US008652809B2

(12) United States Patent
Larsen et al.

(10) Patent No.: US 8,652,809 B2
(45) Date of Patent: *Feb. 18, 2014

(54) METHOD FOR PRODUCING ULTRA-HEAT TREATMENT MILK

(75) Inventors: Niels Erik Larsen, Egä (DK); Jørn Borch Søe, Tilst (DK)

(73) Assignee: DuPont Nutrition Biosciences APS, Copenhagen (DK)

(*) Notice: Subject to any disclaimer, the term of this patent is extended or adjusted under 35 U.S.C. 154(b) by 609 days.

This patent is subject to a terminal disclaimer.

(21) Appl. No.: 12/706,210

(22) Filed: Feb. 16, 2010

(65) Prior Publication Data
US 2010/0215803 A1 Aug. 26, 2010

Related U.S. Application Data

(63) Continuation-in-part of application No. PCT/IB2008/002573, filed on Aug. 14, 2008.

(30) Foreign Application Priority Data

Aug. 17, 2007 (GB) .................................. 0716126.8

(51) Int. Cl.
C12P 19/58 (2006.01)

(52) U.S. Cl.
USPC .............................................. 435/77; 435/7.1

(58) Field of Classification Search
None
See application file for complete search history.

(56) References Cited

U.S. PATENT DOCUMENTS

| 2,888,385 | A | 5/1959 | Grandel |
| 3,260,606 | A | 7/1966 | Azuma |
| 3,368,903 | A | 2/1968 | Johnson |
| 3,520,702 | A | 7/1970 | Menzi |
| 3,634,195 | A | 1/1972 | Melachouris |
| 3,652,397 | A | 3/1972 | Pardun |
| 3,677,902 | A | 7/1972 | Aunstrup |
| 3,817,837 | A | 6/1974 | Rubenstein et. al. |
| 3,850,752 | A | 11/1974 | Schuurs et al. |
| 3,852,260 | A | 12/1974 | Knutsen |
| 3,939,350 | A | 2/1976 | Kronick et al. |
| 3,973,042 | A | 8/1976 | Kosikowski |
| 3,996,345 | A | 12/1976 | Ullman et al. |
| 4,034,124 | A | 7/1977 | Van Dam |
| 4,065,580 | A | 12/1977 | Feldman |
| 4,160,848 | A | 7/1979 | Vidal |
| 4,202,941 | A | 5/1980 | Terada |
| 4,275,149 | A | 6/1981 | Litman et al. |
| 4,277,437 | A | 7/1981 | Maggio |
| 4,366,241 | A | 12/1982 | Tom et al. |
| 4,399,218 | A | 8/1983 | Gauhl |
| 4,567,046 | A | 1/1986 | Inoue et al. |
| 4,683,202 | A | 7/1987 | Mullis |
| 4,689,297 | A | 8/1987 | Good |
| 4,707,291 | A | 11/1987 | Thom |
| 4,707,364 | A | 11/1987 | Barach |
| 4,708,876 | A | 11/1987 | Yokoyama |
| 4,798,793 | A | 1/1989 | Eigtved |
| 4,808,417 | A | 2/1989 | Masuda |
| 4,810,414 | A | 3/1989 | Huge-Jensen |
| 4,814,331 | A | 3/1989 | Kerkenaar |
| 4,816,567 | A | 3/1989 | Cabilly et al. |
| 4,818,695 | A | 4/1989 | Eigtved |
| 4,826,767 | A | 5/1989 | Hansen |
| 4,865,866 | A | 9/1989 | Moore |
| 4,904,483 | A | 2/1990 | Christensen |
| 4,916,064 | A | 4/1990 | Derez |
| 5,112,624 | A | 5/1992 | Johna |
| 5,213,968 | A | 5/1993 | Castle |
| 5,219,733 | A | 6/1993 | Myojo |
| 5,219,744 | A | 6/1993 | Kurashige |
| 5,232,846 | A | 8/1993 | Takeda |
| 5,264,367 | A | 11/1993 | Aalrust |
| 5,273,898 | A | 12/1993 | Ishii |
| 5,288,619 | A | 2/1994 | Brown |
| 5,290,694 | A | 3/1994 | Nakanishi |
| 5,310,679 | A | 5/1994 | Artiss et al. |
| 5,378,623 | A | 1/1995 | Hattori |
| 5,523,237 | A | 6/1996 | Budtz |
| 5,536,661 | A | 7/1996 | Boel |
| 5,558,781 | A | 9/1996 | Buchold |
| 5,650,188 | A | 7/1997 | Gaubert |
| 5,674,707 | A | 10/1997 | Hintz et al. |

(Continued)

FOREIGN PATENT DOCUMENTS

| AR | 249546 | 12/1996 |
| AR | P000105426 | 10/2000 |

(Continued)

OTHER PUBLICATIONS

AACC Method 54-21 Farinograph Method for Flour, from Physical Dough Tests supplied by The British Library, Nov. 3, 1999.
Anderson D, "A Primer in Oils Processing Technology" in Bailey's Industrial Oil and Fat Products, Sixth edition, John Wiley, 2005, vol. 5, chapter 1, p. 1-56. ISBN 978047138401.
Anguita et al, "Purification, Gene Cloning, Amino Acid Sequence Analysis, and Expression of an Extracellular Lipase from an Aeromonas hydrophila Human Isolate", Appl. Environ. Microbiol., vol. 59, No. 8, p. 2411-2417, Aug. 1993.
"AOAC Official method 999.10 (Lead, Cadmium, Zinc, Copper, and Iron in Foods Atomic absorption Spectrophotometry after Microwave Digestion), First Action 1999 NMKL-AOAC Method", AOAC International, pp. 1-3, 2002.

(Continued)

Primary Examiner — Hope Robinson
(74) Attorney, Agent, or Firm — Vedder Price P.C.; Thomas J. Kowalski; Samuel Megerditchian

(57) ABSTRACT

The invention relates to using a lipid acyltransferase polypeptide (SEQ ID NO: 68) in the manufacture of ultra-heat treatment milk (UHT) for improving the stability, the perceptible sensory difference, the smell, and the taste; and for reducing the cholesterol content, and for eliminating or reducing creaming of the UHT milk. The invention also relates to a method of producing UHT milk, wherein the method comprises admixing a lipid acyltransferase with milk and heating the mixture to make it a UHT milk.

19 Claims, 52 Drawing Sheets

(56) References Cited

U.S. PATENT DOCUMENTS

| | | | |
|---|---|---|---|
| 5,677,160 A | 10/1997 | Oester | |
| 5,695,802 A | 12/1997 | Van Den Ouweland | |
| 5,716,654 A | 2/1998 | Groenendaal | |
| 5,741,665 A | 4/1998 | Kato et al. | |
| 5,763,383 A | 6/1998 | Hashida | |
| 5,766,912 A | 6/1998 | Boel | |
| 5,776,741 A | 7/1998 | Pedersen | |
| 5,814,501 A | 9/1998 | Becker | |
| 5,821,102 A | 10/1998 | Berka | |
| 5,824,354 A | 10/1998 | Ritter et al. | |
| 5,827,719 A | 10/1998 | Sandal | |
| 5,830,736 A | 11/1998 | Oxenboll | |
| 5,834,280 A | 11/1998 | Oxenboll | |
| 5,856,163 A | 1/1999 | Hashida | |
| 5,863,759 A | 1/1999 | Boel | |
| 5,869,438 A | 2/1999 | Svendsen | |
| 5,874,558 A | 2/1999 | Boel | |
| 5,879,920 A | 3/1999 | Dale | |
| 5,892,013 A | 4/1999 | Svendsen | |
| 5,912,032 A * | 6/1999 | Komatsu et al. | 426/74 |
| 5,914,306 A | 6/1999 | Svendsen | |
| 5,916,619 A | 6/1999 | Miyazaki | |
| 5,919,746 A | 7/1999 | Hirayama | |
| 5,929,017 A | 7/1999 | Gormsen | |
| 5,965,384 A | 10/1999 | Boel | |
| 5,965,422 A | 10/1999 | Loffler | |
| 5,976,855 A | 11/1999 | Svendsen | |
| 5,989,599 A | 11/1999 | Chmiel | |
| 5,990,069 A | 11/1999 | Andre | |
| 6,001,586 A | 12/1999 | Schellenberger | |
| 6,001,640 A | 12/1999 | Loeffler | |
| 6,020,180 A | 2/2000 | Svendsen | |
| 6,066,482 A | 5/2000 | Steffens | |
| 6,074,863 A | 6/2000 | Svendsen | |
| 6,103,505 A | 8/2000 | Clausen | |
| 6,110,508 A | 8/2000 | Olesen | |
| 6,140,094 A | 10/2000 | Loffler | |
| 6,143,543 A | 11/2000 | Michelsen | |
| 6,143,545 A | 11/2000 | Clausen | |
| 6,146,869 A | 11/2000 | Harris | |
| 6,156,548 A | 12/2000 | Christensen | |
| 6,180,406 B1 | 1/2001 | Stemmer | |
| 6,254,645 B1 | 7/2001 | Kellis | |
| 6,254,903 B1 | 7/2001 | Schuster et al. | |
| 6,344,328 B1 | 2/2002 | Short | |
| 6,350,604 B1 | 2/2002 | Hirayama | |
| 6,358,543 B1 | 3/2002 | Soe | |
| 6,361,974 B1 | 3/2002 | Short | |
| 6,365,204 B1 | 4/2002 | Spendler | |
| 6,432,898 B1 | 8/2002 | Rey | |
| 6,495,357 B1 | 12/2002 | Fuglsang | |
| 6,506,588 B2 | 1/2003 | Tsutsumi | |
| 6,509,182 B2 | 1/2003 | Tsutsumi | |
| 6,511,837 B2 | 1/2003 | Tsutsumi | |
| 6,514,739 B1 | 2/2003 | Udagawa | |
| 6,558,715 B1 | 5/2003 | Rey | |
| 6,582,942 B1 | 6/2003 | Christensen | |
| 6,624,129 B1 | 9/2003 | Borch et al. | |
| 6,645,749 B2 | 11/2003 | Vind | |
| 6,682,922 B2 | 1/2004 | Berka | |
| 6,686,189 B2 | 2/2004 | Rey | |
| 6,726,942 B2 | 4/2004 | Soe et al. | |
| 6,730,346 B2 | 5/2004 | Rey | |
| 6,815,190 B1 | 11/2004 | Abo | |
| 6,852,346 B2 | 2/2005 | Soe | |
| 6,866,837 B2 | 3/2005 | Reubi et al. | |
| 6,936,289 B2 | 8/2005 | Olsen et al. | |
| 6,964,944 B1 | 11/2005 | Callisen et al. | |
| 6,967,035 B2 | 11/2005 | Bojsen et al. | |
| 7,226,771 B2 | 6/2007 | Gramatikova et al. | |
| 7,638,293 B2 * | 12/2009 | De Kreij et al. | 435/15 |
| 7,807,398 B2 * | 10/2010 | De Kreij et al. | 435/15 |
| 7,906,307 B2 * | 3/2011 | Soe et al. | 435/193 |
| 7,955,814 B2 * | 6/2011 | De Kreij et al. | 435/15 |
| 7,960,150 B2 * | 6/2011 | Kolkman et al. | 435/134 |
| 8,003,095 B2 * | 8/2011 | Kreij et al. | 424/94.5 |
| 2002/0098536 A1 | 7/2002 | Norinobu | |
| 2002/0110854 A1 | 8/2002 | Tsutsumi | |
| 2002/0142434 A1 | 10/2002 | Tsutsumi | |
| 2002/0168746 A1 | 11/2002 | Tsutsumi | |
| 2003/0003561 A1 | 1/2003 | Vind | |
| 2003/0028923 A1 | 2/2003 | Lardizabal | |
| 2003/0040450 A1 | 2/2003 | Rey | |
| 2003/0074695 A1 | 4/2003 | Farese | |
| 2003/0100092 A1 | 5/2003 | Berka | |
| 2003/0148495 A1 | 8/2003 | Hastrup | |
| 2003/0180418 A1 | 9/2003 | Rey | |
| 2003/0185939 A1 | 10/2003 | Nielsen | |
| 2003/0215544 A1 | 11/2003 | Nielsen | |
| 2004/0005399 A1 | 1/2004 | Chakrabarti | |
| 2004/0142441 A1 | 7/2004 | Weiss et al. | |
| 2004/0235106 A1 | 11/2004 | Kapeller-Libermann | |
| 2004/0235119 A1 | 11/2004 | Hoppe et al. | |
| 2005/0059130 A1 | 3/2005 | Bojsen | |
| 2005/0059131 A1 | 3/2005 | Bisgard-Frantzen | |
| 2005/0118697 A1 | 6/2005 | Budolfsen | |
| 2005/0142647 A1 | 6/2005 | Wassell | |
| 2006/0040357 A1 | 2/2006 | Bandaru et al. | |
| 2006/0075518 A1 | 4/2006 | Yaver et al. | |
| 2007/0122525 A1 | 5/2007 | Kreij et al. | |
| 2008/0063783 A1 | 3/2008 | Kreij et al. | |
| 2008/0187643 A1 | 8/2008 | Horlacher et al. | |

FOREIGN PATENT DOCUMENTS

| | | |
|---|---|---|
| AR | P040101441 | 4/2004 |
| AT | 110 768 | 8/1987 |
| AU | 570720 | 9/1984 |
| AU | 723031 | 4/1998 |
| AU | 199742798 | 4/1998 |
| AU | 754470 | 11/1999 |
| BR | 8404421-7 | 4/1984 |
| CA | 805618 A | 2/1969 |
| CA | 462382 | 9/1984 |
| CA | 1270781 | 6/1990 |
| CA | 2012723 | 9/1990 |
| CA | 2134597 | 10/1994 |
| CA | 2224143 | 12/1996 |
| CA | 2403025 | 4/2004 |
| CN | 101200754 | 12/2007 |
| DE | 2817087 | 11/1978 |
| DE | 19620649 | 11/1997 |
| DE | 69129988 | 3/1999 |
| DE | 69330066 | 10/2001 |
| DE | 10018787 | 5/2002 |
| DE | 69527835 | 4/2003 |
| DE | 69528070 | 6/2003 |
| DE | 69904161 | 7/2003 |
| DE | 69716711 | 9/2003 |
| DE | 69531538 | 6/2004 |
| DE | 69819782 | 9/2004 |
| DK | 0217/94 | 2/1994 |
| DK | EP0746608 | 10/2003 |
| EP | 0167309 | 1/1986 |
| EP | 0171995 | 2/1986 |
| EP | 0205208 | 12/1986 |
| EP | 0206390 | 12/1986 |
| EP | 0214761 | 3/1987 |
| EP | 0 258 068 | 3/1988 |
| EP | 0257388 | 3/1988 |
| EP | 0260573 | 3/1988 |
| EP | 0334462 | 9/1989 |
| EP | 0195311 | 6/1990 |
| EP | 0375102 | 6/1990 |
| EP | 0426211 | 5/1991 |
| EP | 0445692 | 9/1991 |
| EP | 0449375 | 10/1991 |
| EP | 0468731 | 1/1992 |
| EP | 0493045 | 7/1992 |
| EP | 0583265 | 10/1992 |
| EP | 0513709 | 11/1992 |
| EP | 0542351 | 5/1993 |
| EP | 0558112 | 9/1993 |
| EP | 0258068 | 11/1993 |

(56) References Cited

FOREIGN PATENT DOCUMENTS

| | | |
|---|---|---|
| EP | 0238023 | 12/1993 |
| EP | 0575133 | 12/1993 |
| EP | 0580252 | 1/1994 |
| EP | 0622446 | 1/1994 |
| EP | 0258068 | 8/1994 |
| EP | 0652289 | 5/1995 |
| EP | 0654527 | 5/1995 |
| EP | 0396162 | 9/1995 |
| EP | 0687414 | 12/1995 |
| EP | 0585988 | 3/1996 |
| EP | 0721981 | 7/1996 |
| EP | 0752008 | 1/1997 |
| EP | 0776604 | 6/1997 |
| EP | 0531104 | 8/1997 |
| EP | 0808903 | 11/1997 |
| EP | 0682116 | 12/1997 |
| EP | 0812910 | 12/1997 |
| EP | 0305216 | 3/1998 |
| EP | 0 834 255 | 4/1998 |
| EP | 0847701 | 6/1998 |
| EP | 0548228 | 8/1998 |
| EP | 0866796 | 9/1998 |
| EP | 0702712 | 12/1998 |
| EP | 0882797 | 12/1998 |
| EP | 0897667 | 2/1999 |
| EP | 0913092 | 5/1999 |
| EP | 09913468 | 5/1999 |
| EP | 0321811 | 12/1999 |
| EP | 1131416 | 6/2000 |
| EP | 0739985 | 11/2000 |
| EP | 1057415 | 12/2000 |
| EP | 1071734 | 1/2001 |
| EP | 1073339 | 2/2001 |
| EP | 0659049 | 3/2001 |
| EP | 1103606 | 5/2001 |
| EP | 1108360 | 6/2001 |
| EP | 1138763 | 10/2001 |
| EP | 1145637 | 10/2001 |
| EP | 0191217 | 2/2002 |
| EP | 0869167 | 2/2002 |
| EP | 1 193 314 | 4/2002 |
| EP | 0 746 618 | 8/2002 |
| EP | 0746618 | 8/2002 |
| EP | 1233676 | 8/2002 |
| EP | 0648263 | 9/2002 |
| EP | 0784674 | 9/2002 |
| EP | 1275711 | 1/2003 |
| EP | 1285969 | 2/2003 |
| EP | 1298205 | 4/2003 |
| EP | 0635053 | 6/2003 |
| EP | 0675944 | 6/2003 |
| EP | 0817838 | 6/2003 |
| EP | 1280919 | 6/2003 |
| EP | 0746608 | 8/2003 |
| EP | 0851913 | 5/2004 |
| EP | 1262562 | 6/2004 |
| EP | 1433852 | 6/2004 |
| EP | 0977869 | 7/2004 |
| EP | 0743017 | 9/2004 |
| EP | 0675949 | 10/2004 |
| EP | 0880590 | 10/2004 |
| EP | 0897423 | 10/2004 |
| EP | 1466980 | 10/2004 |
| EP | 0839186 | 11/2004 |
| EP | 1162889 | 2/2005 |
| EP | 1532863 | 5/2005 |
| EP | 1559788 | 8/2005 |
| EP | 1363506 | 11/2005 |
| EP | 1 624 047 A1 | 2/2006 |
| EP | 01624047 A1 | 2/2006 |
| EP | 1 624 047 B1 | 10/2006 |
| EP | 1762622 | 3/2007 |
| EP | 1788080 | 5/2007 |
| ES | 535608 | 9/1984 |
| ES | 535602 | 10/1984 |
| ES | 535609 | 3/1985 |
| GB | 1086550 | 10/1967 |
| GB | 1442418 | 7/1976 |
| GB | 1577933 | 10/1980 |
| GB | 2264429 | 9/1993 |
| GB | 0028701.1 | 11/2000 |
| GB | 2358784 | 8/2001 |
| GB | 0301117.8 | 1/2003 |
| GB | 0301118.6 | 1/2003 |
| GB | 0301119.4 | 1/2003 |
| GB | 0301120.2 | 1/2003 |
| GB | 0301121.0 | 1/2003 |
| GB | 0301122.8 | 1/2003 |
| GB | 2379165 | 3/2003 |
| GB | 2267033 | 11/2003 |
| GB | 0330016.7 | 12/2003 |
| JP | 59183881 | 4/1960 |
| JP | 40116612 | 5/1973 |
| JP | 5476892 | 6/1979 |
| JP | 55131340 | 10/1980 |
| JP | 57-189638 | 11/1982 |
| JP | 57-189637 | 12/1982 |
| JP | 60078529 | 5/1985 |
| JP | 62118883 | 11/1985 |
| JP | 63042691 | 8/1986 |
| JP | 62061590 | 3/1987 |
| JP | 62285749 | 12/1987 |
| JP | 10203974 | 8/1988 |
| JP | 1252294 | 10/1989 |
| JP | 2-49593 | 2/1990 |
| JP | 2-153997 | 6/1990 |
| JP | 04075592 | 3/1992 |
| JP | 6014773 | 3/1992 |
| JP | 4121186 | 4/1992 |
| JP | 15626492 | 6/1992 |
| JP | 04200339 | 7/1992 |
| JP | 4300839 | 10/1992 |
| JP | 4327536 | 11/1992 |
| JP | 04-370055 | 12/1992 |
| JP | 5211852 | 8/1993 |
| JP | 6345800 | 12/1994 |
| JP | 07-079687 | 3/1995 |
| JP | 8268882 | 4/1995 |
| JP | 7231788 | 9/1995 |
| JP | 7330794 | 12/1995 |
| JP | 8143457 | 6/1996 |
| JP | 8266213 | 10/1996 |
| JP | 9040689 | 2/1997 |
| JP | 10155493 | 6/1998 |
| JP | 10155493 A | 6/1998 |
| JP | 11-228986 | 8/1999 |
| JP | 11290078 | 10/1999 |
| JP | 2000226335 | 8/2000 |
| JP | 03/024096 | 7/2001 |
| JP | 3553958 | 5/2004 |
| KR | 93-700773 | 3/1993 |
| KR | 94-10252 | 10/1994 |
| KR | 95-700043 | 1/1995 |
| KR | 95-702583 | 6/1995 |
| KR | 96-704602 | 8/1996 |
| KR | 2001-7012115 | 9/2001 |
| KR | 2003-7008997 | 10/2003 |
| NL | 0784674 | 12/2002 |
| NL | 0869167 | 1/2003 |
| NL | 1073339 | 2/2003 |
| NL | 0746608 | 11/2003 |
| PH | 31068 | 11/1984 |
| RU | 2140751 | 6/1997 |
| RU | 2235775 | 11/1999 |
| RU | 2001117497 | 6/2001 |
| TR | 200101551 | 12/1999 |
| WO | 88/02775 | 4/1988 |
| WO | 88/03365 | 5/1988 |
| WO | 89/01969 | 3/1989 |
| WO | 89/06803 | 7/1989 |
| WO | 91/00920 | 1/1991 |
| WO | 91/06661 | 5/1991 |

(56) References Cited

FOREIGN PATENT DOCUMENTS

| | | |
|---|---|---|
| WO | 91/14772 | 10/1991 |
| WO | WO 91/17243 | 11/1991 |
| WO | 92/05249 | 4/1992 |
| WO | 92/14830 | 9/1992 |
| WO | 92/18645 | 10/1992 |
| WO | 93/01285 | 1/1993 |
| WO | 93/11249 | 6/1993 |
| WO | 93/12812 | 7/1993 |
| WO | 94/01541 | 1/1994 |
| WO | 94/04035 | 3/1994 |
| WO | 94/14940 | 7/1994 |
| WO | 94/14951 | 7/1994 |
| WO | 94/26883 | 11/1994 |
| WO | 95/06720 | 3/1995 |
| WO | 95/09909 | 4/1995 |
| WO | 95/22606 | 8/1995 |
| WO | 95/22615 | 8/1995 |
| WO | 95/22625 | 8/1995 |
| WO | 95/29996 | 11/1995 |
| WO | 95/30744 | 11/1995 |
| WO | WO 95/29996 | 11/1995 |
| WO | 96/09772 | 4/1996 |
| WO | 96/13578 | 5/1996 |
| WO | 96/13579 | 5/1996 |
| WO | 96/13580 | 5/1996 |
| WO | 96/27002 | 9/1996 |
| WO | 96/28542 | 9/1996 |
| WO | 96/30502 | 10/1996 |
| WO | 96/32472 | 10/1996 |
| WO | 96/39851 | 12/1996 |
| WO | 97/04079 | 2/1997 |
| WO | 97/05219 | 2/1997 |
| WO | 97/07202 | 2/1997 |
| WO | 97/11083 | 3/1997 |
| WO | 97/14713 | 4/1997 |
| WO | 97/27237 | 7/1997 |
| WO | 97/27276 | 7/1997 |
| WO | 97/41212 | 11/1997 |
| WO | 97/41735 | 11/1997 |
| WO | 97/41736 | 11/1997 |
| WO | WO 98/00029 | 1/1998 |
| WO | 98/08939 | 3/1998 |
| WO | 98/14594 | 4/1998 |
| WO | WO 98/13479 | 4/1998 |
| WO | WO 98/16112 | 4/1998 |
| WO | 98/18912 | 5/1998 |
| WO | 98/26057 | 6/1998 |
| WO | WO 98/23162 | 6/1998 |
| WO | 98/31790 | 7/1998 |
| WO | WO 98/31790 | 7/1998 |
| WO | 98/41623 | 9/1998 |
| WO | 98/44804 | 10/1998 |
| WO | 98/45453 | 10/1998 |
| WO | 98/50532 | 11/1998 |
| WO | 98/51163 | 11/1998 |
| WO | 98/59028 | 12/1998 |
| WO | 99/33964 | 7/1999 |
| WO | 99/34011 | 7/1999 |
| WO | 99/37782 | 7/1999 |
| WO | 99/42566 | 8/1999 |
| WO | 99/50399 | 10/1999 |
| WO | 99/53001 | 10/1999 |
| WO | 99/53769 | 10/1999 |
| WO | 99/55883 | 11/1999 |
| WO | 00/05396 | 2/2000 |
| WO | 00/28044 | 5/2000 |
| WO | 00/32758 | 6/2000 |
| WO | 00/34450 | 6/2000 |
| WO | 00/36114 | 6/2000 |
| WO | WO 00/32758 | 6/2000 |
| WO | 00/43036 | 7/2000 |
| WO | 00/49164 | 8/2000 |
| WO | 00/58517 | 10/2000 |
| WO | 00/59307 | 10/2000 |
| WO | 00/60063 | 10/2000 |
| WO | 00/61771 | 10/2000 |
| WO | 00/71808 | 11/2000 |
| WO | 00/75295 | 12/2000 |
| WO | 01/16308 | 3/2001 |
| WO | 01/27251 | 4/2001 |
| WO | 01/29222 | 4/2001 |
| WO | WO 00/023461 | 4/2001 |
| WO | 01/34835 | 5/2001 |
| WO | WO 01/39544 | 5/2001 |
| WO | 01/39602 | 6/2001 |
| WO | 01/42433 | 6/2001 |
| WO | 01/47363 | 7/2001 |
| WO | 01/66711 | 9/2001 |
| WO | 01/78524 | 10/2001 |
| WO | WO 01/75083 | 10/2001 |
| WO | 01/83559 | 11/2001 |
| WO | 01/83770 | 11/2001 |
| WO | 01/92502 | 12/2001 |
| WO | 02/00852 | 1/2002 |
| WO | 02/03805 | 1/2002 |
| WO | 02/06457 | 1/2002 |
| WO | WO 02/06508 | 1/2002 |
| WO | 02/14490 | 2/2002 |
| WO | 02/24881 | 3/2002 |
| WO | 02/30207 | 4/2002 |
| WO | WO 02/39828 | 5/2002 |
| WO | 02/055679 | 7/2002 |
| WO | 02/062973 | 8/2002 |
| WO | 02/065854 | 8/2002 |
| WO | 02/066622 | 8/2002 |
| WO | 02/094123 | 11/2002 |
| WO | 03/020923 | 3/2003 |
| WO | WO 03/020923 | 3/2003 |
| WO | WO 03/020941 | 3/2003 |
| WO | WO 2006/031699 | 3/2003 |
| WO | 03/040091 | 5/2003 |
| WO | 03/060112 | 7/2003 |
| WO | 03/070013 | 8/2003 |
| WO | 03/089260 | 10/2003 |
| WO | WO 03/089620 | 10/2003 |
| WO | 03/097825 | 11/2003 |
| WO | WO 03/097835 | 11/2003 |
| WO | 03/099016 | 12/2003 |
| WO | 03/100044 | 12/2003 |
| WO | 03/102118 | 12/2003 |
| WO | WO 03/100044 | 12/2003 |
| WO | 2004/004467 | 1/2004 |
| WO | 2004/018660 | 3/2004 |
| WO | 2004/053039 | 6/2004 |
| WO | 2004/053152 | 6/2004 |
| WO | 2004/059075 | 7/2004 |
| WO | 2004/064537 | 8/2004 |
| WO | 2004/064987 | 8/2004 |
| WO | WO 2004/064537 | 8/2004 |
| WO | WO 2004/064987 | 8/2004 |
| WO | WO 2004/084638 | 10/2004 |
| WO | 2004/097012 | 11/2004 |
| WO | 2004/111216 | 12/2004 |
| WO | 2005/003339 | 1/2005 |
| WO | 2005/005977 | 1/2005 |
| WO | 97/07205 | 2/2005 |
| WO | 2005/056782 | 6/2005 |
| WO | 2005/066347 | 7/2005 |
| WO | 2005066351 | 7/2005 |
| WO | 2005/080540 | 9/2005 |
| WO | 2005/087918 | 9/2005 |
| WO | WO 2005/111203 | 11/2005 |
| WO | 2006/008508 | 1/2006 |
| WO | 2006/008653 | 1/2006 |
| WO | 2006/032279 | 3/2006 |
| WO | WO 2006/045354 | 5/2006 |
| WO | WO 2006/066590 | 6/2006 |
| WO | WO 2008/003420 | 1/2008 |
| WO | WO 2008/036863 | 3/2008 |
| WO | WO 2008/090395 | 7/2008 |
| WO | WO 2008/094847 | 8/2008 |
| WO | WO 2009/002480 | 12/2008 |

(56) References Cited

FOREIGN PATENT DOCUMENTS

| WO | WO 2009/024736 | 2/2009 |
|----|----------------|--------|
| WO | WO 2009/024862 | 2/2009 |
| WO | WO 2009/081094 | 7/2009 |

OTHER PUBLICATIONS

AOCS Introduction to the Processing of Fats and Oils p. 111-16-111-19. Four modules on CD-ROM. American Oil Chemists Society, 2003.
AOCS Method 2c-25 "1997 Moisture and Volatile Matter Air Oven Method" Sampling and Analysis of Commercial Fats and Oils, obtained from The British Library, p. 1, 1997.
AOCS Official Method Ca 20-99: "Analysis of Phosphorus in oil by inductively Coupled Plasma Optical Emission Spectroscopy", Sampling and Analysis of Commercial Fats and Oils, obtained from The British Library, pp. 1-3, 2001.
Archer D.B. & Peberdy, The Molecular Biology of Secreted Enzyme Production by Fungi, Critical Reviews in Biotechnology, 1997, vol. 17, No. 4, p. 273-306.
Arskog and Joergensen, "Baking performance of prior art lipases from *Candida cylindracea* and *Aspergillus foeditus* and their activity on galactolipids in dough", Novozymes Report Jul. 18, 2005, pp. 1-2.
Arskog and Joergensen, "Baking performance of prior art lipases from *Humicola Lanuginosa, Aspergillus tubigensis, Rhizopus delemar* and *Rhizomucor miehei*, and their activity on galactolipids in dough", Novozymes Report Jul. 17, 2005, pp. 1-8.
Aust K., "Applications of lecithin in bakery foods," AIB Research Technical Bulletin, vol. XV, issue 12, Dec. 1993, p. 1-6.
Banas A. et al., "Cellular sterol ester synthesis in plants is performed by an enzyme (Phospholipid: Sterol Acyltransferase) different from the yeast and mammalian Acyl-CoA: Sterol AcylTransferase", Journal of Biological Chemistry, 2005, vol. 280, No. 41, pp. 34626-34634.
Beggs J.D., Transformation of yeast by a replicating hybrid plasmid, Nature (London), 1978, vol. 275, p. 104.
Bessette, "Efficient folding or proteins with multiple disulphide bonds in the *Escherida coli cytoplasm*", Proc. Natl. Acad. Sci. USA, 1999, vol. 96, p. 13703-13708.
Bo Yang et al., "Optimization of Enzymatic Degumming Process for Rapseed Oil," JAOCS, 2006, vol. 83, No. 7, p. 653-658.
Briand et al, "Substrate Specificity of the Lipase from Candida parapsilosis", Lipids, Aug. 1995, vol. 30, No. 8, p. 747-754.
Bru R., López-Nicolás J.M., García-Carmona F., (1995) "Aggregation of polyunsaturated fatty acid in the presence of cyclodextrins", Colloids and Surfaces A: Physiochemical and Engineering Aspects. 97, p. 263-269.
Brunel et al, "High-Level expression of Candida parapsilosis lipase/acyltransferase in Pichia pastoris," J Biotechnology, Jul. 1, vol. 111, No. 1, p. 41-50, 2004.
Buchold H. et. al., "Enzymatische Phosphatidentfernung aus Pflanzenolen'" Technologies, 1993, vol. 95, No. 8, p. 300-304, ISSN:0931-5985.
Bylund G. (ed), 1995, Dairy Processing Handbook, Chapter 2, p. 17-42, Lund, Sweden.
Bylund G. (ed), 1995, Dairy Processing Handbook, Chapter 9, p. 227-246, Lund, Sweden.
Ceci L.N. et al, Oil recovery and lecithin production using water degumming sludge of crude soybean oils, Journal of the Science of Food and Agriculture, 2008, vol. 88, No. 14, p. 2460-2466.
Cereghino et al., Heterologous protein expression in the methylotrophic yeast *Pichia pastoris*, FEMS Microbiology Review, 2000, vol. 24, No. 1, p. 45-66.
Chica et al, "Semi-rational approaches to engineering enzyme activity: combining the benefits of directed evolution and rational design" Current Opinion in Biotechnology, 2005, vol. 16, p. 378-384.
Christou P., Genetic engineering of crop legumes and cereals: current status and recent advances, Agro-Food-Industry Hi-Tech, Mar./Apr. 1994, p. 17-27.

Davis R.H. and de Serres, Genetic and Microbiological Research Techniques for *Neurospora crassa*, Methods Enzymology, 1971, vol. 17A, p. 79-143.
EC 1.1.3.10 (downloaded—Jul. 12, 2010 from http://www.chem.qmul.ac.uk/iubmb/enzyme/EC1/1/3/10.html).
EC 1.1.3.4 (downloaded—Jul. 12, 2010 from http://www.chem.qmul.ac.uk/iubmb/enzyme/EC1/1/3/4.html).
EC 1.1.3.5 (downloaded—Nov. 16, 2009 from http://www.chem.qmul.ac.uk/iubmb/enzyme/EC1/1/3/5.html).
EC 2.3.1.43 (downloaded Apr. 21, 2009 from http://www.chem.qmul.ac.uk/iubmb/enzyme/EC2/3/1/43.html).
EC 2.4.1.19 (Downloaded Jul. 12, 2010 from http://www.chem.qmul.ac.uk/iubmb/enzyme/EC2/4/1/19.html).
EC 3.1.1.26 (downloaded—Dec. 18, 2008 from http://www.chem.qmul.ac.uk/iubmb/enzyme/EC3/1/1/26.html).
EC 3.1.1.3 (downloaded—Dec. 18, 2008 from http://www.chem.qmul.ac.uk/iubmb/enzyme/EC3/1/1/3.html).
EC 3.1.1.32 (downloaded—May 22, 2008 from http://www.chem.qmul.ac.uk/iubmb/enzyme/EC3/1/1/32.html).
EC 3.1.1.4 Phospholipase A2 enzyme Enzyme Entry 1983 (downloaded Apr. 21, 2009 from http://www.chem.qmul.ac.uk/iubmb/enzyme/EC3/1/1/4.html).
EC 3.1.1.5 (downloaded Dec. 18, 2008 from http://www.chem.qmul.ac.uk/iubmb/enzyme/EC3/1/1/5.html).
EC 3.2.1.3 (downloaded Jul. 12, 2010 from http://www.chem.qmul.ac.uk/iubmb/enzyme/EC3/2/1/3.html).
EC 3.2.1.32 (Downloaded Jul. 12, 2010 from http://www.chem.qmul.ac.uk/iubmb/enzyme/EC3/2/1/32.html).
EC 3.2.1.60 (downloaded Apr. 28, 2009 from http://www.chem.qmul.ac.uk/iubmb/enzyme/EC3/2/1/60.html).
Eliasson A-C. and Larssen K., "Chapter 2: Physiochemical Behavior of the Components of Wheat Flour", *Cereals in Breadmaking: a molecular colloidal approach*, Marcel Dekker Inc, 1993, ISBN0824788168, p. 31-45.
Garzillo et al, "Production, Purification, and Characterization of Glucose Oxidase from Penicillium Variable p. 16," Biotechnol. Appl. Biochem., 1995, vol. 22, p. 169-178.
Genbank accession code NC_003888.1:8327480..8328367 (downloaded Apr. 21, 2009), p. 1.
Genbank accession No. AL646052 (downloaded Apr. 21, 2009), pp. 1-2.
Genbank accession No. AL939131.1:265480..266367 (downloaded Apr. 21, 2009), p. 1.
Genbank accession No. CAC42140 (downloaded Apr. 21, 2009), pp. 1-2.
NCBI Accession No. SC07513 (downloaded Apr. 21, 2009), pp. 1.
Genbank accession No. P41734 (downloaded Apr. 21, 2009), pp. 1-4.
NCBI Accession No. Z75034 (downloaded Apr. 21, 2009) p. 1-2.
Hammond E.G. et al., "Soybean Oil" in Bailey's Industrial Oil and Fat Products, Sixth edition, John Wiley, 2005, vol. 3, chapter 13, p. 577-653. ISBN 978047138401.
Hinchcliffe E., Kenny E., "Yeast as a vehicle for the expression of heterologous genes", Yeasts, 1993, vol. 5, Anthony H. Rose and J. Stuart Harrison, eds. 2nd edition, Academic Press Ltd.
Hinnen A. et al., Transformation of yeast, Proceedings of the National Academy of Sciences USA, Apr. 1978, vol. 75, No. 4, p. 1929-1933.
Hollenberg C.P. et al., Production of recombinant proteins by methylotrophic yeasts, Current Opinion in Biotechnology Oct 1997, vol. 8, No. 5, pp. 554-560.
Horwell DC, "The 'peptoid' approach to the design of non-peptide, small molecular agonists and antogonists of neuropeptides", Trends Biotechnol., 1995, vol. 13, No. 4, pp. 132-134.
Hossen, Monjur, "Enzyme catalyzed synthesis of structured phospholipids with conjugated linoleic acid and plant sterols, " A Dissertation by MD Monjur Hossen, May 2005, p. 1-152.
HUI, Bailey's Industrial Oil and Fat Products, 5th edition vol. 2 Edible Oil and Fat Products: Oils and Oilseeds, Wiley Interscience (1996), pp. 513-516. ISBN 0471594261.
International Dairy Federation Bulletin Document 116, 1979, p. 5, "Definition of recombined milk".
Ito H. et al., "Transformation of Intact Yeast Cells Treated with Alkali Cations," J. Bacteriology, 1983, vol. 153, p. 163-168.

(56) References Cited

OTHER PUBLICATIONS

Jost R. et. al., "Milk and Dairy Products," Nestle Product Technology Center, 2007, Wiley-VCH, pp. 1-62, Konolfingen, Switzerland.
Kalscheuer et al, "Synthesis of Novel Lipids in Saccharomyces cerevisiae by Heterologous Expression of an Unspecific Bacterial Acyltransferase," Applied and Environmental Microbiology, vol. 70, No. 12, p. 7119-7125, 2004.
Kane, "Effects of rare codon clusters on high-level expression of heterolgous proteins in *E.coli*" Current Opinion Biotechnology, 1995, vol. 6, p. 494-500.
Kimmel, A. et al. "Preparation of cDNA and the Generation of cDNA Libraries: Overview," Methods in Enzymology, 1987, vol. 152, p. 307-316.
LaVallie T.M., 2-Methoxyestradiol Inhibits Proliferation and Induces Apoptosis Independently of Estrogen Receptors αand β, Current Opinion in Biotechnology, 1995, vol. 6, No. 5, pp. 501-506.
Leon et al., "A new approach to study starchy changes occurring the double-baking process and during bread storage," Z. Lebensn. Unters Forsch A, 1997, vol. 204 pp. 316-320.
McIntyre et al., "Distribution of Glycerophospholipid-Cholesterol Acyltransferase in Selected Bacterial Species," Journal of Bacteriology, Jul. 1979, vol. 139, no. pp. 132-136.
NCBI protein accession code AAK84028.1 GI:15082088, (downloaded Dec. 18, 2009), pp. 1-2.
NCBI protein accession code CAB39707.1 GI:4529178, (downloaded Dec. 18, 2009), pp. 1-2.
NCBI protein accession code CAB62724.1 GI:6562793, (downloaded Dec. 18, 2009), pp. 1-2.
NCBI protein accession code CAB88833.1 GI:7635996, (downloaded Dec. 18, 2009), pp. 1-2.
NCBI protein accession code CAB89450.1; GI:7672261, (downloaded Dec. 18, 2009), pp. 1-2.
NCBI protein accession code CAC01477,1 GI:9716139, (downloaded Dec. 18, 2009), pp. 1-2.
NCBI's Genbank database accession number: 1IVN_A; GID:33357066, (downloaded Oct. 14, 2010), pp. 1-2.
Oil Mill Gazetteer, "Enzymatic Degumming Improves Oil Refining in China," Jul. 2005 vol. 111, p. 2-4.
Phospholipase C, E.C. 3.1.4.3, (downloaded Sep. 8, 2009 from http://www.chem.qmul.ac.uk/iubmb/enzyme/EC3/1/4/3.html), p. 1.
Poldermans B and Schoppink P, "Controlling the baking process and product quality with enzymes", Cereal Foods World, Mar. 1999, 44 (3), p. 132-135.
Potrykus I., Gene Transfer to Plants: assessment of published approaches and results, Annu. Rev. Plant Physiol. Plant Mol. Biol., 1991, vol. 42, p. 205-225.
PreSens Manual HydroPlate® HP96U and HydroPlate® HP96C, pp. 1-15, Aug. 17, 2004.
Seffernick et al, "Melamine Deaminase and Atrazine Chlorohydrolase: 98 Percent Identical but Functionally Different", Journal of Bacteriology, Apr. 2001, vol. 183, No. 8, p. 2405-2410.
Seino et al, "Enzymatic Synthesis of Carbohydrate Esters of Fatty Acid (10 Esterification of Sucrose, Glucose, Fructose and Sorbitol", J. Am. Oil Chem. Soc., Nov. 1984, vol. 61, No. 11, p. 1761-1765.
Sequence alignment of database accession No. Q44268 (database: UNIProtKB/TrEMBL) with SEQ. ID No. 16, (downloaded Jan. 27, 2009), pp. 1-2.
Sequence alignment of database accession No. Q44268 (database: UNIProtKB/TrEMBL) with SEQ. ID No. 70, (downloaded Jan. 27, 2009), pp. 1-2.
Simon RJ et al.,"Peptoids: a modular approach to drug discovery", Proc. Natl. Acad. Sci. USA, 1992, vol. 89, No. 20, pp. 9367-9371.
Stryer, "Conformation and Dynamics," Biochemistry, 2nd Edition, 1981, WH Freeman & Co., San Francisco, p. 16.
Sutrisno, A. et al, "Expression of a gene Encoding Chitinase (pCA 8 ORF) from Aeromonas sp. No. 10S-24 in *Esxherichia coli* and Enzyme Characterization," Journal of Bioscience and Bioengineering, vol. 91, No. 6, pp. 599-602, 2001.

Szuhaj B.F., "Lecithins" in Bailey's Industrial Oil and Fat Products, Sixth edition, John Wiley, 2005, vol. 2, chapter 13, p. 361-456. ISBN 978047138401.
Tanji M.et al., "Lipase hydrolysis of milk fat and its soft fractions", Research Bulletin of Obihiro University, 2001, vol. 22, No. 2, p. 89-94.
Tilden E.B. and Hudson C.S., Preparation and Properties of the Amylases Produced by Bacillus Macerans and Bacillus Polymyxa, J. Bacteriology, 1942, vol. 43, p. 527-544.
Torres C.F. et al., A two steps enzymatic procedure to obtain sterol esters, tocopherols and fatty acid ethyl esters from soybean oil deodorizer distillate, Process Biochemistry, 2007, vol. 42, No. 9, p. 1335-1341.
Trueman L.J., "Heterologous Expression in Yeast," Methods Molecular Biology, vol. 49, p. 341-354 (1995).
Turner G. Vectors for generic manipulation, in Martinelli S.D, Kinghorn J.R. (editors), *Aspergillus*: 50 years on. Progress in industrial microbiology, 1994, vol. 29, p. 641-666.
Verenium Corporation leaflet Purifine® Enzyme"Convert Gums to Oils Significantly Increase Oil Yields no increase in Free Fatty Acids", San Diego, Jan. 2008.
Witkowski et al, "Conversion of a B-Ketoacyl Synthase to a Malonyl Decarboxylase by Replacement of the Active-Site Cysteine with Glutamine," Biochemistry, Sep. 7, 1999, vol. 38, No. 36, p. 11643-11650.
Notification of Reasons for Refusal: JP Application No. 526105, Feb. 12, 2003 (Translation).
Notification of Reasons for Refusal: JP Application No. 526105, Jun. 4, 2002 (Translation).
Written Argument: JP Application No. 97181706.5, (Dec. 9, 1997) (Translation).
U.S. Appl. No. 60/083,277, filed Apr. 28, 1998, Spender, Tina, et al.
Patent Abstracts of Japan; Publication No. 04-370055; Publication Date Dec. 22, 1992.
Patent Abstracts of Japan; Publication No. 07-079687; Publication Date Mar. 28, 1995.
Patent Abstracts of Japan; Publication No. 48016612; Publication Date May 23, 1973.
Delphine Briand et al., "Substrate Specificity of the Lipase from *Candida parapsilosis*" Lipids, 1995, vol. 30, No. 8, pp. 747-754.
Kin-Yu Chan et al., "Direct colorimetric Assay of Free Thiol Groups and Disulfide Bonds in Suspensions of Solubilized and Particulate Cereal Proteins", Cereal Chemistry, 1993, vol. 70, No. 1, pp. 22-26.
Roberto A. Chica et al., "Semi-rational approaches to engineering enzyme activity: combining the benefits of directed evolution and rational design", Current Opinion in Biotechnology, 2005, vol. 16, pp. 378-384.
Rebeca Garcia, et al., "Analysis and Modeling of the Ferulic Acid Oxidation by a Glucose Oxidase-Peroxidase Association. Comparison with a Hexose Oxidase-Peroxidase Association", J. Agric. Food Chem., 2004, vol. 52, pp. 3946-3953.
Anna Maria V. Garzillo et al., "Production, purification and characterization of glucose oxidase from *Penicillium variabile* P16[1]" Biotechnol. Appl. Biochem., 1995, vol. 22, pp. 169-178.
Jennifer L. Seffemick et al., "Melamine Deaminase and Atrazine Chlorohydrolase: 98 Percent Identical but Functionally Different", Journal of Bacteriology, Apr. 2001, vol. 183, No. 8, pp. 2405-2410.
Hajime Seino et al., "Enzymatic Synthesis of Carbohydrate Esters of Fatty Acid (1) Esterification of Sucrose, Glucose, Fructose and Sorbitol", JAOCS, Nov. 1984, vol. 61, No. 11.
Stryer L, Biochemistry, 1981.$2^{nd}$ edition, W H Freeman and Co, San Francisco.
Andrzej Witkowski et al., "Conversion of a β-Ketoacyl Synthase to a Malonyl Decarboxylase by Replacement of the Active-Site Cysteine with Glutamine", Biochemistry, 1999, vol. 38, pp. 11643-11650.
International Dairy Federation Bulletin Document, 1979, doc. 116, p. 5.
AOCS Introduction to the Processing of Fats and Oils, American Oil Chemists Society, 1984, pp. III 16-19.
Verenium Corporation leaflet Purifine Enzyme, Jan. 2008.
Nerland A.H., The Nucleotide Sequence of the Gene Encoding GCAT From *Aeromonas salmonicida* SSP. Salmonicida, Journal of Fish Diseases, 1996, vol. 19, No. 2, pp. 145-150, XP008049669.

(56) References Cited

OTHER PUBLICATIONS

Nerland A.H., Glycerophospholipid-Cholesterol Acyltransferase Precursor, SwissProt, Feb. 11, 2005, XP002318368.
Buckley J. Thomas, Substrate Specificity Of Bacterial Glycerophospholipid Cholesterol Acyltransferase, Biochemistry, 1982, vol. 21, pp. 6699-6703.
Sen, et al., Developments in Directed Evolution for Improving Enzyme Functions, Appl. Biochem. Biotechnol (2007) vol. 143, No. 3, p. 212-223.
Casimir C. Akoh, et al., GDSL Family of Serine Esterases/Lipases, Progress in Lipid Research 43, 2004, p. 534-552.
Donald L. Robertson, et al., Influence Of Active Site Tyrosine Modification On The Secretion And Activity Of The Aeromonas Hydrophila Lipase/Acyltransferase, The Journal of Biological Chemistry, vol. 269, No. 3, Jan. 21, 1994, p. 2146-2150.
Acker, L. "Die Lipide des Getreides, ihre Zusammense and inre Bedeutung", Getreide Mehl Brot (1974) 28:181-187.
Adamzcak, Marek, et al., "Application of Enzymatic Glycerolysis for Production of Monoglycerides from Waste Fats", Polish Journal of Food and Nutrition Science, Mar. 1994.
Adhikari, B., et al., "Stickiness in Foods: A Review of Mechanisms and Test Methods", International Journal of Food Properties, vol. 4, No. 1, 2001.
Agarwal et al., "Lipase Activity of Some Fungi Isolated from Groundnut", Current Science, Dec. 5, 1984, vol. 53, No. 23.
Aires-Barros et al (1994) Isolation and purification of lipases, Cambridge Unversity Press.
Aisaka, Kazuo et al., "Production of Lipoprotein Lipase and Lipase by *Rhizopus* japonicu", Agri. Biol. Chem., vol. 43, No. 10, pp. 2125-2129, 1979.
Akoh, Casimir C., et al., "GDSL family of serine esterases/lipases" Progress in Lipid Research, vol. 43, 2004, pp. 534-552.
Allan Svendsen et al., "Biochemical properties of cloned lipases from the Pseudomonas family", Biochimica et Biophysica Acta, vol. 1259, 1995, pp. 9-17.
Al-Obaidy, K A, Dissertation Abstracts International B (1987) vol. 47(9) 3597, order No. DA8624641, pp. 266.
Amano Enzyme Inc. (2004). Http://www.amano-enzyme.co.jp/english/productuse/oil_fat.html. Dato Jun. 21, 2004.
Amano Enzymes "Enzymes for Gastrointestinal Digestion" Oct. 1997.
Amano Enzymes, Amano Enzyme Europe Ltd, Sep. 1994.
Amin, Neelam S., et al., "Direct transformation of site-saturation libraries in *Bacillus subtilis*", BioTechniques, Dec. 2003, 35:1134-1140.
Andersson, L., et al., "Hydrolysis of galactolipids by human pancreatic lipolytic enzymes and duidenal contents", Journal of Lipid Research, 1995, vol. 36, pp. 1392-1400.
Andreas Sander, Eberhand Eilers, Andrea Heilemann, Edith von Kreis.Fett/lipid 99 (1997) Nr. 4, 115-120.
Angelino, S.A.G.F., et al., "The first European Symposium on Enzymes and Grain Processing".
An-I Yeh et al., "Effects of Oxido-reductants on rheological properties of wheat flour dough and comparison with some characteristics of extruded noodles", Cereal Chemistry, 1999, vol. 76, No. 5, pp. 614-620.
Archer, David B., et al., "Proteolytic degradation of heterologous proteins expressed in *Aspergillus niger*", Biotechnology Letter, vol. 14, No. 5, May 1992, pp. 357-362.
Arcos J.A. et al, "Quantative Enzymatic Production of 6.O-Acylglucose Esters", Biotechnology and Bioengineering 1998 57(5).
Arpigny Jean Louis et al, "Bacterial lipolytic enzymes: Classification and properties", Biochemical Journal, vol. 343, No. 1, Oct. 1, 1999, pp. 177-183, XP002375631.
Atomi, et al.; "Microbial Lipases—from Screening to Design"; pp. 49-51.
August C.A.P.A. et al. "The use of genetic engineering to obtain efficient production of porcine pancreatic phospholipase A2", Biochimica et Biophysica Acta, vol. 1089, 1991, pp. 345-351.

Ausubel, Frederick M., et al., "Short Protocols in Molecular Biology—A Compendium of Methods from Current Protocols in Molecular Biology", 1995, John Wiley & Sons, Inc.
Bachmatova, I., et al., "Lipase of *Pseudomonas mendocina* 3121-1 and its Substrate Specificty", Biologija, 1995.
Balcao V.M., Pavia A.L. Malcata F.X., Enzyme Microb Technhol, May 1, 1996; 18(6):392-416.
Balcao, Victor M and Malcata F. Xavier (1998), Biotechnology Advances, vol. 16, No. 2, pp. 309-341.
Ballance, D.J., et al., "Transformation of *Aspergillus nidulans* by the orotidine-5'-phosphate decarboxylase gene of neurospora crassa", Biochemical and biophysical Research Communications, vol. 112, No. 1, 1983, pp. 284-289.
Ballance, Molecular Industrial Mycology, Systems and Applications for Filamentous Fungi, Leong and Berka (eds.), Marcel Dekker Inc, New York 1991, pp. 1-29.
Barbesgaard, Peder et al Applied Microbiology and Biotechnology (1992) 36: 569-572.
Barnes, P.J., "Lipids in Cereal Technology", Food and Science Technology, Academic Press, 1983.
Basrl, M., et al., "Amidination of Lipase with Hyrdophobic Imidoesters", JAOCS, vol. 69, No. 6, Jun. 1992.
Bateman A and Haft DH (2002) Brief Bioinform 3, 236-245.
Bateman A et al, (2002) Nucleic Acids Res. 30, 276-280.
Bekkers et al, The use of genetic engineering to obtain efficient production of porcine pancreatic phospholipase A2 by *Saccharomyces cerevisiae*, (1991) Biochim Biophys Acta 1089(3), 345-51.
Bengtsson Olivecrona Gunilla et al. Phospholipase activity of milk lipoprotein lipase, Methods in Enzymology, vol. 197, 1991.
Bentley S D et al, Complete genome sequence of the model actinomycete Streptomyces coelicolor A3(2), Nature vol. 417, 2002, pp. 141-147.
Berger K.G. (1990) Recent developments in palm oil. In Oleagineux 45:437-443.
Berks, Ben C., "A common export pathway for proteins binding complex redox cofactors?" Molecular Microbiology, 1996, vol. 22, pp. 393-404.
Beucage S.L. et al, (1981) Tetrahedron Letters 22, p. 1859-1869.
Bilyk, Alexander, et al., "Lipase-catalyzed triglyceride Hydrolysis in Organic Solvent", pp. 320-323, JAOCS, vol. 68, no. 5, May 1991.
Biotekkomet falder hardt til jorden.
Birgitte Hugh-Jensen et al., "Rhizomucor miehei Triglyceride Lipase is Processed and Secreted from Transformed *Aspergillus oryzae*", Lipids, vol. 24, No. 9, 1989.
Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.
Bjorkling, F., et al., "Lipase Catalyzed Organic Synthesis", S. Servie (ed.), Microbial Reagents in Organic Synthesis, pp. 249-260, 1992.
Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.
Bjorkling, Frederik, et al., "Lipase-mediated Formation of Peroxycarboxylic acids used in Catalytic Epoxidation of Alkenes", J. Chem. Soc., Chemical Communications, Issue 19, 1990.
Bjurlin et al. Identification of carboxylesterase activities of commercial triacylglycerol hydrolase (lipase) preparations, Eur. J. Lipid Sci. Technol. 104 (2002) 143-155.
Blain JA et al, The Nature of Mycelial Lipolytic enzymes in filamentous fungi, Ferns Microbiol. Lett., 1978, vol. 3, 85-87.
Blecker et al, Improved emulsifying and foaming of whey proteins after enzymic fat hydrolysis, (1997) J Food Science, vol. 62, No. 1.
Blumenthal, Cynthia Z., "Production of toxic metabolites in *Aspergillus niger*, *Aspergillus oryzae*, and *Trichoderma reesei*: justification of mycotoxin testing in food grade enzyme preparations derived from the three fungi", Regulatory Toxicology and Pharmacology, vol. 39, 2004, p. 214-228.
Boel, Esper, et al.; "Rhizomucor miehei Triglyceride Lipase is Synthesized as a Precursor"; Novo Research Institute; vol. 23; No. 7; Jul. 1988.

(56) References Cited

OTHER PUBLICATIONS

Bornscheuer U T et al, Trends in Biotechnology, Elsevier Publications, Cambridge GB, vol. 20, No. 10, Oct. 1, 2002, pp. 433-437.
Bornscheuer, Uwe T., Lipase-catalyzed syntheses of monoacylglycerols, Enzyme and Microbiol Technology, vol. 17, pp. 578-586, 1995.
Brady, Leo, et al., "A serine protease triad forms the catalytic centre of a triacylglycerol lipase", Nature, vol. 343, 1990.
Brockerhoff, Hans, et al., "Lipolytic Enzymes", Academic Press, 1974.
Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.
Brzozowski, A.M., et al., "A model for interfacial activation in lipases from the structure of a fungal lipase-inhibitor complex", Nature, vol. 351, 1991.
Buckley J. Thomas et al, Journal of Biological Chemistry, vol. 257, No. 6, pp. 3320-3325, 1982.
Buckley, Biochemistry 1983, 22, 5490-5493.
Bulkacz J et al, Biochim. Biophys. Acta (1981) vol. 664, pp. 148-155.
Bulletin of the IDF 294: 1994.
Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.
Butcher, Bronwyn G., et al., Microbiology, 2002, vol. 148, pp. 3983-3992.
Buxton et al, Gene, 1985, 37:207-214.
Carriere et al, "Pancreatic Lipase Structure—Function Relationships by Domain Exchange", American Chemical Society-Biochemistry (1997), 36, pp. 239-248.
Carriére, Frédéric, et al., "Structural basis for the substrate selectivity of pancreatic lipases and some related proteins", Biochemica et Biophysica Acta, vol. 1376, pp. 417-432, 1998.
Caruthers MH et al (1980) Nuc Acids Res Symp Ser 215-23.
Casimir C A et al Progress in Lipid Research, 2004, pp. 534-552.
Castello, Phillippe, et al., "Effect of exogenous lipase on dough lipids during mixing of wheat flours", Cereal Chemistry, 1998, vol. 75, No. 5, pp. 595-601.
Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.
Chakravarti DN et al, Biol. Abstracts, 1981, vol. 72, abstract No. 012592.
Cheng Cheng et al., "Transformation of Trichoderma viride using the *Neurospora crassa* pyr4 gene and its use in the expression of a Taka-amylase A gene from *Aspergillus oryzae*", Curr. Genet., 18: 453-456, 1990.
Christensen et al, "A new and simple method to immobilise lipases by means of granulation", 1998 Nachwachsende Rohstoff 10, 98-105.
Christie, William et al., "New Procedures for Rapid Screening of Leaf Lipid Components from Arabidopsis", Phytochemical Analysis, vol. 9, pp. 53-57, 1998.
Christophersen, Claus, et al., "Enzymatic Characterisation of Novamyl a Thermostable α-Amylase". Starch/Sturke, vol. 50, 1998.
Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.
Chung OK et al, "Recent Research on Wheat Lipids" Bakers Digest Oct. 1981.
Ciuffreda, Pierangela, et al., "Spectrophotometric Assay of Lipase Activity: A New 40nitrophenyl Ester of a Dialkylglycerol Suitable as a Chromogenic Substrate of Pseudomonas cepacia Lipase", Biocatalysis and Biotransformation, vol. 21, No. 3, pp. 123-127, 2003.
Claesson et al., "Techniques for measuring surface forces", Advances in Colloid and Interface Science, vol. 67, 1996, pp. 119-183.
Clausen, Kim, "Enzymatic oil-degumming by a novel microbial phospholipase", European Journal of Lipid Science And Technology, vol. 103, 2001, pp. 333-340.
Clausen, Kim, "New enzyme for degumming", Oils and Fats International, vol. 17, No. 4, Jun. 2001, pp. 24-25.
Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.
Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.
Conference May 6-8, 1999 in Santorini, Greece—Lipases & Lipids Structure, Function and Biotechnological Applications—Slides presented by Charlotte Poulsen.
Cordle et al, "The hydrophobic surface of colipase influences lipase activity at an oil-water interface", Journal of Lipid Research, vol. 39 (1998), 1759-1767.
Coteron, A., et al., "Reactions of Olive Oil and Glycerol over Immobilized Lipases", JAOCS, vol. 75, No. 5, 1998.
Council Directive of Dec. 21, 1988 (89/107/EEC).
Council Regulation (EC) No. 2991/94 5/12/94 Official Journal of the European Communities, Sep. 12, 1994, No. L316/2-7.
Creveld, Lucia D, et al., "Identification of Functional and Unfolding Motions of Cutinase as Obtained from Molecular Dynamics Computer Simulations", Proteins: Structure, Function, and Genetics, 33:253-264, 1998.
Cromie, Susan. Psychrotrophs and their Enzyme residues in cheese milk, The Australian Journal of Dairy Technology, vol. 47, Nov. 1992.
Cui et al., "Purification and characterization of an intracellular carboxylesterase from Arthrobacter viscosus NRRL B-1973", Enzyme and Microbial Technology, vol. 24, pp. 200-208, 1999.
Daboussi et al, Heterologous expression of the *Aspergillus nidulans* regulatory gene nirA in *Fusarium oxysporum*, (1991) Gene 109(1), 155-60.
Daboussi et al., "Transformation of seven species of filamentous fungi using the nitrate reductase gene of *Aspergillus nidulans*", Curr. Genet., 15:453-456, 1989.
Daftary, R.D., et al., "Functional Bread-Making Properties of Wheat Flour Lipids", Food Technology, vol. 22, No. 237, Mar. 1968-1979.
Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.
Dalrymple, Brian D., et al., "Three Neocallimastic patriciarum esterases associated with the degradation of complex polysaccharides are members of a new family of hydrolases", Microbiology, vol. 142, pp. 2605-2614, 1997.
Danisco, "Unique Chance for Better Bread" *Direct, A Newsletter from Danisco Ingredients* (1996).
Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.
Database accession No. P10480 -& Database UniProt 'Online!, Jul. 1, 1989.
Database accession No. Q44268 -& Database UniProt 'Online! Nov. 1, 1996.
Database accession No. Q9F7Y6 Database UniProt 'Online!, Mar. 1, 2001.
Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.
Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.
Database FSTA International Food Information Service (IFIS), Frankfurt/Main, De Weipert D:"Rheologie von Roggenteigen. II. Der

(56) References Cited

OTHER PUBLICATIONS einfluss der enzyme unterschiedlicher spezifitat auf das rheologische verhalten des teiges." XP002077285 see abstract & Getreide, Mehl Und Brot, vol. 26, No. 10, 1972, pp. 275-280.
Database Uniprotkb 1 Jun. 2003, S. Omura et al: "putative secreted hydrolase from *streptomyces avermitilis*" XP002376340 retrieved from EBI, Hinxton, UK Database accession No. Q828T4 abstract.
Database Uniprotkb May 1, 2000, S.D. Bentley et al: "Putative Secreted Hydrolase from *Streptomyces coelicolor*" XP002376339 retrieved from EBI, Hinxton, UK Database accession No. Q9S2A5 abstract.
Davies, Progress in Industrial Microbiology, Martinelli and Kinghorn (eds.), Elsevier, Amsterdam 1994, 29:525-560.
De Haas GH et al, "Purification and Properties of Phospholipase A from Porcine Pancreas" Biochim. Biophys. ACTA, 1968, vol. 139, pp. 103-117.
Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.
Dellaporta, et al.; "A Plant DNA Minipreparation Version II"; Plant Molecular Biology Reporter(1983); vol. 1(4); pp. 19-21.
Derewenda et al, "The crystal and molecular structure of the Rhizomuxor miehei Triacylglyceride Lipase at 1•9 ÅResolution", J. Mol. Biol. 1992, 227:818-839.
Derewenda, Urszula, et al., "Catalysis at the Interface: The Anatomy of a Conformational Change in a Triglyceride Lipase", Biochemistry, vol. 31, pp. 1532-1541, 1992.
Directive 2000/36/EC. Http://europa.eu.int/scadplus/leg/en/lvb/121122b.htm. Dato: Apr. 16, 2004.
Drost-Lustenberger, Cornelia, et al., "Lipopan F BG—application and mechanism of a new lipase for bread baking", Cereal Food, 2003.
Drost-Lustenberger, Cornelia, et al., "Lipopan F BG—unlocking the natural strengthening potential in dough", Cereal Food, 2004.
Duan, Rui Dong, Fat Digestion and Absorption (2000), p. 25-46, publisher AOCS Press, Champaign III Coden 69ACBA Conference; general review written in English.
Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.
Ducancel, Frederic, et al., "Complete amino acid sequence of a PLA2 from the tiger snake Notechis sculatus scutatus as deduced from a complementary DNA", Nucleic Acids Research, vol. 16, No. 18, 1988.
Dugi KA et al, "Human hepatic and lipoprotein lipase: the loop covering the catalytic site mediates lipase substrate specificity", Journal of Biological Chemistry (1995), vol. 270, pp. 25, 396 - pp. 25, 401.
Dutilh & Groger, "Improvement of Product Attributes of Mayonnaise by Enzymic Hydrolysis of Egg Yolk with Phospholipase A2", 1981 J. Sci. Food Agric. 32, 451-458.
Eddine et al, "Cloning and expression analysis of NhL1, a gene encoding an extracellular lipase from the fungal pea pathogen Nextria *haematococca* MP VI (*Fusarium solani* f. sp. pisi) that is expressed in planta", Mol. Genet. Genomics (2001) 265: 215-224.
EFEMA Index of Food Emulsifiers Jan. 2004, 4th Edition.
Elyk, Alexander, et al., "Lipase-Catalyzed ", JAOCS, vol. 08, No. 5, May 1991, pp. 320-323.
Engelhorn and Raab, "Rapid Electroblotting of Small DNA Fragments from Polyacrylamide Gels", Biotechniques (1991) 11(5):594-6.
Engelhorn et al., "Rapid Electroblotting of Small DNA Fragments from Polyacrylamide Gels"; Biotechniques(1991); vol. 11(5); pp. 594-596.
Enzymes in food processing (3rd Ed.), Academic press 1993.
EPO, Mobay Chemical Corporation—Decision of the Technical Board of Appeal 3.3.1 dated Jul. 1, 1982, *Official Journal EPO*, Oct. 1982, pp. 394-402.
Ettinger, William F. et al., "Structure of Cutinase Gene, cDNA, and the Derived Amino Acid Sequence from Phytopathogenic Fungi", Biochemistry, vol. 26, pp. 7883-7892, 1987.

Euromonitor International, "The World Market for Dairy Products—Introduction, Executive Summary, Operating Environment, World Market Overview, Key Trends and Developments" in *Euromonitor, Strategy 2000*, Feb. 2001.
European Parliament and Council Directive No. 95/2/EC of Feb. 20, 1995 on food additives other than colours and sweeteners.
European Parliament and Council Directive No. 98/72/EC of Oct. 15, 1998 amending Directive 95/2/EC on food additives other than colours and sweeteners.
Eurpean Journal of Biochemistry, vol. 166, 1987, Published by Springer International on behalf of the Federation of European Biochemical Societies.
Ezra, David, et al., "Coronamycins, peptide antibiotics produced by a verticillate *Streptomyces* sp. (MSU-2110) endophytic on *Monstera* sp.", Microbiology, 2004, vol. 150, p. 785-793.
Fauvel, et al.; "Purification of Two Lipases With High Phospholipase A, Activity from Guinea-Pig Pancreas"; Biochimica et Biophysica Acta(1981); vol. 663; pp. 446-456.
Fernandez-Garcia et al., "The use of lipolytic and proteolytic enzymees in the manufacture of manchego type cheese from ovine and bovine milk", 1994 J. Dairy Sci. 77: 2139-2149.
Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.
Ferrer et al, 2000, J. Chem. Technol. Biotechnol. 75, 569-576.
Finizym Technical Information, Novo Enzymes, 1981.
Fødevarenubusteriet (2003). Bekendtgørelse om indhold af transfedtsyrer I olier og fedtstoffer. Bekendtgørelse nr. 160 af Nov. 3, 2003.
Food R&D. Dairy fields ingredient technology section.
Forman, Todd, "Enzymes Used in Bread Baking: An Application Update", Technical Bulletin, vol. XXVI, Issue 10, Oct. 2004.
Fox, et al.; "Isolation and some Properties of Extracellular Heat-Stable Lipases: from *Pseudomonas Fluorescens* Strain AFT 36"; Journal of Dairy Research (1988); vol. 50; pp. 77-89.
Frenken N. et at (1992) Appl. Envir. Microbiol. 58 3787-3791.
Frohman, et al.; "Rapid Production of Full-Length cDNAS from Rare transcripts: Amplification using a single gene-specific oligonucleotide primer"; Proc. Natl. Acad. Sci, USA (1988); vol. 85; pp. 8998-9002.
Fugman, Douglas A et al Biochemica et Biophysica acia 795 (1984) 191-195.
Galliard T and Dennis S (1974) Phytochemistry vol. 13, pp. 1731-1735.
Galliard, "The Enzymic Breakdown of Lipids in Potato Tuber by Phospholipid—And Galactolipid—Acyl Hydrolase Activities and by Lipoxygenase", Phytochemistry, 1970, vol. 9, pp. 1725-1734.
Gan, Z. et al., "Rapid Communication—Antisera agains: Wheat Diacylgalactosylglycerol (MGDG) and Diacyldigalactosylglycerol (DGDG)", Journal of Cereal Science, vol. 18, pp. 207-210, 1993.
Ganghro AB & Dahot MU, Sci Int. (Lahore), 1992, vol. 4, pp. 169-172.
Gemel, Joanna et al., "Comparison of galactolipase activity and free fatty acid levels in chloroplasts of chill-sensitive and chill resistant plants", European Journal of Biochemistry, vol. 166, 1987.
Geus et at (1987) Nucleic Acids Research 15(9) p. 3743-3759.
Gilbert, E. Jane, et al., "Purification and properties of extracellular lipase from Pseudomonal aeruginosa EF2", Journal of General Microbiology, 1991, vol. 137, pp. 2223-2229.
Gillian, B., Turgeon et al., "*Cochliobolus heterostrophus* using the *Aspergillus nidulans* amdS gene", Mol Gen Genet, 201: 450-453, 1985.
Godfrey, Tony, et al., "Industrial Enzymology Second Edition".
Food Enzymes: Stalingase L, Gist-brocades Food Ingredients.
Frenken N. et al (1992) Appl. Envir. Microbiol. 58 3787-3791.
Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.

(56) References Cited

OTHER PUBLICATIONS

Gan, Z. et al., "Rapid Communication—Antisera agains: Wheat Diacylgalactosylglycerol (MGDG) and Diacyldigalactosyiglycerol (DGDG)", Journal of Cereal Science, vol. 18, pp. 207-210, 1993.
Geus et al (1987) Nucleic Acids Research 15(9) p. 3743-3759.
Goodey et al, Yeast Biotechnology, Berry et al (eds.), Allen and Unwin, London 1987, pp. 401-429.
Graille J, Lipid Technology, vol. 5, No. 1, 1993, pp. 11-16.
GRAS Notification dated Apr. 11, 2001 by Novozymes for Lecitase® and Lipopanlm™ F.
Greenough et al (1996) Food Chem Toxicology 34:161-166 and PubMed abstract in respect thereof.
Haas and Berka, 1991, Gene, 109:107-113.
Haas, et al., "Enzymatic Phosphatidylcholine Hydrolysis in Organic Solvents: An Examination of Selected Commercially Available Lipases", JAOCS, vol. 71, No. 5, May 1994, pp. 483-490.
Haas, et al.; "Lipases of the Genera *Rhizopus* and *Rhizomucor*. Versatile Catalysts in Nature and the Laboratory"; Food Biotechnology Micro-organisims (1995); pp. 549-588.
Haggag H F et al. Egypt J Food Sci vol. 22, No. 1 pp. 99-107 (1994).
Hansen, Chr., Danisco and Novozymes, Apr. 3, 2002, Food Ingredients day, R&D—the main ingredients for growth.
Hara, et al.; "Comparative Study of Comercially Available Lipases in Hydrolysis Reaction of Phosphatidylcholine"; JAOCS (1997); vol. 74; No. 9, pp. 1129-1132.
Hawker, Kim L., et al., "Heterologous expression and regulation of the *Neurospora crassa* nit-4 pathway-specific regulartory gene for nitrate assimilation in *Aspergillus nidulans*", Gene., vol. 100, pp. 237-240, 1991.
Helmsing, "Purification and Properties of Galactolipase", Biochim., Biophys., Acta, vol. 178, pp. 519-533, 1969.
Henderson, H.E., et al., "Structure-function relationships of lipoprotein lipase: mutation analysis and mutagenesis of the loop region", Journal of Lipid Research, vol. 34, 1993, pp. 1593-1602.
Henke, Erik, et al., "Activity of Lipases and Esterases towards Tertiary Alcohols: Insights into Structure-Function Relationships", Angew. Chem. Int. Ed., 2002, vol. 41, No. 17.
Hernquist L & Anjou K (1993) Diglycerides as a stabilizer of the β'-crystal form in margarines and fats, in Fette Seifen Anstrichmittel 2:64-66.
Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.
Hilton S et al, Biochemistry vol. 29, No. 38, 1990, pp. 9072-9078.
Hilton S, Buckley JT, J Biol Chem. 1991 Jan 15; 266(2): 997-1000.
Hirayama O et al, Biochim Biophys Acta. 1975, vol. 384(1), p. 127-137.
Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.
Höfelmann et al, J. Food Sci., 1985, 50:1721-1731.
Holmquist et al., "Lipases from Rhizomucor miehei and Humicola lanuginosa: Modification of the Lid covering the active site alters enantioselectivity", Journal of Protein Chemistry, vol. 12, No. 6, 1993.
Holmquist et al., "Probing a Functional Role of Glu87 and Trp89 in the Lid of Humicola lanuginosa Lipase through Transesterification Reactions in Organic Solvent", Journal of Protein Chemistry, 1995, vol. 14, No. 4, pp. 217-224.
Holmquist et al., "Trp89 in the Lid of Humicola lanuginosa Lipase is Important for Efficient Hydrolysis of Tributyrin", Lipids, vol. 29, No. 9, 1994.
Horn T et al, (1980) Nuc Acids Res Symp Ser 225-232.
Hoshino, et al.; "Calcium Ion Regulates the Release of Lipase of *Fusarium oxysporum*"; J. Biochem (1991); vol. 110; pp. 457-461.
Hoshino, et al.; "Purification and Some Characteristics of Extracellular Lipase from *Fusarium oxysporum f. sp. lini*"; Biosci. Biotech. Biochem (1992); pp. 660-664.

Hoshino, Tamotsu, et al., "Purfication and Some Characteristics of Extracellular Lipase from Fusarium oxysporum", Biosci. Biotech. Biochem., vol. 56, No. 4, pp. 660-664, 1992.
Hossen, Monjur and Hernandez, Ernesto, Lipids, vol. 39, Aug. 2004, pp. 777-782.
Hou Ching T, Journal of Industrial Microbiology, vol. 13, No. 4, 1994, pp. 242-248.
Hübner et al., "Interactions at the lipid-water interface", Chemistry and physics of Lipids, vol. 96, 1998, pp. 99-123.
Hugh-Jensen, Birgitte, et al., "Rhizomucor miehei Triglyceride Lipase is Processed and Secreted from Transformed *Aspergillus oryzae*", Lipids, vol. 24, No. 9, pp., 1989.
Icard-Verniere, Christele, et al., "Effects of mixing conditions on pasta dough development on biochemical changes", Cereal Chemistry, 1999, vol. 76, No. 4, pp. 558-565.
Igrejas, Gilberto, et al., "Genetic and Environmental Effects on Puroindoline-a and Puroindoline -b Content and their Relationship to Technological Properties in French Bread Wheats", Journal of Cereal Science, vol. 34, 2001, pp. 37-47.
Ikeda H et al, Nature Biotech, vol. 21, 2003, p. 526-531.
Industrial enzymology (2nd Ed.), The Macmillan press 1996.
Ishihara et al Biochimica et Biophysica Acta 388 (1975) 413-422.
Isobe and Nokihara, Febs. Lett., 1993, 320:101-106.
Isobe K et al, Journal of Molecular Catalysis B: Enzymatic 1 (1995), pp. 37-43.
Iwai and Tsujisaka (in Lipases, Borgström and Brockman (eds.), Elsevier, Amsterdam, 1984, pp. 443-468.
Izco et al. Adv Food Sci vol. 21 N 3/4, (10-116) 1999.
Jacob, Jules S., et al., "The Effects of Galactolipid Depletion on the Structure of a Photosynthetic Membrane", The Journal of Cell Biology, vol. 103, Oct. 1986, pp. 1337-1347.
Jacobsberg B. & Oh C.H. (1976) Studies in Palm Oil Crystallisation, in Journal of the American Oil Chemist Society 53:609-616.
Jan-Willem F. A. Simons et al., "Cloning, purification and characterisation of the lipase from *Staphylococcus epidermidis*", Eur. J. Biochem., vol. 253, pp. 675-683, 1998.
Jeng-yen Lin, Matthew, "Wheat Polar Lipids—A Theseis Submitted to the Graduate Faculty of the North Dakota State University of Agriculture and Applied Science", May 1972.
Jong et al.; "American Type Culture Collection Catalogue of Filamentous FUNGI"; Eighteenth edition (1991).
Joshi, et al.; "Specificity of Fungal Lipase in Hydrolytic Cleavage of Oil"; Acta Microbiologica Hungarica (1987); vol. 34(2); pp. 111-114.
Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.
Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.
Kaniuga Z, Acta Biochim Pol. (1997), vol. 44(1), p. 21-35.
Kapur J & Sood ML, J. Parasit., 1986, vol. 72, pp. 346-347.
Kasai, Naoya, et al., "Chiral C3 epoxides and halophydrins: Their preparation and synthetic application", Journal of Molecular Catalysis B: Enzymatic, vol. 4, 1998, pp. 237-252.
Kawamura and Doi, J. Of Bacteriology Oct 1984, p. 442-444.
Keller, R.C.A., et al., "Competitive Adsorption Behaviour of Wheat Flour Components and Emulsifiers at an Air-Water Interface", Journal of Cereal Science, vol. 25, 1997, pp. 175-183.
Keum J S et al. Korean J Dairy Sci 15 (2): 103-117 1993.
Kim, Hyung Kwoun, et al., Expression and characterization of Ca2+-independent lipase from *Bacillus pumilus* B26, Biochimica et Biophysica Acta, vol. 1583, 2002, pp. 205-212.
Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.
Kimura, Yoshiharu, et al., "Application of Immobilized Lipase to Hydrolysis of Triacylglyceride", Eur J. Appl Microbiol Biotechnol, 1983, vol. 17, pp. 107-112.
King et al, Molecular and Cell Biology of Yeasts, Walton and Yarronton (eds.), Blackie, Glasgow, 1989, pp. 107-133.

(56) References Cited

OTHER PUBLICATIONS

Kirk, Ole, et al., "Fatty Acid Specificity in Lipase-Catalyzed Synthesis of Glucoside Esters" Biocatalysis, 1992, vol. 6, pp. 127-134.
Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.
Klein, Robert R., et al., "Additive Effects of Acyl-Binding Site Mutations on the Fatty Acid Selectivity of Rhizopus delemar Lipase", JAOCS, vol. 74, No. 11, 1997.
Kocak et al, Milchwissenschaft 51(1), 1996.
Kochubei et al Role of lipids in the organization of the closest surroundings of the reaction centers(1976) Institute of Plant Physiology.
Kochubei S M et al, Biophysics (1981), vol. 26(2), p. 299-304.
Kochubei S M et al, Mol Biol (Mosk) (1975), vol. 9(2), (p. 190-193) p. 150-153.
Kochubei SM et al, Mol Biol (Mosk) (1978),(vol. 1, p. 47-54) p. 32-37.
Kolkovski et al (1991) Fish Nutrition in Practice, Biarritz (France), Jun. 24-27.
Kostal, Jan, et al., "Enhanced Arsenic Accumulation in Engineered Bacterial Cells Expressing ArsR", Applied and Environmental Microbiology, Aug. 2004, pp. 4582-4587.
Kouker, et al.; "Specific and Sensitive Plate Assay for Bacterial Lipases"; Applied and Environmental Microbiology (1987); vol. 53(1); pp. 211-213.
Krishna, Sajja Hari, et al., "Enantioselective transesterification of a tertiary alcohol by lipase A from Candida antarctica", Tetrahedron: Asymmetry, vol. 13, 2002, pp. 2693-2696.
Kristensen A.C.J. (2004) Preparation of margarine and spreads by enzyme-generated emulsifiers. Master thesis, The Royal Veterinary and Agricultural University, Frederiksberg, Copenhagen.
Krog, Cereal Foods World, The American Association of Cereal Chemists, p. 10, Jan. 1979, vol. 24, No. 1, pp. 10-11.
Krupa, Zbigniew et al., "Requirement of Galactolipids for Photosystem J Activity in Lyophilized Spinach Chloroplasts", Biochimica et Biophysica Acta, 408, pp. 26-34, 1975.
Kuipers, Oscar P., et al., "Enhanced Activity and Altered Specificity of Phospholipase A2 by Deletion of a Surface Loop", Science, vol. 244, 1989.
Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.
Kuwabara, et al., "Purification and Some Properties of Water-soluble Phospholipase B from *Torulaspora delbrueckii*", J. Biochem., vol. 104, pp. 236-241, 1988.
Kuwabara, et al., "Purification and Some Properties of Water-soluble Phospholipase", Agric. Biol. Chem., vol. 52, No. 10, pp. 2451-2458, 1988.
Kweon et al., "Phospholipid Hydolysate and Antistaling Amylase Effects on Retrogradation of Starch in Bread", Journal of Food Science, vol. 59, No. 5, 1994.
Larsen N G et al, Journal of Cereal Science (1990), vol. 12(2), p. 155-164.
Lee, Keun Hyeung, et al., "Identification and characterization of the antimicrobial peptide corresponding to C-terminal B-sheet domain of tenecin 1, an antibacterial protein of larvae of *Tenebrio molitor*", Biochem. J., 1996, vol. 334, pp. 99-105.
Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.
Leidich et al., "Cloning and Disruption of caPLB1, a Phospholipase B Gene Involved in the Pathogenicity of *Candida albicans*", The Journal of Biological Chemistry, vol. 273, No. 40, oo.26078-26086, 1998.
Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, J Agric. Food. Chem. (1993), 41, 1000-1005.
Lima, Vera L.M., et al., "Lecithin-cholesterol acyltransferase (LCAT) as a plasma glycoprotein: an overview", Carbohydrate Polymers, vol. 55, 2004, pp. 179-191.
Lin M J Y et al, Cereal Chemistry (1974), vol. 51(1), p. 34-45.
Lin S et al, Enzyme and Microbial Technology 18 (1996), pp. 383-387.
Lipase A "Amano" 6 Assay Note and Product Specification from Armano Pharmaceutical Co Ltd Nagoya Japan, Dec. 16, 1985.
Lipase A "Amano" 6 Assay Note and Product Specification from Armano Pharmaceutical Co Ltd Nagoya Japan, Aug. 27, 1985.
Lipase A "Amano" 6 product sheet, Apr. 1, 1999.
Lipase SP677 as a Baking Enzyme, from Novo Nordisk, Denmark, Mar. 17, 1994.
Lipopan F: Keep the quality—cut your costs 2000 Novozymes A/S. www.enzymes.novo.dk/cgl-bin/bvisapi.dll/biotimes/one_article.jsp?id=16947&lang=en&t=b1.
Litthauer, Derek, et al., "Pseudomonas luteola lipase: A new member of the 320-residue Pseudomonas lipase family", Enzyme and Microbial Technology, vol. 30, pp. 209-215, 2002.
Llustenberger, Cornelia, et al., "Application of Noopazyme in Asian Noodles and Non-Durum Pasta", Cereal Food, 2002-18584-01, p. 1, vol. 11.
Llustenberger, Cornelia, et al., "Enzymes in Frozen Dough and Parbaked Bread", Cereal Food, 2001-17056-01, p. 1, vol. 19.
Longhi, Sonia, et al., "Atomic Resolution (1.0 Å) Crystal Structure of *Fusarium solani* Cutinase: Stereochemical Analysis" J. Mol. Biol. vol. 268, pp. 779-799, 1997.
Lozano et al., "Over-stabilization of Candida antarctica lipase B by ionic liquids in ester synthesis", Biotechnology Letters, vol. 23, pp. 1529-1533, 2001.
Luzi, Paola et al, Genomics (1995), vol. 26(2), p. 407-409.
Madsen J.S. & Qvist K.B. (1997) J. Food Sci. 62, 579-582.
Mao, Cungui, et al., "Cloning and Characterization of a *Saccharomyces cerevisiae* Alkaline Ceramidase with Specificity for Dihydroceramide", The Journal of Biological Chemistry, vol. 275, No. 40, 2000, pp. 31369-31378.
Maria Teres Neves Petersen, PhD, "Total Internal Reflection Fluorescence Flow System with Electrochemical Control", TIRF-EC Flow System, Sep. 2002.
Marion D et al—Chapter 6, pp. 131-p. 167 of "Interactions The Keys to Cereal Quality" 1998 ISBN 0913250-99-6 (ed. Hamer & Hoseney).
Marion D et al pp. 245-260 of Wheat Structure Biochemistry & Functionality (ed Schofield JP) ISBN 085404777-8 published in 2000—(It states that it is the Proceedings of Conference organised by Royal Soc of Chemistry Food Chemistry Group held on Apr. 10-12, 1995, in Reading, UK. However, it is unclear why there was such a delay).
Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.
Martinelli et al., "The Role of Glu87 and Trp89 in the lid of Humicola lanuginosa lipase", Protein Engineering, vol. 9, No. 6, 1996, pp. 519-524.
Martinez, Chrislaine, et al., "Engineering cysteine mutants to obtain crystallographic phases with a cutinase from *Fusarium solani* pisi", Protein Engineering, vol. 6, No. 2, pp. 157-165, 1993.
Martinez, Diego, et al., "Genome sequence of the lignocellulose degrading fungus *Phanerochaete chrysosporium* strain RP78", Nature Biology, May 2, 2004.
Mase et al., "Purification and Characterization of a new Lipase from *Fusarium* sp. TM-30", Biosci. Biotech. Biochem., vol. 59, No. 9, pp. 1771-1772, 1995.
Mason, Research Disclosure, Kenneth Mason Publications, Westbourne GB No. 390, Oct. 1996, pp. 661-662.
Masuda, Naoko, et al., "Primary structure of protein moiety of *Penicillium notatum* phospholipase B deduced from the Cdna", Eur. J. Biochem., vol. 202, pp. 783-787, 1991.
Matos AR, Lipid Catabolism: Lipid Degradation, 2000, p. 779-781.

(56) References Cited

OTHER PUBLICATIONS

Matos, A.R., et al., "A patatin-like protein with galactolipase activity is induced by drought stress in *Vigna unguiculata* leaves", Biochemical Society Transactions, vol. 28, part 6, 2000.
Matos, AR et al, Febs Letters, 491 (2001) p. 188-192.
Matsuda H et al, Biochim Biophys Acta, (1979), vol. 573(1), p. 155-165.
Matsuoka, et al.; "Purification and properties of a Phospholipase C That has High Activity toward Sphingomyelin from *Aspergillus Saitoi*"; Biotiechonology and Applied Biochemistry (1987); vol. 9, pp. 401-409.
Matthes et al, (1984) EMBO J. 3, p. 801-805.
McAuley, Katherine E., et al., "Structure of a feruloyl esterase from *Aspergillus niger*", Acta Crystallographica, Section D, pp. 878-887, 2004.
McCoy M G et al, Journal of Lipid Research (2002), vol. 43, pp. 921-929.
McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.
McNeill, Gerald P., et al., "High-Yield Enzymatic Glycerolysis of Fats and Oils", JAOCS, vol. 68, No. 1, Jan. 1991.
McNeill, Gerald P., et al., "Selective Distribution of Saturated Fatty Acids into the Monoglyceride Fraction During Enzymatic Glycerolysis", JAOCS, vol. 69, No. 11, Nov. 1992.
Memo: From Charlotte Johanson?, "Short introduction/ status on Ferulic Acid Esterases and Acetyl Xylan Esterases", Jan. 9, 2004.
Meyer, V., et al., "Transcriptional regulation of the Antifungal Protein in *Aspergillus giganteus*", Mol Genet Genomics, 2002, vol. 266, pp. 747-757.
Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.
Mielgo, I., et al., "Covalent immobilisation of manganese peroxidases (MnP) from *Phanerochaete chrysosporium* and *Bjerkandera* sp. BOS55", Enzyme and Microbial Technology, vol. 32, 2003, pp. 769-775.
Miller, Byron S., et al., "A Comparison of Cereal, Fungal, and Bacterial Alpha-Amylases as Supplements for Breadmaking", Food Technology, Jan. 1953.
Ministerio da Ciencia e Tecnologia, *Diario Oficial da Uniao*, Jul. 15, 2003.
Mogensen, Jesper E., et al., "Activation, Inhibition, and Destabilization of Thermomyces lanuginosus Lipase by Detergents", Biochemistry, vol. 44, pp. 1719-1730, 2005.
Molecular Biological Methods for *Bacillus*—Chapter 3 (Ed. C.R. Harwood and S.M. Cutting) 1990, John Wiley and Sons Ltd, Chichester, UK.
Mølgaard, Anne, et al., "Rhamnogalacturonan acetylesterase elucidates the structure and function of a new family of hydrolases", Structure, vol. 9, No. 4, 2000.
Molochnaya Promyshlennost 1980 No. 11 21-25, 47—abstract from Food Sci & Tech Abs.
Monographs for Emulsifiers for Foods, EFEMA Nov. 1985 2nd Edition.
Moore, Charles M., et al., "Metal ion homeostasis in *Bacillus subtilis*", Current Opinion in Microbiology, 2005, vol. 8, pp. 188-195.
Morgan, Keith R., et al., "Stalling in Starch Breads: The Effect of Antistaling α-Amylase", Starch/Stärke, vol. 49, 1997, pp. 59-66.
Morgan-Jones, Gareth; "Notes on Coelomycetes.II. Concerning the Fusicoccum Anamorph of Botryosphaneria Ribis"; vol. XXX, pp. 117-125; Oct.-Dec. 1987.
Morinaga et al Biotechnology (1984) 2, p. 636-639.
Morten, T. & A., Letter, Rodovre, Jul. 2004.
Mukherjee, Kumar D. et al., "Enrichment of y-linolenic acid from fungal oil by lipase-catalysed reactions", Appl. Microbiol Biotechnol (1991), vol. 35, pp. 579-584.
Murakami, Nobutoshi, et al., "Enzymatic Transformation of Glyceroglycolipids into sn-1 and sn-2 Lysoglyceroglycolipids by use of *Rhizopus arrhizus* Lipase", Tetrahedron, vol. 50, No. 7, pp. 1993-2002, 1994.
Mustranta, Annikka, et al., "Comparison of Lipases and Phosphlipases in the Hydrolysis of Phospholipids", Process Biochemistry, vol. 30, No. 5, pp. 393-401, 1995.
Nagano, et al.; "Cloning and Nucleotide Sequence of cDNA Encoding a Lipase from *Fusarium keteroporum*"; J. Biochem (1994); vol. 116; pp. 535-540.
Nagao et al, J. Biochem 124, 1124-1129, 1998.
Nagao et al, J. of Bioscience and Bioengineering vol. 89, No. 5, 446-450, 2000.
Nagao et al, J. of Molecular Catalysis B: Enzymatic 17 (2002) 125-132.
Nagao et al, JAOCS vol. 78, No. 2, 2001.
Nagao, Toshihiro et al., "Cloning and Nucleotide Sequence of CDNA Encoding a Lipase from *Fusarium heterosporum*", J. Biochem., vol. 116, pp. 535-540, 1994.
Nagao, Toshihiro et al., "Expression of Lipase cDNA from *Fusarium heterosporum* by *Saccharomyces cereviisiae*: High-Level Production and Purification", Journal of Fermentation and Bioengineering, 1996, vol. 81, No. 6, pp. 488-492.
Nagodawlthana et al., "Enzymes in Food Processing", Third Edition, 1993, Academic Press, Inc.
National Research Council (U.S.) Committee on Specifications of the Food Chemicals Codex, "Lipase Activity" in *Food Chemicals Codex* (1981) National Academy Press, Washington, D.C. pp. 492-493.
Needleman & Wunsch (1970), J. of Molecular Biology 48, 443-453.
Nelson and Long, Analytical Biochemistry (1989), 180, p. 147-151.
Nerland A H, Journal of Fish Diseases, vol. 19, No. 2, 1996, pp. 145-150.
Ness, Jon. E., et al., "DNA shuffling of subgenomic sequences of subtilisin" Nature Biotechnology, vol. 17, Sep. 1999.
Nestle Research Center, Brochure for "Food Colloids 2006" in Montreux, Switzerland, Apr. 23-26, 2006.
Neugnot Virginie et al, European Journal of Biochemistry, 2002, vol. 269, pp. 1734-1745.
Newport, G., et al., "KEX2 Influences *Candida albicans* Proteinase Secretion and Hyphal Formation", The Journal of Biological Chemistry, 1997, vol. 272, No. 46, pp. 28954-28961.
Nicolas, Anne, et al., "Contribution of Cutinase Serine 42 Side Chain to the Stabilization of the Oxyanion Transition State", Biochemistry, vol. 35, pp. 398-410, 1996.
Nierle W et al, Fette Seifen Anstrichmittel (1981), vol. 83(10), p. 391-395.
Nierle, W., et al., "Versuche zur Verlangerung der Haltbarkeit von Dartoffelprodukten", Chem. Mikrobiol. Technol. Lebensm., 1975, vol. 3, pp. 172-175.
Nobutoshi M et al, Tetrahedron Letters (1991), vol. 31(1), p. 1331-1334.
Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".
Novozymes Memo—Test of lipases for EP1193314B1, Jul. 6, 2005.
Novozymes Report 2002 Annual Report.
Novozymes, "Biowhitening—a new concept for steamed bread", *BioTimes*, Jan. 2005.
Novozymes, "Breakthrough: Less Fattening Fried Food" *BioTimes*, Jun. 2001, No. 2.
Novozymes, "Enzymes for dough strengthening", 2001.
Novozymes, "Lipopan F BG- application and mechanism of a new lipase for bread baking" (Draft) *Cereal Food* (2003) (Author: Drost-Lustenberger, C. et al.).
Novozymes, "Product Sheet for Lipopan F BG"; *Cereal Food*, (2001).
Novozymes, "Product Sheet for Lipopan FS BG", *Cereal Food* (2002).
Novozymes, "Product Sheet for Lipopan S BG", *Cereal Food* (2002).
Novozymes, "Strong sales for lipase that makes dough stronger" *BioTimes*, Dec. 2003.

(56) References Cited

OTHER PUBLICATIONS

Novozymes, "The Novozyme Touch: Make your mark on the future".
Novozymes, "The perfect roll every time for steers", *BioTimes*, Sep. 2003.
Novozymes, "The value of innovation", *BioTimes*, Mar. 2004.
Novozymes, "The vital role of technical service in baking", *BioTimes*, Jun. 2004.
Novozymes, Lipopan F BG, Product Data Sheet.
Ohm, J.B., et al., "Relationships of Free Lipids with Quality Factors in Hard Winter Wheat Flours", Cereal Chem., vol. 79, No. 2, pp. 274-278, 2002.
Ohta, S. et al., "Application of Enzymatic Modification of Phospholipids on Breadmaking", Abstract from AACC 68th Annual Meeting in Kansas City, MO, Oct. 30-Nov. 3, 1983, published in Cerial Foods World, p. 561.
Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.
Okiy D.A. (1977) Partial glycerides and palm oil Crystallisation, in Journal of Science and Food Agriculture 28:955.
Okiy D.A. (1978) Interaction of triglycerides and diglycerides of palm oil, in Oleagineux 33:625-628.
Okiy D.A., Wright, W.B., Berger, K.G. & Morton I.D. (1978), The physical properties of modified palm oil, in Journal of Science of Food and Agriculture 29:1061-1068.
Oluwatosin, Yemisi E., et al., "Phenotype: a Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.
Orberg, Marie-Louise, "Self-assembly Structures Formed by Wheat Polar Lipids and their Interaction with Lipases", Master of Scient Thesis, Apr. 2005.
Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.
Osman, Mohamed, et al., "Lipolytic activity of *Alternaria alternata* and *Fusarium oxysporum* and certain properties of their lipids", Microbios Letters, vol. 39, pp. 131-135, 1988.
O'Sullivan et al, J Plant Physiol, vol. 313, (1987) p. 393-404.
Palomo, Jose M., et al., "Enzymatic production of (3S, 4R)-(-)-4-(4'-fluorophenyl)-6-oxo-piperidin-3-carboxylic acid using a commerical preparation of lipase A from *Candida antarctica*: the role of a contaminant esterase" Tetrahedron: Asymmetry, vol. 13, 2002, pp. 2653-2659.
Palomo, Jose M., et al., "Enzymatic resolution of (±)-glycidyl butyrate in aquenous media. Strong modulation of the properties of the lipase from *Rhizopus oryzae* via immobilization techniques", Tetrahedron: Asymmetry, vol. 15, 2004, pp. 1157-1161.
Palomo, Jose M., et al., "Modulation of the enantioselectivity of *Candida antarctica* B lipase via conformational engineering: kinetic resolution of (±)-α-hydroxy-phenylacetic acid derivatives", Tetrahedron: Asymmetry, vol. 13, 2002, pp. 1337-1345.
Patent Abstracts of Japan vol. 016, No. 528 (C-1001), Oct. 29, 1992 & JP 04 200339 A see abstract.
Patent Abstracts of Japan vol. 095, No. 001, Feb. 28, 1995 & JP 06 296467 A see abstract.
Peelman F, et al, Protein Science Mar. 1998; 7(3): 587-99.
Penninga et al, Biochemistry (1995), 3368-3376.
Persson, Mattias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the *Humicola lanuginosa* Lipase", Biochemistry, 1998, vol. 37, pp. 12375-12383.
Peters, Günther H., et al., "Theoretical Investigation of the Dynamics of the Active Site Lid in *Rhizomucor* miehei Lipase", Biophysical Journal, vol. 71, 1996, pp. 119-129.
Plijter J and JHGM Mutsaers, The surface rheological properties of dough and the influence of lipase on it, Gist-brocades, Bakery Ingredients Division, Oct. 1994.
Plou et al, J. Biotechnology 92 (2002) 55-66.
Ponte J G, Cereal Chemistry (1969), vol. 46(3), p. 325-329.
Punt and van den Hondel, Meth. Enzym., 1992, 216:447-457.
Pyler, E.J., "Baking Science and Technology Third Edition", vol. 1, 1988.
Pyler, E.J., "Baking Science and Technology Third Edition", vol. II, 1988.
Queener et al. (1994) Ann N Y Acad Sci. 721, 178-193.
Rambosek and Leach, CRC Crit. Rev. Biotechnol., 1987, 6:357-393.
Rapp, Peter, et al., "Formation of extracellular lipases by filamentous fungi, yeasts, and bacteria", Enzyme Microb. Technol., 1992, vol. 14, Nov.
Rapp, Peter; "Production, regulation, and some properties of lipase activity from *Fusarium Oxysporum* f. sp. *vasinfectum*"; Enzyme and Microbial Technology(1995); vol. 17; pp. 832-838.
Reetz M.T., Jaeger K.E. Chem Phys Lipids. Jun. 1998; 93(1-2): 3-14.
Reetz Manfred T, Current Opinion in Chemical Biology, Apr. 2002, vol. 6, No. 2, pp. 145-150.
Reiser J et al. (1990) Adv Biochem Eng Biotechnol. 43, 75-102.
Richardson and Hyslop, "Enzymes: XI—Enzymes Added To Foods During Processing" in *Food Chemistry*, Marcel Dekker, Inc., New York, NY 1985.
Arskog and Joergensen, "Baking performance of prior art lipases from *Candida cylindracea* and *Aspergillus foeditus* and their actiivty on galactolipids in dough", Novozymes Report 2005.
Arskog and Joergensen, "Baking performance of prior art lipases from *Humicola lanuginosa*, *Aspergillus tubigensis*, *Rhizopus delemar* and *Rhizomucor miehei*, and their actiivty on galactolipids in dough", Novozymes Report 2005.
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) Gene 122(1), 155-61.
Roberts, et al.; "Extracellular Lipase Production by Fungi from Sunflower Seed"; Mycologia(1987); vol. 79(2); pp. 265-273.
Robertson et al, Journal of Biological Chemistry, 1994, 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via *Rhizopus arrhizus* Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in *Vigna unguiculata* leaves and influence of drought stress", Physiologia Plantarum, vol. 104, pp. 577-586, 1998.
Sahsah, Y., et al., "Purification and characterization of a soluble lipolytic acylhydrolase from Cowpea (*Vigna unguiculata* L.) leaves", Biochimica et Biophysica Acta, vol. 1215, pp. 66-73, 1994.
Saiki R.K. et al Science (1988) 239, pp. 487-491.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.

(56) References Cited

OTHER PUBLICATIONS

Sambrook et al, Chapters 1, 7, 9, 11, 12 and 13—Molecular Cloning a laboratory manual, Cold Spring Harbor Laboratory Press (1989).
Sambrook, J., et al. "A Laboratory Manual, Second Edition", Plasmid Vectors, 1989.
Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.
Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).
Saxena, et al.; "Purification Strategies for Microbial Lipases"; Journal of Microbilogical Methods (2003); pp. 1-18.
Scheib et al.; "Stereoselectivity of Mucorales lipases toward triradylglycerols—A simple solution to a complex problem"; Protein Science (1999); vol. 8; pp. 215-221.
Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.
Scopes, Robert K., "Section 8.4: Ultrafiltration" in *Protein Purification Principles and Practice, Third Edition* (1994) Springer-Verlag, New York, p. 267-269.
Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.
Shimada et al, J. of Bioscience and Bioengineering vol. 91, No. 6, 529-538 (2001).
Shimada et al, J. of Fermentation and Bioengineering vol. 75, No. 5, 349-352 (1993).
Shimada et al, JAOCS vol. 71, No. 9, (Sep. 1994).
Shin, et al.; "Butyl-Toyopearl 650 as a New Hydrophobic Adsorbent for Water-Soluable Enzyme Proteins"; Analytical Biochemistry(1984); vol. 138; pp. 259-261.
Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.
Si, Joan Qi; "New Enzymes for the Baking Industry"; Food Tech Europe (1996) pp. 60-64.
Sias Bet al, Biochemistry, (2004), vol. 43(31), p. 10138-10148.
Siew W.L. & Ng W.L. (1999) Influence of diglycerides on crystalisation of palm oil, in Journal of Science of Food and Agriculture 79:722-726.
Siew W.L. & Ng W.L. (2000) Differential scanning thermograms of palm oil triglycerides in the presence of diglycerides, in Journal of Oil Palm Research 12:107.
Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.
Skovgaard, et al.;"Comparison of Intra- and extracellualr isozyme banding patterns of *Fusarium oxysporum*"; Mycol. Res. (1998); vol. 102(9); pp. 1077-1084.
Slotboom et al Chem. Phys. Lipids 4 (1970) 15-29.
Smith, George P.; "The Progeny of sexual PCR"; Nature; vol. 370; No. 18; Aug. 4, 1994.
Smith, Timothy L., et al., "The promoter of the glucoamylase-encoding gene of *Aspergillus niger* functions in *Ustilago maydis*", Gene. 88, 259-262, 1990.
Solares, Laura F., et al., "Enzymatic resolution of new carbonate intermediates for the synthesis of (S)-(+)-zopiclone", Tetrahedron: Asymmetry, vol. 13, 2002, pp. 2577-2582.
Sols and De Le Fuente, "On the substrate specificity of glucose oxidase", Biochem et Biophysica Acta (1957) 24:206-7.
Sonntag N.O.V. (1982a) Glycerolysis of Fats and methyl esters—status, review and critique, in Journal of American Oil Chemist Society 59:795-802A.

Soragni, Elisabetta, et al., "A nutrient-regulated, dual localization phospholipase A2 in the symbiotic fungus" The EMBO Journal, vol. 20, No. 18, pp. 5079-5090, 2001.
Sosland, Josh, "Alive and kicking", Milling & Baking News, Feb. 24, 2004.
Soumanou, Mohamed M., et al., "Two-Step Enzymatic Reaction for the Synthesis of Pure Structured Triacylglycerides", JAOCS, vol. 75, No. 6, 1998.
Spendler, et al., "Functionality and mechanism of a new 2nd generation lipase for baking industry" -Abstract. 2001 AACC Annual Meeting; Symposia at Charlotte, NC. Oct. 14-18, 2001.
Spradlin J E, Biocatalysis in Agric. Technol., ACS Symposium, 389(3), 24-43 (1989).
Sreekrishna K et al (1988) J Basic Microbiol. 28(4), 265-78.
Stadler et al., "Understanding Lipase Action and Selectivity", CCACAA, vol. 68, No. 3, pp. 649-674, 1995.
Steinstraesser, et al., "Activity of Novispirin G10 against *Pseudomonas aeruginosa* In Vitro and in Infected Burns", Antimicrobial Agents and Chemotherapy, Jun. 2002, vol. 46, No. 6, pp. 1837-1844.
Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.
Stemmer, Willem P.C.; "Rapid evolution of a protein in vitro by DNA shuffling"; Affymax Research Institute, Nature, vol. 370, Aug. 4, 1994.
Sternberg, M., "Purification of Industrial Enzymes with Polyacrylic Acids", Process Biochemistry, Sep. 1976.
Strickland, James A., et al., "Inhibition of Diabrotica Larval Growth by Patatin, the Lipid Acyl Hydrolase from Potato Tubers", Plant Physiol, vol. 109, pp. 667-674, 1995.
Sudbery et al (1988) Biochem Soc Trans. 16(6), 1081-3.
Sugatani, Junko, et al., "Studies of a Phospholipase B from Penicillium Notatum Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Sugiyama et al., "Molecular cloning of a second phospholipase B gene, caPLB2 from *Candida albicans*", Medical Mycology, vol. 37, 1999.
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the *Pseudomonas* family", Biochimica et Biophysica Acta, vol. 1259, 1995, pp. 9-17.
Sweigard, James A., et al., "Cloning and analysis of CUT1, a cutinase gene from *Magnaporthe grisea*", Mol. Gen. Genet., 232:174-182, 1992.
Swinkels et al (1993) Antonie van Leeuwenhoek 64, 187-201.
Sztajer H et al Acta Biotechnol, vol. 8, 1988, pp. 169-175.
Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.
Terasaki, Masaru, et al., "Glycerolipid Acyl Hydrolase Activity in the Brown Alga *Cladosiphon okamuranus* Tokida", Biosci. Biotechnol. Biochem., vol. 67, No. 9, pp. 1986-1989, 2003.
The New Enzyme Operatives, Ingredient Technology, 50, Aug. 1997.
Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et al 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.
Toida J et al, Bioscience, Biotechnology, and Biochemistry, Jul 1995, vol. 59, No. 7, pp. 1199-1203.
Tombs and Blake, Biochim. Biophys (1982) 700:81-89.
Topakas, E., et al. "Purification and characterization of a feruloyl esterase from *Fusarium oxysporum* catalyzing esterification of phenolic acids in ternary water—organic solvent mixtures", Journal of Biotechnology, vol. 102, 2003, pp. 33-44.
Torossian and Bell (Biotechnol. Appl. Biochem., 1991, 13:205-211.

(56) References Cited

OTHER PUBLICATIONS

Tsao et al. (1973) J Supramol Struct. 1(6), 490-7.
Tsuchiya, Atsushi et al, Fems Microbiology Letters, vol. 143, pp. 63-67.
Tsuneo Yamane et al., "Glycerolysis of Fat by Lipase", Laboratory of Bioreaction Engineering, vol. 35, No. 8, 1986.
Tsychiya, Atsushi, et al., "Cloning and nucleotide sequence of the mono- and diacylglycerol lipase gene (mdlB) of *Aspergillus oryzae*", FEMS Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.
Turner, Progress in Industrial Microbiology, Martinelli and Kinghorn (eds.), Elsevier, Amsterdam, 1994, 29:641-666.
Unknown, *Studies on Lipase* (1964) p. 21.
Uppenberg, Jonas, et al., "Crystallographic and Molecular-Modeling Studies of Lipase B from *Candida antarctia* Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from *Candida antarctica*", Structure 1994, vol. 2, No. 4.
Upton C et al TIBS Trends in Biochemical Sciences, Elsevier Publication (1995), vol. 20, pp. 178-179.
USDA, "Production of an Industrially Useful Fungal Lipase by a Genetically Altered Strain of *E. coli*", *New Technology*.
Uusitalo et al. (1991) J Biotechnol. 17(1), 35-49.
Uwajima T et al, Agricultural and Biological Chemistry, 43(12), pp. 2633-2634, 1979.
Uwajima T et al, Agricultural and Biological Chemistry, 44(9), pp. 2039-2045, 1980.
Vaidehi, et al.; "Lipase Activity of Some Fungi Isolated from Groundnut"; Current Science (1984); vol. 53(23); p. 1253.
van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.
van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.
van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.
van Oort, Maarten G et al, Biochemistry 1989 9278-9285.
Vaysse et al J. of Biotechnology 53 (1997) 41-46.
Villenueva, Inform, vol. 8, No. 6, Jun. 1997.
Vujaklija, Dušica, et al., "A novel streptomycete lipase: cloning, sequencing and high-level expression of the *Streptomyces rimosus* GDS (L)-lipase gene", Arch. Microbiol, vol. 178, pp. 124-130, 2002.
Wahnelt S.V., Meusel D, & Tülsner M, (1991) Zur kenntnis des diglyceride influsses auf das kristallisationsverhalten von Fetten, in Fat Science Technology 4:117-121.
Waninge, Rianne, et al., "Milk membrane lipid vesicle structures studied with Cryo-TEM", Colloids and Surfaces B: Biointerfaces 31 (2003), pp. 257-264.
Warmuth et al, 1992, Bio Forum 9, 282-283.
Watanabe et al. Bio sci Biochem 63(5) 820-826, 1999.
Watanabe, Yasuo et al., "Cloning and sequencing of phospholipase B gene from the yeast *Torulaspora delbrueckii*", FEMS Microbiology Letters, vol. 124, 1994, pp. 29-34.
Webb EC, Enzyme Nomenclature, 1992, p. 310.
Weber et al. J Agric Food Chem 1985, 33, 1093-1096.
Wen-Chen Suen et al., "Improved activity and thermostability of *Candida antarctica* lipase B by DNA family shuffling", Protein Engineering, Design & Selection, vol. 17, No. 2, pp. 133-140, 2004.
West S.; "Olive and Other Edible Oils"; Industrial Enzymology (1996); pp. 295-299.
Whitehead, Michael, et al., "Transformation of a nitrate reductase deficient mutant of *Penicillium chrysogenum* with the corresponding *Aspergillus niger* and *A. nidulans* niaD genes", Mol Gen Genet, 216: 408-411, 1989.
Wilhelm et al., "A Novel Lipolytic Enzyme Located in the Outer Membrane of *Pseudomonas aeruginosa*", Journal of Bacteriology, vol. 181, No. 22, Nov. 1999, pp. 6977-6986.
Winnacker, Chapter 11, pp. 424-431 In From genes to clones: introduction to gene technology, VCH (1987).
Winnacker, E. "Chapter 11: Identification of Recombinant DNA" in *From Genes to Clones: Introduction to Gene Technology*, 1987 John Wiley & Sons.
Winther, Ole, et al., "Teaching computers to fold proteins", Physical Review, vol. 70, No. 030903, 2004.
Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.
Witt, Wolfgang et al., "Secretion of Phospholipase B From *Saccharomyces cerevisiae*", Biochimica et Biophysica Acta, vol. 795, 1984, pp. 117-124.
Wood et al., Eds., "Biomass, Part B, Lignin, Pectin, and Chitin", Methods in Enzymology (1988) vol. 161, Academic Press, San Diego.
Xu, Jun, et al., "Intron requirement for AFP gene expression in *Trichoderma viride*", Microbiology, 2003, vol. 149, pp. 3093-3097.
Yamaguchi et al, 1991, Gene 103:61-67.
Yamane et al., "High-Yield Diacylglycerol Formation by Solid-Phase Enzymatic Glycerolysis of Hydrogenated Beef Tallow", JAOCS, vol. 71, No. 3, Mar. 1994.
Yamauchi, Asao et al., "Evolvability of random polypetides through functional selection within a small library", Protein Engineering, vol. 15, No. 7, pp. 619-626, 2002.
Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.
Zaks, Aleksey, et al., "Enzyme-catalyzed processes in organic solvents", Proc. Natl. Acad. Sci. USA, vol. 82, pp. 3192-3196, May 1985.
Zaks, Aleksey, et al., "The Effect of Water on Enzyme Action in Organic Media", The Journal of Biological Chemistry, vol. 263, No. 17, Issue of Jun. 15, pp. 8017-8021, 1988.
Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.
Zangenbert, Niels Honberg, et al., "A dynamic in vitro lipolysis model II. Evaluation of the model", European Journal of Pharmaceutical Sciences, vol. 14, 2001, pp. 237-244.
Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.
U.S. Appl. No. 03/119,164, filed Jun. 26, 2003, Udagawa.
U.S. Appl. No. 60/039,791, filed Mar. 4, 1997, Clausen.
U.S. Appl. No. 60/189,780, filed Mar. 16, 2000, Soe.
U.S. Appl. No. 60/489,441, filed Jul. 23, 2003, Kreji.

* cited by examiner

FIGURE 1

SEQ ID No. 16

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

FIGURE 2

(SEQ ID No. 1)

```
  1  MKKWFVCLLG LVALTVQAAD SRPAFSRIVM FGDSLSDTGK MYSKMRGYLP
 51  SSPPYYEGRF SNGPVWLEQL TKQFPGLTIA NEAEGGATAV AYNKISWNPK
101  YQVINNLDYE VTQFLQKDSF KPDDLVILWV GANDYLAYGW NTEQDAKRVR
151  DAISDAANRM VLNGAKQILL FNLPDLGQNP SARSQKVVEA VSHVSAYHNQ
201  LLLNLARQLA PTGMVKLFEI DKQFAEMLRD PQNFGLSDVE NPCYDGGYVW
251  KPFATRSVST DRQLSAFSPQ ERLAIAGNPL LAQAVASPMA RRSASPLNCE
301  GKMFWDQVHP TTVVHAALSE RAATFIANQY EFLAH*
```

FIGURE 3

(SEQ ID No. 2)

```
  1 ivafGDSlTd geayygdsdg ggwgagladr Ltallrlrar prgvdvfnrg isGrtsdGrl
 61 ivDalvallF laqslglpnL pPYLsgdflr GANFAsagAt Ilptsgpfli QvqFkdfksq
121 vlelrqalgl lqellrllpv ldakspdlvt imiGtNDlit saffgpkste sdrnvsvpef
181 kdnlrqlikr Lrsnngarii vlitlvilnl gplGClPlkl alalassknv dasgclerln
241 eavadfneal relaiskled qlrkdglpdv kgadvpyvDl ysifqdldgi qnpsayvyGF
301 ettkaCCGyG gryNynrvCG naglcnvtak aCnpssylls flfwDgfHps ekGykavAea
361 l
```

FIGURE 4

(SEQ ID No. 3)

```
  1 mkkwfvcllg lvaltvqaad srpafsrivm fgdslsdtgk myskmrgylp ssppyyegrf
 61 sngpvwleql tnefpgltia neaeggptav aynkiswnpk yqvinnldye vtqflqkdsf
121 kpddlvilwv gandylaygw nteqdakrvr daisdaanrm vlngakeill fnlpdlgqnp
181 sarsqkvvea ashvsayhnq lllnlarqla ptgmvklfei dkqfaemlrd pqnfglsdqr
241 nacyggsyvw kpfasrsast dsqlsafnpq erlaiagnpl laqavaspma arsastlnce
301 gkmfwdqvhp ttvvhaalse paatfiesqy eflah
```

FIGURE 5

SEQ ID No. 4

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

FIGURE 6

SEQ ID No. 5

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 7

SEQ ID No. 6

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 8

SEQ ID No. 7

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

FIGURE 9

(SEQ ID No. 8)

```
              10         20         30         40         50         60
              |          |          |          |          |          |
       MNLRQWMGAA TAALALGLAA CGGGGTDQSG NPNVAKVQRM VVFGDSLSDI GTYTPVAQAV 70         80         90        100        110        120
              |          |          |          |          |          |
       GGGKFTNPG  PIWAETVAAQ LGVTLTPAVM GYATSVQNCP KAGCFDYAQG GSRVTDPNGI 130        140        150        160        170        180
              |          |          |          |          |          |
       GHNGGAGALT YPVQQQLANF YAASNNTFNG NNDVVFVLAG SNDIFFWTTA AATSGSGVTP 190        200        210        220        230        240
              |          |          |          |          |          |
       AIATAQVQQA ATDLVGYVKD MIAKGATQVY VFNLPDSSLT PDGVASGTTG QALLHALVGT 250        260        270        280        290        300
              |          |          |          |          |          |
       FNTTLQSGLA GTSARIIDFN AQLTAAIQNG ASFGFANTSA RACDATKINA LVPSAGGSSL 310        320        330        340
              |          |          |          |
       FCSANTLVAS GADQSYLFAD GVHPTTAGHR LIASNVLARL LADNVAH
```

FIGURE 10 (SEQ ID No. 9)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalraggal glrvpadpdq pwpplpprgt ldvrrddvhw areylvpwig rrlrgessgd
241 hvtakgtlsp daiktriaav a
```

FIGURE 11

(SEQ ID No. 10)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

FIGURE 12

(SEQ ID No. 11)

```
  1 mtrgrdggag apptkhrall aaivtlivai saaiyagasa ddgsrdhalq aggrlprgda
 61 apastgawvg awatapaaae pgtettglag rsvrnvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsglsr fqrdvlertn vkavvvvlgv ndvlnspela drdailtglr tlvdraharg
361 lrvvgatitp fggyggytea retmrqevne eirsgrvfdt vvdfdkalrd pydprrmrsd
421 ydsgdhlhpg dkgyarmgav idlaalkgaa pvka
```

FIGURE 13 (SEQ ID No. 12)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdicvimvga ndvthrmpat rsvrhlssav rrlrtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeaas
301 eagtevaaam ptgprgpwal lkrrrrrrvs eaepsspsgv
```

FIGURE 14 (SEQ ID No. 13)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswmya
121 vtgarmadlt aqvtraaqre pelvavmaga ndacrsttsa mtpvadfraq feeamatlrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

FIGURE 15 (SEQ ID No. 14)

```
  1 mrlsrraata sallltpala lfgasaavsa priqatdyva lgdsyssgvg agsydsssgs
 61 ckrstksypa lwaashtgtr fnftacsgar tgdvlakqlt pvnsgtdlvs itiggndagf
121 adtmttcnlq gesaclaria karayiqqtl paqldqvyda idsrapaaqv vvlgyprfyk
181 lggscavgls eksraainaa addinavtak raadhgfafg dvnttfaghe lcsgapwlhs
241 vtlpvensyh ptangqskgy lpvlnsat
```

FIGURE 16 (SEQ ID No. 15)

```
  1 MKKWFVCLLG LIALTVQAAD TRPAFSRIVM FGDSLSDTGK MYSKMRGYLP
 51 SSPPYYEGRF SNGPVWLEQL IKQFPGLTIA NEAEGGATAV AYNKISWNPK
101 YQVINNLDYE VTQFLQKDSF KPDDLVILWV GANDYLAYGW NTEQDAKRVR
151 DAISDAANRM VLNGAKQILL FNLPDLGQNP SARSQKVVEA VSHVSAYHNK
201 LLLNLARQLA PTGMVKLFEI DKQFAEMLRD PQNFGLSDVE NPCYDGGYVW
251 KPFATRSVST DRQLSAFSPQ ERLAIAGNPL LAQAVASPMA RRSASPLNCE
301 GKMFWDQVHP TTVVHAALSE RAATFIETQY EFLAHG*
```

FIGURE 17 (SEQ ID No. 19)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalraggal glrvpadpdq pwpplpprgt ldvrrddvhw areylvpwig rrlrgessgd
241 hvtakgtlsp daiktriaav a
```

FIGURE 18   (SEQ ID No. 25)

```
  1 MFKFKKNFLV GLSAALMSIS LFSATASAAS ADSRPAFSRI VMFGDSLSDT
 51 GKMYSKMRGY LPSSPPYYEG RFSNGPVWLE QLIKQFPGLT IANEAEGGAT
101 AVAYNKISWN PKYQVINNLD YEVTQFLQKD SFKPDDLVIL WVGANDYLAY
151 GWNTEQDAKR VRDAISDAAN RMVLNGAKQI LLFNLPDLGQ NPSARSQKVV
201 EAVSHVSAYH NQLLLNLARQ LAPTGMVKLF EIDKQFAEML RDPQNFGLSD
251 VENPCYDGGY VWKPFATRSV STDRQLSAFS PQERLAIAGN PLLAQAVASP
301 MARRSASPLN CEGKMFWDQV HPTTVVHAAL SERAATFIAN QYEFLAH**
```

FIGURE 19

(SEQ ID NO. 26)

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYRPTSTGHQSGYLPVLNANSST

Figure 20

SEQ ID No. 27

<ins>2P 00058717</ins>
```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIGURE 21

(SEQ ID No. 28)
```
  1 mgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 22

(SEQ ID No. 29)

```
  1 mrttviaasa llllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 23

(SEQ ID No. 30)

ZP_00094165

```
  1 mgqvklfarr capvllalag lapaatvare aplaegaryv algssfaagp gvgpnapgsp
 61 ercgrgtlny phllaealkl dlvdatcsga tthhvlgpwn evppqidsvn gdtrlvtlti
121 ggndvsfvgn ifaaacekma spdprcgkwr eiteeewqad eermrsivrq iharaplarv
181 vvvdyitvlp psgtcaamai spdrlaqsrs aakrlarita rvareegasl lkfshisrrh
241 hpcsakpwsn glsapaddgi pvhpnrlgha eaaaalvklv klmk //
```

FIGURE 24

SEQ ID No. 31

NP_625998.

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
//
```

FIGURE 25

SEQ ID No. 32

NP_827753.
```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
//
```

FIGURE 26

SEQ ID No. 33

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIGURE 27

(SEQ ID No. 34)

ADSRPAFSRIVMFGDSLSDTGKMYSKMRGYLPSSPPYYEGRFSNGPVWLEQLTNEFPGLTIANEAEGGPT
AVAYNKISWNPKYQVINNLDYEVTQFLQKDSFKPDDLVILWVGANDYLAYGWNTEQDAKRVRDAISDAAN
RMVLNGAKEILLFNLPDLGQNPSARSQKVVEAASHVSAYHNQLLLNLARQLAPTGMVKLFEIDKQFAEML
RDPQNFGLSDQRNACYGGSYVWKPFASRSASTDSQLSAFNPQERLAIAGNPLLAQAVASPMAARSASTLN
CE
GKMFWDQVHPTTVVHAALSEPAATFIESQYEFLAH

FIGURE 28

(SEQ ID No. 35)

```
  1  ADTRPAFSRI VMFGDSLSDT GKMYSKMRGY LPSSPPYYEG RFSNGPVWLE QLTKQFPGLT
 61  IANEAEGGAT AVAYNKISWN PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPFATRSV
241  STDRQLSAFS PQERLAIAGN PLLAQAVASP MARRSASPLN CEGKMFWDQV HPTTVVHAAL
301  SERAATFIET QYEFLAHG
```

FIGURE 29

(SEQ ID No. 36)

ACAGGCCGATGCACGGAACCGTACCTTTCCGCAGTGAAGCGCTCTCCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCCGTAGCCGGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGGCTCGTACCGGATGATGTGCAGATCCAAAGAATT

FIGURE 30

(SEQ ID NO. 37):

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIGURE 31

SEQ ID No. 38

```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIGURE 32

(SEQ ID No. 39)

```
   1 ggtggtgaac cagaacaccc ggtcgtcggc gtgggcgtcc aggtgcaggt gcaggttctt
  61 caactgctcc agcaggatgc cgccgtggcc gtgcacgatg gccttgggca ggcctgtggt
 121 ccccgacgag tacagcaccc atagcggatg gtcgaacggc agcggggtga actccagttc
 181 cgcgccttcg cccgcggctt cgaactccgc caggacagg gtgtcggcga cagggccgca
 241 gcccaggtac ggcaggacga cggtgtgctg caggctgggc atgccgtcgc gcagggcttt
 301 gagcacgtca cggcggtcga agtccttacc gccgtagcgg tagccgtcca cggccagcag
 361 cactttcggt tcgatctgcg cgaaccggtc gaggacgctg cgcacccga agtcggggga
 421 acaggacgac caggtcgcac cgatcgcggc gcaggcgagg aatgcggccg tcgcctcggc
 481 gatgttcggc aggtaggcca cgacccggtc gccggggccc accccgaggc tgcggagggc
 541 cgcagcgatc gcggcggtgc gggtccgcag ttctccccag gtccactcgg tcaacggccg
 601 gagttcggac gcgtgccgga tcgccacggc tgatgggtca cggtcgcgga agatgtgctc
 661 ggcgtagttg agggtggcgc cggggaacca gacggcgccg ggcatggcgt cggaggcgag
 721 cactgtggtg tacggggtgg cggcgcgcac ccggtagtac tcccagatcg cggaccagaa
 781 tccttcgagg tcggttaccg accagcgcca cagtgcctcg tagtccggtg cgtccacacc
 841 gcggtgctcc cgcacccagc gggtgaacgc ggtgaggttg gcgcgttctt tgcgctcctc
 901 gtcgggactc cacaggatcg gcggctgcgg cttgagtgtc atgaaacgcg accccttcgt
 961 ggacggtgcg gatgcggtga gcgtcgggtg cctcccctaa cgctccccgg tgacggagtg
1021 ttgtgcacca catctagcac gcgggacgcg gaaaccgtat ggagaaaaca cctacaaccc
1081 cggccgaacg gtgggtttcg gccacactta ggggtcgggt gcctgcttgc cgggcagggc
1141 agtcccgggg tgctgtggtg cgggcgggag ggctgtcgct tcgaggtgtg ccggcgggac
1201 actccgggcc tcagccgtac ccgcaacggg gacagttctc ctccccttccg ggctggatgg
1261 tcccttcccc cgaaatgcgg cgagatctcc cagtcagccc ggaaaacacc cgctgtgccc
1321 aggtactctt tgcttcgaac agacaggccg gacggtccac gggggaggtt tgtgggcagc
1381 ggaccacgtg cggcgaccag acgacggttg ttcctcggta tccccgctct tgtacttgtg
1441 acagcgctca cgctggtctt ggctgtcccg acggggcgcg agacgctgtg gcgcatgtgg
1501 tgtgaggcca cccaggactg gtgcctgggg gtgccggtcg actcccgcg acagcctgca
1561 gaggacggcg agtttctgct gctttctccg gtccaggcag cgacctgggg gaactattac
1621 gcgctcgggg attcgtactc ttcgggggac ggggcccgcg actactatcc cggcaccgcg
1681 gtgaagggcg gttgctggcg gtccgctaac gcctatccgg agctggtcgc cgaagcctac
1741 gacttcgccg gacacttgtc gttcctggcc tgcagcggcc agcgcggcta cgccatgctt
1801 gacgctatcg acgaggtcgg ctcgcagctg gactggaact ccctcacac gtcgctggtg
1861 acgatcggga tcggcggcaa cgatctgggg ttctccacgg ttttgaagac ctgcatggtg
1921 cgggtgccgc tgctggacag caagcgtgc aggaccagg aggacgctat ccgcaagcgg
1981 atggcgaaat tcgagacgac gtttgaagag ctcatcagcg aagtgcgcac ccgcgcgccg
2041 gacgccggga tccttgtcgt gggctacccc cggatttttc cggaggaacc gaccggcgcc
2101 tactacacgc tgaccgcgag caaccagcgg tggctcaacg aaaccattca ggagttcaac
2161 cagcagctcg ccgaggctgt cgcggtccac gacgaggaga ttgccgcgtc gggcggggtg
2221 ggcagcgtgg agttcgtgga cgtctaccac gcgttggacg gccacgagat cggctcggac
2281 gagccgtggg tgaacggggt gcagttgcgg gacctcgcca ccggggtgac tgtggaccgc
2341 agtaccttcc accccaacgc cgctgggcac cgggcggtcg gtgagcgggt catcgagcag
2401 atcgaaaccg gcccggccg tccgctctat gccactttcg cggtggtggc ggggcgacc
2461 gtggacactc tcgcgggcga ggtggggtga cccggcttac cgtccggccc gcaggtctgc
2521 gagcactgcg gcgatctggt ccactgccca gtgcagttcg tcttcggtga tgaccagcgg
2581 cggggagagc cggatcgttg agccgtgcgt gtctttgacg agcacacccc gctgcaggag
2641 ccgttcgcac agttctcttc cggtggccag agtcgggtcg acgtcgatcc cagcccacag
2701 gccgatgctg cgggccgcga ccacgccgtt gccgaccagt tggtcgaggc gggcgcgcag
2761 cacggggcg agggcgcgga catggtccag gtaagggccg tcgcggacga ggctccaccac
2821 ggcagtgccg accgcgcagg cgagggcgtt gccgccgaag tgctgccgt gctggccggg
2881 gcggatcacg tcgaagactt ccgcgtcgcc taccgccgcc gccacgggca ggatgccgcc
2941 gcccagcgct tgccgaaca ggtagatatc ggcgtcgact ccgctgtggt cgcaggcccg
```

FIGURE 33

(SEQ ID No. 40)

```
  1 vgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 34

(SEQ ID No. 41)

```
  1 mrttviaasa llllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 35

(SEQ ID No. 42)

```
   1 ttctggggtg ttatggggtt gttatcggct cgtcctgggt ggatcccgcc aggtggggta
  61 ttcacggggg acttttgtgt ccaacagccg agaatgagtg ccctgagcgg tgggaatgag
 121 gtgggcgggg ctgtgtcgcc atgaggggc ggcgggctct gtggtgcccc gcgaccccg
 181 gccccggtga gcggtgaatg aaatccggct gtaatcagca tcccgtgccc acccccgtcgg
 241 ggaggtcagc gcccggagtg tctacgcagt cggatcctct cggactcggc catgctgtcg
 301 gcagcatcgc gctcccgggt cttggcgtcc ctcggctgtt ctgcctgctg tccctggaag
 361 gcgaaatgat caccggggag tgatacaccg gtggtctcat cccggatgcc cacttcggcg
 421 ccatccggca attcgggcag ctccgggtgg aagtaggtgg catccgatgc gtcggtgacg
 481 ccatagtggg cgaagatctc atcctgctcg agggtgctca ggccactctc cggatcgata
 541 tcgggggcgt ccttgatggc gtccttgctg aaaccgaggt gcagcttgtg ggcttccaat
 601 ttcgcaccac ggagcgggac gaggctggaa tgacggccga agagcccgtg gtggacctca
 661 acgaaggtgg gtagtcccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aatgggtgg tgggagccct ggtcgcggtt
 961 ccgtgggagg cgccgtgccc cgcaggatcg tcggcatcgg cggatctggc cggtaccccg
1021 cggtgaataa aatcattctg taaccttcat cacggttggt tttaggtatc cgccccttc
1081 gtcctgaccc cgtcccggc gcgcgggagc ccgcgggttg cggtagacag gggagacgtg
1141 gacaccatga ggacaacggt catcgcagca agcgcattac tccttctcgc cggatgcgcg
1201 gatggggccc gggaggagac cgccggtgca ccgccgggtg agtcctccgg gggcatccgg
1261 gaggagggg cggaggcgtc gacaagcatc accgacgtct acatcgccct cggggattcc
1321 tatgcggcga tgggcgggcg ggatcagccg ttacggggtg agccgttctg cctgcgctcg
1381 tccggtaatt acccggaact cctccacgca gaggtcaccg atctcacctg ccagggggcg
1441 gtgaccgggg atctgctcga acccaggacg ctggggggagc gcacgctgcc ggcgcaggtg
1501 gatgcgctga cggaggacac caccctggtc accctctcca tcggggcaa tgacctcgga
1561 ttcggggagg tggcgggatg catccgggaa cggatcgccg gggagaacgc tgatgattgc
1621 gtggacctgc tggggggaaac catcggggag cagctcgatc agcttccccc gcagctggac
1681 cgcgtgcacg aggctatccg ggaccgcgcc ggggacgcgc aggttgtggt caccggttac
1741 ctgccgctcg tgtctgccgg ggactgcccc gaactggggg atgtctccga ggcggatcgt
1801 cgttgggcgg ttgagctgac cgggcagatc aacgagaccg tgcgcgaggc ggccgaacga
1861 cacgatgccc tctttgtcct gcccgacgat gccgatgagc acaccagttg tgcacccca
1921 cagcagcgct gggcggatat ccagggccaa cagaccgatg cctatccgct gcacccgacc
1981 tccgccggcc atgaggcgat ggccgccgcc gtccgggacg cgctgggcct ggaaccggtc
2041 cagccgtagc gccgggcgcg cgcttgtcga cgaccaaccc atgccaggct gcagtcacat
2101 ccgcacatag cgcgcgcggg cgatggagta cgcaccatag aggatgagcc cgatgccgac
2161 gatgatgagc agcacactgc cgaagggttg ttccccgagg gtgcgcagag ccgagtccag
2221 acctgcggcc tgctccggat catgggccca accggcgatg acgatcaaca ccccaggat
2281 cccgaaggcg ataccacggg cgacataacc ggctgttccg gtgatgatga tcgcggtccc
2341 gaccatgcc gaccccgcac ccgctcccag atcctcccgg aaatcccgtg tggccccctt
2401 ccagaggttg tagacacccg cccccagtac caccagcccg gcgaccacaa ccagcaccac
2461 accccagggt tgggatagga cggtggcggt gacatcggtg gcggtctccc catcggaggt
2521 gctgccgccc cgggcgaagg tggaggtggt caccgccagg gagaagtaga ccatggccat
2581 gaccgccccc ttggccctt ccttgaggtc ctcgcccgcc agcagctggc tcaattgcca
2641 gagtcccagg gccgccaggg cgatgacggc aacccacagg aggaactgcc cacccggagc
2701 ctccgcgatg gtggccaggg cacctgaatt cgaggcctca tcacccgaac cgccggatcc
2761 agtggcgatg cgcaccgcga tccacccgat gaggatgtgc agtatgccca ggacaatgaa
2821 accacctctg gccaggtgg tcagcgcggg gtggtcctcg gcctggtcgg cagcccgttc
2881 gatcgtccgt ttcgcggatc tggtgtcgcc cttatccata gctcccattg aaccgccttg
2941 aggggtgggc ggccactgtc agggcggatt gtgatctgaa ctgtgatgtt ccatcaaccc
```

FIGURE 36

(SEQ ID No. 43)

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
```

Figure 37

(SEQ ID No. 44)

```
   1 cccggcggcc cgtgcaggag cagcagccgg cccgcgatgt cctcgggcgt cgtcttcatc
  61 aggccgtcca tcgcgtcggc gaccggcgcc gtgtagttgg cccggacctc gtcccaggtg
 121 cccgcggcga tctggcgggt ggtgcggtgc gggccgcgcc gagggagac gtaccagaag
 181 cccatcgtca cgttctccgg ctgcggttcg ggctcgtccg ccgctccgtc cgtcgcctcg
 241 ccgagcacct tctcggcgag gtcggcgctg gtcgccgtca ccgtgacgtc ggcgcccgg
 301 ctccagcgcg agatcagcag cgtccagccg tcgccctccg ccagcgtcgc gctgcggtcg
 361 tcgtcgcggg cgatccgcag cacgcgcgcg ccgggcggca gcagcgtggc gccggaccgt
 421 acgcggtcga tgttcgccgc gtgcgagtac ggctgctcac ccgtggcgaa acgccgagg
 481 aacagcgcgt cgacgacgtc ggacggggag tcgctgtcgt ccacgttgag ccggatcggc
 541 agggcttcgt gcgggttcac ggacatgtcg ccatgatcgg gcaccggcc gccgcgtgca
 601 cccgctttcc cgggcacgca cgacaggggc tttctcgccg tcttccgtcc gaacttgaac
 661 gagtgtcagc catttcttgg catggacagt tccagtcaac gcgcgtagct gctaccacgg
 721 ttgtggcagc aatcctgcta agggaggttc catgagacgt ttccgacttg tcggcttcct
 781 gagttcgctc gtcctcgccg ccggcgccg cctcaccggg gcagcgaccg cccaggcggc
 841 ccaacccgcc gccgccgacg gctatgtggc cctcggcgac tcctactcct cggggtcgg
 901 agcgggcagc tacatcagct cgagcggcga ctgcaagcgc agcacgaagg cccatcccta
 961 cctgtgggcg gccgcccact cgccctccac gttcgacttc accgcctgtt cggcgcccg
1021 tacgggtgat gttctctccg gacagctcgg cccgctcagc tccggcaccg gcctcgtctc
1081 gatcagcatc ggcggcaacg acgcggtt cgccgacacc atgacgacct gtgtgctcca
1141 gtccgagagc tcctgcctgt cgcggatcgc caccgccgag gcgtacgtcg actcgacgct
1201 gcccggcaag ctcgacggcg tctactcgg aatcagcgac aaggcgccga acgcccacgt
1261 cgtcgtcatc ggctaccgc gcttctacaa gctcggcacc acctgcatcg gcctgtccga
1321 gaccaagcgg acggcgatca acaaggcctc cgaccacctc aacaccgtcc tcgcccagcg
1381 cgccgccgcc cacggcttca ccttcggcga cgtacgcacc accttcaccg gccacgagct
1441 gtgctccggc agcccctggc tgcacagcgt caactggctg aacatcggcg agtcgtacca
1501 cccaccgcg gccggccagt ccggtggcta cctgccggtc ctcaacggcg ccgcctgacc
1561 tcaggcggaa ggagaagaag aaggagcgga gggagacgag gagtgggagg cccgcccga
1621 cggggtcccc gtcccgtct ccgtctccgt cccggtcccg caagtcaccg agaacgccac
1681 cgcgtcggac gtggcccgca ccggactccg cacctccacg cgcacggcac tctcgaacgc
1741 gccggtgtcg tcgtgcgtcg tcaccaccac gccgtcctgg cgcgagcgct cgccgcccga
1801 cgggaaggac agcgtccgcc accccggatc ggagaccgac ccgtccgcgg tcacccaccg
1861 gtagccgacc tccgggggca gccgcccgac cgtgaacgtc gccgtgaacg cgggtgcccg
1921 gtcgtgcggc ggcggacagg cccccgagta gtgggtgcgc gagcccacca cggtcacctc
1981 caccgactgc gctgcggggc
```

FIGURE 38

(SEQ ID No. 45)

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
```

FIGURE 39

SEQ ID No. 46

```
   1 ccaccgccgg gtcggcggcg agtctcctgg cctcggtcgc ggagaggttg gccgtgtagc
  61 cgttcagcgc ggcgccgaac gtcttcttca ccgtgccgcc gtactcgttg atcaggccct
 121 tgcccttgct cgacgcggcc ttgaagcggt gcccttctt gagcgtgacg atgtagctgc
 181 ccttgatcgc ggtggggggag ccggcggcga gcaccgtgcc ctcggccggg gtggcctggg
 241 cgggcagtgc ggtgaatccg cccacgaggg cgccggtcgc cacggcggtt atcgcggcga
 301 tccggatctt cttgctacgc agctgtgcca tacgagggag tcctcctctg ggcagcggcg
 361 cgcctggtg gggcgcaggg ctgtggggg tgcgcgcgtc atcacgcaca cggccctgga
 421 gcgtcgtgtt ccgccctggg ttgagtaaag cctcggccat ctacgggggt ggctcaaggg
 481 agttgagacc ctgtcatgag tctgacatga gcacgcaatc aacggggccg tgagcacccc
 541 ggggcgaccc cggaaagtgc cgagaagtct tggcatggac acttcctgtc aacacgcgta
 601 gctggtacga cggttacggc agagatcctg ctaaaggag gttccatgag acgttcccga
 661 attacggcat acgtgacctc actcctcctc gccgtcggct gcgccctcac cggggcagcg
 721 acggcgcagg cgtccccagc cgccgcggcc acgggctatg tggccctcgg cgactcgtac
 781 tcgtccggtg tcggcgccgg cagctacctc agctccagcg gcgactgcaa gcgcagttcg
 841 aaggcctatc cgtacctctg gcaggccgcg cattcaccct cgtcgttcag tttcatggct
 901 tgctcggcg ctcgtacggg tgatgtcctg gccaatcagc tcggcaccct gaactcgtcc
 961 accggcctgc tctccctcac catcggaggc aacgacgcgg gcttctccga cgtcatgacg
1021 acctgtgtgc tccagtccga cagcgcctgc ctctcccgca tcaacacggc gaaggcgtac
1081 gtcgactcca ccctgccggg ccaactcgac agcgtgtaca cggcgatcag cacgaaggcc
1141 ccgtcggccc atgtggccgt gctgggctac ccccgcttct acaaactggg cggctcctgc
1201 ctcgcgggct tctcggagac caagcggtcc gccatcaacg acgcggccga ctatctgaac
1261 agcgccatcg ccaagcgcgc cgccgaccac ggcttcacct tcggcgacgt caagagcacc
1321 ttcaccggcc atgagatctg ctccagcagc acctggctgc acagtctcga cctgctgaac
1381 atcggccagt cctaccaccc gaccgcggcc ggccagtccg gcggctatct gccggtcatg
1441 aacagcgtgg cctgagctcc cacggcctga attttaagg cctgaatttt taaggcgaag
1501 gtgaaccgga agcggaggcc ccgtccgtcg gggtctccgt cgcacaggtc accgagaacg
1561 gcacggagtt ggacgtcgtg cgcaccgggt cgcgcacctc gacggcgatc tcgttcgaga
1621 tcgttccgct cgtgtcgtac gtggtgacga acacctgctt ctgctgggtc tttccgccgc
1681 tcgccgggaa ggacagcgtc ttccagcccg gatcgggac ctcgcccttc ttggtcaccc
1741 agcggtactc cacctcgacc ggcaccggg ccaccgtgaa ggtcgccgtg aacgtgggcg
1801 cctgggcggt gggcggcggg caggcaccgg agtagtcggt gtgcacgccg gtgaccgtca
1861 ccttcacgga ctgggccggc ggggtcgtcg taccgccgcc gccaccgccg cctcccggag
1921 tggagcccga gctgtggtcg cccccgccgt cggcgttgtc gtcctcgggg gttttcgaac
```

FIGURE 40

SEQ ID No. 47

```
  1 mgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 41

SEQ ID No. 48

```
  1    ctgcagacac cgccccgcc ttctcccgga tcgtcatgtt cggcgactcc ctcagcgaca
 61    ccggcaagat gtactccaag atgcgcggct acctgccgtc ctccccgccg tactacgagg
121    gccgcttctc gaacggcccg gtctggctgg agcagctgac gaagcagttc cccggcctga
181    cgatcgccaa cgaggccgag gggggcgcga ccgcagtcgc ctacaacaag atctcctgga
241    acccgaagta ccaggtcatt aacaacctcg actacgaggt cacccagttc ttgcagaagg
301    actcgttcaa gcccgacgac ctggtcatcc tgtgggtggg cgccaacgac tacctggcct
361    acggttggaa cacggagcag gacgccaagc gggtgcgcga cgccatctcg gacgcggcaa
421    accgcatggt cctgaacggc gcgaagcaga tcctgctgtt caacctgccc gacctgggcc
481    agaacccgtc cgcccgctcc cagaaggtcg tcgaggccgt ctcgcacgtg tccgcctacc
541    acaacaagct gctcctcaac ctcgcccggc agctcgcccc gacgggcatg gtcaagctgt
601    tcgagatcga caagcagttc gcggagatgc tgcgcgaccc cagaacttc ggcctgagcg
661    acgtggagaa cccgtgctac gacggcggct acgtgtggaa gccgttcgcc acccggtccg
721    tctcgaccga ccggcagctg tcggccttct cgccccagga gcgcctggcg atcgctggca
781    acccgctcct ggcacaggcg gtagcttcgc cgatggcctg ccgtcggcc tcgcccctca
841    actgcgaggg caagatgttc tgggaccagg tccacccac caccgtggtc cacgccgccc
901    tctcggagcg cgccgccacc ttcatcgaga cccagtacga gttcctcgcc cactagtcta
961    gaggatcc
```

Figure 42

1. L131
2. S.avermitilis
3. T.fusca
4. Consensus

```
                 1                                                50
1   (1)   --------MRLTRSLSAASVIVFALLLALLGISPAQAAG-----------
2   (1)   --------MRRSRITAYVTSLLLAVGCALTGAATAQASPA----------
3   (1)   VGSGPRAATRRRLFLGIPALVLVTALTLVLAVPTGRETLWRMWCEATQDW
4   (1)           MRRSRFLA  ALILLTLA AL GAA ARAAP 51                                                100
1   (32)  -----------------------------P-AYVALGDSYSSGNGAGSYID
2   (33)  -----------------------------AAATGYVALGDSYSSGVGAGSYLS
3   (51)  CLGVPVDSRGQPAEDGEFLLLSPVQAATWGNYYALGDSYSSGDGARDYYP
4   (51)                          A A  YVALGDSYSSG GAGSY 101                                               150
1   (53)  SSGD----CHRSNNAYPARWAAANAP---SSFTFAACSGAVTTDVIN----
2   (57)  SSGD----CKRSSKAYPYLWQAAHSP---SSFSFMACSGARTGDVLA----
3   (101) GTAVKGGCWRSANAYPELVAEAYDFA--GHLSFLACSGQRGYAMLDAIDE
4   (101) SSGD    C RSTKAYPALWAAAHA    SSFSF ACSGARTYDVLA 151                                               200
1   (93)  --NQLGALNAST--GLVSITIGGNDAGFADAMTTCVTS------SDSTCL
2   (97)  --NQLGTLNSST--GLVSLTIGGNDAGFSDVMTTCVLQ------SDSACL
3   (149) VGSQLDWNSPHT--SLVTIGIGGNDLGFSTVLKTCMVR------VPLLDS
4   (151)    QL LNS T  LVSITIGGNDAGFAD MTTCVL      SDSACL 201                                               250
1   (133) NRLATATNYINTTLLA-------RLDAVYSQIKARAPNARVVVLGYPRMY
2   (137) SRINTAKAYVDSTLPG-------QLDSVYTAISTKAPSAHVAVLGYPRFY
3   (191) KACTDQEDAIRKRMAKF----ETTFEELISEVRTRAPDARILVVGYPRIF
4   (201)  RIA AK YI  TLPA        RLDSVYSAI TRAP ARVVVLGYPRIY 251                                               300
1   (176) LASNPWYCLGLSNTKRAAINTTADTLNSVISSRATAH----------GF
2   (180) KLGG-SCLAGLSETKRSAINDAADYLNSAIAKRAADH----------GF
3   (237) PEEPTGAYYTLTASNQRWLNETIQEFNQQLAEAVAVHDEEIAASGGVGSV
4   (251)     SG  LGLS TKRAAINDAAD LNSVIAKRAADH           GF 301                                               350
1   (215) RFGDVRPTFNNHELFFGNDWLHSLTLP-----------------VWESYH
2   (218) TFGDVKSTFTGHEICSSSTWLHSLDLLN----------------IGQSYH
3   (287) EFVDVYHALDGHEIGSDEPWVNGVQLRDLATG---------VTVDRSTFH
4   (301) TFGDV  TF GHELCSA  PWLHSLTLP                V  SYH 351                                               395
1   (248) PTSTGHQSGYLPVLNANSST-------------------------
2   (252) PTAAGQSGGYLPVMNSVA---------------------------
3   (328) PNAAGHRAVGERVIEQIETGPGRPLYATFAVVAGATVDTLAGEVG
4   (351) PTA GHAAGYLPVLNSI T
```

FIGURE 43

SEQ ID No 17 which is the amino acid sequence of a lipid acyltransferase from *Candida parapsilosis*;

```
MRYFAIAFLL INTISAFVLA PKKPSQDDFY TPPQGYEAQP LGSILKTRNV PNPLTNVFTP VKVQNAWQLL
VRSEDTFGNP NAIVTTIIQP FNAKKDKLVS YQTFEDSGKL DCAPSYAIQY GSDISTLTTQ GEMYYISALL
DQGYYVVTPD YEGPKSTFTV GLQSGRATLN SLRATLKSGN LTGVSSDAET LLWGYSGGSL ASGWAAAIQK
EYAPELSKNL LGAALGGFVT NITATAEAVD SGPFAGIISN ALAGIGNEYP DFKNYLLKKV SPLLSITYRL
GNTHCLLDGG IAYFGKSFFS
RIIRYFPDGW DLVNQEPIKT ILQDNGLVYQ PKDLTPQIPL FIYHGTLDAI VPIVNSRKTF QQWCDWGLKS
GEYNEDLTNG HITESIVGAP AALTWIINRF NGQPPVDGCQ HNVRASNLEY PGTPQSIKNY FEAALHAILG
FDLGPDVKRD KVTLGGLLKL ERFAF
```

FIGURE 44

SEQ ID No 18 which is the amino acid sequence of a lipid acyltransferase from *Candida parapsilosis*;

```
MRYFAIAFLL INTISAFVLA PKKPSQDDFY TPPQGYEAQP LGSILKTRNV PNPLTNVFTP VKVQNAWQLL
VRSEDTFGNP NAIVTTIIQP FNAKKDKLVS YQTFEDSGKL DCAPSYAIQY GSDISTLTTQ GEMYYISALL
DQGYYVVTPD YEGPKSTFTV GLQSGRATLN SLRATLKSGN LTGVSSDAET LLWGYSGGSL ASGWAAAIQK
EYAPELSKNL LGAALGGFVT NITATAEAVD SGPFAGIISN ALAGIGNEYP DFKNYLLKKV SPLLSITYRL
GNTHCLLDGG IAYFGKSFFS RIIRYFPDGW DLVNQEPIKT ILQDNGLVYQ PKDLTPQIPL FIYHGTLDAI
VPIVNSRKTF QQWCDWGLKS GEYNEDLTNG HITESIVGAP AALTWIINRF NGQPPVDGCQ HNVRASNLEY
PGTPQSIKNY FEAALHAILG FDLGPDVKRD KVTLGGLLKL ERFAFHHHHH H
```

```
1DEO      T T V Y  L  A G D S T M A K R - - - - - - - - - - - - - - - - - - G G G S G T N G W G E Y L
          s1s1s1s1 s1 s1s1h?h?h?h?                                            h1h1h1h1h1
1IVN      A D T L L  I  L G D S L S A G - - - - - - - - - - - - - - - - - - Y R M S A S A A W P A L L
          s1s1s1s1 s1 s1s1h h h h                                             h1h1h1h1h1
P10480       I V  M  F G D S L S D T g k m  y s k m  r g y l  p s g s  p y  y c G R F S N G P V W L E Q L

1DEOm     T T V Y  L  A G D S T M A K R - - - - - - - - - - - - - - - - - - G G G S G T N G W G E Y L
          s1s1s1s1 s1 s1s1h?h?h?h?                                            h1h1h1h1h1
1IVNm     A D T L L  I  L G D S L S A G - - - - - - - - - - - - - - - - - - Y R M S A S A A W P A L L
          s1s1s1s1 s1 s1s1h h h h                                             h1h1h1h1h1
P10480m      I V  M  F G D S L S D T g k m  y s k m  r g y l  p s s  p y  y e G R F S N G P V W L E Q L

1DEO      A S Y L S  A  T V - - - - - - - - - - - -  V N D A V  P G R S - - - A R S Y T R E G R F E N I A S VV
          h1h1h1 s2 s2 s2                    s2s2 s2 s2 s2       h3  h3h3 h3h3h3h3h3h3h3h3h3h3h3h3
1IVN      N D K W q  s  k - - - - - - - - - - - t s v  V N A S I S G D T - - - - - S Q Q G L A R I P A L L K Q
          h1h1h1 s2?s2?                       s2?s2s2s2s2 s2 s2 s2              h3?h3h3h3h3 h3h3h3h3h3h3
P10480    T N E F P  G  L T i a n e a e g g p  t a v a  Y N K I S W N P K y  q v i N N L D Y E V T Q F T Q K D S F

1DEOm     A S Y L S  A  T V - - - - - - - - - - - -  V N D A V  G R S - -      A R S Y T R E G R F E N I A
          h1h1h1 s2 s2 s2                    s2s2 s2 s2 s2       h3    h3h3h3h3h3 h3h3h3h3h3
1IVNm     N D K W q  s  k - - - - - - - - - - - t n v  V N A S I S G D T - - - - S Q Q G L A    R L P A L L
          h1h1h1 s2?s2?                       s2?s2s2s2s2 s2 s2 s2              h3h3h3h3h3  h3h3h3h3h3
P10480m   N E F P  G  L T i a n e a e g g p  t a v a  Y N K I S W N P K      y q v i N N L D Y E V T Q F L Q

1DEO      T A G D Y  V  I V E F G H N D G s  l s t d  n  g  r  t  d c z  q  t q  s E V C Y S V V D G V N E T I L T F P
          s4s4 s4 s4s4s4 s4                  ? ? ? ?  ?  ?  ?  ?  ? ? ?  ?  ? ?  ? ? s?s?s?s?s?s?s?s?s?s?s?s?h4h4h4
1IVN      H Q P R W  V  L V E L G G N D G - - - - - - - - - - - - - - - - - - - L R G F Q D Q Q T E
          h3  s4s4s4s4 s4 s4s4                                                 h4h4h4h4h4
P10480    R P D D L  V  I L N V G A N D Y - - - - - - - - - - - - - - - - - L A Y G W N T E Q D A R R V P

1DEOm     D  V V T  A  G D Y V I V E F G H N  D G g  l  s  t d n g r t  d c  s g t q s E V C Y S V V D G V N E T I
          h3h3     s4 s4s4s4s4s4            ?  ?  ? ? ? ? ? ? ? ? ?  ? ?  ? ? ? ? s?s?s?s?s?s?s?s?s?s?s?s?s?
1IVNm     K Q H Q F       R W V L V E L G G N  D G - - - - - - - - - - - - - - - - - L R G F Q P
          h3h3h3      s4s4s4s4 s4 s4                                                    h4
P10480m K D S F K  P  D D L V I L N V G A N  D Y - - - - - - - - - - - - - - - - - - L A Y G W N T E Q D A

1DEO      A Y L E N  A  A K L F T - A R G A K - - - - - V I L S S Q T P - - - - N K E W E T G T F V N S P T R
          h4h4h4h4h4 h4 h4h4h4h4h4 h4             s5 s5 s5 s5 s5
1IVN      G T L R Q  I  L Q D V K a A N A E P  l l m q  i R L P A N Y G R - - - - - - - - - - - - - - R Y
          h4h4h4h4h4 h4 h4h4h4h4h4h4    s5s5s5 s5s5s5s5?s5?s5?s5?                                       h5
P10480    Q A I S D  A  A N R M V - L N G A K - - - - - E I L L P N L P d  i g g s P S A R S Q S V V E A A S HV
```

FIGURE 50B

```
1DEOm    LTPPA Y LENAAKLFTAK GAKV I L S S Q T P N N P W E T G T F V N S P T P
         h4h4h4h4 h4 h4h4h4h4h4h4h4h4h4h4h4    s5s5s5 s5 s5 s5
1IVNm    QQTEQ T LRQILQSVKaA NAEP I l m q i P L P A N Y G R - - - - - - - - R Y N E A
         h4h4h4h4 h4 h4h4h4h4h4h4h4h4h4h4h4    s5s5s5 s5 s5 s5 s5?s5?s5?s5?           h5h5h5h5h5h5
P10480mK RVRD A ISDAANRMVLN GAKE I L L F N L P d l g q p P S A R S Q K V V E A A S H V S A

1DEO     FVEYA E LAAEVA - - - - - - - - - - - - - - - G V E Y V D H W S Y V D S I Y P T L G N A t v n
         h5h5h5h5h5 h5 h5h5h5h5h5h5                                  s6 s6 s6s6?h6h6h6h6h6h6h6h6h6h6h6   h h h h
1IVN     NEAFS A IYPKLAke - - - - - - - - - - - f D V P L L P F F M E E V Y L K P Q W - - - - - -
         h5h5h5h5h5 h5 h5h5h5h5h5h5h5h5                              h5    s6 s6 s6s6?  h6h6h6h6h6   s
P10460   S A Y E N Q L L L N L A r q l a p t g m v k l f e i D K Q F A E M L R D P Q N F G L S D Q R N a c y

1DEOm    FVEYA E LAAEVA - - - - - - - - - - - - - - - G V E Y V D H W S Y V D S I Y E P L G N A t v n - -
         h5h5h5h5 h5 h5h5h5h5h5h5h5                                  s6 s6 s6 s6?h6h6 h6h6h6h6h6h6h6h6     h h h h
1IVNm    PSAI Y PKLAke - - - - - - - - - - f D V P L L P P F M E E V Y         I K P Q W - - - -
         h5h5h5h5h5 h5 h5h5h5            h5    s6 s6 s6 s6?  h6 h6 h6 h6h6
P10460mY H N Q L L L N L A r q l a p t g m v k l f e i D K Q T A E M L P D P Q N F G L S D Q R N a c y g g

1DEO     - - - - - - - - - - - - - - - - - - - - - - - - - - - - - - - - - - - - - - - - - - - - - - -

1IVN     - - - - - - - - - - - - - - - - - - - - - - - - - - - - - - - - - - - - - - - - - - - - - - -

P10480   g q s y v w k p f a s r s a s t a r q l s a f n p q e r l a i a g n p l l a q a v a s p m a a r s a

1DEOm    - - - - - - - - - - - - - - - - - - - - - - - - - - - - - - - - - - - - - - - - - - - - - - -

1IVNm    - - - - - - - - - - - - - - - - - - - - - - - - - - - - - - - - - - - - - - - - - - - - - - -

P10460ms y v w k p f a s t s a s t d s q l s a f n p q e r l s i a g n p l l a q a v a s p m a a r s a s t

1DEO     - - - - - s y F P I D H T E T S P A G A E V V A E A F L K A V V C T G T S L K S V L T T T S F E G
         h                      s?s?s? h7h7h7h7 h7 h7 h7 h7 h7 h7 h7 h7 h7 h7h7 h7h7h7h7   h?h?h?
1IVN     - - - - - - M Q D D G I H P N R D A Q P F I A D W M A K Q L Q P L V N H D S L E
         s s            s s    h7h7h7 h7 h7 h7 h7 h7 h7 h7 h7 h7h7 h7h7h7h7
P10480   s t l n c e g k M F W D Q V H P T T V V H A A L S E P A A T F I E S Q Y E F L A H -

1DEOm    - - - - s y F P I D H T E T S P A G A E V V A E A F L K A V V C T G T S L K S V L T T T S F E G T C
         h                    s?s?s?h7h7 h7h7h7h7 h7 h7 h7 h7 h7 h7 h7 h7h7 h?h?     h?h?h?
1IVNm    - - - - - - M Q D D G I H P N R D A Q P F I A D W M A K Q L Q P L V N H D S L E
         s s s     s?h7h7h7h7h7h7h7 h7h7h7h7 h? h? h7 h7 h7 h7 h7 h7 h7
P10480ml n c e g k M F W D Q V H P T T V V H A A L S E P A A T F I E S Q Y E F L A H -
```

FIGURE 51

```
                        10        20        30        40        50        60
        ....*....|....*....|....*....|....*....|....*....|....*....|
1IVN_A       4  LLILGDSLSAG------------------YRMSASAAWPALLNDKWqsk--------- 34
P10480      28  IVMFGDSLSDTgkmyskmrgylpssppyyeGRFSNGPVWLEQLTNEFPGLTianeaeggp 87

70        80        90       100       110       120
        ....*....|....*....|....*....|....*....|....*....|....*....|
1IVN_A      35  -tsvVNASISGDT-----------------------SQQGLARLPALLKQHQPRW 65
P10480      88  tavaYNKISWNPKyq------------------------vINNLDYEVTQFLQKDSFKPDDL 125

130       140       150       160       170       180
        ....*....|....*....|....*....|....*....|....*....|....*....|
1IVN_A      66  VLVELGGNDG-----------------------------LRGFQPQQTEQT 87
P10480     126  VILWVGANDY----------------------LA--YGWNTEQDAKRVRDA 152

190       200       210       220       230       240
        ....*....|....*....|....*....|....*....|....*....|....*....|
1IVN_A      88  LRQILQDVKaANAEPllmqiRLPANYGR------------------------- 115
P10480     153  ISDAANRMV-LNGAK-----EILLFNLPdlg--------------qnP 180

250       260       270       280       290       300
        ....*....|....*....|....*....|....*....|....*....|....*....|
1IVN_A     116  -------------RYNEAFSAIYPKLAke-----------------fDVPLLPFFME 142
P10480     181  SARSQKVVEAASHVSAYHNQLLLNLArqlaptg----------mvklfeiDKQFAEMLRD 230

310       320       330       340       350       360
        ....*....|....*....|....*....|....*....|....*....|....*....|
1IVN_A     143  EVYLKPQW-------------------------------- 150
P10480     231  PQNFGLSDQRNacyggsyvwkpfasrsastdsqlsafnpqerlaiagnplllaqavaspma 290

370       380       390       400
        ....*....|....*....|....*....|....*....|
1IVN_A     151  ----------MQDDGI--------HPNRDAQPFIADWM 170
P10480     291  arsastlncegkMFWDQV--------HPTTVVHAALSEPA 322
```

FIGURE 52

```
                     1                                               50
P10480      (1)   MKKWFVCLLGLVALTVQAADSRPAFSRIVMFGDSLSDTGKMYSKMRGYLP
A. sal      (1)   ------------------ADTRPAFSRIVMFGDSLSDTGKMYSKMRGYLP
A. hyd      (1)   ------------------ADSRPAFSRIVMFGDSLSDTGKMYSKMRGYLP
Consensus   (1)                     AD*RPAFSRIVMFGDSLSDTGKMYSKMRGYLP
                    51                                              100
P10480     (51)   SSPPYYEGRFSNGPVWLEQLTNEFPGLTIANEAEGGPTAVAYNKISWNPK
A. sal     (33)   SSPPYYEGRFSNGPVWLEQLTKQFPGLTIANEAEGGATAVAYNKISWNPK
A. hyd     (33)   SSPPYYEGRFSNGPVWLEQLTKQFPGLTIANEAEGGATAVAYNKISWNPK
Consensus  (51)   SSPPYYEGRFSNGPVWLEQLT**FPGLTIANEAEGG*TAVAYNKISWNPK
                   101                                              150
P10480    (101)   YQVINNLDYEVTQFLQKDSFKPDDLVILWVGANDYLAYGWNTEQDAKRVR
A. sal     (83)   YQVINNLDYEVTQFLQKDSFKPDDLVILWVGANDYLAYGWNTEQDAKRVR
A. hyd     (83)   YQVINNLDYEVTQFLQKDSFKPDDLVILWVGANDYLAYGWNTEQDAKRVR
Consensus (101)   YQVINNLDYEVTQFLQKDSFKPDDLVILWVGANDYLAYGWNTEQDAKRVR
                   151                                              200
P10480    (151)   DAISDAANRMVLNGAKEILLFNLPDLGQNPSARSQKVVEAASHVSAYHNQ
A. sal    (133)   DAISDAANRMVLNGAKQILLFNLPDLGQNPSARSQKVVEAVSHVSAYHNK
A. hyd    (133)   DAISDAANRMVLNGAKQILLFNLPDLGQNPSARSQKVVEAVSHVSAYHNQ
Consensus (151)   DAISDAANRMVLNGAK*ILLFNLPDLGQNPSARSQKVVEA*SHVSAYHN*
                   201                                              250
P10480    (201)   LLLNLARQLAPTGMVKLFEIDKQFAEMLRDPQNFGLSDQRNACYGGSYVW
A. sal    (183)   LLLNLARQLAPTGMVKLFEIDKQFAEMLRDPQNFGLSDVENPCYDGGYVW
A. hyd    (183)   LLLNLARQLAPTGMVKLFEIDKQFAEMLRDPQNFGLSDVENPCYDGGYVW
Consensus (201)   LLLNLARQLAPTGMVKLFEIDKQFAEMLRDPQNFGLSD**N*CY*G*YVW
                   251                                              300
P10480    (251)   KPFASRSASTDSQLSAFNPQERLAIAGNPLLAQAVASPMAARSASTLNCE
A. sal    (233)   KPFATRSVSTDRQLSAFSPQERLAIAGNPLLAQAVASPMARRSASPLNCE
A. hyd    (233)   KPFATRSVSTDRQLSAFSPQERLAIAGNPLLAQAVASPMARRSASPLNCE
Consensus (251)   KPFA*RS*STD*QLSAF*PQERLAIAGNPLLAQAVASPMA*RSAS*LNCE
                   301                              336
P10480    (301)   GKMFWDQVHPTTVVHAALSEPAATFIESQYEFLAH-
A. sal    (283)   GKMFWDQVHPTTVVHAALSERAATFIETQYEFLAHG
A. hyd    (283)   GKMFWDQVHPTTVVHAALSERAATFIANQYEFLAH-
Consensus (301)   GKMFWDQVHPTTVVHAALSE*AATFI**QYEFLAH*
```

FIGURE 53

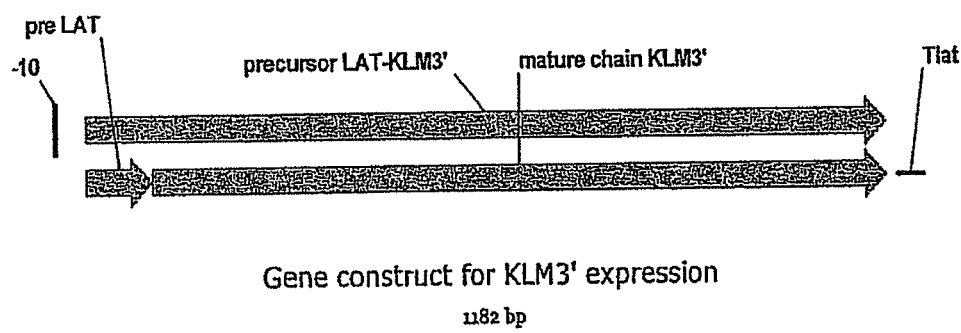

Gene construct for KLM3' expression 1182 bp

FIGURE 55

```
                                                              -35
    1   GCTTTTCTTT TGGAAGAAAA TATAGGGAAA ATGGTACTTG TTAAAAATTC GGAATATTIA
        CGAAAAGAAA ACCTTCTTTT ATATCCCTTT TACCATGAAC AATTTTTAAG CCTTATAAAT
           -10                                     M  K  Q  Q  K  R  L
   61   TACAATATCA TATGTTTCAC ATTGAAAGGG GAGGAGAATC ATGAAACAAC AAAAACGGCT
        ATGTTATAGT ATACAAAGTG TAACTTTCCC CTCCTCTTAG TACTTTGTTG TTTTTGCCGA
         Y  A  R  L  L  T  L  L  P  F  A  L  I  F  L  L  P  H  S  A  A
  121   TTACGCCCGA TTGCTGACGC TGTTATTTGC GCTCATCTTC TTGCTGCCTC ATTCTGCAGC
        AATGCGGGCT AACGACTGCG ACAATAAACG CGAGTAGAAG AACGACGGAG TAAGACGTCG
         S  A  A  D  T  R  P  A  F  S  R  I  V  M  F  G  D  S  L  S
  181   TTCAGCAGCA GATACAAGAC CGGCGTTTAG CCGGATCGTC ATGTTTGGAG ATAGCCTGAG
        AAGTCGTCGT CTATGTTCTG GCCGCAAATC GGCCTAGCAG TACAAACCTC TATCGGACTC
         D  T  G  K  M  Y  S  K  M  R  G  Y  L  P  S  S  P  P  Y  Y
  241   CGATACGGGC AAAATGTATA GCAAAATGAG AGGCTATCTT CCGTCAAGCC CGCCGTATTA
        GCTATGCCCG TTTTACATAT CGTTTTACTC TCCGATAGAA GGCAGTTCGG GCGGCATAAT
         E  G  R  F  S  N  G  P  V  W  L  E  Q  L  T  K  Q  F  P  G
  301   TGAAGGCCGC TTTAGCAATG GACCGGTCTG GCTGGAACAA CTGACGAAAC AATTTCCGGG
        ACTTCCGGCG AAATCGTTAC CTGGCCAGAC CGACCTTGTT GACTGCTTTG TTAAAGGCCC
         L  T  I  A  N  E  A  E  G  G  A  T  A  V  A  Y  N  K  I  S
  361   ACTGACGATC GCTAATGAAG CAGAAGGAGG AGCAACAGCG GTCGCCTATA ACAAAATCAG
        TGACTGCTAG CGATTACTTC GTCTTCCTCC TCGTTGTCGC CAGCGGATAT TGTTTTAGTC
         W  D  P  K  Y  Q  V  I  N  N  L  D  Y  E  V  T  Q  F  L  Q
  421   CTGGGACCCG AAATATCAGG TCATCAACAA CCTGGACTAT GAAGTCACAC AGTTTCTTCA
        GACCCTGGGC TTTATAGTCC AGTAGTTGTT GGACCTGATA CTTCAGTGTG TCAAAGAAGT
         K  D  S  F  K  P  D  D  L  V  I  L  W  V  G  A  N  D  Y  L
  481   GAAAGACAGC TTTAAACCGG ATGATCTGGT CATCCTTTGG GTCGGCGCCA ATGATTATCT
        CTTTCTGTCG AAATTTGGCC TACTAGACCA GTAGGAAACC CAGCCGCGGT TACTAATAGA
         A  Y  G  W  N  T  E  Q  D  A  K  R  V  R  D  A  I  S  D  A
  541   GGCGTATGGC TGGAACACAG AACAAGATGC CAAAAGAGTC AGAGATGCCA TCAGCGATGC
        CCGCATACCG ACCTTGTGTC TTGTTCTACG GTTTTCTCAG TCTCTACGGT AGTCGCTACG
         A  N  R  M  V  L  N  G  A  K  Q  I  L  L  F  N  L  P  D  L
  601   CGCTAATAGA ATGGTCCTGA ACGGCGCCAA ACAAATCCTG CTGTTTAACC TGCCGGATCT
        GCGATTATCT TACCAGGACT TGCCGCGGTT TGTTTAGGAC GACAAATTGG ACGGCCTAGA
         G  Q  N  P  S  A  R  S  Q  K  V  V  E  A  V  S  H  V  S  A
  661   GGGACAAAAT CCGAGCGCCA GAAGCCAAAA AGTCGTCGAA GCAGTCAGCC ATGTCAGCGC
        CCCTGTTTTA GGCTCGCGGT CTTCGGTTTT TCAGCAGCTT CGTCAGTCGG TACAGTCGCG
         Y  H  N  K  L  L  L  N  L  A  R  Q  L  A  P  T  G  M  V  K
  721   CTATCATAAC AAACTGCTGC TGAACCTGGC AAGACAATTG GCACCGACGG GAATGGTTAA
        GATAGTATTG TTTGACGACG ACTTGGACCG TTCTGTTAAC CGTGGCTGCC CTTACCAATT
         L  F  E  I  D  K  Q  F  A  E  M  L  R  D  P  Q  N  F  G  L
  781   ATTGTTTGAA ATTGACAAAC AGTTTGCCGA AATGCTGAGA GATCCGCAAA ATTTTGGCCT
        TAACAAACTT TAACTGTTTG TCAAACGGCT TTACGACTCT CTAGGCGTTT TAAAACCGGA
         S  D  V  E  N  P  C  Y  D  G  Y  V  W  K  P  F  A  T  R
  841   GAGCGATGTC GAAAACCGT GCTATGATGG CGGATATGTC TGGAAACCGT TTGCCACAAG
        CTCGCTACAG CTTTTGGGCA CGATACTACC GCCTATACAG ACCTTTGGCA AACGGTGTTC
         S  V  S  T  D  R  Q  L  S  A  F  S  P  Q  E  R  L  A  I  A
  901   AAGCGTCAGC ACGGATAGAC AACTGTCAGC GTTTAGCCCG CAAGAAAGAC TGGCAATCGC
        TTCGCAGTCG TGCCTATCTG TTGACAGTCG CAAATCGGGC GTTCTTTCTG ACCGTTAGCG
         G  N  P  L  L  A  Q  A  V  A  S  P  M  A  R  R  S  A  S  P
  961   CGGAAATCCG CTTTTGGCAC AAGCAGTTGC TTCACCGATG GCAAGAAGAT CAGCAAGCCC
        GCCTTTAGGC GAAAACCGTG TTCGTCAACG AAGTGGCTAC CGTTCTTCTA GTCGTTCGGG
         L  N  C  E  G  K  M  F  W  D  Q  V  H  P  T  T  V  V  H  A
 1021   GCTGAATTGC GAAGGCAAAA TGTTTTGGGA TCAGGTCCAT CCGACAACAG TTGTCCATGC
        CGACTTAACG CTTCCGTTTT ACAAAACCCT AGTCCAGGTA GGCTGTTGTC AACAGGTACG
         R  L  S  E  R  A  A  T  F  I  E  T  Q  Y  E  F  L  A  H  G
 1081   TGCCCTTTCA GAAAGAGCGG CGACGTTTAT CGAAACACAG TATGAATTTC TGGCCCATGG
        ACGGGAAAGT CTTTCTCGCC GCTGCAAATA GCTTTGTGTC ATACTTAAAG ACCGGGTACC
        -stop
 1141   CTGAGTTAAC AGAGGACGGA TTTCCTGAAG GAAATCCGTT TTTTTATTTT AAGCTTGGAG
        GACTCAATTG TCTCCTGCCT AAAGGACTTC CTTTAGGCAA AAAAATAAAA TTCGAACCTC
 1201   ACAAGGTAAA GGATAAAACC TCGAG
        TGTTCCATTT CCTATTTTGG AGCTC
```

FIGURE 57 (SEQ ID No 49)

```
   1  ATGAAACAAC AAAAACGGCT TTACGCCCGA TTGCTGACGC TGTTATTTGC
      TACTTTGTTG TTTTTGCCGA AATGCGGGCT AACGACTGCG ACAATAAACG

51  GCTCATCTTC TTGCTGCCTC ATTCTGCAGC TTCAGCAGCA GATACAAGAC
      CGAGTAGAAG AACGACGGAG TAAGACGTCG AAGTCGTCGT CTATGTTCTG

101  CGGCGTTTAG CCGGATCGTC ATGTTTGGAG ATAGCCTGAG CGATACGGGC
      GCCGCAAATC GGCCTAGCAG TACAAACCTC TATCGGACTC GCTATGCCCG

151  AAAATGTATA GCAAAATGAG AGGCTATCTT CCGTCAAGCC CGCCGTATTA
      TTTTACATAT CGTTTTACTC TCCGATAGAA GGCAGTTCGG GCGGCATAAT

201  TGAAGGCCGC TTTAGCAATG GACCGGTCTG GCTGGAACAA CTGACGAAAC
      ACTTCCGGCG AAATCGTTAC CTGGCCAGAC CGACCTTGTT GACTGCTTTG

251  AATTTCCGGG ACTGACGATC GCTAATGAAG CAGAAGGAGG AGCAACAGCG
      TTAAAGGCCC TGACTGCTAG CGATTACTTC GTCTTCCTCC TCGTTGTCGC

301  GTCGCCTATA ACAAAATCAG CTGGGACCCG AAATATCAGG TCATCAACAA
      CAGCGGATAT TGTTTTAGTC GACCCTGGGC TTTATAGTCC AGTAGTTGTT

351  CCTGGACTAT GAAGTCACAC AGTTTCTTCA GAAAGACAGC TTTAAACCGG
      GGACCTGATA CTTCAGTGTG TCAAAGAAGT CTTTCTGTCG AAATTTGGCC

401  ATGATCTGGT CATCCTTTGG GTCGGCGCCA ATGATTATCT GGCGTATGGC
      TACTAGACCA GTAGGAAACC CAGCCGCGGT TACTAATAGA CCGCATACCG

451  TGGAACACAG AACAAGATGC CAAAAGAGTC AGAGATGCCA TCAGCGATGC
      ACCTTGTGTC TTGTTCTACG GTTTTCTCAG TCTCTACGGT AGTCGCTACG

501  CGCTAATAGA ATGGTCCTGA ACGGCGCCAA ACAAATCCTG CTGTTTAACC
      GCGATTATCT TACCAGGACT TGCCGCGGTT TGTTTAGGAC GACAAATTGG

551  TGCCGGATCT GGGACAAAAT CCGAGCGCCA GAAGCCAAAA AGTCGTCGAA
      ACGGCCTAGA CCCTGTTTTA GGCTCGCGGT CTTCGGTTTT TCAGCAGCTT

601  GCAGTCAGCC ATGTCAGCGC CTATCATAAC AAACTGCTGC TGAACCTGGC
      CGTCAGTCGG TACAGTCGCG GATAGTATTG TTTGACGACG ACTTGGACCG

651  AAGACAATTG GCACCGACGG GAATGGTTAA ATTGTTTGAA ATTGACAAAC
      TTCTGTTAAC CGTGGCTGCC CTTACCAATT TAACAAACTT TAACTGTTTG

701  AGTTTGCCGA AATGCTGAGA GATCCGCAAA ATTTTGGCCT GAGCGATGTC
      TCAAACGGCT TTACGACTCT CTAGGCGTTT TAAAACCGGA CTCGCTACAG

751  GAAAACCCGT GCTATGATGG CGGATATGTC TGGAAACCGT TTGCCACAAG
      CTTTTGGGCA CGATACTACC GCCTATACAG ACCTTTGGCA AACGGTGTTC

801  AAGCGTCAGC ACGGATAGAC AACTGTCAGC GTTTAGCCCG CAAGAAAGAC
      TTCGCAGTCG TGCCTATCTG TTGACAGTCG CAAATCGGGC GTTCTTTCTG

851  TGGCAATCGC CGGAAATCCG CTTTTGGCAC AAGCAGTTGC TTCACCGATG
      ACCGTTAGCG GCCTTTAGGC GAAAACCGTG TTCGTCAACG AAGTGGCTAC

901  GCAAGAAGAT CAGCAAGCCC GCTGAATTGC GAAGGCAAAA TGTTTTGGGA
      CGTTCTTCTA GTCGTTCGGG CGACTTAACG CTTCCGTTTT ACAAACCCT

951  TCAGGTCCAT CCGACAACAG TTGTCCATGC TGCCCTTTCA GAAAGAGCGG
      AGTCCAGGTA GGCTGTTGTC AACAGGTACG ACGGGAAAGT CTTTCTCGCC

1001  CGACGTTTAT CGAAACACAG TATGAATTTC TGGCCCATGG CTGA
      GCTGCAAATA GCTTTGTGTC ATACTTAAAG ACCGGGTACC GACT
```

FIGURE 58 (SEQ ID No. 50)

```
  1  ATGAAAAAAT GGTTTGTGTG TTTATTGGGA TTGGTCGCGC TGACAGTTCA GGCAGCCGAC
 61  AGCCGTCCCG CCTTCTCCCG GATCGTGATG TTTGGCGACA GCCTCTCCGA TACCGGCAAG
121  ATGTACAGCA AGATGCGCGG TTACCTCCCC TCCAGCCCCC CCTACTATGA GGGCCCGTTC
181  TCCAACGGGC CCGTCTGGCT GGAGCAGCTG ACCAACGAGT TCCCGGGCCT GACCATAGCC
241  AACGAGGCGG AAGGCGGACC GACCGCCGTG GCTTACAACA AGATCTCCTG GAATCCCAAG
301  TATCAGGTCA TCAACAACCT GGACTACGAG GTCACCCAGT TCCTGCAAAA AGACAGCTTC
361  AAGCCGGACG ATCTGGTGAT CCTCTGGGTC GGCGCCAACG ACTATCTGGC CTATGGCTGG
421  AACACAGAGC AGGATGCCAA GCGGGTGCGC GACGCCATCA GCGATGCGGC CAACCGCATG
481  GTGCTGAACG GCGCCAAGGA GATACTGCTG TTCAACCTGC GGATCTGGG CCAGAACCCC
541  TCGGCCCGCA GCCAGAAGGT GGTCGAGGCG GCCAGCCATG TCTCCGCCTA CCACAACCAG
601  CTGCTGCTGA ACCTGGCACG CCAGCTGGCT CCCACCGGCA TGGTGAAGCT GTCGAGATC
661  GACAAGCAGT TTGCCGAGAT GCTGCGTGAT CCGCAGAACT TCGGCCTGAG CGACCAGAGG
721  AACGCCTGCT ACGGTGGCAG CTATGTATGG AAGCCGTTTG CCTCCCGCAG CGCCAGCACC
781  GACAGCCAGC TCTCCGCCTT CAACCCGCAG GAGCGCCTCG CCATCGCCGG CAACCCGCTG
841  CTGGCCCAGG CCGTCGCCAG CCCCATGGCT GCCCGCAGCG CCAGCACCCT CAACTGTGAG
901  GGCAAGATGT CTGGGATCA GGTCCACCCC ACCACTGTCG TGCACGCCGC CCTGAGCGAG
961  CCCGCCGCCA CCTTCATCGA GAGCCAGTAC GAGTTCCTCG CCCAC
```

FIGURE 59 (SEQ ID No. 51)

```
  1  ATGAAAAAAT GGTTTGTTTG TTTATTGGGG TTGATCGCGC TGACAGTTCA GGCAGCCGAC
 61  ACTCGCCCCG CCTTCTCCCG GATCGTGATG TTCGGCGACA GCCTCTCCGA TACCGGCAAA
121  ATGTACAGCA AGATGCGCGG TTACCTCCCC TCCAGCCCGC CCTACTATGA GGGCCGTTTC
181  TCCAACGGAC CCGTCTGGCT GGAGCAGCTG ACCAAGCAGT TCCCGGGTCT GACCATCGCC
241  AACGAAGCGG AAGGCGGTGC CACTGCCGTG GCTTACAACA AGATCTCCTG GAATCCCAAG
301  TATCAGGTCT ACAACAACCT GGACTACGAG GTCACCCAGT TCTTGCAGAA AGACAGCTTC
361  AAGCCGGACG ATCTGGTGAT CCTCTGGGTC GGTGCCAATG ACTATCTGGC ATATGGCTGG
421  AATACGGAGC AGGATGCCAA GCGAGTTCGC GATGCCATCA GCGATGCGGC CAACCGCATG
481  GTACTGAACG GTGCCAAGCA GATACTGCTG TTCAACCTGC GGATCTGGG CCAGAACCCC
541  TCAGCCCGCA GTCAGAAGGT GGTCGAGGCG GTCAGCCATG TCTCCGCCTA TCACAACAAG
601  CTGCTGCTGA ACCTGGCACG CCAGCTGGCC CCCACCGGCA TGGTAAAGCT GTTCGAGATC
661  GACAAGCAAT TTGCCGAGAT GCTGCGTGAT CCGCAGAACT TCGGCCTGAG CGACGTCGAG
721  AACCCCTGCT ACGACGGCGG CTATGTGTGG AAGCCGTTTG CCACCCGCAG CGTCAGCACC
781  GACGCCAGC TCTCCGCCTT CAGTCCGCAG GAACGCCTCG CCATCGCCGG CAACCCGCTG
841  CTGGCACAGG CCGTTGCCAG TCCTATGGCC CGCCGCAGCG CCAGCCCCT CAACTGTGAG
901  GGCAAGATGT CTGGGATCA GGTACACCCG ACCACTGTCG TGCACGCAGC CCTGAGCGAG
961  CGCGCCGCCA CCTTCATCGA GACCCAGTAC GAGTTCCTCG CCCACGGATG A
```

FIGURE 60 (SEQ ID No. 52)

```
  1  ATGCCGAAGC CTGCCCTTCG CCGTGTCATG ACCGCGACAG TCGCCGCCGT CGGCACGCTC
 61  GCCCTCGGCC TCACCGACGC CACCGCCCAC GCCGCGCCCG CCCAGGCCAC TCCGACCCTG
121  GACTACGTCG CCCTCGGCGA CAGCTACAGC GCCGGCTCCG GCGTCCTGCC CGTCGACCCC
181  GCCAACCTGC TCTGTCTGCG CTCGACGGCC AACTACCCCC ACGTCATCGC GGACACGACG
241  GGCGCCCGCC TCACGGACGT CACCTGCGGC GCCGCCGACA CCGCCGACTT CACGCGGGCC
301  CAGTACCCGG GCGTCGCACC CCAGTTGGAC GCGCTCGGCA CCGGCACGGA CCTGGTCACG
361  CTCACCATCG GCGGCAACGA CAACAGCACC TTCATCAACG CCATCACGGC CTGCGGCACG
421  GCGGGTGTCC TCAGCGGCGG CAAGGGCAGC CCCTGCAAGG ACAGGCACGG CACCTCCTTC
481  GACGACGAGA TCGAGGCCAA CACGTACCCC GCGCTCAAGG AGGCGCTGCT CGGCGTCCGC
541  GCCAGGGCTC CCCACGCCAG GGTGGCGGCT CTCGGCTACC CGTGGATCAC CCCGGCCACC
601  GCCGACCCGT CCTGCTTCCT GAAGCTCCCC CTCGCCGCCG GTGACGTGCC CTACCTGCGG
661  GCCATCCAGG CACACCTCAA CGACGCGGTC CGGCGGGCCG CCGAGGAGAC CGGAGCCACC
721  TACGTGGACT TCTCCGGGGT GTCCGACGGC CACGACGCTC GCGAGGCCCC CGGCACCCGC
781  TGGATCGAAC CGCTGCTCTT CGGGCACAGC CTCGTTCCCG TCCACCCCAA CGCCCTGGGC
841  GAGCGGCGCA TGGCCGAGCA CACGATGGAC GTCCTCGGCC TGGACTGA
```

FIGURE 61 (SEQ ID No. 53)

```
  1 TCAGTCCAGG CCGAGGACGT CCATCGTGTG CTCGGCCATG CGCCGCTCGC CCAGGGCGTT
 61 GGGGTGGACG GGAACGAGGC TGTGCCCGAA GAGCAGCGGT TCGATCCAGC GGGTGCCGGG
121 GGCCTCGCAG GCGTCGTGGC CGTCGGACAC CCCGGAGAAG TCCACGTAGG TGGCTCCGGT
181 CTCCTCGGCG GCCCGCCGGA CCGCGTCGTT GAGGTGTGCC TGGATGGCCC GCAGGTAGGG
241 CACGTCACCG GCGGCGAGGG GGAGCTTCAG GAAGCAGGAC GGGTCGGCGG TGGCCGGGGT
301 GATCCACGGG TAGCCGAGAG CCGCCACCCT GGCGTGGGGA GCCCTGGCGC GGACGCCGAG
361 CAGCGCCTCC TTGAGCGCGG GGTACGTGTT GGCCTCGATC TCGTCGTCGA AGGAGGTGCC
421 GTGCCTGTCC TTGCAGGGGC TGCCCTTGCC GCCGCTGAGG ACACCCGCCG TGCCGCAGGC
481 CGTGATGGCG TTGATGAAGG TGCTGTTGTC GTTGCCGCCG ATGGTGAGCG TGACCAGGTC
541 CGTGCCGGTG CCGAGCGCGT CCAACTGGGG TGCGACGCCC GGGTACTGGG CCCGCGTGAA
601 GTCGGCGGTC TGCGCGGCGC CGCAGGTGAC GTCCGTGAGG CGGGCGCCCG TCGTGTCCGC
661 GATGACGTGG GGGTAGTTGG CCGTCGAGCG CAGACAGAGC AGGTTGGCGG GGTCGACGGG
721 CAGGACGCCG GAGCCGGCGC TGTAGCTGTC GCCGAGGGCG ACGTAGTCCA GGGTCGGAGT
781 GGCCTGGGCG GGCGCGGCGT GGGCGGTGGC GTCGGTGAGG CCGAGGGCGA GCGTGCCGAC
841 GGCGGCGACT GTCGCGGTCA TGACACGGCG AAGGGCAGGC TTCGGCAT
```

FIGURE 62 (SEQ ID No. 54)

```
  1 ATGGATTACG AGAAGTTTCT GTTATTTGGG GATTCCATTA CTGAATTTGC TTTTAATACT
 61 AGGCCCATTG AAGATGGCAA AGATCAGTAT GCTCTTGGAG CCGCATTAGT CAACGAATAT
121 ACGAGAAAAA TGGATATTCT TCAAAGAGGG TTCAAAGGGT ACACTTCTAG ATGGGCGTTG
181 AAAATACTTC CTGAGATTTT AAAGCATGAA TCCAATATTG TCATGGCCAC AATATTTTTG
241 GGTGCCAACG ATGCATGCTC AGCAGGTCCC CAAAGTGTCC CCCTCCCCGA ATTTATCGAT
301 AATATTCGTC AAATGGTATC TTTGATGAAG TCTTACCATA TCCGTCCTAT TATAATAGGA
361 CCGGGGCTAG TAGATAGAGA GAAGTGGGAA AAAGAAAAAT CTGAAGAAAT AGCTCTCGGA
421 TACTTCCGTA CCAACGAGAA CTTTGCCATT TATTCCGATG CCTTAGCAAA ACTAGCCAAT
481 GAGGAAAAAG TTCCCTTCGT GGCTTTGAAT AAGGCGTTTC AACAGGAAGG TGGTGATGCT
541 TGGCAACAAC TGCTAACAGA TGGACTGCAC TTTTCCGGAA AAGGGTACAA AATTTTTCAT
601 GACGAATTAT TGAAGGTCAT TGAGACATTC TACCCCCAAT ATCATCCCAA AAACATGCAG
661 TACAAACTGA AAGATTGGAG AGATGTGCTA GATGATGGAT CTAACATAAT GTCTTGA
```

FIGURE 63 (SEQ ID No. 55)

```
atgaacctgc gtcaatggat gggcgccgcc acggctgccc ttgccttggg cttggccgcg   60
tgcggggggcg gtgggaccga ccagagcggc aatcccaatg tcgccaaggt gcagcgcatg  120
gtggtgttcg gcgacagcct gagcgatatc ggcacctaca cccccgtcgc gcaggcggtg  180
ggcggcggca agttcaccac caacccgggc ccgatctggg ccgagaccgt ggccgcgcaa  240
ctgggcgtga cgctcacgcc ggcggtgatg ggctacgcca cctccgtgca gaattgcccc  300
aaggccggct gcttcgacta tgcgcagggc ggctcgcgcg tgaccgatcc gaacggcatc  360
ggccacaacg gcggcgcggg ggcgctgacc tacccggttc agcagcagct cgccaacttc  420
tacgcggcca gcaacaacac attcaacggc aataacgatg tcgtcttcgt gctggccggc  480
agcaacgaca ttttcttctg gaccactgcg gcggccacca gcggctccgg cgtgacgccc  540
gccattgcca cggcccaggt gcagcaggcc gcgacggacc tggtcggcta tgtcaaggac  600
atgatcgcca agggtgcgac gcaggtctac gtgttcaacc tgcccgacag cagcctgacg  660
ccggacggcg tggcaagcgg cacgaccggc caggcgctgc tgcacgcgct ggtgggcacg  720
ttcaacacga cgctgcaaag cgggctggcc ggcacctcgg cgcgcatcat cgacttcaac  780
gcacaactga ccgcggcgat ccagaatggc gcctcgttcg gcttcgccaa caccagcgcc  840
cgggcctgcg acgccaccaa gatcaatgcc ctggtgccga gcgccggcgg cagctcgctg  900
ttctgctcgg ccaacacgct ggtggcttcc ggtgcggacc agagctacct gttcgccgac  960
ggcgtgcacc cgaccacggc cggccatcgc ctgatcgcca gcaacgtgct ggcgcgcctg 1020
ctggcggata acgtcgcgca ctga                                        1044
```

FIGURE 64 (SEQ ID No. 56)

```
  1 gtgatcgggt cgtacgtggc ggtgggggac agcttcaccg agggcgtcgg cgaccccggc
 61 cccgacgggg cgttcgtcgg ctgggccgac cggctcgccg tactgctcgc ggaccggcgc
121 cccgaggcg acttcacgta cacgaacctc gccgtgcgcg gcaggtcct cgaccagatc
181 gtggcggaac aggtcccgcg ggtcgtcgga ctcgcgcccg acctcgtctc gttcgcggcg
241 ggcggcaacg acatcatccg gcccggcacc gatcccgacg aggtcgccga gcggttcgag
301 ctggcggtgg ccgcgctgac cgccgcggcc ggaaccgtcc tggtgaccac cgggttcgac
361 acccgggggg tgcccgtcct caagcacctg cgcggcaaga tcgccacgta caacgggcac
421 gtccgcgcca tcgccgaccg ctacggctgc ccgtgctcg acctgtggtc gctgcggagc
481 gtccaggact gcagggcgtg ggacgccgac cggctgcacc tgtcgccgga ggggcacacc
541 cgggtggcgc tgcgcgcggg gcaggccctg ggcctgcgcg tcccgccgga ccctgaccag
601 ccctggccgc ccctgccgcc gcgcggcacg ctcgacgtcc ggcgcgacga cgtgcactgg
661 gcgcgcgagt acctggtgcc gtggatcggg cgccggctgc ggggcgagtc gtcggcgac
721 cacgtgacgg ccaagggac gctgtcgccg gacgccatca agacgcggat cgccgcggtg
781 gcctga
```

FIGURE 65 (SEQ ID No. 57)

```
  1 atgcagacga accccgcgta caccagtctc gtcgccgtcg gcgactcctt caccgagggc
 61 atgtcggacc tgctgcccga cggctcctac cgtgctggg ccgacctcct cgccacccgg
121 atggcggccc gctcccccgg cttccggtac gccaacctgg cggtgcgcgg gaagctgatc
181 ggacagatcg tcgacgagca ggtggacgtg gccgccgcca tgggagccga cgtgatcacg
241 ctggtcgcg ggctcaacga cacgctgcgg cccaagtgcg acatggcccg ggtgcgggac
301 ctgctgaccc aggccgtgga acggctcgcc ccgcactgcg agcagctggt gctgatgcgc
361 agtcccggtc gccagggtcc ggtgctggag cgcttccggc cccgcatgga ggccctgttc
421 gccgtgatcg acgacctggc cgggcggcac ggcgccgtgg tcgtcgacct gtacggggcc
481 cagtcgctgg ccgaccctcg gatgtgggac gtggaccggc tgcacctgac cgccgagggc
541 caccgccggg tcgcggaggc ggtgtggcag tcgctcggcc acgagcccga ggaccccgag
601 tggcacgcgc cgatcccggc gacgccgccg ccggggtggg tgacgcgcag gaccgcggac
661 gtccggttcg cccggcagca cctgctgccc tggataggcc gcaggctgac cgggcgctcg
721 tccggggacg gcctgccggc caagcgcccg gacctgctgc ctacgagga ccccgcacgg
781 tga
```

FIGURE 66 (SEQ ID No. 58)

```
   1 atgacccggg gtcgtgacgg gggtgcgggg gcgcccccca ccaagcaccg tgccctgctc
  61 gcggcgatcg tcaccctgat agtggcgatc tccgcggcca tatacgccgg agcgtccgcg
 121 gacgacggca gcagggacca cgcgctgcag gccgaggcc gtctcccacg aggagacgcc
 181 gccccgcgt ccaccggtgc ctgggtgggc gcctgggcca ccgcaccggc cgcggccgag
 241 ccgggcaccg agacgaccgg cctggcgggc cgctccgtgc gcaacgtcgt gcacacctcg
 301 gtcggcggca ccggcgcgcg gatcaccctc tcgaacctgt acgggcagtc gccgctgacc
 361 gtcacacacg cctcgatcgc cctggccgcc gggcccgaca ccgccgccgc gatcgccgac
 421 accatgcgcc ggctcacctt cggcggcagc gcccgggtga tcatcccggc gggcggccag
 481 gtgatgagcg acaccgcccg cctcgccatc ccctacgggg cgaacgtcct ggtcaccacg
 541 tactccccca tcccgtccgg gccggtgacc taccatccgc aggcccggca gaccagctac
 601 ctggccgacg gcgaccgcac ggcggacgtc accgccgtcg cgtacaccac ccccacgccc
 661 tactgcgct acctgaccgc cctcgacgtg ctgagccacg aggccgacgg cacggtcgtg
 721 gcgttcggcg actccatcac cgacggcgcc cgctcgcaga gcgacgccaa ccaccgctgg
 781 accgacgtcc tcgccgcacg cctgcacgag gcggcggggcg acggccggga cacgccccgc
 841 tacagcgtcg tcaacgaggg catcagcggc aaccggctcc tgaccagcag gccggggcgg
 901 ccggccgaca acccgagcgg actgagccgg ttccagcggg acgtgctgga acgcaccaac
 961 gtcaaggccg tcgtcgtcgt cctcggcgtc aacgacgtcc tgaacagccc ggaactcgcc
1021 gaccgcgacg ccatcctgac cggcctgcgc accctcgtcg accgggcgca cgcccgggga
1081 ctgcgggtcg tcggcgccac gatcacgccg ttcggcggct acggcggcta caccgaggcc
1141 cgcgagacga tgcggcagga ggtcaacgag gagatccgct ccggccgggt cttcgacacg
1201 gtcgtcgact tcgacaaggc cctgcgcgac ccgtacgacc cgcgccggat gcgctccgac
1261 tacgacagcg gcgaccacct gcaccccggc gacaagggt acgcgcgcat gggcgcggtc
1321 atcgacctgg ccgcgctgaa gggcgcggcg ccggtcaagg cgtag
```

FIGURE 67 (SEQ ID No. 59)

```
   1 atgacgagca tgtcgagggc gagggtggcg cggcggatcg cggccggcgc ggcgtacggc
  61 ggcggcggca tcggcctggc gggagcggcg gcggtcggtc tggtggtggc cgaggtgcag
 121 ctggccagac gcagggtggg ggtgggcacg ccgacccggg tgccgaacgc gcagggactg
 181 tacgcgcggca ccctgccac ggccggcgac ccgccgctgc ggctgatgat gctgggcgac
 241 tccacggccg ccgggcaggg cgtgcaccgg gccgggcaga cgccgggcgc gctgctggcg
 301 tccgggctcg cggcggtggc ggagcggccg gtgcggctgg ggtcggtcgc ccagccgggg
 361 gcgtgctcgg acgacctgga ccggcaggtg gcgctggtgc tcgccgagcc ggaccgggtg
 421 cccgacatct gcgtgatcat ggtcggcgcc aacgacgtca cccaccggat gccggcgacc
 481 cgctcggtgc ggcacctgtc ctcggcggta cggcggctgc gcacggccgg tgcggaggtg
 541 gtggtcggca cctgtccgga cctgggcacg atcgagcggg tgcggcagcc gctgcgctgg
 601 ctggccggc gggcctcacg gcagctcgcg gcggcacaga ccatcggcgc cgtcgagcag
 661 ggcgggcgca cggtgtcgct gggcgacctg ctgggtccgg agttcgcgca gaacccgcgg
 721 gagctcttcg gccccgacaa ctaccacccc tccgccgagg ggtacgccac ggccgcgatg
 781 gcggtactgc cctcggtgtg cgccgcgctc ggcctgtggc cggccgacga ggagcacccg
 841 gacgcgctgc gccgcgaggg cttcctgccg gtggcgcgcg cggcggcgga ggcggcgtcc
 901 gaggcgggta cggaggtcgc cgccgccatg cctacggggc ctcggggggcc ctgggcgctg
 961 ctgaagcgcc ggagacggcg tcgggtgtcg gaggcggaac cgtccagccc gtccggcgtt
1021 tga
```

FIGURE 68 (SEQ ID No. 60)

```
   1 atgggtcgag ggacggacca gcggacgcgg tacggccgtc gccgggcgcg tgtcgcgctc
  61 gccgccctga ccgccgccgt cctgggcgtg ggcgtggcgg gctgcgactc cgcctgggac
 121 gactcacccg ctccttccgg cagcccgtcg aagcggacga ggacggccgc cgcctgggac
 181 accagcccgg cgtccgtcgc cgccgtgggc gactccatca cgcgcggctt cgacgcctgt
 241 gcggtgctgt cggactgccc ggaggtgtcg tgggcgaccg gcagcagcgc gaaggtcgac
 301 tgctggccg tacggctgct ggggaaggcg gacgcggccg agcacagctg gaactacgcg
 361 gtcaccgggg cccggatggc ggacctgacc gctcaggtga cgcgggcggc gcagcgcgag
 421 ccggagctgg tggcggtgat ggccggggcg aacgacgcgt gccggtccac gacctcggcg
 481 atgacgccgg tggcggactt ccgggcgcag ttcgaggagg cgatggccac cctgcgcaag
 541 aagctcccca aggcgcaggt gtacgtgtcg agcatcccgg acctcaagcg gctctggtcc
 601 cagggccgca ccaacccgct gggcaagcag gtgtggaagc tcggcctgtg ccgtcgatg
 661 ctgggcgacg cggactccct ggactcggcg gcgacctgc ggcgcaacac ggtgcgcgac
 721 cgggtggcgg actacaacga ggtgctgcgg gaggtctgcg cgaaggaccg gcggtgccgc
 781 agcgacgacg gcgcggtgca cgagttccgg ttcggcacgg accagttgag ccactgggac
 841 tggttccacc cgagtgtgga cggccaggcc cggctggcgg agatcgccta ccgcgcggtc
 901 accgcgaaga tccctga
```

FIGURE 69 (SEQ ID No. 61)

```
   1 ttcatcacaa cgatgtcaca acaccggcca tccgggtcat ccctgatcgt gggaatgggt
  61 gacaagcctt cccgtgacga aagggtcctg ctacatcaga aatgacagaa atcctgctca
 121 gggaggttcc atgagactgt cccgacgcgc ggccacggcg tccgcgctcc tcctcacccc
 181 ggcgctcgcg ctcttcggcg cgagcgccgc cgtgtccgcg ccgcgaatcc aggccaccga
 241 ctacgtggcc ctcggcgact cctactcctc ggggtcggc gcggggcagct acgacagcag
 301 cagtggctcc tgtaagcgca gcaccaagtc ctacccggcc ctgtgggccg cctcgcacac
 361 cggtacgcgg ttcaacttca ccgcctgttc gggcgcccgc acaggagacg tgctggccaa
 421 gcagctgacc ccggtcaact ccggcaccga cctggtcagc attaccatcg gcggcaacga
 481 cgcgggcttc gccgacacca tgaccacctg caacctccag ggcgagagcg cgtgcctggc
 541 gcggatcgcc aaggcgcgcg cctacatcca gcagacgctg cccgcccagc tggaccaggt
 601 ctacgacgcc atcgacagcc gggcccccgc agcccaggtc gtcgtcctgg gctaccccgcg
 661 cttctacaag ctgggcggca gctgcgccgt cggtctctcg gagaagtccc gcgcggccat
 721 caacgccgcc gccgacgaca tcaacgccgt caccgccaag cgcgccgccg accacggctt
 781 cgccttcggg gacgtcaaca cgaccttcgc cgggcacgag ctgtgctccg gcgccccctg
 841 gctgcacagc gtcacccttc ccgtgagaa ctcctaccac cccacggcca acggacagtc
 901 caaggctac ctgccgtcc tgaactccgc cacctgatcc gcggctact ccgccccctga
 961 cgaagtcccg cccccggcg gggcttcgcc gtaggtcgc gtaccgcgt cgcccgtcgc
1021 gccggtggcc ccgccgtacg tgccgccgcc cccggacgcg gtcggttc
```

FIGURE 70 (SEQ ID No. 62)

```
   1 ATGAAAAAAT GGTTTGTGTG TTTATTGGGA TTGGTCGCGC TGACAGTTCA
     TACTTTTTTA CCAAACACAC AAATAACCCT AACCAGCGCG ACTGTCAAGT

51 GGCAGCCGAC AGTCGCCCCG CCTTTTCCCG GATCGTGATG TTCGGCGACA
     CCGTCGGCTG TCAGCGGGGC GGAAAAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAACAGT TCCCGGGTCT GACCATCGCC AACGAAGCGG
     CCTCGTCGAC TGGTTTGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC CTATGGCTGG AACACGGAGC AGGATGCCAA GCGGGTTCGC
     TGATAGACCG GATACCGACC TTGTGCCTCG TCCTACGGTT CGCCCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCTCGCA
     CTATGACGAC AAGTTGGACG GCCTAGACCC GGTCTTGGGC AGTCGAGCGT

551 GTCAGAAGGT GGTCGAGGCG GTCAGCCATG TCTCCGCCTA TCACAACCAG
     CAGTCTTCCA CCAGCTCCGC CAGTCGGTAC AGAGGCGGAT AGTGTTGGTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGC GAACCAGTAC GAGTTCCTCG
     GGACTCGCTC GCGCGGCGGT GGAAGTAGCG CTTGGTCATG CTCAAGGAGC

1001 CCCAC TGA
     GGGTG ACT
```

FIGURE 71 (SEQ ID No. 63)

```
   1 ATGAAAAAAT GGTTTGTTTG TTTATTGGGG TTGATCGCGC TGACAGTTCA
     TACTTTTTTA CCAAACAAAC AAATAACCCC AACTAGCGCG ACTGTCAAGT

51 GGCAGCCGAC ACTCGCCCCG CCTTCTCCCG GATCGTGATG TTCGGCGACA
     CCGTCGGCTG TGAGCGGGGC GGAAGAGGGC CTAGCACTAC AAGCCGCTGT

101 GCCTCTCCGA TACCGGCAAA ATGTACAGCA AGATGCGCGG TTACCTCCCC
     CGGAGAGGCT ATGGCCGTTT TACATGTCGT TCTACGCGCC AATGGAGGGG

151 TCCAGCCCGC CCTACTATGA GGGCCGTTTC TCCAACGGAC CCGTCTGGCT
     AGGTCGGGCG GGATGATACT CCCGGCAAAG AGGTTGCCTG GGCAGACCGA

201 GGAGCAGCTG ACCAAGCAGT TCCCGGGTCT GACCATCGCC AACGAAGCGG
     CCTCGTCGAC TGGTTCGTCA AGGGCCCAGA CTGGTAGCGG TTGCTTCGCC

251 AAGGCGGTGC CACTGCCGTG GCTTACAACA AGATCTCCTG GAATCCCAAG
     TTCCGCCACG GTGACGGCAC CGAATGTTGT TCTAGAGGAC CTTAGGGTTC

301 TATCAGGTCA TCAACAACCT GGACTACGAG GTCACCCAGT TCTTGCAGAA
     ATAGTCCAGT AGTTGTTGGA CCTGATGCTC CAGTGGGTCA AGAACGTCTT

351 AGACAGCTTC AAGCCGGACG ATCTGGTGAT CCTCTGGGTC GGTGCCAATG
     TCTGTCGAAG TTCGGCCTGC TAGACCACTA GGAGACCCAG CCACGGTTAC

401 ACTATCTGGC ATATGGCTGG AATACGGAGC AGGATGCCAA GCGAGTTCGC
     TGATAGACCG TATACCGACC TTATGCCTCG TCCTACGGTT CGCTCAAGCG

451 GATGCCATCA GCGATGCGGC CAACCGCATG GTACTGAACG GTGCCAAGCA
     CTACGGTAGT CGCTACGCCG GTTGGCGTAC CATGACTTGC CACGGTTCGT

501 GATACTGCTG TTCAACCTGC CGGATCTGGG CCAGAACCCG TCAGCCCGCA
     CTATGACGAC AAGTTGGACG GCCTAGACCC GGTCTTGGGC AGTCGGGCGT

551 GTCAGAAGGT GGTCGAGGCG GTCAGCCATG TCTCCGCCTA TCACAACAAG
     CAGTCTTCCA CCAGCTCCGC CAGTCGGTAC AGAGGCGGAT AGTGTTGTTC

601 CTGCTGCTGA ACCTGGCACG CCAGCTGGCC CCCACCGGCA TGGTAAAGCT
     GACGACGACT TGGACCGTGC GGTCGACCGG GGGTGGCCGT ACCATTTCGA

651 GTTCGAGATC GACAAGCAAT TTGCCGAGAT GCTGCGTGAT CCGCAGAACT
     CAAGCTCTAG CTGTTCGTTA AACGGCTCTA CGACGCACTA GGCGTCTTGA

701 TCGGCCTGAG CGACGTCGAG AACCCCTGCT ACGACGGCGG CTATGTGTGG
     AGCCGGACTC GCTGCAGCTC TTGGGGACGA TGCTGCCGCC GATACACACC

751 AAGCCGTTTG CCACCCGCAG CGTCAGCACC GACCGCCAGC TCTCCGCCTT
     TTCGGCAAAC GGTGGGCGTC GCAGTCGTGG CTGGCGGTCG AGAGGCGGAA

801 CAGTCCGCAG GAACGCCTCG CCATCGCCGG CAACCCGCTG CTGGCACAGG
     GTCAGGCGTC CTTGCGGAGC GGTAGCGGCC GTTGGGCGAC GACCGTGTCC

851 CCGTTGCCAG TCCTATGGCC CGCCGCAGCG CCAGCCCCCT CAACTGTGAG
     GGCAACGGTC AGGATACCGG GCGGCGTCGC GGTCGGGGGA GTTGACACTC

901 GGCAAGATGT TCTGGGATCA GGTACACCCG ACCACTGTCG TGCACGCAGC
     CCGTTCTACA AGACCCTAGT CCATGTGGGC TGGTGACAGC ACGTGCGTCG

951 CCTGAGCGAG CGCGCCGCCA CCTTCATCGA GACCCAGTAC GAGTTCCTCG
     GGACTCGCTC GCGCGGCGGT GGAAGTAGCT CTGGGTCATG CTCAAGGAGC

1001 CCCACGGATG A
     GGGTGCCTAC T
```

FIGURE 72 (SEQ ID No. 24)

```
   1  ATGTTTAAGT TTAAAAAGAA TTTCTTAGTT GGATTATCGG CAGCTTTAAT
      TACAAATTCA AATTTTTCTT AAAGAATCAA CCTAATAGCC GTCGAAATTA

51  GAGTATTAGC TTGTTTTCGG CAACCGCCTC TGCAGCTAGC GCCGACAGCC
      CTCATAATCG AACAAAAGCC GTTGGCGGAG ACGTCGATCG CGGCTGTCGG

101  GTCCCGCCTT TTCCCGGATC GTGATGTTCG GCGACAGCCT CTCCGATACC
      CAGGGCGGAA AAGGGCCTAG CACTACAAGC CGCTGTCGGA GAGGCTATGG

151  GGCAAAATGT ACAGCAAGAT GCGCGGTTAC CTCCCCTCCA GCCCGCCCTA
      CCGTTTTACA TGTCGTTCTA CGCGCCAATG GAGGGGAGGT CGGGCGGGAT

201  CTATGAGGGC CGTTCTCCA ACGGACCCGT CTGGCTGGAG CAGCTGACCA
      GATACTCCCG GCAAAGAGGT TGCCTGGGCA GACCGACCTC GTCGACTGGT

251  AACAGTTCCC GGGTCTGACC ATCGCCAACG AAGCGGAAGG CGGTGCCACT
      TTGTCAAGGG CCCAGACTGG TAGCGGTTGC TTCGCCTTCC GCCACGGTGA

301  GCCGTGGCTT ACAACAAGAT CTCCTGGAAT CCCAAGTATC AGGTCATCAA
      CGGCACCGAA TGTTGTTCTA GAGGACCTTA GGGTTCATAG TCCAGTAGTT

351  CAACCTGGAC TACGAGGTCA CCCAGTTCTT GCAGAAAGAC AGCTTCAAGC
      GTTGGACCTG ATGCTCCAGT GGGTCAAGAA CGTCTTTCTG TCGAAGTTCG

401  CGGACGATCT GGTGATCCTC TGGGTCGGTG CCAATGACTA TCTGGCCTAT
      GCCTGCTAGA CCACTAGGAG ACCCAGCCAC GGTTACTGAT AGACCGGATA

451  GGCTGGAACA CGGAGCAGGA TGCCAAGCGG GTTCGCGATG CCATCAGCGA
      CCGACCTTGT GCCTCGTCCT ACGGTTCGCC CAAGCGCTAC GGTAGTCGCT

501  TGCGGCCAAC CGCATGGTAC TGAACGGTGC CAAGCAGATA CTGCTGTTCA
      ACGCCGGTTG GCGTACCATG ACTTGCCACG GTTCGTCTAT GACGACAAGT

551  ACCTGCCGGA TCTGGGCCAG AACCCGTCAG CTCGCAGTCA GAAGGTGGTC
      TGGACGGCCT AGACCCGGTC TTGGGCAGTC GAGCGTCAGT CTTCCACCAG

601  GAGGCGGTCA GCCATGTCTC CGCCTATCAC AACCAGCTGC TGCTGAACCT
      CTCCGCCAGT CGGTACAGAG GCGGATAGTG TTGGTCGACG ACGACTTGGA

651  GGCACGCCAG CTGGCCCCCA CCGGCATGGT AAAGCTGTTC GAGATCGACA
      CCGTGCGGTC GACCGGGGGT GGCCGTACCA TTTCGACAAG CTCTAGCTGT

701  AGCAATTTGC CGAGATGCTG CGTGATCCGC AGAACTTCGG CCTGAGCGAC
      TCGTTAAACG GCTCTACGAC GCACTAGGCG TCTTGAAGCC GGACTCGCTG

751  GTCGAGAACC CCTGCTACGA CGGCGGCTAT GTGTGGAAGC CGTTTGCCAC
      CAGCTCTTGG GGACGATGCT GCCGCCGATA CACACCTTCG GCAAACGGTG

801  CCGCAGCGTC AGCACCGACC GCCAGCTCTC CGCCTTCAGT CCGCAGGAAC
      GGCGTCGCAG TCGTGGCTGG CGGTCGAGAG GCGGAAGTCA GGCGTCCTTG

851  GCCTCGCCAT CGCCGGCAAC CCGCTGCTGG CACAGGCCGT TGCCAGTCCT
      CGGAGCGGTA GCGGCCGTTG GGCGACGACC GTGTCCGGCA ACGGTCAGGA

901  ATGGCCCGCC GCAGCGCCAG CCCCCTCAAC TGTGAGGGCA AGATGTTCTG
      TACCGGGCGG CGTCGCGGTC GGGGGAGTTG ACACTCCCGT TCTACAAGAC

951  GGATCAGGTA CACCCGACCA CTGTCGTGCA CGCAGCCCTG AGCGAGCGCG
      CCTAGTCCAT GTGGGCTGGT GACAGCACGT GCGTCGGGAC TCGCTCGCGC

1001  CCGCCACCTT CATCGCGAAC CAGTACGAGT TCCTCGCCCA CTGATGA
      GGCGGTGGAA GTAGCGCTTG GTCATGCTCA AGGAGCGGGT GACTACT
```

FIGURE 73

SEQ ID No. 68

```
  1  ADTRPAFSRI VMFGDSLSDT GKMYSKMRGY LPSSPPYYEG RFSNGPVWLE QLTKQFPGLT
 61  IANEAEGGAT AVAYNKISWD PKYQVINNLD YEVTQFLQKD SFKPDDLVIL WVGANDYLAY
121  GWNTEQDAKR VRDAISDAAN RMVLNGAKQI LLFNLPDLGQ NPSARSQKVV EAVSHVSAYH
181  NKLLLNLARQ LAPTGMVKLF EIDKQFAEML RDPQNFGLSD VENPCYDGGY VWKPF

236  RSASPLNCEG KMFWDQVHPT TVVHAALSER AATFIETQYE FLAHG
```

METHOD FOR PRODUCING ULTRA-HEAT TREATMENT MILK

INCORPORATION BY REFERENCE

This application is a continuation-in-part application of international patent application Serial No. PCT/IB2008/002573 filed Aug. 14, 2008, which published as PCT Publication No. WO 2009/024862 on Feb. 26, 2009, which claims benefit of European patent application Serial No. GB0716126.8 filed Aug. 17, 2007.

Reference is made to the following related applications: US 2002-0009518, US 2004-0091574, WO2004/064537, WO2004/064987, WO2005/066347, WO2005/066351, U.S. Application Ser. No. 60/764,430 filed on 2 Feb. 2006, WO2006/008508, International Patent Application Number PCT/IB2007/000558 and U.S. application Ser. No. 11/671,953.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

SEQUENCE LISTING

The instant application contains a Sequence Listing which has been submitted in ASCII format via EFS-Web and is hereby incorporated by reference in its entirety. Said ASCII copy, created on May 16, 2013 is named 43049.00.2092_SL.txt and is 194,613 bytes in size.

FIELD OF THE PRESENT INVENTION

The present invention relates to a process for the manufacture of UHT milk, a process for enzymatic treatment of UHT milk, an enzymatically treated UHT milk and uses of an enzyme for the treatment of UHT milk to provide new and unexpected technical advantages.

BACKGROUND OF THE PRESENT INVENTION

Lipid acyltransferases are known to be advantageous in food applications. Lipid acyltransferases have been found to have significant acyltransferase activity in foodstuffs. This activity has surprising beneficial applications in methods of preparing foodstuffs.

For instance, WO 2004/064537 pertains to a method for the in situ production of an emulsifier by use of a lipid acyltransferase and the advantages associated therewith.

International Patent Application No. PCT/IB2001/000558 relates to the expression of lipid acyltransferases in (heterologous) host cell and is incorporated herein by reference.

Heat treatment in the production of long-life products is often called "sterilisation". This means that the product is exposed to such powerful heat treatment that all relevant microorganisms and most of the heat resistant enzymes are inactivated. Such products have excellent keeping qualities and can be stored for long periods of time at ambient temperatures. Many dairies can therefore distribute these products over long distances and thereby find new markets.

Typically two methods are used for the production of sterilised (otherwise known as long-life milk for ambient storage), namely in-container sterilisation or UHT treatment followed by aseptic packaging in packages protecting the product against light and atmospheric oxygen. The present invention is applicable to long-life milk produced by any method, e.g. UHT milk.

There are many advantages for the producer, retailer and consumer if the product does not require refrigeration and can be stored for long periods without spoiling.

These products are often called UHT-products, particularly UHT milk or UHT flavoured milks.

Milk exposed to UHT treatment must be of a very good quality. It is particularly important that the proteins in the raw milk do not cause thermal instability, which can be the case if the raw milk is of bad quality. A milk is unsuitable for UHT treatment if it is sour, has the wrong salt balance and/or contains too many serum proteins, typical of colostrum.

When milk is kept at a high temperature for a long time, certain chemical reaction products are formed, which results in discolouration (browning). It also acquires a cooked and caramel flavour, and there is occasionally a great deal of sedimentation. These defects are largely avoided by heat treatment at a higher temperature for a short time. It is important that the optimum time/temperature combination is chosen to enable satisfactory spore destruction while keeping heat damage to the milk to a minimum.

It has been shown that when milk is heated (e.g. pasteurised at 70-80° C. for 5-20 seconds), an effect known as the "cream plug phenomenon" is evident. Heat treatment of milk may be detrimental to the stability of the milk.

The principal constituents of milk are water, fat, proteins, lactose (milk sugar) and minerals (salts). Milk also contains smaller amounts of other substances such as pigments, enzymes, vitamins, phospholipids (substances with fat like properties), sterols and gases.

The many lipids of milk, together forming the 'milk fat', have a very complicated composition and structure, even more complicated than most other naturally occurring fats. Typically milk fat consists of triglycerides, di- and monoglycerides, fatty acids, sterols, carotenoids and vitamins (A, D, E and K). Other components include phospholipids, lipoproteins, glycerides, cerebrosides, proteins, nucleic acids, enzymes, metals and water.

Phospholipids are the most surface-active class, as they are amphipolar. As the molecular size is relatively large, they are hardly soluble, neither in water nor in fat. In both liquids they tend to form lamellar bilayers. Phospholipids of milk are generally seen in close connection with proteins, especially when located in the membrane(s) of milk fat globules. The main part of phospholipids in milk is Lecithins, which are surface active at moderate hydrophilicity. Thus lecithin can be seen as a suspending and dispersing agent or as an emulsifier for O/W emulsions as well as for W/O emulsions.

Phospholipids comprises 0.8-1.0% of the natural milk fat. The main types of phospholipids/lecithin in milk are phosphatidylcholine and phosphatidylethanolamine.

Sterols are highly insoluble in water, and show very little surface activity. They easily associate with phospholipids. The cholesterol may be considered an unwanted ingredient in milk when considering the nutritional value of milk. Cholesterol comprises 0.3-0.4% of the natural milk fat.

EP 1 532 863 relates to the use of a phospholipase to treat a cheese milk or a cheese milk fraction.

Tanji et al (Res. Bull. Obihiro Univ., 22 (2001): 89-94) relates to the use of lipases to enhance flavour in butter oil at 40° C.

JP 57-189637 and JP57-189638 pertains to the treatment of milk to produce fermented or acidic milk drinks using phospholipases—where the enzymatic treatment is done at 30-45° C.

Citation or identification of any document in this application is not an admission that such document is available as prior art to the present invention.

SUMMARY OF THE INVENTION

Aspects of the present invention are presented in the claims and in the following commentary.

It has surprisingly been found that the stability, particularly the long term stability, of UHT milk can be significantly improved by exposing milk or a portion thereof during UHT milk production to a lipid acyltransferase as defined herein.

Even more surprisingly the inventors of the present invention have found that the enzymatic treatment can be carried out without an additional heating step. Hence the adverse effects of heating the milk twice, i.e. once for enzymatic treatment and then again for the UHT treatment can be avoided. This has many advantages as described below.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

According to a first aspect of the present invention there is provided a method of producing UHT milk, wherein said method comprises admixing a lipid acyltransferase and milk or a fraction thereof; and treating the enzyme treated milk by ultra-heat treatment to produce UHT milk.

"Ultra-heat treatment (UHT)" is a process where the milk is heated to approximately 130-150° C. and held there for a few seconds, such as one to three seconds, preferably two seconds. The terms "ultra-heat treatment" and "ultra-high temperature treatment" and "high temperature treatment" are used synonymously herein.

In one embodiment, the term "ultra-heat treatment" as used herein is meant to encompass both in-container sterilisation and/or UHT treatment followed by aseptic packaging in packages protecting the product against light and atmospheric oxygen.

As one skilled in the art will appreciate, the UHT heat treatment time and temperature combination will be established based upon the product to be treated and may vary to some degree.

The UHT milk after heat treatment may be sent to a Sterile tank to give a buffer prior to filling.

Filling is usually done in a sterile atmosphere where the UHT packing machine flushes the package with Nitrogen and also keeps the area within the filling heads flooded with Nitrogen to eliminate any air contamination.

According to a second aspect of the present invention there is provided a use of a lipid acyltransferase in the manufacture of UHT milk for improving the stability, particularly the long term stability, of the UHT milk.

The term "improving the stability" as used herein means that there is a reduction in the amount of creaming and/or sedimentation and/or flocculation and/or phase separation following storage (preferably following storage for at least 24 hours). Suitably the storage may be at a temperature of between about 5° C. and 35° C.

In one embodiment, the term "improving the stability" as used herein means that there is a reduction in the amount of creaming without formation of a sediment layer following storage (preferably following storage for at least 24 hours). Suitably the storage may be at a temperature of between about 5° C. and 35° C.

Creaming may be measured objectively by Turbiscan (as taught herein in the Examples section) and/or subjectively by the Stress Test (as taught herein in the Examples section).

Flocculation may be measured objectively by Turbiscan (as taught herein in the Examples section) and/or subjectively by the Stress Test (as taught herein in the Examples section).

Sedimentation may be measured by the Sedimentation Test (as taught herein in the Examples section).

Phase separation may be measured visually or by Turbiscan (as taught herein in the Examples section).

The term "improving the long term stability" as used herein means that there is a reduction in the amount of creaming (preferably without formation of a sediment layer) and/or sedimentation and/or flocculation and/or phase separation following storage over a prolonged period of time (preferably following storage for about 1-12 months, more preferably following storage for about 3-12 months, preferably following storage for up to about 6 months, preferably following storage for up to about 12 months, more preferably following storage for at least about 6 months). Suitably the storage may be at a temperature between about 5° C. and 35° C.

According to a third aspect of the present invention there is provided a use of a lipid acyltransferase in the manufacture of UHT milk for improving the perceptible sensory difference of the UHT milk. Suitably the perceptible sensory difference of the UHT milk may be measured using the "triangle test" taught herein under.

In one aspect the "perceptible sensory difference" includes improved smell and/or taste, for example a reduced cooked taste and/or aroma and/or a reduced rancidity taste and/or aroma.

According to a fourth aspect of the present invention there is provided a use of a lipid acyltransferase in the manufacture of UHT milk for reducing the cholesterol content in the UHT milk.

A reduction in cholesterol can be measured by Thin Layer Chromatography (TLC) and/or Gas Liquid Chromatography (GLC).

According to a fifth aspect of the present invention there is provided a use of a lipid acyltransferase in the manufacture of UHT milk for eliminating or reducing creaming (preferably without formation of a sediment layer) in the UHT milk.

Suitably the improvement in the stability, particularly the long term stability, and/or the improvement in the perceptible sensory difference and/or the improvement in smell and/or taste and/or the reduction in cholesterol content and/or reduction in creaming (preferably without formation of a sediment layer) of the UHT milk means an improvement when the enzymatically treated UHT milk (treated with enzymes in accordance with the present invention) is compared with UHT milk which has not been enzymatically treated and/or compared with UHT milk which has been treated with a phospholipase (in particular either a phospholipase A1 enzyme classified as E.C. 3.1.1.32 or a phospholipase A2 enzyme classified as EC.3.1.1.4).

Suitably the improvement in the stability, particularly the long term stability, and/or the improvement in the perceptible sensory difference and/or the improvement in smell and/or taste and/or the reduction in cholesterol content and/or reduction in creaming (preferably without formation of a sediment layer) of the UHT milk may mean an improvement when the enzymatically treated UHT milk (treated with enzymes in accordance with the present invention) is compared with UHT milk which has been treated with one or more of the following phospholipases: Phospholipase A1 from *Fusarium oxysporum* (Lipopan F™) and/or a phospholipase from *Fusarium heterosporum* and/or a phospholipase A1 from *Fusarium venenatum* (YieldMax™) and/or a phospholipase from *Aspergillus niger* and/or a phospholipase A2 from *Streptomyces violaceoruber* and/or a phospholipase A2 from porcine pancreas and/or a phospholipase A2 from *Tuber borchii*.

Suitably the improvement in the stability, particularly the long term stability, and/or the improvement in the perceptible sensory difference and/or the improvement in smell and/or taste and/or the reduction in cholesterol content and/or reduction in creaming (preferably without formation of a sediment layer) of the UHT milk may mean an improvement when the enzymatically treated UHT milk is compared with UHT milk which has been treated with a phospholipase A1 from *Fusarium oxysporum* (Lipopan F™).

Preferably it is advantageous to admix the lipid acyltransferase with the milk or a portion thereof before it is undergoes high temperature treatment. In other words the lipid acyltransferase may be added to raw milk or a portion thereof, and the enzyme-treated raw milk or portion thereof then undergoes ultra-heat treatment (resulting in UHT milk or a portion thereof).

In one embodiment of the present invention, the present invention may provide a method of producing UHT milk, wherein said method comprises comprising admixing a lipid acyltransferase and UHT milk or a fraction thereof. Suitably, in some embodiments the lipid acyltransferase may be added to the milk or a portion thereof after the ultra-heat treatment of the milk.

Preferably the lipid acyltransferase is added to the milk and incubated therewith at a temperature of less than about 20° C., preferably less than about 10° C.

Preferably the lipid acyltransferase is added to the milk and incubated therewith at a temperature of between about 1° C. and about 10° C., preferably between about 3° C. and about 7° C., more preferably about 5° C.

Preferably the incubation time is effective to ensure that there is at least 5% transferase activity, preferably at least 10% transferase activity, preferably at least 15%, 20%, 25% 26%, 28%, 30%, 40% 50%, 60% or 75% transferase activity.

The transferase activity is measured by the molar amount of cholesterol ester formed by acyltransfer from phospholipids or triacylglycerides in milk to cholesterol relative to the amount of cholesterol originally available Transferase activity=(Mol/l cholesterol ester(*t*)−Mol/l cholesterol ester(0))×100 Mol/l cholesterol(0)

Where:
Cholesterol ester(t)=the amount of cholesterol ester to the time t
Cholesterol ester(0)=the amount of cholesterol ester to the time 0
Cholesterol (0)=the amount of cholesterol in milk to the time 0
Cholesterol and cholesterol ester are determined by GLC Gas Chromatography:
Gas Chromatography is used to measure the content of cholesterol and cholesterol-ester in the milk samples.
The following CG setup is used:
Perkin Elmer Autosystem 9000 Capillary Gas Chromatograph equipped with WCOT fused silica column 12.5 m×0.25 mm ID×0.1μ film thickness 5% phenyl-methyl-silicone (CP Sil 8 CB from Chrompack).
Carrier gas: Helium.
Injector. PSSI cold split injection (initial temp 50° C. heated to 385° C.), volume 1.0 μl
Detector FID: 395° C.

| | Oven program (used since 30.10.2003): | | |
|---|---|---|---|
| | 1 | 2 | 3 |
| Oven temperature, ° C. | 90 | 280 | 350 |
| Isothermal, time, min. | 1 | 0 | 10 |
| Temperature rate, ° C./min. | 15 | 4 | |

Preparation of Milk Samples for Gc Analysis:
The milk lipids are extracted according to Mojonnier AOAC 989.05 using ethanol, $NH_3$, MTBE (methyl-tert-butyl ether) and p-ether. The lipid fraction is redissolved in heptane/pyridine (2:1) containing heptadecan as internal standard and cholesterol is measured by GC.

Preparing samples for cholesterol-ester measurements Squalane is added as an additional internal standard. The lipid fraction is redissolved in hexane and cholesterol-esters are concentrated using a $NH_2$ Bond Elut column and hexane eluation. Samples are redissolved in heptane/pyridine (2:1) and cholesterol-esters are measured by CG.

Preferably the combination of temperature and the incubation time is effective to ensure that there is at least 5% transferase activity, preferably at least 10% transferase activity, preferably at least 15%, 20%, 25% 26%, 28%, 30%, 40% 50%, 60% or 75% transferase activity.

Suitably the incubation time may be from 5 minutes up to 30 hours, suitably the incubation time may be from 45 minutes up to 30 hours.

In one embodiment the incubation time may be from about 10 hours to about 30 h, preferably from about 15 to 25 hours, more preferably about 20 hours.

In a preferred embodiment the enzymatic treatment takes place at about 3° C. to about 10° C. (preferably about 5° C.) for at least 10 hours, preferably between about 10 and 25 hours, more preferably about 20 hours.

The use of lower temperatures in combination with effective incubation times leads to significant advantages in the present invention.

In the methods and/or uses of the present invention preferably the milk (UHT milk) is not heated during enzymatic treatment.

Preferably in the methods and/or uses of the present invention the milk is only heated once (when it is ultra-heat treated to provide a UHT milk). Therefore, preferably the milk (e.g. UHT milk) in the present invention does not undergo more than one heating step during it production.

In some aspects, the lipid acyltransferase for use in any one of the methods and/or uses of the present invention may comprise a GDSX (SEQ ID NO: 120) motif and/or a GANDY (SEQ ID NO: 118) motif. Preferably, the lipid acyltransferase enzyme is characterised as an enzyme which possesses acyltransferase activity and which comprises the amino acid sequence motif GDSX (SEQ ID NO: 117), wherein X is one or more of the following amino acid residues L, A, V, I, F, Y, H, Q, T, N, M or S.

Suitably, the nucleotide sequence encoding a lipid acyltransferase or lipid acyltransferase for use in any one of the methods and/or uses of the present invention may be obtainable, preferably obtained, from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*. Preferably, the lipid acyltransferase is obtainable, preferably obtained, from an organism from the genus *Aeromonas*.

In some aspects of the present invention, the nucleotide sequence encoding a lipid acyltransferase for use in any one of the methods and/or uses of the present invention encodes a lipid acyltransferase that comprises an aspartic acid residue at a position corresponding to N-80 in the amino acid sequence of the *Aeromonas hydrophila* lipid acyltransferase shown as SEQ ID NO: 35.

In some aspects of the present invention, the lipid acyltransferase for use in any one of the methods and/or uses of the present invention is a lipid acyltransferase that comprises an aspartic acid residue at a position corresponding to N-80 in the amino acid sequence of the *Aeromonas hydrophila* lipid acyltransferase shown as SEQ ID NO: 35.

In addition or in the alternative, the nucleotide sequence encoding a lipid acyltransferase for use in any one of the methods and/or uses of the present invention encodes a lipid acyltransferase that may comprise the amino acid sequence shown as SEQ ID NO: 16, or an amino acid sequence which has 75% or more homology thereto. Suitably, the nucleotide sequence encoding a lipid acyltransferase encodes a lipid acyltransferase that may comprise the amino acid sequence shown as SEQ ID NO: 16.

In addition or in the alternative, the nucleotide sequence encoding a lipid acyltransferase for use in any one of the methods and/or uses of the present invention encodes a lipid acyltransferase that may comprise the amino acid sequence shown as SEQ ID NO: 68, or an amino acid sequence which has 75% or more homology thereto. Suitably, the nucleotide sequence encoding a lipid acyltransferase encodes a lipid acyltransferase that may comprise the amino acid sequence shown as SEQ ID NO: 68.

In one embodiment the lipid acyltransferase for use in any on of the methods and/or uses of the present invention has an amino acid sequence shown in SEQ ID NO: 16 or SEQ ID NO: 68, or has an amino acid sequence which has at least 75% identity therewith, preferably at least 80%, preferably at least 85%, preferably at least 95%, preferably at least 98% identity therewith.

The term "UHT milk" means herein any long-life milk designed for ambient storage. In particular "UHT milk" means any milk which has been heat-treated using to make it long-life milk, this includes flavoured and unflavoured products.

Suitably, the method may comprise a step of removing the enzyme and/or denaturing the enzyme.

Suitably the enzyme for use in the present invention may be an immobilised enzyme.

The milk product of the present invention is a UHT milk or a UHT flavoured milk.

It is not intended to cover herein cheese milk (i.e. a milk which is not a UHT milk and which is used in the subsequent preparation of cheese) and/or cheese or cheese products produced from a milk which is not UHT milk.

One advantage of the present invention is that the stability, particularly the long term stability, of UHT milk can be significantly improved.

A further advantage is that the unwanted physical effect of "creaming" of UHT milk is prevented and/or reduced compared with UHT milk which has not been enzymatically treated and/or compared with UHT milk which during its manufacture has been treated with a phospholipase (in particular either a phospholipase A1 enzyme classified as E.C. 3.1.1.32 or a phospholipase A2 enzyme classified as EC.3.1.1.4) (rather than the lipid acyltransferase as described herein).

The term "creaming" as used herein means the undesirable gravitational rise of fat globules to the top of the milk (e.g. in a container) over time.

A further advantage of the present invention may be the reduction of surface tension in UHT milk treated in accordance with the present invention compared with UHT milk which has not been enzymatically treated and/or compared with UHT milk which during its manufacture has been treated with a phospholipase (in particular either a phospholipase A1 enzyme classified as E.C. 3.1.1.32 or a phospholipase A2 enzyme classified as EC.3.1.1.4) (rather than the lipid acyltransferase as described herein).

A further advantage of the present invention may be the reduction of fouling of the UHT plant (e.g. of the plant tubes and/or steel surfaces) when using the UHT milk treated in accordance with the present invention compared with UHT milk which has not been enzymatically treated and/or compared with UHT milk which during its manufacture has been treated with a phospholipase (in particular either a phospholipase A1 enzyme classified as E.C. 3.1.1.32 or a phospholipase A2 enzyme classified as EC.3.1.1.4) (rather than the lipid acyltransferase as described herein).

A further advantage of the present invention may be a reduction in free fatty acids in UHT milk treated in accordance with the present invention compared with UHT milk which during its manufacture has been treated with a phospholipase (in particular either a phospholipase A1 enzyme classified as E.C. 3.1.1.32 or a phospholipase A2 enzyme classified as EC.3.1.1.4) (rather than the lipid acyltransferase as described herein).

Even more surprisingly the inventors of the present invention have found that the enzymatic treatment can be carried out without an additional heating step. In particular the enzymatic treatment using the lipid acyltransferase in accordance with the present invention may be carried out at temperatures as low as approximately 1-25° C., preferably as low as approximately 1-10° C., preferably between about 3 and about 7° C., more preferably about 5° C. Hence the adverse effects of heating the milk twice, i.e. once for the UHT treatment and then again for enzymatic treatment, can be avoided. This has many advantages including:
  a) that the process is more economic and is therefore advantageous for producers of the UHT milk;
  b) heating of the milk can lead to adverse effects such as a breakdown in stability of the constituents of the milk, the present invention reduces significantly this disadvantageous property; and/or
  c) less changes in organoleptic properties.

A further advantage of the present invention is a reduced cholesterol content in the UHT milk which may have major health benefits.

Suitably the improvement in any of the characteristics taught herein (such as creaming) may be compared with UHT milk which has been treated with one or more of the following phospholipases: Phospholipase A1 from *Fusarium oxysporum* (Lipopan F™) and/or a phospholipase A1 from *Fusarium venenatum* (YieldMax™) and/or a phospholipase from *Fusarium heterosporum* and/or a phospholipase from *Aspergillus niger* and/or a phospholipase A2 from *Streptomyces violaceoruber* and/or a phospholipase A2 from porcine pancreas and/or a phospholipase A2 from *Tuber borchii*; preferably Phospholipase A1 from *Fusarium oxysporum* (Lipopan F™).

Host Cell

The host organism can be a prokaryotic or a eukaryotic organism.

In one embodiment of the present invention the lipid acyl transferase according to the present invention in expressed in a host cell, for example a bacterial cells, such as a *Bacillus* spp, for example a *Bacillus licheniformis* host cell.

Alternative host cells may be fungi, yeasts or plants for example.

It has been found that the use of a *Bacillus licheniformis* host cell results in increased expression of a lipid acyltransferase when compared with other organisms, such as *Bacillus subtilis*.

A lipid acyltransferase from *Aeromonas salmonicida* has been inserted into a number of conventional expression vectors, designed to be optimal for the expression in *Bacillus subtilis, Hansenula polymorpha, Schizosaccharomyces pombe* and *Aspergillus tubigensis*, respectively. Only very low levels were, however, detected in *Hansenula polymorpha, Schizosaccharomyces pombe* and *Aspergillus tubigensis*. The expression levels were below 1 µg/ml, and it was not possible to select cells which yielded enough protein to initiate a commercial production (results not shown). In contrast, *Bacillus licheniformis* was able to produce protein levels, which are attractive for an economically feasible production.

In particular, it has been found that expression in *B. licheniformis* is approximately 100-times greater than expression in *B. subtilis* under the control of aprE promoter or is approximately 100-times greater than expression in *S. lividans* under the control of an A4 promoter and fused to cellulose (results not shown herein).

The host cell may be any *Bacillus* cell other than *B. subtilis*. Preferably, said *Bacillus* host cell being from one of the following species: *Bacillus licheniformis; B. alkalophilus; B. amyloliquefaciens; B. circulans; B. clausii; B. coagulans; B. firmus; B. lautus; B. lentus; B. megaterium; B. pumilus* or *B. stearothermophilus*.

The term "host cell"—in relation to the present invention includes any cell that comprises either a nucleotide sequence encoding a lipid acyltransferase as defined herein or an expression vector as defined herein and which is used in the recombinant production of a lipid acyltransferase having the specific properties as defined herein.

Suitably, the host cell may be a protease deficient or protease minus strain and/or an α-amylase deficient or α-amylase minus strain.

The term "heterologous" as used herein means a sequence derived from a separate genetic source or species. A heterologous sequence is a non-host sequence, a modified sequence, a sequence from a different host cell strain, or a homologous sequence from a different chromosomal location of the host cell.

A "homologous" sequence is a sequence that is found in the same genetic source or species i.e. it is naturally occurring in the relevant species of host cell.

The term "recombinant lipid acyltransferase" as used herein means that the lipid acyltransferase has been produced by means of genetic recombination. For instance, the nucleotide sequence encoding the lipid acyltansferase has been inserted into a cloning vector, resulting in a *B. licheniformis* cell characterised by the presence of the heterologous lipid acyltransferase.

Regulatory Sequences

In some applications, a lipid acyltransferase sequence for use in the methods and/or uses of the present invention may be obtained by operably linking a nucleotide sequence encoding same to a regulatory sequence which is capable of providing for the expression of the nucleotide sequence, such as by the chosen host cell (such as a *B. licheniformis* cell).

By way of example, a vector comprising the nucleotide sequence of the present invention operably linked to such a regulatory sequence, i.e. the vector is an expression vector, may be used.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of regulatory regions, e.g. promoter, secretion leader and terminator regions that are not regulatory regions for the nucleotide sequence encoding the enzyme in nature.

Suitably, the nucleotide sequence of the present invention may be operably linked to at least a promoter.

Suitably, the nucleotide sequence encoding a lipid acyltransferase may be operably linked to at a nucleotide sequence encoding a terminator sequence. Examples of suitable terminator sequences for use in any one of the vectors, host cells, methods and/or uses of the present invention include: an .alpha.-amylase terminator sequence (for instance, CGGGACTTACCGAAAGAAACCATCAAT-GATGGTTTCTTTTTTGTTCATAAA—SEQ ID NO: 64), an alkaline protease terminator sequence (for instance, CAA-GACTAAAGACCGTTCGCCCGTTTTTG-CAATAAGCGGGCGAATCTTACATAAAAATA—SEQ ID NO: 65), a glutamic-acid specific terminator sequence (for instance, ACGGCCGTTAGATGTGACAGCCCGTTC-CAAAAGGAAGCGGGCTGTCTTCGTGTATTATTGT— SEQ ID NO: 66), a levanase terminator sequence (for instance, TCTTTTAAAGGAAAGGCTGGAATGCCCG-GCATTCCAGCCACATGATCATCGTTT—SEQ ID NO: 67) and a subtilisin E terminator sequence (for instance, GCT-GACAAATAAAAAGAAGCAGGTATGGAG-GAACCTGCTTCTTTTTACTATTATTG—SEQ ID NO: 119). Suitably, the nucleotide sequence encoding a lipid acyltransferase may be operably linked to an .alpha.-amylase terminator, such as a *B. licheniformis* .alpha.-amylase terminator.

Promoter

The promoter sequence to be used in accordance with the present invention may be heterologous or homologous to the sequence encoding a lipid acyltransferase.

The promoter sequence may be any promoter sequence capable of directing expression of a lipid acyltransferase in the host cell of choice.

Suitably, the promoter sequence may be homologous to a *Bacillus* species, for example *B. licheniformis*. Preferably, the promoter sequence is homologous to the host cell of choice.

Suitably the promoter sequence may be homologous to the host cell. "Homologous to the host cell" means originating within the host organism; i.e. a promoter sequence which is found naturally in the host organism.

Suitably, the promoter sequence may be selected from the group consisting of a nucleotide sequence encoding: an α-amylase promoter, a protease promoter, a subtilisin promoter, a glutamic acid-specific protease promoter and a levansucrase promoter.

Suitably the promoter sequence may be a nucleotide sequence encoding: the LAT (e.g. the alpha-amylase promoter from *B. licheniformis*, also known as AmyL), AprL (e.g. subtilisin Carlsberg promoter), EndoGluC (e.g. the glutamic-acid specific promoter from *B. licheniformis*), AmyQ (e.g. the alpha amylase promoter from *B. amyloliquefaciens* alpha-amylase promoter) and SacB (e.g. the *B. subtilis* levansucrase promoter).

Other examples of promoters suitable for directing the transcription of a nucleic acid sequence in the methods of the present invention include: the promoter of the *Bacillus lentus* alkaline protease gene (aprH),; the promoter of the *Bacillus subtilis* alpha-amylase gene (amyE); the promoter of the *Bacillus stearothermophilus* maltogenic amylase gene (amyM); the promoter of the *Bacillus licheniformis* penicillinase gene (penP); the promoters of the *Bacillus subtilis* xylA and xylB genes; and/or the promoter of the *Bacillus thuringiensis* subsp. *tenebrionis* CryIIIA gene.

In a preferred embodiment, the promoter sequence is an α-amylase promoter (such as a *Bacillus licheniformis* α-amylase promoter). Preferably, the promoter sequence comprises the −35 to −10 sequence of the *B. licheniformis* α-amylase promoter—see FIGS. 53 and 55.

The "−35 to −10 sequence" describes the position relative to the transcription start site. Both the "−35" and the "−10" are boxes, i.e. a number of nucleotides, each comprising 6 nucleotides and these boxes are separated by 17 nucleotides. These 17 nucleotides are often referred to as a "spacer". This is illustrated in FIG. 55, where the −35 and the −10 boxes are underlined. For the avoidance of doubt, where "−35 to −10 sequence" is used herein it refers to a sequence from the start of the −35 box to the end of the −10 box i.e. including both the −35 box, the 17 nucleotide long spacer and the −10 box.

Signal Peptide

The lipid acyltransferase produced by a host cell by expression of the nucleotide sequence encoding the lipid acyltransferase may be secreted or may be contained intracellularly depending on the sequence and/or the vector used.

A signal sequence may be used to direct secretion of the coding sequences through a particular cell membrane. The signal sequences may be natural or foreign to the lipid acyltransferase coding sequence. For instance, the signal peptide coding sequence may be obtained form an amylase or protease gene from a *Bacillus* species, preferably from *Bacillus licheniformis*.

Suitable signal peptide coding sequences may be obtained from one or more of the following genes: maltogenic α-amylase gene, subtilisin gene, beta-lactamase gene, neutral protease gene, prsA gene, and/or acyltransferase gene.

Preferably, the signal peptide is a signal peptide of *B. licheniformis* .alpha.-amylase, *Aeromonas* acyltransferase (for instance, mkkwfvellglialtvqa—SEQ ID NO: 21), *B. subtilis* subtilisin (for instance, mrskklwisllfaltliftmafsnmsaqa—SEQ ID NO: 22) or *B. licheniformis* subtilisin (for instance, mmrkksfwfgmltafmlyftmefsdsasa—SEQ ID NO: 23) Suitably, the signal peptide may be the signal peptide of *B. licheniformis* α-amylase.

However, any signal peptide coding sequence capable of directing the expressed lipid acyltransferase into the secretory pathway of a *Bacillus* host cell (preferably a *B. licheniformis* host cell) of choice may be used.

In some embodiments of the present invention, a nucleotide sequence encoding a signal peptide may be operably linked to a nucleotide sequence encoding a lipid acyltransferase of choice.

The lipid acyltransferase of choice may be expressed in a host cell as defined herein as a fusion protein.

Expression Vector

The term "expression vector" means a construct capable of in vivo or in vitro expression.

Preferably, the expression vector is incorporated in the genome of the organism, such as a *B. licheniformis* host. The term "incorporated" preferably covers stable incorporation into the genome.

The nucleotide sequence encoding a lipid acyltransferase as defined herein may be present in a vector, in which the nucleotide sequence is operably linked to regulatory sequences such that the regulatory sequences are capable of providing the expression of the nucleotide sequence by a suitable host organism (such as *B. licheniformis*), i.e. the vector is an expression vector.

The vectors of the present invention may be transformed into a suitable host cell as described above to provide for expression of a polypeptide having lipid acyltransferase activity as defined herein.

The choice of vector, e.g. plasmid, cosmid, virus or phage vector, genomic insert, will often depend on the host cell into which it is to be introduced. The present invention may cover other forms of expression vectors which serve equivalent functions and which are, or become, known in the art.

Once transformed into the host cell of choice, the vector may replicate and function independently of the host cell's genome, or may integrate into the genome itself.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Lipid Acyl Transferase

The nucleotide sequence encoding a lipid acyl transferase for use in any one of the methods and/or uses of the present invention may encode a natural lipid acyl transferase or a variant lipid acyl transferase.

The lipid acyl transferase for use in any one of the methods and/or uses of the present invention may be a natural lipid acyl transferase or a variant lipid acyl transferase.

For instance, the nucleotide sequence encoding a lipid acyl transferase for use in the present invention may be one as described in WO2004/064537, WO2004/064987, WO2005/066347, or WO2006/008508. These documents are incorporated herein by reference.

The term "lipid acyl transferase" as used herein preferably means an enzyme that has acyltransferase activity (generally classified as E.C. 2.3.1.x, for example 2.3.1.43), whereby the enzyme is capable of transferring an acyl group from a lipid to one or more acceptor substrates, such as one or more of the following: a sterol; a stanol; a carbohydrate; a protein; a protein subunit; a sugar alcohol, such as ascorbic acid and/or glycerol—preferably glycerol and/or a sterol, such as cholesterol.

Preferably, the lipid acyl transferase for use in any one of the methods and/or uses of the present invention is a lipid acyltransferase that is capable of transferring an acyl group from a phospholipid (as defined herein) to a sugar alcohol, such as ascorbic acid and/or glycerol and/or a sterol, preferably glycerol or a sterol, most preferably a sterol (e.g. cholesterol).

For some aspects the "acyl acceptor" according to the present invention may be any compound comprising a hydroxy group (—OH), such as for example, polyvalent alcohols, including glycerol; sterols; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof. Preferably, the "acyl acceptor" according to the present invention is not water. Preferably, the "acyl acceptor" according to the present invention is a sugar alcohol, such as a polyol, most preferably glycerol. For the purpose of this invention ascorbic acid is also considered a sugar-alcohol.

The acyl acceptor is preferably not a monoglyceride.

The acyl acceptor is preferably not a diglyceride

In one aspect, the lipid acyltransferase for use in any one of the methods and/or uses of the present invention is a lipid acyltransferase that may, as well as being able to transfer an acyl group from a lipid to glycerol, additionally be able to transfer the acyl group from a lipid to one or more of the following: a carbohydrate, a protein, a protein subunit, sterol and/or a stanol, preferably it is capable of transferring to both a sugar alcohol, such as ascorbic acid and/or glycerol, most preferably a sterol such as cholesterol, and/or plant sterols/stanols.

Preferably, the lipid substrate upon which the lipid acyl acts is one or more of the following lipids: a phospholipid, such as a lecithin, e.g. phosphatidylcholine and/or phosphatidylethanolamine.

This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

For some aspects, preferably the lipid acyl transferase for use in any one of the methods and/or uses of the present invention is a lipid acyltransferase that is incapable, or substantially incapable, of acting on a triglyceride and/or a 1-monoglyceride and/or 2-monoglyceride.

For some aspects, preferably the lipid acyl transferase for use in any one of the methods and/or uses of the present invention is a lipid acyltransferase that does not exhibit triacylglycerol lipase activity (E.C. 3.1.1.3) or does not exhibit significant triacylglycerol lipase activity (E.C. 3.1.1.3).

The ability to hydrolyse triglyceride (E.C. 3.1.1.3 activity) may be determined by lipase activity is determined according to Food Chemical Codex (3rd Ed., 1981, pp 492-493) modified to sunflower oil and pH 5.5 instead of olive oil and pH 6.5. The lipase activity is measured as LUS (lipase units sunflower) where 1 LUS is defined as the quantity of enzyme which can release 1 [mu]mol of fatty acids per minute from sunflower oil under the above assay conditions. Alternatively the LUT assay as defined in WO9845453 may be used. This reference is incorporated herein by reference.

The lipid acyl transferase for use in any one of the methods and/or uses of the present invention may be a lipid acyltransferase which is substantially incapable of acting on a triglyceride may have a LUS/mg of less than 1000, for example less than 500, such as less than 300, preferably less than 200, more preferably less than 100, more preferably less than 50, more preferably less than 20, more preferably less than 10, such as less than 5, less than 2, more preferably less than 1 LUS/mg. Alternatively LUT/mg activity is less than 500, such as less than 300, preferably less than 200, more preferably less than 100, more preferably less than 50, more preferably less than 20, more preferably less than 10, such as less than 5, less than 2, more preferably less than 1 LUT/mg.

The lipid acyl transferase for use in any one of the methods and/or uses of the present invention may be a lipid acyltransferase which is substantially incapable of acting on a monoglyceride. This may be determined by using monooleate (M7765 1-Oleoyl-rac-glycerol 99%) in place of the sunflower oil in the LUS assay. 1 MGHU is defined as the quantity of enzyme which can release 1 [mu]mol of fatty acids per minute from monoglyceride under the assay conditions.

The lipid acyl transferase for use in any one of the methods and/or uses of the present invention is a lipid acyltransferase which is preferably substantially incapable of acting on a triglyceride may have a MGHU/mg of less than 5000, for example less than 1000, for example less than 500, such as less than 300, preferably less than 200, more preferably less than 100, more preferably less than 50, more preferably less than 20, more preferably less than 10, such as less than 5, less than 2, more preferably less than 1 MGHU/mg.

Suitably, the lipid acyltransferase for use in any one of the methods and/or uses of the present invention is a lipid acyltransferase that may exhibit one or more of the following phospholipase activities: phospholipase A2 activity (E.C. 3.1.1.4) and/or phospholipase A1 activity (E.C. 3.1.1.32). The lipid acyl transferase may also have phospholipase B activity (E.C 3.1.1.5).

Suitably, for some aspects the lipid acyltransferase may be capable of transferring an acyl group from a phospholipid to a sugar alcohol, preferably glycerol and/or ascorbic acid.

Suitably, for some aspects the lipid acyltransferase may be capable of transferring an acyl group from a phospholipid to a stanol and/or sterol, preferably cholesterol.

For some aspects, preferably the lipid acyltransferase for use any one of the methods and/or uses of the present invention encodes a lipid acyltransferase that is capable of transferring an acyl group from a phospholipid to a sterol and/or a stanol to form at least a sterol ester and/or a stanol ester.

The lipid acyltransferase may be capable of transferring an acyl group from a lipid to a polyol such as glycerol, and/or a sterol such as cholesterol or plant sterol/stanols. Thus, in one embodiment the "acyl acceptor" according to the present invention may be glycerol and/or cholesterol or plant sterol/stanols.

Preferably, the lipid acyltransferase enzyme may be characterised using the following criteria:

the enzyme possesses acyl transferase activity which may be defined as ester transfer activity whereby the acyl part of an original ester bond of a lipid acyl donor is transferred to an acyl acceptor, preferably glycerol or cholesterol, to form a new ester; and the enzyme comprises the amino acid sequence motif GDSX (SEQ ID NO: 117), wherein X is one or more of the following amino acid residues L, A, V, I, F, Y, H, Q, T, N, M or S.

Preferably, X of the GDSX motif is L or Y (SEQ ID NO: 121). More preferably, X of the GDSX motif is L (SEQ ID NO: 122). Thus, preferably the enzyme according to the present invention comprises the amino acid sequence motif GDSL (SEQ ID NO: 122).

The GDSX (SEQ ID NO: 120) motif is comprised of four conserved amino acids.

Preferably, the serine within the motif is a catalytic serine of the lipid acyl transferase enzyme. Suitably, the serine of the GDSX (SEQ ID NO: 120) motif may be in a position corresponding to Ser-16 in *Aeromonas hydrophila* lipid acyltransferase enzyme taught in Brumlik & Buckley (Journal of Bacteriology April 1996, Vol. 178, No. 7, p 2060-2064).

To determine if a protein has the GDSX (SEQ ID NO: 120) motif according to the present invention, the sequence is preferably compared with the hidden markov model profiles (HMM profiles) of the pfam database in accordance with the procedures taught in WO2004/064537 or WO2004/064987, incorporated herein by reference.

Preferably the lipid acyl transferase enzyme can be aligned using the Pfam00657 consensus sequence (for a full explanation see WO2004/064537 or WO2004/064987).

Preferably, a positive match with the hidden markov model profile (HMM profile) of the pfam00657 domain family indicates the presence of the GDSL (SEQ ID NO: 122) or GDSX (SEQ ID NO: 120) domain according to the present invention.

Preferably when aligned with the Pfam00657 consensus sequence the lipid acyltransferase for use in the methods or uses of the invention may have at least one, preferably more than one, preferably more than two, of the following, a GDSX (SEQ ID NO: 120) block, a GANDY (SEQ ID NO: 118) block, a HPT block. Suitably, the lipid acyltransferase may have a GDSX (SEQ ID NO: 120) block and a GANDY (SEQ ID NO: 118) block. Alternatively, the enzyme may have a GDSX (SEQ ID NO: 120) block and a HPT block. Preferably the enzyme comprises at least a GDSX (SEQ ID NO: 120) block. See WO2004/064537 or WO2004/064987 for further details.

Preferably, residues of the GANDY (SEQ ID NO: 118) motif are selected from GANDY (SEQ ID NO: 118), GGNDA (SEQ ID NO: 123), GGNDL (SEQ ID NO: 124), most preferably GANDY (SEQ ID NO: 118).

Preferably, when aligned with the Pfam00657 consensus sequence the enzyme for use in the methods or uses of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference A. hydrophilia polypeptide sequence, namely SEQ ID ID NO: 1: 28hid, 29hid, 30hid, 31hid, 32gly, 33Asp, 34Ser, 35hid, 130hid, 131Gly, 132Hid, 133Asn, 134Asp, 135hid, 309His.

The pfam00657 GDSX (SEQ ID NO: 120) domain is a unique identifier which distinguishes proteins possessing this domain from other enzymes.

The pfam00657 consensus sequence is presented in FIG. 3 as SEQ ID NO: 2. This is derived from the identification of the pfam family 00657, database version 6, which may also be referred to as pfam00657.6 herein.

The consensus sequence may be updated by using further releases of the pfam database (for example see WO2004/064537 or WO2004/064987).

In one embodiment, the lipid acyl transferase enzyme for use in any one of the methods and/or uses of the present invention is a lipid acyltransferase that may be characterised using the following criteria:
(i) the enzyme possesses acyl transferase activity which may be defined as ester transfer activity whereby the acyl part of an original ester bond of a lipid acyl donor is transferred to acyl acceptor, preferably glycerol or cholesterol, to form a new ester, preferably monoglyceride or cholesterol ester respectfully;
(ii) the enzyme comprises the amino acid sequence motif GDSX (SEQ ID NO: 117), wherein X is one or more of the following amino acid residues L, A, V, I, F, Y, H, Q, T, N, M or S;
(iii) the enzyme comprises His-309 or comprises a histidine residue at a position corresponding to His-309 in the *Aeromonas hydrophila* lipid acyltransferase enzyme shown in FIGS. 2 and 4 (SEQ ID NO: 1 or SEQ ID NO: 3).

Preferably, the amino acid residue of the GDSX motif is L (SEQ ID NO: 122).

In SEQ ID NO: 3 or SEQ ID NO: 1 the first 18 amino acid residues form a signal sequence. His-309 of the full length sequence, that is the protein including the signal sequence, equates to His-291 of the mature part of the protein, i.e. the sequence without the signal sequence.

In one embodiment, the lipid acyl transferase enzyme for use any one of the methods and uses of the present invention is a lipid acyltransferase that comprises the following catalytic triad: Ser-34, Asp-306 and His-309 or comprises a serine residue, an aspartic acid residue and a histidine residue, respectively, at positions corresponding to Ser-34, Asp-306 and His-309 in the *Aeromonas hydrophila* lipid acyl transferase enzyme shown in FIG. 4 (SEQ ID NO: 3) or FIG. 2 (SEQ ID NO: 1). As stated above, in the sequence shown in SEQ ID NO: 3 or SEQ ID NO: 1 the first 18 amino acid residues form a signal sequence. Ser-34, Asp-306 and His-309 of the full length sequence, that is the protein including the signal sequence, equate to Ser-16, Asp-288 and His-291 of the mature part of the protein, i.e. the sequence without the signal sequence. In the pfam00657 consensus sequence, as given in FIG. 3 (SEQ ID NO: 2) the active site residues correspond to Ser-7, Asp-345 and His-348.

In one embodiment, the lipid acyl transferase enzyme for use any one of the methods and/or uses of the present invention is a lipid acyltransferase that may be characterised using the following criteria:
the enzyme possesses acyl transferase activity which may be defined as ester transfer activity whereby the acyl part of an original ester bond of a first lipid acyl donor is transferred to an acyl acceptor to form a new ester; and
the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-306 and His-309, respectively, in the *Aeromonas hydrophila* lipid acyltransferase enzyme shown in SEQ ID NO: 3 or SEQ ID NO: 1.

Suitably, the lipid acyltransferase enzyme for use in any one of the methods and/or uses of the present invention may be encoded by one of the following nucleotide sequences:
(a) the nucleotide sequence shown as SEQ ID NO: 36 (see FIG. 29); (b) the nucleotide sequence shown as SEQ ID NO: 39 (see FIG. 32); (c) the nucleotide sequence shown as SEQ ID NO: 42 (see FIG. 35); (d) the nucleotide sequence shown as SEQ ID NO: 44 (see FIG. 37); (e) the nucleotide sequence shown as SEQ ID NO: 46 (see FIG. 39); (f) the nucleotide sequence shown as SEQ ID NO: 48 (see FIG. 41); (g) the nucleotide sequence shown as SEQ ID NO: 49 (see FIG. 57); (h) the nucleotide sequence shown as SEQ ID NO: 50 (see FIG. 58); (i) the nucleotide sequence shown as SEQ ID NO: 51 (see FIG. 59); (j) the nucleotide sequence shown as SEQ ID NO: 52 (see FIG. 60); (k) the nucleotide sequence shown as SEQ ID NO: 53 (see FIG. 61); (1) the nucleotide sequence shown as SEQ ID NO: 54 (see FIG. 62); (m) the nucleotide sequence shown as SEQ ID NO: 55 (see FIG. 63); (n) the nucleotide sequence shown as SEQ ID NO: 56 (see FIG. 64); (o) the nucleotide sequence shown as SEQ ID NO: 57 (see FIG. 65); (p) the nucleotide sequence shown as SEQ ID NO: 58 (see FIG. 66); (q) the nucleotide sequence shown as SEQ ID NO: 59 (see FIG. 67); (r) the nucleotide sequence shown as SEQ ID NO: 60 (see FIG. 68); (s) the nucleotide sequence shown as SEQ ID NO: 61 (see FIG. 69); (t) the nucleotide sequence shown as SEQ ID NO: 62 (see FIG. 70); (u) the nucleotide sequence shown as SEQ ID NO: 63 (see FIG. 71); (v) or a nucleotide sequence which has 70% or more, preferably 75% or more, identity with any one of the sequences shown as SEQ ID NO: 36, SEQ ID NO: 39, SEQ ID NO: 42, SEQ ID NO: 44, SEQ ID NO: 46, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62 or SEQ ID NO: 63.

Suitably the nucleotide sequence may have 80% or more, preferably 85% or more, more preferably 90% or more and even more preferably 95% or more identity with any one of the sequences shown as SEQ ID NO: 36, SEQ ID NO: 39, SEQ ID NO: 42, SEQ ID NO: 44, SEQ ID NO: 46, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62 or SEQ ID NO: 63.

In one embodiment, the nucleotide sequence encoding a lipid acyltransferase enzyme for use any one of the methods and uses of the present invention is a nucleotide sequence which has 70% or more, preferably 75% or more, identity with any one of the sequences shown as: SEQ ID NO: 49, SEQ ID NO: 50, SEQ ID NO: 51, SEQ ID NO: 62, and SEQ ID NO: 63. Suitably the nucleotide sequence may have 80% or more, preferably 85% or more, more preferably 90% or more and even more preferably 95% or more identity with any one of the sequences shown as: SEQ ID NO: 49, SEQ ID NO: 50, SEQ ID NO: 51, SEQ ID NO: 62, and SEQ ID NO: 63.

In one embodiment, the nucleotide sequence encoding a lipid acyltransferase enzyme for use in any one of the methods and uses of the present invention is a nucleotide sequence which has 70% or more, 75% or more, 80% or more, preferably 85% or more, more preferably 90% or more and even more preferably 95% or more identity the sequence shown as SEQ ID NO: 49.

Suitably, the lipid acyl transferase enzyme for use any one of the methods and/or uses of the present invention may be a lipid acyltransferase that comprises one or more of the following amino acid sequences:
(i) the amino acid sequence shown as SEQ ID NO: 3 (ii) the amino acid sequence shown as SEQ ID NO: 4 (iii) the amino acid sequence shown as SEQ ID NO: 5 (iv) the amino acid sequence shown as SEQ ID No. 6 (v) the amino acid sequence shown as SEQ ID No. 7 (vi) the amino acid sequence shown as SEQ ID NO: 8 (vii) the amino acid sequence shown as SEQ ID NO: 9 (viii) the amino acid sequence shown as SEQ ID NO: 10 (ix) the amino acid sequence shown as SEQ ID NO: 11 (x) the amino acid sequence shown as SEQ ID NO: 12 (xi) the amino acid sequence shown as SEQ ID NO: 13 (xii) the amino acid sequence shown as SEQ ID NO: 14 (xiii) the amino acid sequence shown as SEQ ID NO: 1 (xiv) the amino acid sequence shown as SEQ ID No. 15 (xv) the amino acid sequence shown as SEQ ID NO: 16 (xvi) the amino acid sequence shown as SEQ ID NO: 17 (xvii) the amino acid sequence shown as SEQ ID NO: 18 (xviii) the amino acid sequence shown as SEQ ID NO: 34 (xix) the amino acid sequence shown as SEQ ID NO: 35 or an amino acid sequence which has 75%, 80%, 85%, 90%, 95%, 98% or more identity with any one of the sequences shown as SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 or SEQ ID NO: 15, SEQ ID NO: 16, SEQ ID NO: 17, SEQ ID NO: 18, SEQ ID NO: 34 or SEQ ID NO: 35.

Suitably, the lipid acyl transferase enzyme for use any one of the methods and uses of the present invention may be a lipid acyltransferase that comprises either the amino acid sequence shown as SEQ ID NO: 3 or as SEQ ID NO: 4 or SEQ ID NO: 1 or SEQ ID NO: 15 or SEQ ID NO: 16, or SEQ ID NO: 34 or SEQ ID NO: 35 or comprises an amino acid sequence which has 75% or more, preferably 80% or more, preferably 85% or more, preferably 90% or more, preferably 95% or more, identity with the amino acid sequence shown as SEQ ID NO: 3 or the amino acid sequence shown as SEQ ID NO: 4 or the amino acid sequence shown as SEQ ID NO: 1 or the amino acid sequence shown as SEQ ID No. 15 or the amino acid sequence shown as SEQ ID NO: 16 or the amino acid sequence shown as SEQ ID NO: 34 or the amino acid sequence shown as SEQ ID NO: 35.

Suitably the lipid acyl transferase enzyme for use any one of the methods and/or uses of the present invention may be a lipid acyltransferase that comprises an amino acid sequence which has 80% or more, preferably 85% or more, more preferably 90% or more and even more preferably 95% or more identity with any one of the sequences shown as SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 1, SEQ ID NO: 15, SEQ ID NO: 16, SEQ ID NO: 17, SEQ ID NO: 18, SEQ ID NO: 34 or SEQ ID NO: 35.

Suitably, the lipid acyl transferase enzyme for use any one of the methods and/or uses of the present invention may be a lipid acyltransferase that comprises one or more of the following amino acid sequences:
(a) an amino acid sequence shown as amino acid residues 1-100 of SEQ ID NO: 3 or SEQ ID NO: 1;
(b) an amino acid sequence shown as amino acids residues 101-200 of SEQ ID NO: 3 or SEQ ID NO: 1;
(c) an amino acid sequence shown as amino acid residues 201-300 of SEQ ID NO: 3 or SEQ ID NO: 1; or
(d) an amino acid sequence which has 75% or more, preferably 85% or more, more preferably 90% or more, even more preferably 95% or more identity to any one of the amino acid sequences defined in (a)-(c) above.

Suitably, the lipid acyl transferase enzyme for use in methods and uses of the present invention may comprise one or more of the following amino acid sequences:
(a) an amino acid sequence shown as amino acid residues 28-39 of SEQ ID NO: 3 or SEQ ID NO: 1;
(b) an amino acid sequence shown as amino acids residues 77-88 of SEQ ID NO: 3 or SEQ ID NO: 1;

(c) an amino acid sequence shown as amino acid residues 126-136 of SEQ ID NO: 3 or SEQ ID NO: 1;

(d) an amino acid sequence shown as amino acid residues 163-175 of SEQ ID NO: 3 or SEQ ID NO: 1;

(e) an amino acid sequence shown as amino acid residues 304-311 of SEQ ID NO: 3 or SEQ ID NO: 1; or (f) an amino acid sequence which has 75% or more, preferably 85% or more, more preferably 90% or more, even more preferably 95% or more identity to any one of the amino acid sequences defined in (a)-(e) above.

In one aspect, the lipid acyl transferase enzyme for use any one of the methods and/or uses of the present invention is a lipid acyltransferase that may be the lipid acyl transferase from *Candida parapsilosis* as taught in EP 1 275 711. Thus in one aspect the lipid acyl transferase for use in the method and uses of the present invention may be a lipid acyl transferase comprising one of the amino acid sequences taught in SEQ ID NO: 17 or SEQ ID NO: 18.

Much by preference, the lipid acyl transferase enzyme for use in any one of the methods and uses of the present invention is a lipid acyltransferase that may be a lipid acyl transferase comprising the amino acid sequence shown as SEQ ID No. 16, or an amino acid sequence which has 75% or more, preferably 85% or more, more preferably 90% or more, even more preferably 95% or more, even more preferably 98% or more, or even more preferably 99% or more identity to SEQ ID NO: 16. This enzyme could be considered a variant enzyme.

In one aspect, the lipid acyltransferase enzyme for use any one of the methods and/or uses of the present invention is a lipid acyltransferase that may be a lecithin:cholesterol acyltransferase (LCAT) or variant thereof (for example a variant made by molecular evolution)

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the lipid acyltransferase enzyme for use any one of the methods and/or uses of the present invention is a lipid acyltransferase that may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NCIMB 41204 and NCIMB 41205, respectively.

A lipid acyltransferase enzyme for use in any one of the methods and/or uses of the present invention may be a phospholipid glycerol acyl transferase. Phospholipid glycerol acyl transferases include those isolated from *Aeromonas* spp., preferably *Aeromonas hydrophila* or *A. salmonicida*, most preferably *A. salmonicida* or variants thereof.

Most preferred lipid acyl transferases for use in the present invention are encoded by SEQ ID NOS: 1, 3, 4, 15, 16, 34 and 35. It will be recognised by the skilled person that it is preferable that the signal peptides of the acyl transferase has been cleaved during expression of the transferase. The signal peptide of SEQ ID NOS: 1, 3, 4, 15 and 16 are amino acids 1-18. Therefore the most preferred regions are amino acids 19-335 for SEQ ID NO: 1 and SEQ ID NO: 3 (*A. hydrophilia*) and amino acids 19-336 for SEQ ID NO: 4, SEQ ID NO: 15 and SEQ ID NO: 16. (*A. salmonicida*). When used to determine the homology of identity of the amino acid sequences, it is preferred that the alignments as herein described use the mature sequence.

In one embodiment, suitably the lipid acyl transferase for use in the present invention comprises (or consists of) the amino acid sequence shown in SEQ ID NO: 16 or comprises (or consists of) an amino acid sequence which has at least 70%, at least 75%, at least 85%, at least 90%, at least 95%, at least 98% identity to SEQ ID NO: 16.

In one embodiment, suitably the lipid acyl transferase for use in the present invention is encoded by a nucleotide sequence comprising (or consisting of) a nucleotide sequence shown in SEQ ID NO: 68 or comprises (or consists of) a nucleotide sequence which has at least 70%, at least 75%, at least 85%, at least 90%, at least 95%, at least 98% identity to SEQ ID No. 68.

Therefore the most preferred regions for determining homology (identity) are amino acids 19-335 for SEQ ID NOS: 1 and 3 (*A. hydrophilia*) and amino acids 19-336 for SEQ ID Nos. 4, 15 and 16. (*A. salmonicida*). SEQ ID Nos. 34 and 35 are mature protein sequences of a lipid acyl transferase from *A. hydrophilia* and *A. salmonicida* respectively which may or may not undergo further post-translational modification.

A lipid acyltransferase enzyme for use any one of the methods and uses of the present invention may be a lipid acyltransferase that may also be isolated from *Thermobifida*, preferably *T. fusca*, most preferably that encoded by SEQ ID NO: 28.

Suitable lipid acyltransferases for use in accordance with the present invention and/or in the methods of the present invention may comprise any one of the following amino acid sequences and/or be encoded by the following nucleotide sequences:

a) a nucleic acid which encodes a polypeptide exhibiting lipid acyltransferase activity and is at least 70% identical (preferably at least 80%, more preferably at least 90% identical) with the polypeptide sequence shown in SEQ ID NO: 16 or with the polypeptide shown in SEQ ID NO: 68; b) a (isolated) polypeptide comprising (or consisting of) an amino acid sequence as shown in SEQ ID NO: 16 or SEQ ID NO: 68 or an amino acid sequence which is at least 70% identical (preferably at least 80% identical, more preferably at least 90% identical) with SEQ ID NO: 16 or SEQ ID NO: 68; c) a nucleic acid encoding a lipid acyltransferase, which nucleic acid comprises (or consists of) a nucleotide sequence shown as SEQ ID NO: 49 or a nucleotide sequence which is at least 70% identical (preferably at least 80%, more preferably at least 90% identical) with the nucleotide sequence shown as SEQ ID NO: 49; d) a nucleic acid which hybridises under medium or high stringency conditions to a nucleic acid probe comprising the nucleotide sequence shown as SEQ ID NO: 49 and encodes for a polypeptide exhibiting lipid acyltransferase activity; e) a nucleic acid which is a fragment of the nucleic acid sequences specified in a), c) or d); or f) a polypeptide which is a fragment of the polypeptide specified in b).

A lipid acyltransferase enzyme for use any one of the methods and uses of the present invention may be a lipid acyltransferase that may also be isolated from *Streptomyces*, preferable *S. avermitis*, most preferably that encoded by SEQ ID NO: 32. Other possible enzymes for use in the present invention from *Streptomyces* include those encoded by SEQ ID Nos. 5, 6, 9, 10, 11, 12, 13, 14, 31, and 33.

An enzyme for use in the invention may also be isolated from *Corynebacterium*, preferably *C. efficiens*, most preferably that encoded by SEQ ID NO: 29.

Suitably, the lipid acyltransferase enzyme for use any one of the methods and/or uses of the present invention may be a lipid acyltransferase that comprises any one of the amino acid sequences shown as SEQ ID Nos. 37, 38, 40, 41, 43, 45, or 47 or an amino acid sequence which has at least 70%, 75%, 80%, 85%, 90%, 95%, 96%, 97% or 98% identity therewith, or may be encoded by any one of the nucleotide sequences shown as SEQ ID Nos. 36, 39, 42, 44, 46, or 48 or a nucleotide sequence which has at least 70%, 75%, 80%, 85%, 90%, 95%, 96%, 97% or 98% identity therewith.

In one embodiment, the nucleotide sequence encoding a lipid acyltransferase enzyme for use any one of the methods and/or uses of the present invention is selected from the group consisting of:
 a) a nucleic acid comprising a nucleotide sequence shown in SEQ ID NO: 36;
 b) a nucleic acid which is related to the nucleotide sequence of SEQ ID NO: 36 by the degeneration of the genetic code; and
 c) a nucleic acid comprising a nucleotide sequence which has at least 70% identity with the nucleotide sequence shown in SEQ ID NO: 36.

In one embodiment, the lipid acyltransferase enzyme for use any one of the methods and/or uses of the present invention is a lipid acyltransferase that comprises an amino acid sequence as shown in SEQ ID NO: 37 or an amino acid sequence which has at least 60% identity thereto.

In a further embodiment the lipid acyltransferase enzyme for use any one of the methods and/or uses of the present invention may be a lipid acyltransferase comprising any one of the amino acid sequences shown as SEQ ID NOS: 37, 38, 40, 41, 43, 45 or 47 or an amino acid sequence which has at least 70%, 75%, 80%, 85%, 90%, 95%, 96%, 97% or 98% identity therewith, or may be encoded by any one of the nucleotide sequences shown as SEQ ID No. 39, 42, 44, 46 or 48 or a nucleotide sequence which has at least 70%, 75%, 80%, 85%, 90%, 95%, 96%, 97% or 98% identity therewith.

In a further embodiment the lipid acyltransferase enzyme for use any one of the methods and/or uses of the present invention may be a lipid acyltransferase comprising any one of amino sequences shown as SEQ ID NOS: 38, 40, 41, 45 or 47 or an amino acid sequence which has at least 70%, 75%, 80%, 85%, 90%, 95%, 96%, 97% or 98% identity therewith for the uses described herein.

In a further embodiment the lipid acyltransferase for use in any one of the methods and/or uses of the present invention may be a lipid acyltransferase comprising any of amino sequences shown as SEQ ID NOS: 38, 40, or 47 or an amino acid sequence which has at least 70%, 75%, 80%, 85%, 90%, 95%, 96%, 97% or 98% identity therewith for the uses described herein.

More preferably in one embodiment the lipid acyltransferase for use in any one of the methods and/or uses of the present invention may be a lipid acyltransferase comprising the amino acid sequence shown as SEQ ID NOS: 47 or an amino acid sequence which has at least 70%, 75%, 80%, 85%, 90%, 95%, 96%, 97% or 98% identity therewith.

In another embodiment the lipid acyltransferase for use in any one of the methods and uses of the present invention may be a lipid acyltransferase comprising the amino acid sequence shown as SEQ ID NOS: 43 or 44 or an amino acid sequence which has at least 80%, 85%, 90%, 95%, 96%, 97% or 98% identity therewith.

In another embodiment the lipid acyltransferase for use in any one of the methods and uses of the present invention may be a lipid acyltransferase comprising the amino acid sequence shown as SEQ ID NO: 41 or an amino acid sequence which has at least 70%, 75%, 80%, 85%, 90%, 95%, 96%, 97% or 98% identity therewith.

In one embodiment the lipid acyltransferase for use in any one of the methods and uses of the present invention may be encoded by a nucleic acid selected from the group consisting of:
 a) a nucleic acid comprising a nucleotide sequence shown in SEQ ID NO: 36;
 b) a nucleic acid which is related to the nucleotide sequence of SEQ ID NO: 36 by the degeneration of the genetic code; and
 c) a nucleic acid comprising a nucleotide sequence which has at least 70% identity with the nucleotide sequence shown in SEQ ID NO: 36.

In one embodiment the lipid acyltransferase according to the present invention may be a lipid acyltransferase obtainable, preferably obtained, from the *Streptomyces* strains L130 or L131 deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 25 Jun. 2004 under accession numbers NCIMB 41226 and NCIMB 41227, respectively.

Suitable nucleotide sequences encoding a lipid acyltransferase for use in any one of the methods and/or uses of the present invention may encode a polynucleotide encoding a lipid acyltransferase (SEQ ID NO: 16); or may encode an amino acid sequence of a lipid acyltransferase (SEQ ID NO: 16).

A suitable lipid acyltransferases for use in any one of the methods and/or uses of the present invention may be an amino acid sequence which may be identified by alignment to the L131 (SEQ ID NO: 37) sequence using Align X, the Clustal W pairwise alignment algorithm of Vector NTI using default settings.

An alignment of the L131 and homologues from *S. avermitilis* and *T. fusca* illustrates that the conservation of the GDSX (SEQ ID NO: 120) motif (GDSY (SEQ ID NO: 125) in L131 and *S. avermitilis* and *T. fusca*), the GANDY (SEQ ID NO: 118) box, which is either GGNDA (SEQ ID NO: 123) or GGNDL (SEQ ID NO: 124), and the HPT block (considered to be the conserved catalytic histidine). These three conserved blocks are highlighted in FIG. 42.

When aligned to either the pfam Pfam00657 consensus sequence (as described in WO04/064987) and/or the L131 sequence herein disclosed (SEQ ID No 37) it is possible to identify three conserved regions, the GDSX (SEQ ID NO: 120) block, the GANDY (SEQ ID NO: 118) block and the HTP block (see WO04/064987 for further details).

When aligned to either the pfam Pfam00657 consensus sequence (as described in WO04/064987) and/or the L131 sequence herein disclosed (SEQ ID NO: 37)
 i) The lipid acyltransferase for use in any one of the methods and uses of the present invention may be a lipid acyltransferase that has a GDSX (SEQ ID NO: 120) motif, more preferably a GDSX (SEQ ID NO: 120) motif selected from GDSL (SEQ ID NO: 122) or GDSY (SEQ ID NO: 125) motif
 and/or
 ii) The lipid acyltransferase for use in any one of the methods and uses of the present invention may be a lipid acyltransferase that, has a GANDY (SEQ ID NO: 118) block, more preferably a GANDY (SEQ ID NO: 118) block comprising amino GGNDx (SEQ ID NO: 126), more preferably GGNDA (SEQ ID NO: 123) or GGNDL (SEQ ID NO: 124).

and/or iii) The lipid acyltransferase for use in any one of the methods and uses of the present invention may be a lipid acyltransferase that has preferably an HTP block.
and preferably iv) the lipid acyltransferase for use in any one of the methods and uses of the present invention may be a lipid acyltransferase that has preferably a GDSX (SEQ ID NO: 120) or GDSY (SEQ ID NO: 125) motif, and a GANDY (SEQ ID NO: 118) block comprising amino GGNDx (SEQ ID NO: 126), preferably GGNDA (SEQ ID NO: 123) or GGNDL (SEQ ID NO: 124), and a HTP block (conserved histidine).

Without wishing to be bound by theory the reaction of the lipid acyltransferase and lecithin naturally present in the UHT milk can be used to change the surface activity of the native components of the milk and/or it can be used to reduce the amount of cholesterol in the milk.

The lipid acyltransferase as used herein may be referred to as a glycerophospholipid cholesterol acyltransferase. In other words the lipid acyltransferase for use in the present invention preferably has the ability to "hydrolyse" phospholipids and at the same time esterify cholesterol with the free fatty acid from the hydrolyzation this is effective a tranferase reaction (i.e. an interesterification and/or a transesterification reaction.

The degree of "hydrolysis" can be described as the ratio of phosphatidylcholine (PC) and/or phosphatidylethanolamine (PE) converted into lyso-PC or lyso-PE respectively. By the enzymatic hydrolyzation of PC into lyso-PC, the ratio between the hydrophilic part of the phospholipid molecule (polar head group) and the hydrophobic part (fatty acid chains) is altered. By removing one fatty acid (saturated and/or unsaturated fatty acids) the hydrophobic part is reduced, thus making the entire molecule more hydrophilic. Furthermore the sterical molecule conformation may be changed, which may influence phase structures (e.g. micellation) formed by the molecules in dispersion, as well as interactions with other molecules like e.g. milk proteins.

Lyso-lecithin products are known to possess improved emulsifying properties. With a high degree of interesterification and/or transesterification it is possible to obtain smaller mean oil droplet sizes in a comparative emulsification test.

By changing cholesterol into cholesterol-ester along with a change of PC and PE to lyso-PC and lyso-PE (which both have superior surface activity compared to normal PC/PE) it is possible to produce UHT milk products without cholesterol and with improved emulsion stability. This is important in the production of UHT milk and in particular in the production of flavored UHT milk, where one of the main defects is related to low emulsion stability and a high rate of creaming.

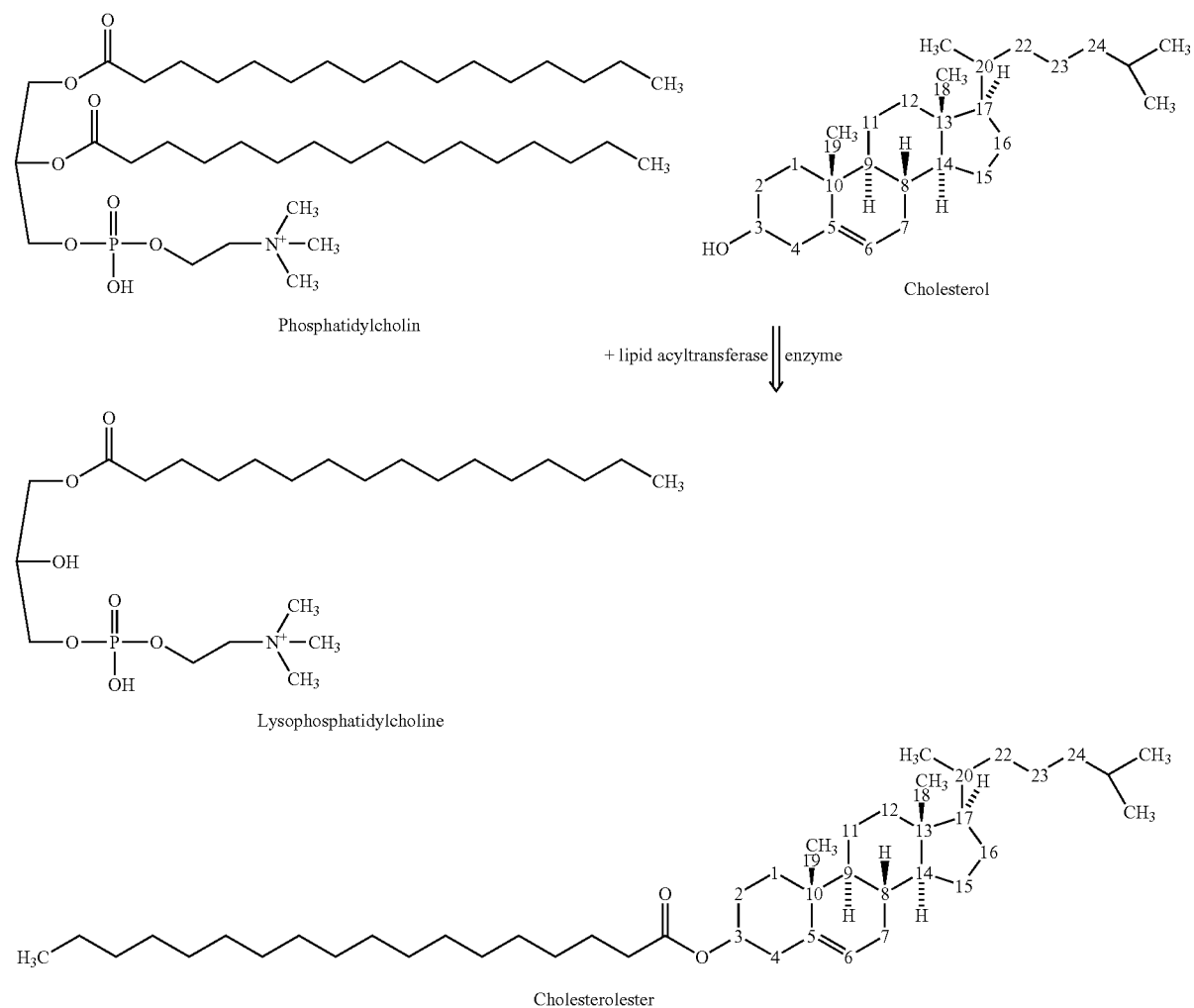

The use of the lipid acyltransferase as defined herein results in smaller particles in the milk which is an advantage in UHT milk, where creaming is very often seen as a defect.

The function of lipid acyltransferase is that cholesterol and phospholipids will be changed into cholesterol-esters and lyso-phospholipids, giving two resulting components with surface-active properties in relation to O/W emulsions. It has been shown that lipid acyltransferases promote increased stability against creaming as well as reduced cholesterol level in UHT milk. Thus the final products will contain no or significantly reduced cholesterol and have an improved emulsion stability.

The enzyme according to the present invention is preferably not a phospholipase enzyme, such as a phospholipase A1 classified as E.C. 3.1.1.32 or a phospholipase A2 classified as E.C. 3.1.1.4.

Variant Lipid Acyl Transferase

In a preferred embodiment the nucleotide sequence encoding a lipid acyltransferase for use in any one of the methods and/or uses of the present invention may encode a lipid acyltransferase that is a variant lipid acyl transferase.

Variants which have an increased activity on phospholipids, such as increased hydrolytic activity and/or increased transferase activity, preferably increased transferase activity on phospholipids may be used.

Preferably the variant lipid acyltransferase is prepared by one or more amino acid modifications of the lipid acyl transferases as defined hereinabove.

Suitably, the lipid acyltransferase for use in any one of the methods and uses of the present invention may be a lipid acyltransferase that may be a variant lipid acyltransferase, in which case the enzyme may be characterised in that the enzyme comprises the amino acid sequence motif GDSX (SEQ ID NO: 117), wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7 (as defined WO2005/066347 and hereinbelow).

For instance the variant lipid acyltransferase may be characterised in that the enzyme comprises the amino acid sequence motif GDSX (SEQ ID NO: 117), wherein X is one or more of the following amino acid residues L, A, V, I, F, Y, H, Q, T, N, M or S, and wherein the variant enzyme comprises one or more amino acid modifications compared with a parent sequence at any one or more of the amino acid residues detailed in set 2 or set 4 or set 6 or set 7 (as defined in WO2005/066347 and hereinbelow) identified by said parent sequence being structurally aligned with the structural model of P10480 defined herein, which is preferably obtained by structural alignment of P10480 crystal structure coordinates with 1IVN.PDB and/or 1DEO.PDB as defined WO2005/066347 and hereinbelow.

In a further embodiment a lipid acyltransferase for use in any one of the methods and/or uses of the present invention may be a variant lipid acyltransferase that may be characterised in that the enzyme comprises the amino acid sequence motif GDSX (SEQ ID NO: 117), wherein X is one or more of the following amino acid residues L, A, V, I, F, Y, H, Q, T, N, M or S, and wherein the variant enzyme comprises one or more amino acid modifications compared with a parent sequence at any one or more of the amino acid residues taught in set 2 identified when said parent sequence is aligned to the pfam consensus sequence (SEQ ID NO: 2—FIG. 3) and modified according to a structural model of P 10480 to ensure best fit overlap as defined WO2005/066347 and hereinbelow.

Suitably a lipid acyltransferase for use in any one of the methods and uses of the present invention may be a variant lipid acyltransferase enzyme that may comprise an amino acid sequence, which amino acid sequence is shown as SEQ ID NO: 34, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 1, SEQ ID NO: 15, SEQ ID NO: 25, SEQ ID NO: 26, SEQ ID NO: 27, SEQ ID NO: 28, SEQ ID NO: 29, SEQ ID NO: 30—SEQ ID NO: 32, SEQ ID NO: 33 or SEQ ID NO: 35 except for one or more amino acid modifications at any one or more of the amino acid residues defined in set 2 or set 4 or set 6 or set 7 (as defined WO2005/066347 and hereinbelow) identified by sequence alignment with SEQ ID NO: 34.

Alternatively the lipid acyltransferase may be a variant lipid acyltransferase enzyme comprising an amino acid sequence, which amino acid sequence is shown as SEQ ID NO: 34, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 1, SEQ ID NO: 15, SEQ ID NO: 25, SEQ ID NO: 26, SEQ ID NO: 27, SEQ ID NO: 28, SEQ ID NO: 29, SEQ ID NO: 30, SEQ ID NO: 32, SEQ ID NO: 33 or SEQ ID NO: 35 except for one or more amino acid modifications at any one or more of the amino acid residues defined in set 2 or set 4 or set 6 or set 7 as defined WO2005/066347 and hereinbelow, identified by said parent sequence being structurally aligned with the structural model of P10480 defined herein, which is preferably obtained by structural alignment of P10480 crystal structure coordinates with 1IVN.PDB and/or 1DEO.PDB as taught within WO2005/066347 and hereinbelow.

Alternatively, the lipid acyltransferase may be a variant lipid acyltransferase enzyme comprising an amino acid sequence, which amino acid sequence is shown as SEQ ID NO: 34, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 1, SEQ ID NO: 15, SEQ ID NO: 25, SEQ ID NO: 26, SEQ ID NO: 27, SEQ ID NO: 28, SEQ ID NO: 29, SEQ ID NO: 30, SEQ ID NO: 32, SEQ ID NO: 33 or SEQ ID NO: 35 except for one or more amino acid modifications at any one or more of the amino acid residues taught in set 2 identified when said parent sequence is aligned to the pfam consensus sequence (SEQ ID NO: 2) and modified according to a structural model of P10480 to ensure best fit overlap as taught within WO2005/066347 and hereinbelow.

Preferably, the parent enzyme is an enzyme which comprises, or is homologous to, the amino acid sequence shown as SEQ ID NO: 34 and/or SEQ ID NO: 15 and/or SEQ ID No. 35.

Preferably, the lipid acyltransferase may be a variant enzyme which comprises an amino acid sequence, which amino acid sequence is shown as SEQ ID NO: 34 or SEQ ID NO: 35 except for one or more amino acid modifications at any one or more of the amino acid residues defined in set 2 or set 4 or set 6 or set 7 as defined in WO2005/066347 and hereinbelow.

Definition of Sets

Amino Acid Set 1:

Amino acid set 1 (note that these are amino acids in 1IVN—FIG. 53 and FIG. 54) (residues at positions 8-12, 69-76, and 106-110 disclosed as SEQ ID NOS 127-129, respectively) Gly8, Asp9, Ser10, Leu11, Ser12, Tyr15, Gly44, Asp45, Thr46, Glu69, Leu70, Gly71, Gly72, Asn73, Asp74, Gly75, Leu76, Gln106, Ile107, Arg108, Leu109, Pro110, Tyr113, Phe121, Phe139, Phe140, Met141, Tyr145, Met151, Asp154, His157, Gly155, Ile156, Pro158 The highly conserved motifs, such as GDSX (SEQ ID NO: 120) and catalytic residues, were deselected from set 1 (residues underlined). For the avoidance of doubt, set 1 defines the amino acid residues within 10 .ANG. of the central carbon atom of a glycerol in the active site of the 1IVN model.

Amino Acid Set 2:

Amino acid set 2 (note that the numbering of the amino acids refers to the amino acids in the P10480 mature sequence) (residues at positions 159-172 disclosed as SEQ ID NO: 130)

Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Met209, Leu210, Arg211, Asn215, Lys284, Met285, Gln289 and Val290.

Table of Selected Residues in Set 1 Compared with Set 2 (Column 1 Discloses Residues at Positions 8-12, 69-76, 106-110, and 154-158, as SEQ ID NOS 127-129 And 131, Respectively; Column 2 Discloses Residues at Positions 32-36, 129-136, and 306-310 as SEQ ID NOS 132-134, Respectively; Column 4 Discloses Residues at Positions 159-172 as SEQ ID NO: 130):

| IVN model IVN A. hyd homologue | | | P10480 Mature sequence Residue |
|---|---|---|---|
| PFAM | Structure | | Number |
| Gly8 | Gly32 | | |
| Asp9 | Asp33 | | |
| Ser10 | Ser34 | | |
| Leu11 | Leu35 | | Leu17 |
| Ser12 | Ser36 | | Ser18 |
| | | | Lys22 |
| | | | Met23 |
| Tyr15 | Gly58 | | Gly40 |
| Gly44 | Asn98 | | Asn80 |
| Asp45 | Pro99 | | Pro81 |
| Thr46 | Lys100 | | Lys82 |
| | | | Asn87 |
| | | | Asn88 |
| Glu69 | Trp129 | | Trp111 |
| Leu70 | Val130 | | Val112 |
| Gly71 | Gly131 | | |
| Gly72 | Ala132 | | Ala114 |
| Asn73 | Asn133 | | |
| Asp74 | Asp134 | | |
| Gly75 | Tyr135 | | Tyr117 |
| Leu76 | Leu136 | | Leu118 |
| Gln106 | | Pro174 | Pro156 |
| Ile107 | | Gly177 | Gly159 |
| Arg108 | | Gln178 | Gln160 |
| Leu109 | | Asn179 | Asn161 |
| Pro110 | | 180 to 190 | Pro162 |
| Tyr113 | | | Ser163 |
| | | | Ala164 |
| | | | Arg165 |
| | | | Ser166 |
| | | | Gln167 |
| | | | Lys168 |
| | | | Val169 |
| | | | Val170 |
| | | | Glu171 |
| | | | Ala172 |
| Phe121 | His198 | Tyr197 | Tyr179 |
| | | His198 | His180 |
| | | Asn199 | Asn181 |
| Phe139 | Met227 | | Met209 |
| Phe140 | Leu228 | | Leu210 |
| Met141 | Arg229 | | Arg211 |
| Tyr145 | Asn233 | | Asn215 |
| | | | Lys284 |
| Met151 | Met303 | | Met285 |
| Asp154 | Asp306 | | |
| Gly155 | Gln307 | | Gln289 |
| Ile156 | Val308 | | Val290 |
| His157 | His309 | | |
| Pro158 | Pro310 | | |

Amino Acid Set 3:

Amino acid set 3 is identical to set 2 but refers to the *Aeromonas salmonicida* (SEQ ID NO: 4) coding sequence, i.e. the amino acid residue numbers are 18 higher in set 3 as this reflects the difference between the amino acid numbering in the mature protein (SEQ ID NO: 34) compared with the protein including a signal sequence (SEQ ID NO: 3).

The mature proteins of *Aeromonas salmonicida* GDSX ('GDSX' disclosed as SEQ ID NO: 120) (SEQ ID NO: 4) and *Aeromonas hydrophila* GDSX ('GDSX' disclosed as SEQ ID NO: 120) (SEQ ID NO: 34) differ in five amino acids. These are Thr3Ser, Gln182Lys, Glu309Ala, Ser310Asn, and Gly318-, where the salmonicida residue is listed first and the hydrophila residue is listed last. The hydrophila protein is only 317 amino acids long and lacks a residue in position 318. The *Aeromonas salmonicida* GDSX ('GDSX' disclosed as SEQ ID NO: 120) has considerably high activity on polar lipids such as galactolipid substrates than the *Aeromonas hydrophila* protein. Site scanning was performed on all five amino acid positions.

Amino Acid Set 4:

Amino acid set 4 is S3, Q182, E309, S310, and -318.

Amino Acid Set 5:

F13S, D15N, S18G, S18V, Y30F, D116N, D116E, D157 N, Y226F, D228N Y230F.

Amino Acid Set 6:

Amino acid set 6 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, -318. Residues at positions 159-172 and 179-182 disclosed as SEQ ID NOS 130 and 135, respectively.

The numbering of the amino acids in set 6 refers to the amino acids residues in P 10480 (SEQ ID NO: 3)—corresponding amino acids in other sequence backbones can be determined by homology alignment and/or structural alignment to P10480 and/or 1IVN.

Amino Acid Set 7:

Amino acid set 7 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, -318, Y30X (where X is selected from A, C, D, E, G, H, I, K, L, M, N, P, Q, R, S, T, V, or W), Y226X (where X is selected from A, C, D, E, G, H, I, K, L, M, N, P, Q, R, S, T, V, or W), Y230X (where X is selected from A, C, D, E, G, H, I, K, L, M, N, P, Q, R, S, T, V, or W), S18X (where X is selected from A, C, D, E, F, H, I, K, L, M, N, P, Q, R, T, W or Y), D157X (where X is selected from A, C, E, F, G, H, I, K, L, M, P, Q, R, S, T, V, W or Y). Residues at positions 159-172 and 179-182 disclosed as SEQ ID NOS 130 and 135, respectively.

The numbering of the amino acids in set 7 refers to the amino acids residues in P10480 (SEQ ID NO: 3)—corresponding amino acids in other sequence backbones can be determined by homology alignment and/or structural alignment to P10480 and/or 1IVN).

Suitably, the variant enzyme comprises one or more of the following amino acid modifications compared with the parent enzyme:
S3E, A, G, K, M, Y, R, P, N, T or G
E309Q, R or A, preferably Q or R
-318Y, H, S or Y, preferably Y.

Preferably, X of the GDSX motif is L (SEQ ID NO: 122). Thus, preferably the parent enzyme comprises the amino acid motif GDSL (SEQ ID NO: 122).

Suitably, said first parent lipid acyltransferase may comprise any one of the following
amino acid sequences: SEQ ID NO: 34, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 1, SEQ ID NO: 15, SEQ ID NO: 25, SEQ ID NO: 26, SEQ ID NO: 27, SEQ ID NO: 28, SEQ ID NO: 29, SEQ ID NO: 30, SEQ ID NO: 32, SEQ ID NO: 33 or SEQ ID NO: 35.

Suitably, said second related lipid acyltransferase may comprise any one of the following amino acid sequences: SEQ ID NO: 3, SEQ ID NO: 34, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 1, SEQ ID NO: 15, SEQ ID NO: 25, SEQ ID NO: 26, SEQ ID NO: 27, SEQ ID NO: 28, SEQ ID NO: 29, SEQ ID NO: 30, SEQ ID NO: 32, SEQ ID NO: 33 or SEQ ID NO: 35.

The variant enzyme must comprise at least one amino acid modification compared with the parent enzyme. In some embodiments, the variant enzyme may comprise at least 2, preferably at least 3, preferably at least 4, preferably at least 5, preferably at least 6, preferably at least 7, preferably at least 8, preferably at least 9, preferably at least 10 amino acid modifications compared with the parent enzyme.

When referring to specific amino acid residues herein the numbering is that obtained from alignment of the variant sequence with the reference sequence shown as SEQ ID NO: 34 or SEQ ID NO: 35.

In one aspect preferably the variant enzyme comprises one or more of the following amino acid substitutions:
S3A, C, D, E, F, G, H, I, K, L, M, N, P, Q, R, T, V, W, or Y; and/or
L17A, C, D, E, F, G, H, I, K, M, N, P, Q, R, S, T, V, W, or Y; and/or
S18A, C, D, E, F, H, I, K, L, M, N, P, Q, R, T, W, or Y; and/or
K22A, C, D, E, F, G, H, I, L, M, N, P, Q, R, S, T, V, W, or Y; and/or
M23A, C, D, E, F, G, H, I, K, L, N, P, Q, R, S, T, V, W, or Y; and/or
Y30A, C, D, E, G, H, I, K, L, M, N, P, Q, R, S, T, V, or W; and/or
G40A, C, D, E, F, H, I, K, L, M, N, P, Q, R, S, T, V, W, or Y; and/or
N80A, C, D, E, F, G, H, I, K, L, M, P, Q, R, S, T, V, W, or Y; and/or
P81A, C, D, E, F, G, H, I, K, L, M, N, Q, R, S, T, V, W, or Y; and/or
K82A, C, D, E, F, G, H, I, L, M, N, P, Q, R, S, T, V, W, or Y; and/or
N87A, C, D, E, F, G, H, I, K, L, M, P, Q, R, S, T, V, W, or Y; and/or
N88A, C, D, E, F, G, H, I, K, L, M, P, Q, R, S, T, V, W, or Y; and/or
W111A, C, D, E, F, G, H, I, K, L, M, N, P, Q, R, S, T, V, W or Y; and/or
V112A, C, D, E, F, G, H, I, K, L, M, N, P, Q, R, S, T, W, or Y; and/or
A114C, D, E, F, G, H, I, K, L, M, N, P, Q, R, S, T, V, W, or Y; and/or
Y117A, C, D, E, F, G, H, I, K, L, M, N, P, Q, R, S, T, V, or W; and/or
L118A, C, D, E, F, G, H, I, K, M, N, P, Q, R, S, T, V, W, or Y; and/or
P156A, C, D, E, F, G, H, I, K, L, M, N, Q, R, S, T, V, W, or Y; and/or
D157A, C, E, F, G, H, I, K, L, M, P, Q, R, S, T, V, W, or Y; and/or
G159A, C, D, E, F, H, I, K, L, M, N, P, Q, R, S, T, V, W, or Y; and/or
Q160A, C, D, E, F, G, H, I, K, L, M, N, P, R, S, T, V, W, or Y; and/or
N161A, C, D, E, F, G, H, I, K, L, M P, Q, R, S, T, V, W, or Y; and/or
P162A, C, D, E, F, G, H, I, K, L, M, N, Q, R, S, T, V, W, or Y; and/or
S163A, C, D, E, F, G, H, I, K, L, M, N, P, Q, R, T, V, W, or Y; and/or
A164C, D, E, F, G, H, I, K, L, M, N, P, Q, R, S, T, V, W, or Y; and/or
R165A, C, D, E, F, G, H, I, K, L, M, N, P, Q, S, T, V, W, or Y; and/or
S166A, C, D, E, F, G, H, I, K, L, M, N, P, Q, R, T, V, W, or Y; and/or
Q167A, C, D, E, F, G, H, I, K, L, M, N, P, R, S, T, V, W, or Y; and/or
K168A, C, D, E, F, G, H, I, L, M, N, P, Q, R, S, T, V, W, or Y; and/or
V169A, C, D, E, F, G, H, I, K, L, M, N, P, Q, R, S, T, W, or Y; and/or
V170A, C, D, E, F, G, H, I, K, L, M, N, P, Q, R, S, T, W, or Y; and/or
E171A, C, D, F, G, H, I, K, L, M, N, P, Q, R, S, T, V, W, or Y; and/or
A172C, D, E, F, G, H, I, K, L, M, N, P, Q, R, S, T, V, W, or Y; and/or
Y179A, C, D, E, F, G, H, I, K, L, M, N, P, Q, R, S, T, V, or W; and/or
H180A, C, D, E, F, G, I, K, L, M, P, Q, R, S, T, V, W, or Y; and/or
N181A, C, D, E, F, G, H, I, K, L, M, P, Q, R, S, T, V, W, or Y; and/or
Q182A, C, D, E, F, G, H, I, K, L, M, N, P, R, S, T, V, W, or Y, preferably K; and/or
M209A, C, D, E, F, G, H, I, K, L, N, P, Q, R, S, T, V, W, or Y; and/or
L210 A, C, D, E, F, G, H, I, K, M, N, P, Q, R, S, T, V, W, or Y; and/or
R211A, C, D, E, F, G, H, I, K, L, M, N, P, Q, S, T, V, W, or Y; and/or
N215 A, C, D, E, F, G, H, I, K, L, M, N, P, Q, R, S, T, V, W, or Y; and/or Y226A, C, D, E, G, H, I, K, L, M, N, P, Q, R, S, T, V, or W; and/or
Y230A, C, D, E, G, H, I, K, L, M, N, P, Q, R, S, T, V or W; and/or
K284A, C, D, E, F, G, H, I, L, M, N, P, Q, R, S, T, V, W, or Y; and/or
M285A, C, D, E, F, G, H, I, K, L, N, P, Q, R, S, T, V, W, or Y; and/or
Q289A, C, D, E, F, G, H, I, K, L, M, N, P, R, S, T, V, W, or Y; and/or
V290A, C, D, E, F, G, H, I, K, L, M, N, P, Q, R, S, T, W, or Y; and/or
E309A, C, D, F, G, H, I, K, L, M, N, P, Q, R, S, T, V, W, or Y; and/or
S310A, C, D, E, F, G, H, I, K, L, M, N, P, Q, R, T, V, W, or Y.

In addition or alternatively thereto there may be one or more C-terminal extensions. Preferably the additional C-terminal extension is comprised of one or more aliphatic amino acids, preferably a non-polar amino acid, more preferably of I, L, V or G. Thus, the present invention further provides for a variant enzyme comprising one or more of the following C-terminal extensions: 318I, 318L, 318V, 318G.

Preferred variant enzymes may have a decreased hydrolytic activity against a phospholipid, such as phosphatidylcholine (PC), may also have an increased transferase activity from a phospholipid.

Preferred variant enzymes may have an increased transferase activity from a phospholipid, such as phosphatidylcholine (PC), these may also have an increased hydrolytic activity against a phospholipid.

Modification of one or more of the following residues may result in a variant enzyme having an increased absolute transferase activity against phospholipid:
S3, D157, S310, E309, Y179, N215, K22, Q289, M23, H180, M209, L210, R211, P81, V112, N80, L82, N88; N87

Specific preferred modifications which may provide a variant enzyme having an improved transferase activity from a phospholipid may be selected from one or more of the following:
S3A, C, D, E, F, G, H, I, K, L, M, N, P, Q, R, T, V, W or Y; preferably N, E, K, R, A, P or M, most preferably S3A
D157A, C, E, F, G, H, I, K, L, M, N, P, Q, R, S, T, V, W or Y; preferably D157S, R, E, N, G, T, V, Q, K or C
S310A, C, D, E, F, G, H, I, K, L, M, N, P, Q, R, T, V, W or Y; preferably S310T
-318 E
E309A, C, D, E, F, G, H, I, K, L, M, N, P, Q, R, T, V, W or Y; preferably E309 R, E, L, R or A
Y179A, C, D, E, F, G, H, I, K, L, M, N, P, Q, R, S, T, V or W; preferably Y179 D, T, E, R, N, V, K, Q or S, more preferably E, R, N, V, K or Q
N215A, C, D, E, F, G, H, I, K, L, M, P, Q, R, S, T, V, W or Y; preferably N215 S, L, R or Y
K22A, C, D, E, F, G, H, I, L, M, N, P, Q, R, S, T, V, W or Y; preferably K22 E, R, C or A
Q289A, C, D, E, F, G, H, I, K, L, M, N, P, R, S, T, V, W or Y; preferably Q289 R, E, G, P or N
M23A, C, D, E, F, G, H, I, K, L N, P, Q, R, S, T, V, W or Y; preferably M23 K, Q, L, G, T or S
H180A, C, D, E, F, G, I, K, L, M, P, Q, R, S, T, V, W or Y; preferably H180 Q, R or K
M209 A, C, D, E, F, G, H, I, K, L, N, P, Q, R, S, T, V, W or Y; preferably M209 Q, S, R, A, N, Y, E, V or L
L210A, C, D, E, F, G, H, I, K, M, N, P, Q, R, S, T, V, W or Y; preferably L210 R, A, V, S, T, I, W or M
R211A, C, D, E, F, G, H, I, K, L, M, N, P, Q, S, T, V, W or Y; preferably R211T P81A, C, D, E, F, G, H, I, K, L, M, N, Q, R, S, T, V, W or Y; preferably P81G
V112A, C, D, E, F, G, H, I, K, L, M, N, P, Q, R, S, T, W or Y; preferably V112C
N80A, C, D, E, F, G, H, I, K, L, M, P, Q, R, S, T, V, W or Y; preferably N80 R, G, N, D, P, T, E, V, A or G
L82A, C, D, E, F, G, H, I, M, N, P, Q, R, S, T, V, W or Y; preferably L82N, S or E
N88A, C, D, E, F, G, H, I, K, L, M, P, Q, R, S, T, V, W or Y; preferably N88C
N87A, C, D, E, F, G, H, I, K, L, M, P, Q, R, S, T, V, W or Y; preferably N87M or G Preferred modification of one or more of the following residues results in a variant enzyme having an increased absolute transferase activity against phospholipid:
S3 N, R, A, G
M23 K, Q, L, G, T, S
H180 R
L82 G
Y179 E, R, N, V, K or Q
E309 R, S, L or A One preferred modification is N80D. This is particularly the case when using the reference sequence SEQ ID NO: 35 as the backbone. Thus, the reference sequence may be SEQ ID NO: 16. This modification may be in combination with one or more further modifications. Therefore in a preferred embodiment of the present invention the nucleotide sequence encoding a lipid acyltransferase for use in any one of the methods and uses of the present invention may encode a lipid acyltransferase that comprises SEQ ID No. 35 or an amino acid sequence which has 75% or more, preferably 85% or more, more preferably 90% or more, even more preferably 95% or more, even more preferably 98% or more, or even more preferably 99% or more identity to SEQ ID NO: 35.

As noted above, when referring to specific amino acid residues herein the numbering is that obtained from alignment of the variant sequence with the reference sequence shown as SEQ ID NO: 34 or SEQ ID NO: 35

Much by preference, the nucleotide sequence encoding a lipid acyltransferase for use in any one of the methods and uses of the present invention may encode a lipid comprising the amino acid sequence shown as SEQ ID NO: 16 or the amino acid sequence shown as SEQ ID NO: 68, or an amino acid sequence which has 70% or more, preferably 75% or more, preferably 85% or more, more preferably 90% or more, even more preferably 95% or more, even more preferably 98% or more, or even more preferably 99% or more identity to SEQ ID NO: 16 or SEQ ID NO: 68. This enzyme may be considered a variant enzyme.

For the purposes of the present invention, the degree of identity is based on the number of sequence elements which are the same. The degree of identity in accordance with the present invention for amino acid sequences may be suitably determined by means of computer programs known in the art, such as Vector NTI 10 (Invitrogen Corp.). For pairwise alignment the score used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

Suitably, the nucleotide sequence encoding a lipid acyltransferase or the lipid acyl transferase enzyme for use in the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium*.

Suitably, the nucleotide sequence encoding a lipid acyltransferase or the lipid acyl transferase enzyme for use in the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Streptomyces thermosacchari, Streptomyces avermitilis Lactobacillus helveticus, Desulfitobacterium dehalogenans, Bacillus sp, Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis Thermobifida fusca* and *Corynebacterium efficiens*.

In one aspect, preferably the nucleotide sequence encoding a lipid acyltransferase for use in any one of the methods and/or uses of the present invention encodes a lipid acyl transferase enzyme according to the present invention is obtainable, preferably obtained or derived, from one or more of *Aeromonas* spp., *Aeromonas hydrophila* or *Aeromonas salmonicida*.

In one aspect, preferably the lipid acyltransferase for use in any one of the methods and/or uses of the present invention is a lipid acyl transferase enzyme obtainable, preferably obtained or derived, from one or more of *Aeromonas* spp., *Aeromonas hydrophila* or *Aeromonas salmonicida*.

Enzymes which function as lipid acyltransferases in accordance with the present invention can be routinely identified using the assay taught herein below:

Assay for Transferase Activity

The transferase activity is preferably measured by the molar amount of cholesterol ester formed by acyltransfer from phospholipids and/or lipids in milk to cholesterol relative to the amount of cholesterol originally available.

Milk is incubated with enzyme or water (as control) for 30 minutes at 40° C.

Milk lipids are isolated by solvent extraction and the isolated lipids are analysed by GLC.

Based on GLC analysis the amount of cholesterol (CHL), cholesterol ester (CHLE) and free fatty acids (FFA) are calculated.

$$\% \text{ Transferase} = \frac{(CHLE(t) - CHLE(0)) \times 100}{CHLE(t) - CHLE(0) + (FFA(t) - FFA(0))}$$

Where
CHLE(0)=Mol/l Cholesterol ester Control
CHLE(t)=Mol/l Cholesterol ester Enzyme treatment
FFA(0)=Mol/l Free fatty acids Control
FFA(t)=Mol/l Free fatty acids Enzyme treatment
GLC Analysis May be Carried Out as Follows:
GLC Analysis Perkin Elmer Autosystem 9000 Capillary Gas Chromatograph equipped with WCOT fused silica column 12.5 m×0.25 mm ID×0.1µ film thickness 5% phenyl-methyl-silicone (CP Sil 8 CB from Chrompack).
Carrier gas: Helium.
Injector. PSSI cold split injection (initial temp 50° C. heated to 385° C.), volume 1.0 µl
Detector FID: 395° C.

| | Oven program: | | |
|---|---|---|---|
| | 1 | 2 | 3 |
| Oven temperature, ° C. | 90 | 280 | 350 |
| Isothermal, time, min. | 1 | 0 | 10 |
| Temperature rate, ° C./min. | 15 | 4 | |

Sample preparation: 30 mg of sample was dissolved in 9 ml Heptane:Pyridin, 2:1 containing internal standard heptadecane, 0.5 mg/ml. 300 µl sample solution was transferred to a crimp vial, 300 µl MSTFA (N-Methyl-N-trimethylsilyl-trifluoraceamid) was added and reacted for 20 minutes at 60° C.

Calculation: Response factors for mono-di-triglycerides and free fatty acid were determined from Standard 2 (mono-di-triglyceride), for Cholesterol, Cholesteryl palmitate and Cholesteryl stearate the response factors were determined from pure reference material (weighing for pure material 10 mg).

Using this assay, lipid acyltransferases/lipid acyl transferase in accordance with the present invention are those which have at least 5% transferase activity, preferably at least 10% transferase activity, preferably at least 15%, 20%, 25% 26%, 28%, 30%, 40% 50%, 60% or 75% transferase activity.

The term "transferase" as used herein is interchangeable with the term "lipid acyltransferase".

Suitably, the lipid acyltransferase as defined herein catalyses one or more of the following reactions: interesterification, transesterification, alcoholysis, hydrolysis.

The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule.

The term "without increasing or without substantially increasing the free fatty acids" as used herein means that preferably the lipid acyl transferase according to the present invention has 100% transferase activity (i.e. transfers 100% of the acyl groups from an acyl donor onto the acyl acceptor, with no hydrolytic activity); however, the enzyme may transfer less than 100% of the acyl groups present in the lipid acyl donor to the acyl acceptor. In which case, preferably the acyltransferase activity accounts for at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following the "Assay for Transferase Activity" given above.

In some aspects of the present invention, the term "without substantially increasing free fatty acids" as used herein means that the amount of free fatty acid in a edible oil treated with an lipid acyltransferase according to the present invention is less than the amount of free fatty acid produced in the edible oil when an enzyme other than a lipid acyltransferase according to the present invention had been used, such as for example as compared with the amount of free fatty acid produced when a conventional phospholipase enzyme, e.g. Lecitase Ultra™ (Novozymes A/S, Denmark), had been used.

The term 'milk' as used herein may comprise milk from either animal or vegetable origin. It is possible to use milk from animal sources such as buffalo, (traditional) cow, sheep, goat etc. either individually or combined. Vegetable milks such as soya milk may also be used, normally in combination with the animal milk, typically at a low percentage (of vegetable milk) say below 15%, or below 20%, or below 25% v/v. The term milk preferably does not comprise cheese milk and cream.

The term 'essentially consists' as used herein, when referring to a product or composition, preferably means that the product or composition, may consist of other products or compositions but only to a maximum concentration of, preferably 10%, such as 5%, such as 3%, such as 2% or 1%, or 0.5% or 0.1%.

For the enzyme modification of milk and/or cream for example it may be preferable to use a temperature of less than about 30° C. for example, suitably less than 20° C. for example, suitably less than 10° C. for example. Suitable temperatures of between 1-30° C. may be used, such as between 3-20° C. for example, such as between 1-10° C.

The enzyme according to the present invention may be used with one or more other suitable food grade enzymes. Thus, it is within the scope of the present invention that, in addition to the enzyme of the invention, at least one further enzyme is added to the foodstuff Such further enzymes include starch degrading enzymes such as endo- or exoamylases, pullulanases, debranching enzymes, hemicellulases including xylanases, cellulases, oxidoreductases, e.g. peroxidases, phenol oxidases, glucose oxidase, pyranose oxidase, sulfhydryl oxidase, or a carbohydrate oxidase such as one which oxidises maltose, for example hexose oxidase (HOX), lipases, phospholipases, glycolipases, galactolipases and proteases.

In one embodiment the enzyme may be Dairy HOX™, which acts as an oxygen scavenger to prolong shelf life of cheese while providing browning control in pizza ovens. Therefore in a one aspect the present invention relates to the use of an enzyme capable of reducing the maillard reaction in a foodstuff (see WO02/39828 incorporated herein by reference), such as a dairy product, for example cheese, wherein the enzyme is preferably a maltose oxidising enzyme such as carbohydrate oxidase, glucose oxidase and/or hexose oxidase, in the process or preparing a food material and/or foodstuff according to the present invention.

In one preferred embodiment the lipid acyltransferase is used in combination with a lipase having one or more of the following lipase activities: glycolipase activity (E.C. 3.1.1.26, triacylglycerol lipase activity (E.C. 3.1.1.3), phospholipase A2 activity (E.C. 3.1.1.4) or phospholipase A1 activity (E.C. 3.1.1.32). Suitably, lipolytice enzymes are well know within the art and include by way of example the following lipolytic enzymes: LIPOPAN® F and/or LECITASE® ULTRA (Novozymes A/S, Denmark), phospholipase A2 (e.g. phospholipase A2 from LIPOMOD™ 22L from Biocatalysts, LIPOMAX™ from Genecor), LIPOLASE® (Novozymes A/S, Denmark), the lipases taught in WO03/97835, EP 0 977 869 or EP 1 193 314. This combination of a lipid acyl transferase as defined herein and a lipase may be particularly preferred in dough or baked products or in fine food products such as cakes and confectionary.

In some embodiments, it may also be beneficial to combine the use of lipid acyltransferase with a lipolytic enzymes such as rennet paste prepared from calf, lamb, kid stomachs, or Palatase A750L (Novo), Palatase M200L (Novo), Palatase M1000 (Novo), or Piccantase A (DSM), also Piccantase from animal sources from DSM (K, KL, L & C) or Lipomod 187, Lipomod 338 (Biocatalysts). These lipases are used conventionally in the production of cheese to produce cheese flavours. These lipases may also be used to produce an enzymatically-modified foodstuff, for example a dairy product (e.g. cheese), particularly where said dairy product consists of, is produced from or comprises butterfat. A combination of the lipid acyltransferase with one or more of these lipases may have a beneficial effect on flavour in the dairy product (e.g. cheese for instance).

The use of lipases in combination with the enzyme of the invention may be particularly advantageous in instances where some accumulation of free fatty acids maybe desirable, for example in cheese where the free fatty acids can impart a desirable flavour, or in the preparation of fine foods. The person skilled in the art will be able to combine proportions of lipolytic enzymes, for example LIPOPAN® F and/or LECITASE® ULTRA (Novozymes A/S, Denmark), phospholipase A2 (e.g. phospholipase A2 from LIPOMOD™ 22L from Biocatalysts, LIPOMAX™ from Genecor), LIPOLASE® (Novozymes A/S, Denmark), the lipases taught in WO03/97835, EP 0 977 869 or EP 1 193,314 and the lipid acyltransferase of the present invention to provide the desired ratio of hydrolytic to transferase activity which results in a preferred technical effect or combination of technical effects in the foodstuff (such as those listed herein under 'Technical Effects').

It may also be beneficial to combine the use of lipid acyltransferase with a phospholipase, such as phospholipase A1, phospholipase A2, phospholipase B, Phospholipase C and/or phospholipase D.

The combined use may be performed sequentially or concurrently, e.g. the lipid acyl transferase treatment may occur prior to or during the further enzyme treatment. Alternatively, the further enzyme treatment may occur prior to or during the lipid acyl transferase treatment.

In the case of sequential enzyme treatments, in some embodiments it may be advantageous to remove the first enzyme used, e.g. by heat deactivation or by use of an immobilised enzyme, prior to treatment with the second (and/or third etc.) enzyme.

Post-Transcription and Post-Translational Modifications

Suitably the lipid acyltransferase in accordance with the present invention may be encoded by any one of the nucleotide sequences taught herein.

Depending upon the host cell used post-transcriptional and/or post-translational modifications may be made. It is envisaged that the lipid acyltransferase for use in the present methods and/or uses encompasses lipid acyltransferases which have undergone post-transcriptional and/or post-translational modification.

By way of example only, the expression of the nucleotide sequence shown herein as SEQ ID NO: 49 (see FIG. 57) in a host cell (such as *Bacillus licheniformis* for example) results in post-transcriptional and/or post-translational modifications which lead to the amino acid sequence shown herein as SEQ ID NO: 68 (see FIG. 73).

SEQ ID No. 68 is the same as SEQ ID NO: 16 (shown herein in FIG. 1) except that SEQ ID NO: 68 has undergone post-translational and/or post-transcriptional modification to remove 38 amino acids.

Isolated

In one aspect, the lipid acyltransferase is a recovered/isolated lipid acyltransferase. Thus, the lipid acyltransferase produced may be in an isolated form.

In another aspect, the nucleotide sequence encoding a lipid acyltransferase for use in the present invention may be in an isolated form.

The term "isolated" means that the sequence or protein is at least substantially free from at least one other component with which the sequence or protein is naturally associated in nature and as found in nature.

Purified

In one aspect, the lipid acyltransferase may be in a purified form.

In another aspect, the nucleotide sequence encoding a lipid acyltransferase for use in the present invention may be in a purified form.

The term "purified" means that the sequence is in a relatively pure state—e.g. at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labeled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984) 2, p 646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. No. 6,344,328, U.S. Pat. No. 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, In addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate As will be apparent to a person skilled in the art, using molecular evolution tools an enzyme may be altered to improve the functionality of the enzyme.

Suitably, the nucleotide sequence encoding a lipid acyltransferase used in the invention may encode a variant lipid acyltransferase, i.e. the lipid acyltransferase may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSX (SEQ ID NO: 120), GANDY (SEQ ID NO: 118) and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the nucleotide sequence encoding a lipid acyltransferase for use in any one of the methods and/or uses of the present invention may encode a lipid acyltransferase that may be a variant with enhanced enzyme activity on polar lipids, preferably phospholipids and/or glycolipids when compared to the parent enzyme. Preferably, such variants also have low or no activity on lyso polar lipids. The enhanced activity on polar lipids, phospholipids and/or glycolipids may be the result of hydrolysis and/or transferase activity or a combination of both.

Variant lipid acyltransferases may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme may have increased activity on triglycerides, and/or may also have increased activity on one or more of the following, polar lipids, phospholipids, lecithin, phosphatidylcholine, glycolipids, digalactosyl monoglyceride, monogalactosyl monoglyceride.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J. Biol. Chem. 1991 Jan. 15: 266 (2): 997-1000; Robertson et al J. Biol. Chem. 1994 Jan. 21; 269(3):2146-50; Brumlik et al J. Bacteriol 1996 April; 178 (7): 2060-4; Peelman et al Protein Sci. 1998 March; 7(3):587-99.

Amino Acid Sequences

The present invention also encompasses the use of amino acid sequences encoded by a nucleotide sequence which encodes a lipid acyltransferase for use in any one of the methods and/or uses of the present invention.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 μg of the freeze-dried material may be dissolved in 50 μl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen. 135 µl of water and 5 µg of endoproteinase Lys-C in 5 µl of water may be added to the above reaction mixture and the digestion may be carried out at 37° C. under nitrogen for 24 hours. The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Sequence Identity or Sequence Homology

Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons.

Calculation of maximum % homology therefore firstly requires the production of an optimal alignment, taking into consideration gap penalties. A suitable computer program for carrying out such an alignment is the Vector NTI (Invitrogen Corp.). Examples of other software that can perform sequence comparisons include, but are not limited to, the BLAST™ package (see Ausubel et al 1999 Short Protocols in Molecular Biology, 4.sup.th Ed—Chapter 18), and FASTA (Altschul et al 1990 J. Mol. Biol. 403-410). Both BLAST™ and FASTA are available for offline and online searching (see Ausubel et al 1999, pages 7-58 to 7-60). However, for some applications, it is preferred to use the Vector NTI program. A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST™ suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), *Gene* 73(1), 237-244).

Once the software has produced an optimal alignment, it is possible to calculate % homology, preferably % sequence identity. The software typically does this as part of the sequence comparison and generates a numerical result.

Should Gap Penalties be used when determining sequence identity, then preferably the following parameters are used for pairwise alignment:

| FOR BLAST ™ | |
|---|---|
| GAP OPEN | 0 |
| GAP EXTENSION | 0 |

| FOR CLUSTAL | DNA | PROTEIN | |
|---|---|---|---|
| WORD SIZE | 2 | 1 | K triple |
| GAP PENALTY | 15 | 10 | |
| GAP EXTENSION | 6.66 | 0.1 | |

In one embodiment, preferably the sequence identity for the nucleotide sequences is determined using CLUSTAL with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

In one embodiment the degree of amino acid sequence identity in accordance with the present invention may be suitably determined by means of computer programs known in the art, such as Vector NTI 10 (Invitrogen Corp.). For pairwise alignment the matrix used is preferably BLOSUM62 with Gap opening penalty of 10.0 and Gap extension penalty of 0.1.

Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the degree of identity with regard to an amino acid sequence may be determined over the whole sequence.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | | |
|---|---|---|---|
| ALIPHATIC | Non-polar | G A P | |
| | | I L V | |
| | Polar - uncharged | C S T M | |
| | | N Q | |
| | Polar - charged | D E | |
| | | K R | |
| AROMATIC | | H F W Y | |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses the use of sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses the use of sequences that are complementary to sequences that are capable of hybridising under high stringency conditions or intermediate stringency conditions to nucleotide sequences encoding polypeptides having the specific properties as defined herein.

More preferably, the present invention encompasses the use of sequences that are complementary to sequences that are capable of hybridising under high stringency conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to the use of nucleotide sequences that can hybridise to the nucleotide sequences discussed herein (including complementary sequences of those discussed herein).

The present invention also relates to the use of nucleotide sequences that are complementary to sequences that can hybridise to the nucleotide sequences discussed herein (including complementary sequences of those discussed herein).

Also included within the scope of the present invention are the use of polynucleotide sequences that are capable of hybridising to the nucleotide sequences discussed herein under conditions of intermediate to maximal stringency.

In a preferred aspect, the present invention covers the use of nucleotide sequences that can hybridise to the nucleotide sequences discussed herein, or the complement thereof, under stringent conditions (e.g. 50° C. and 0.2×SSC).

In a more preferred aspect, the present invention covers the use of nucleotide sequences that can hybridise to the nucleotide sequences discussed herein, or the complement thereof, under high stringency conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Organism

The term "organism" in relation to the present invention includes any organism that could comprise a nucleotide sequence according to the present invention or a nucleotide sequence encoding for a polypeptide having the specific properties as defined herein and/or products obtained therefrom.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a promoter not associated with a sequence encoding a lipid acyltransferase in nature.

Transformation of Host Cells/Organism

The host organism can be a prokaryotic or a eukaryotic organism.

Examples of suitable prokaryotic hosts include bacteria such as E. coli and Bacillus licheniformis, preferably B. licheniformis.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of Aspergillus as a host microorganism is described in EP 0 238 023.

Another host organism can be a plant. A review of the general techniques used for transforming plants may be found in articles by Potrykus (Annu Rev Plant Physiol Plant Mol Biol [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera Thermomyces, Acremonium, Aspergillus, Penicillium, Mucor, Neurospora, Trichoderma and the like.

Methods referred to on transforming filamentous fungi are reviewed in U.S. Pat. No. 5,741,665 which states that standard techniques for transformation of filamentous fungi and culturing the fungi are well known in the art. An extensive review of techniques as applied to N crassa is found, for example in Davis and de Serres, Methods Enzymol (1971) 17A: 79-143.

Further teachings on transforming filamentous fungi are reviewed in U.S. Pat. No. 5,674,707.

In one aspect, the host organism can be of the genus Aspergillus, such as Aspergillus niger.

A transgenic Aspergillus according to the present invention can also be prepared by following, for example, referred to in Turner G. 1994 (Vectors for genetic manipulation. In: Martinelli S. D., Kinghorn J. R. (Editors) Aspergillus: 50 years on. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5):200-6, Archer & Peberdy Crit. Rev Biotechnol (1997) 17(4):273-306.

Transformed Yeast

In another embodiment, the transgenic organism can be a yeast.

A review of the principles of heterologous gene expression in yeast are provided in, for example, Methods Mol Biol (1995), 49:341-54, and Curr Opin Biotechnol (1997) October; 8(5):554-60

In this regard, yeast—such as the species Saccharomyces cerevisi or Pichia pastoris (see FEMS Microbiol Rev (2000 24(1):45-66), may be used as a vehicle for heterologous gene expression.

A review of the principles of heterologous gene expression in Saccharomyces cerevisiae and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

For the transformation of yeast, several transformation protocols have been developed. For example, a transgenic

*Saccharomyces* according to the present invention can be prepared by following the teachings of Hinnen et al., (1978, *Proceedings of the National Academy of Sciences of the USA* 75, 1929); Beggs, J D (1978, *Nature*, London, 275, 104); and Ito, H et al (1983, J Bacteriology 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces, Yarrowinia* spp., *Saccharomyces* spp., including *S. cerevisiae*, or *Schizosaccharomyce* spp. including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO01/39544).

Transformed Plants/Plant Cells

A host organism suitable for the present invention may be a plant. A review of the general techniques may be found in articles by Potrykus (*Annu Rev Plant Physiol Plant Mol Biol* 42:205-225) and Christou (Agro-Food-Industry Hi-Tech March/April 1994 17-27), or in WO01/16308. The transgenic plant may produce enhanced levels of phytosterol esters and phytostanol esters, for example.

Therefore the present invention also relates to a method for the production of a transgenic plant with enhanced levels of phytosterol esters and phytostanol esters, comprising the steps of transforming a plant cell with a lipid acyltransferase as defined herein (in particular with an expression vector or construct comprising a lipid acyltransferase as defined herein), and growing a plant from the transformed plant cell.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of secretion leader sequences not associated with a nucleotide sequence encoding a lipid acyltransferase in nature are those originating from the fungal amyloglucosidase (AG) gene (glaA—both 18 and 24 amino acid versions e.g. from *Aspergillus*), the α-factor gene (yeasts e.g. *Saccharomyces, Kluyveromyces* and *Hansenula*) or the α-amylase gene (*Bacillus*).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Also, recombinant immunoglobulins may be produced as shown in U.S. Pat. No. 4,816,567.

Fusion Proteins

The lipid acyltransferase for use in the present invention may be produced as a fusion protein, for example to aid in extraction and purification thereof. Examples of fusion protein partners include glutathione-S-transferase (GST), 6×His (SEQ ID NO: 136), GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):501-6.

The amino acid sequence of a polypeptide having the specific properties as defined herein may be ligated to a non-native sequence to encode a fusion protein. For example, for screening of peptide libraries for agents capable of affecting the substance activity, it may be useful to encode a chimeric substance expressing a non-native epitope that is recognised by a commercially available antibody.

BRIEF DESCRIPTION OF THE DRAWINGS

The detailed description, given by way of example, but not intended to limit the invention solely to the specific embodiments described, may best be understood in conjunction with the accompanying drawings, in which:

FIG. 1 shows the amino acid sequence of a mutant *Aeromonas salmonicida* mature lipid acyltransferase (GCAT) with a mutation of Asn80Asp (notably, amino acid 80 is in the mature sequence) (SEQ ID NO: 16);

FIG. 2 shows an amino acid sequence (SEQ ID NO: 1) a lipid acyl transferase from *Aeromonas hydrophila* (ATCC #7965);

FIG. 3 shows a pfam00657 consensus sequence from database version 6 (SEQ ID NO: 2);

FIG. 4 shows an amino acid sequence (SEQ ID NO: 3) obtained from the organism *Aeromonas hydrophila* (P10480; GI:121051);

FIG. 5 shows an amino acid sequence (SEQ ID NO: 4) obtained from the organism *Aeromonas salmonicida* (AAG098404; GI:9964017);

FIG. 6 shows an amino acid sequence (SEQ ID NO: 5) obtained from the organism *Streptomyces coelicolor* A3(2) (Genbank accession number NP.sub.—631558);

FIG. 7 shows an amino acid sequence (SEQ ID NO: 6) obtained from the organism *Streptomyces coelicolor* A3(2) (Genbank accession number: CAC42140);

FIG. 8 shows an amino acid sequence (SEQ ID NO: 7) obtained from the organism *Saccharomyces cerevisiae* (Genbank accession number P41734);

FIG. 9 shows an amino acid sequence (SEQ ID NO: 8) obtained from the organism *Ralstonia* (Genbank accession number: AL646052);

FIG. 10 shows SEQ ID NO: 9. Scoe1 NCBI protein accession code CAB39707.1 GI:4539178 conserved hypothetical protein [*Streptomyces coelicolor* A3(2)];

FIG. 11 shows an amino acid shown as SEQ ID NO: 10. Scoe2 NCBI protein accession code CAC01477.1 GI:9716139 conserved hypothetical protein [*Streptomyces coelicolor* A3 (2)];

FIG. 12 shows an amino acid sequence (SEQ ID NO: 11) Scoe3 NCBI protein accession code CAB88833.1 GI:7635996 putative secreted protein. [*Streptomyces coelicolor* A3(2)];

FIG. 13 shows an amino acid sequence (SEQ ID NO: 12) Scoe4 NCBI protein accession code CAB89450.1 GI:7672261 putative secreted protein. [*Streptomyces coelicolor* A3(2)];

FIG. 14 shows an amino acid sequence (SEQ ID NO: 13) Scoe5 NCBI protein accession code CAB62724.1 GI:6562793 putative lipoprotein [*Streptomyces coelicolor* A3 (2)];

FIG. 15 shows an amino acid sequence (SEQ ID NO: 14) Srim1 NCBI protein accession code AAK84028.1 GI:15082088 GDSL-lipase ('GDSL' disclosed as SEQ ID NO: 122) [*Streptomyces rimosus*];

FIG. 16 shows an amino acid sequence (SEQ ID NO: 15) of a lipid acyltransferase from *Aeromonas salmonicida* subsp. *Salmonicida* (ATCC#14174);

FIG. 17 shows SEQ ID NO: 19. Scoe 1 NCBI protein accession code CAB39707.1 GI:4539178 conserved hypothetical protein [*Streptomyces coelicolor* A3(2)];

FIG. 18 shows an amino acid sequence (SEQ ID NO: 25) of the fusion construct used for mutagenesis of the *Aeromonas hydrophila* lipid acyltransferase gene. The underlined amino acids is a xylanase signal peptide;

FIG. 19 shows a polypeptide sequence of a lipid acyltransferase enzyme from *Streptomyces* (SEQ ID NO: 26);

FIG. 20 shows a polypeptide sequence of a lipid acyltransferase enzyme from *Thermobifida* (SEQ ID NO: 27);

FIG. 21 shows a polypeptide sequence of a lipid acyltransferase enzyme from *Thermobifida* (SEQ ID NO: 28);

FIG. 22 shows a polypeptide of a lipid acyltransferase enzyme from *Corynebacterium efficiens* GDSX (SEQ ID NO: 120) 300 amino acid (SEQ ID NO: 29);

FIG. 23 shows a polypeptide of a lipid acyltransferase enzyme from *Novosphingobium aromaticivorans* GDSX (SEQ ID NO: 120) 284 amino acid (SEQ ID NO: 30);

FIG. 24 shows a polypeptide of a lipid acyltransferase enzyme from *Streptomyces coelicolor* GDSX (SEQ ID NO: 120) 269 aa (SEQ ID NO: 31);

FIG. 25 shows a polypeptide of a lipid acyltransferase enzyme from *Streptomyces avermitilis*\GDSX (SEQ ID NO: 120) 269 amino acid (SEQ ID NO: 32);

FIG. 26 shows a polypeptide of a lipid acyltransferase enzyme from *Streptomyces* (SEQ ID NO: 33);

FIG. 27 shows an amino acid sequence (SEQ ID NO: 34) obtained from the organism *Aeromonas hydrophila* (P10480; GI:121051) (notably, this is the mature sequence);

FIG. 28 shows the amino acid sequence (SEQ ID NO: 35) of a mutant *Aeromonas salmonicida* mature lipid acyltransferase (GCAT) (notably, this is the mature sequence);

FIG. 29 shows a nucleotide sequence (SEQ ID NO: 36) from *Streptomyces thermosacchari*;

FIG. 30 shows an amino acid sequence (SEQ ID NO: 37) from *Streptomyces thermosacchari*;

FIG. 31 shows an amino acid sequence (SEQ ID NO: 38) from *Thermobifida fusca*/GDSX (SEQ ID NO: 120) 548 amino acid;

FIG. 32 shows a nucleotide sequence (SEQ ID NO: 39) from *Thermobifida fusca*;

FIG. 33 shows an amino acid sequence (SEQ ID NO: 40) from *Thermobifida fusca*/GDSX (SEQ ID NO: 120);

FIG. 34 shows an amino acid sequence (SEQ ID NO: 41) from *Corynebacterium efficiens*/GDSX (SEQ ID NO: 120) 300 amino acid;

FIG. 35 shows a nucleotide sequence (SEQ ID NO: 42) from *Corynebacterium efficiens*;

FIG. 36 shows an amino acid sequence (SEQ ID NO: 43) from *S. coelicolor*/GDSX (SEQ ID NO: 120) 268 amino acid;

FIG. 37 shows a nucleotide sequence (SEQ ID No: 44) from *S. coelicolor*;

FIG. 38 shows an amino acid sequence (SEQ ID NO: 45) from *S. avermitilis*;

FIG. 39 shows a nucleotide sequence (SEQ ID NO: 46) from *S. avermitilis*;

FIG. 40 shows an amino acid sequence (SEQ ID NO: 47) from *Thermobifida fusca*/GDSX (SEQ ID NO: 120);

FIG. 41 shows a nucleotide sequence (SEQ ID NO: 48) from *Thermobifida fusca*/GDSX (SEQ ID NO: 120);

FIG. 42 shows an alignment of the L131 (SEQ ID NO: 26) and homologues from *S. avermitilis* (SEQ ID NO: 32) and *T. fusca* (SEQ ID NO: 40) illustrates that the conservation of the GDSX (SEQ ID NO: 120) motif (GDSY (SEQ ID NO: 125) in L131 and *S. avermitilis* and *T. fusca*), the GANDY (SEQ ID NO: 118) box, which is either GGNDA (SEQ ID NO: 123) or GGNDL (SEQ ID NO: 124), and the HPT block (considered to be the conserved catalytic histidine). These three conserved blocks are highlighted. Consensus sequence fragments disclosed as SEQ ID NOS 71-94, respectively, in order of appearance;

FIG. 43 shows SEQ ID No 17 which is the amino acid sequence of a lipid acyltransferase from *Candida parapsilosis*;

FIG. 44 shows SEQ ID No 18 which is the amino acid sequence of a lipid acyltransferase from *Candida parapsilosis*;

Figure 48:
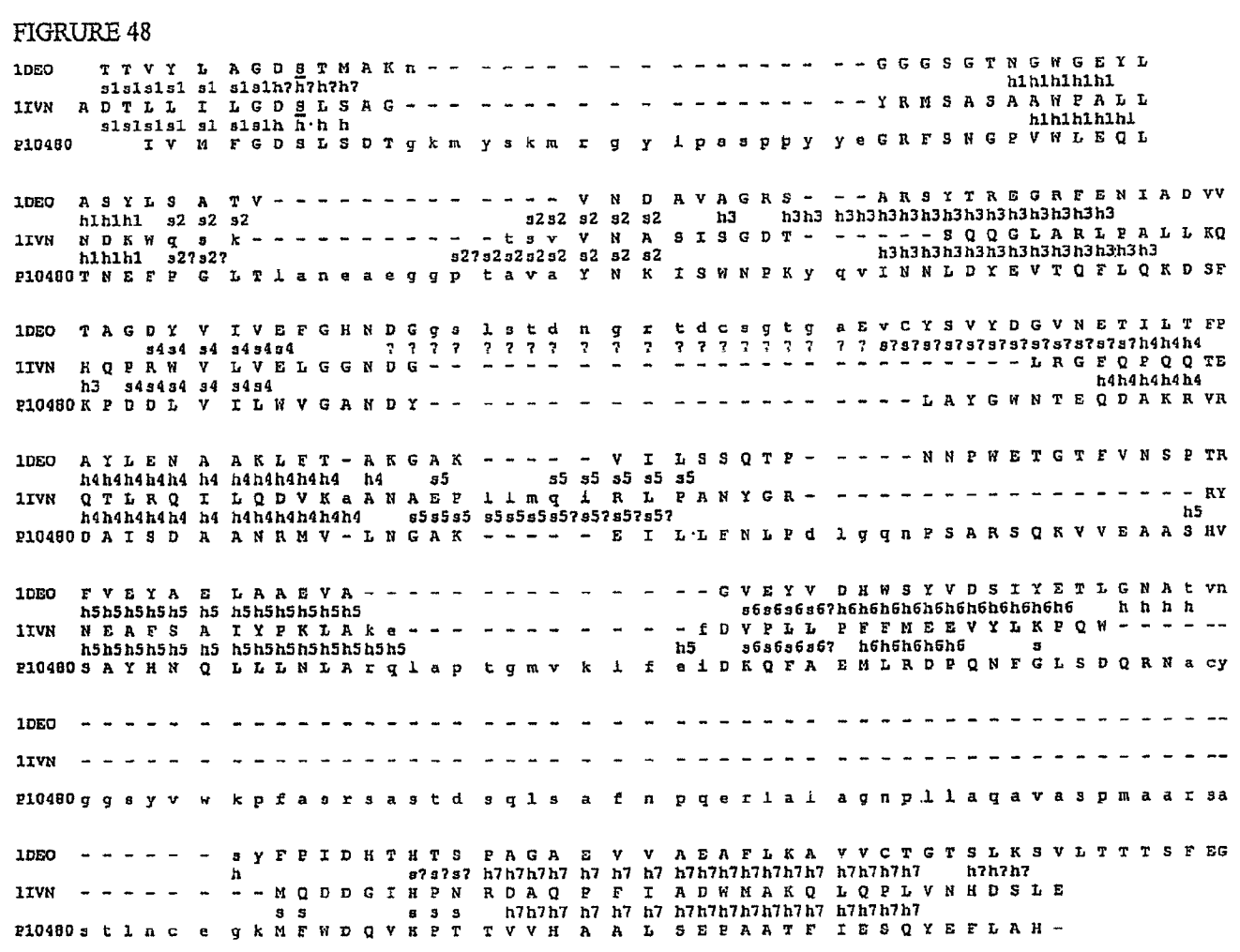

FIG. 48 shows alignment 1 (SEQ ID NOS 20, 96, and 97, respectively, in order of appearance);

Figure 49:
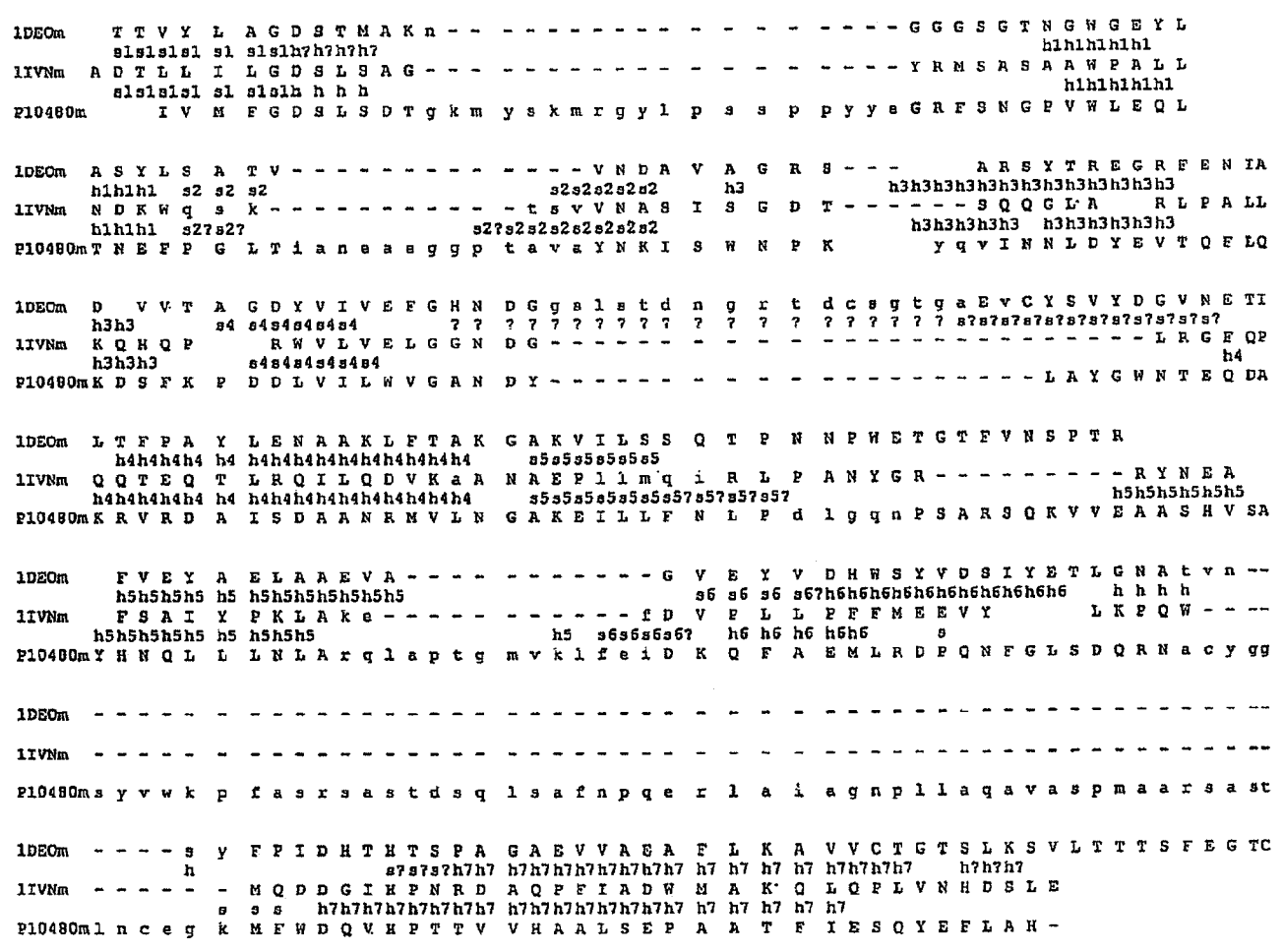

FIG. 49 shows alignment 2 (SEQ ID NOS 95-97, respectively, in order of appearance);

FIGS. 50A-B and 51 show an alignment of 1IVN to P10480 (P10480 is the database sequence for *A. hydrophila* enzyme), this alignment was obtained from the PFAM database and used in the model building process (FIG. 50A-B discloses SEQ ID NOS 20, 96-97, and 95-97, and FIG. 51 discloses SEQ ID NOS 98-99, all respectively, in order of appearance); and FIG. 52 shows an alignment where P10480 is the database sequence for *Aeromonas hydrophila*. This sequence is used for the model construction and the site selection. Note that the full protein (SEQ ID NO: 3) is depicted, the mature protein (equivalent to SEQ ID NO: 34) starts at residue 19. A. sal is *Aeromonas salmonicida* (SEQ ID NO: 35) GDSX (SEQ ID NO: 120) lipase, A. hyd is *Aeromonas hydrophila* (SEQ ID NO: 137) GDSX (SEQ ID NO: 120) lipase. The consensus sequence contains a * at the position of a difference between the listed sequences (consensus sequence fragments disclosed as SEQ ID NOS 102-114, respectively, in order of appearance).

FIG. 53 shows a gene construct used in Example 1;

FIG. 55 shows the sequence of the XhoI insert containing the LAT-KLM3' precursor gene, the −35 and −10 boxes are underlined (figure discloses the DNA sequence as SEQ ID NO: 115 and the protein sequence as SEQ ID NO: 116);

FIG. 57 shows a nucleotide sequence from *Aeromonas salmonicida* (SEQ ID NO: 49) including the signal sequence (preLAT—positions 1 to 87);

FIG. 58 shows a nucleotide sequence (SEQ ID NO: 50) encoding a lipid acyl transferase according to the present invention obtained from the organism *Aeromonas hydrophila;*

FIG. 59 shows a nucleotide sequence (SEQ ID NO: 51) encoding a lipid acyl transferase according to the present invention obtained from the organism *Aeromonas salmonicida;*

FIG. 60 shows a nucleotide sequence (SEQ ID NO: 52) encoding a lipid acyl transferase according to the present invention obtained from the organism *Streptomyces coelicolor* A3(2) (Genbank accession number NC.sub.—003888.1:8327480.8328367);

FIG. 61 shows a nucleotide sequence (SEQ ID NO: 53) encoding a lipid acyl transferase according to the present invention obtained from the organism *Streptomyces coelicolor* A3(2) (Genbank accession number AL939131.1: 265480.266367);

FIG. 62 shows a nucleotide sequence (SEQ ID NO: 54) encoding a lipid acyl transferase according to the present invention obtained from the organism *Saccharomyces cerevisiae* (Genbank accession number Z75034);

FIG. 63 shows a nucleotide sequence (SEQ ID NO: 55) encoding a lipid acyl transferase according to the present invention obtained from the organism *Ralstonia;*

FIG. 64 shows a nucleotide sequence shown as SEQ ID NO: 56 encoding NCBI protein accession code CAB39707.1 GI:4539178 conserved hypothetical protein [*Streptomyces coelicolor* A3 (2)];

FIG. 65 shows a nucleotide sequence shown as SEQ ID NO: 57 encoding Scoe2 NCBI protein accession code CAC01477.1 GI:9716139 conserved hypothetical protein [*Streptomyces coelicolor* A3(2)];

FIG. 66 shows a nucleotide sequence shown as SEQ ID NO: 58 encoding Scoe3 NCBI protein accession code CAB88833.1 GI:7635996 putative secreted protein. [*Streptomyces coelicolor* A3 (2)];

FIG. 67 shows a nucleotide sequence shown as SEQ ID NO: 59 encoding Scoe4 NCBI protein accession code CAB89450.1 GI:7672261 putative secreted protein. [*Streptomyces coelicolor* A3(2)];

FIG. 68 shows a nucleotide sequence shown as SEQ ID NO: 60, encoding Scoe5 NCBI protein accession code CAB62724.1 GI:6562793 putative lipoprotein [*Streptomyces coelicolor* A3 (2)];

FIG. 69 shows a nucleotide sequence shown as SEQ ID NO: 61 encoding Srim1 NCBI protein accession code AAK84028.1 GI:15082088 GDSL-lipase ('GDSL' disclosed as SEQ ID NO: 122) [*Streptomyces rimosus*];

FIG. 70 shows a nucleotide sequence (SEQ ID NO: 62) encoding a lipid acyltransferase from *Aeromonas hydrophila* (ATCC #7965);

FIG. 71 shows a nucleotide sequence (SEQ ID NO: 63) encoding a lipid acyltransferase from *Aeromonas salmonicida* subsp. *Salmonicida* (ATCC#14174);

FIG. 72 shows a nucleotide sequence (SEQ ID NO: 24) encoding an enzyme from *Aeromonas hydrophila* including a xylanase signal peptide;

FIG. 73 shows the amino acid sequence of a mutant *Aeromonas salmonicida* mature lipid acyltransferase (GCAT) with a mutation of Asn80Asp (notably, amino acid 80 is in the mature sequence)—shown herein as SEQ ID No. 16—and after undergoing post-translational modification as SEQ ID NO: 68—amino acid residues 235 and 236 of SEQ ID No. 68 are not covalently linked following post-translational modification. The two peptides formed are held together by one or more S-S bridges. Amino acid 236 in SEQ ID NO: 68 corresponds with the amino acid residue number 274 in SEQ ID No. 16 shown herein;

The invention will now be further described by way of the following non-limiting examples.

EXAMPLE 1

Expression of KLM3' in *Bacillus licheniformis*

Figure 45:
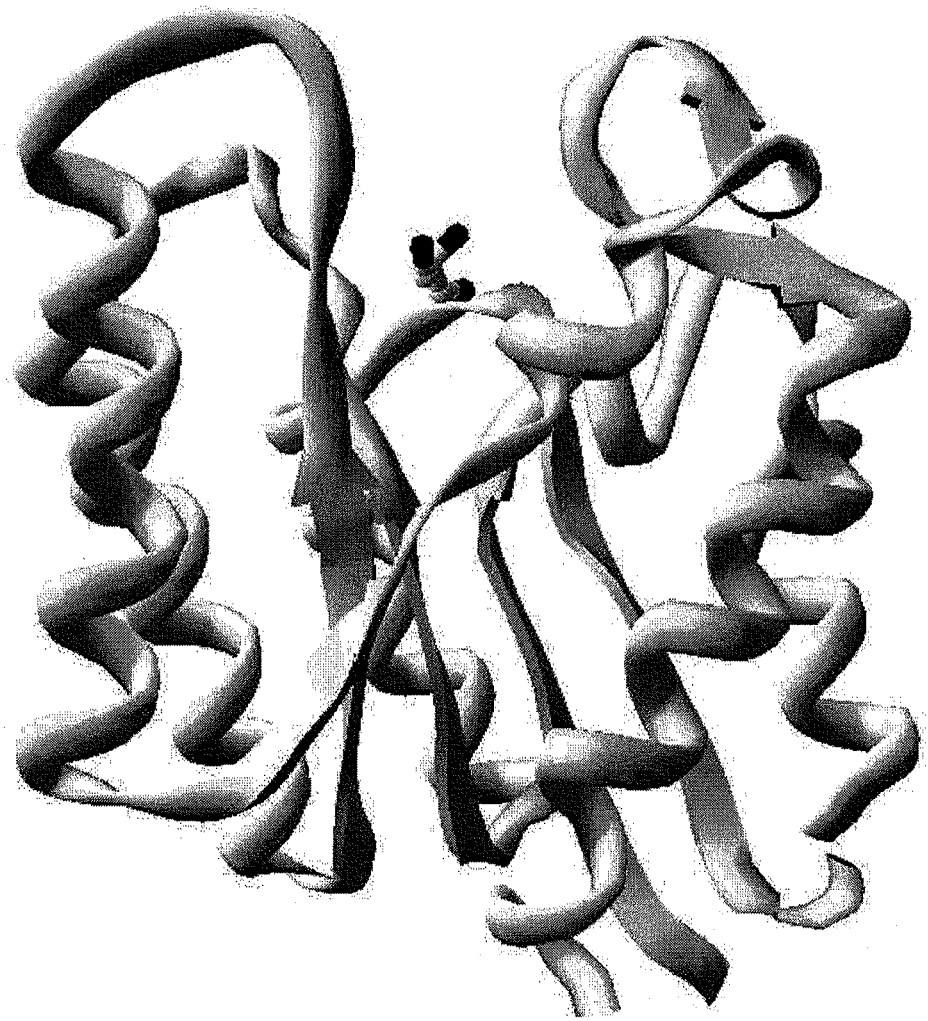
FIG. 45 shows a ribbon representation of the 1IVN.PDB crystal structure which has glycerol in the active site. The Figure was made using the Deep View Swiss-PDB viewer.
Figure 46:
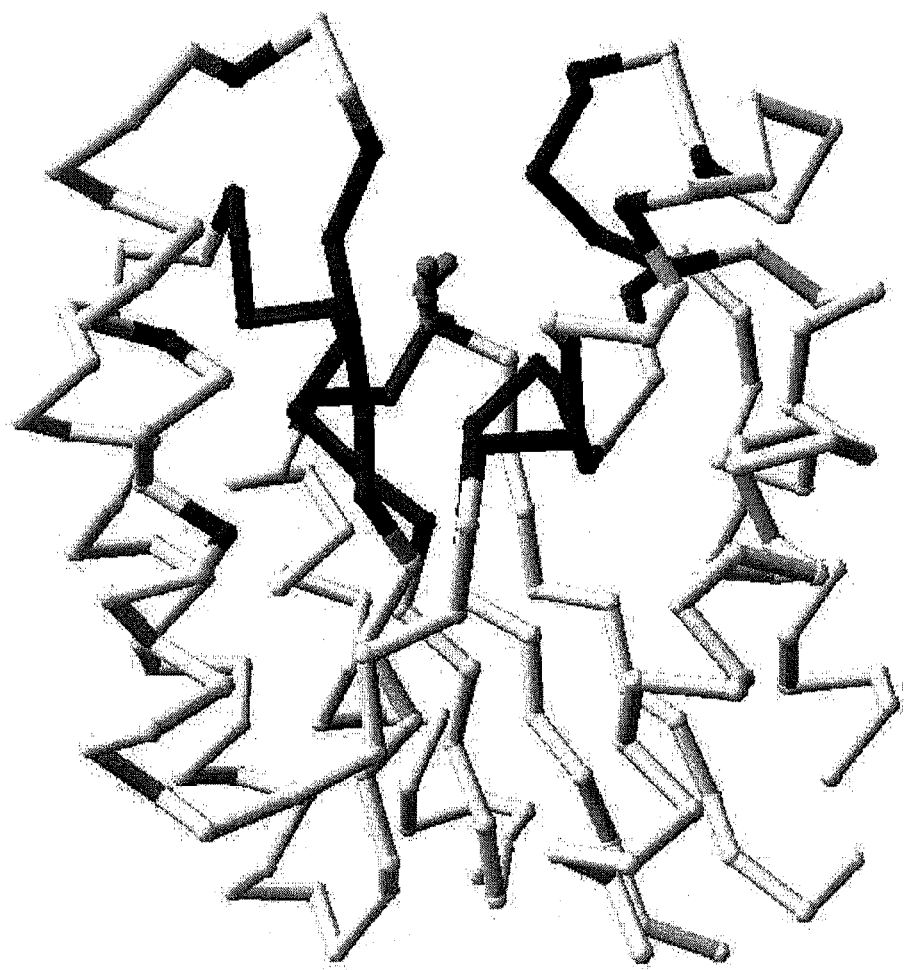
FIG. 46 shows 1IVN.PDB Crystal Structure—Side View using Deep View Swiss-PDB viewer, with glycerol in active site—residues within 10 Å of active site glycerol are coloured black.
Figure 47:
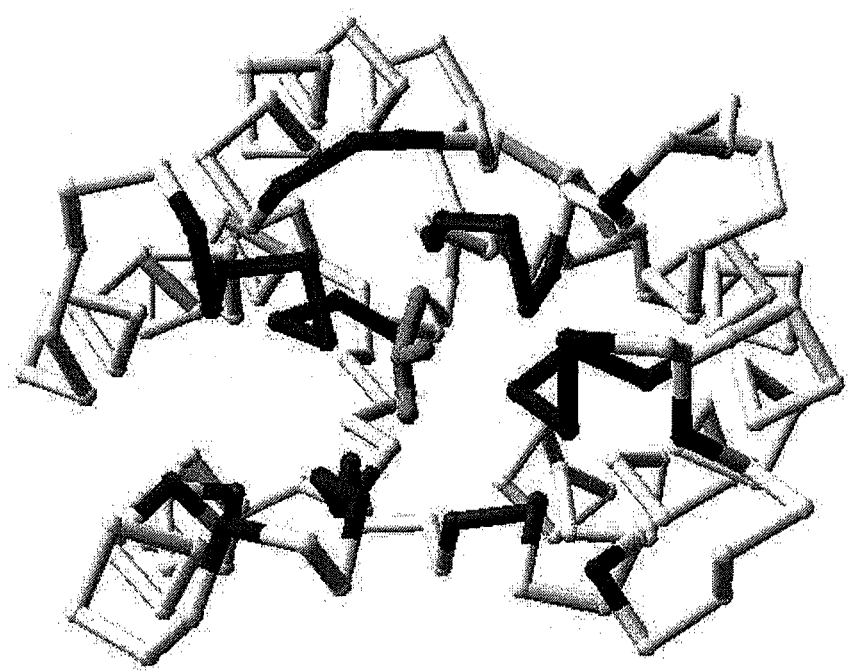
FIG. 47 shows 1IVN.PDB Crystal Structure—Top View using Deep View Swiss-PDB viewer, with glycerol in active site—residues within 10 Å of active site glycerol are coloured black.
Figure 54:
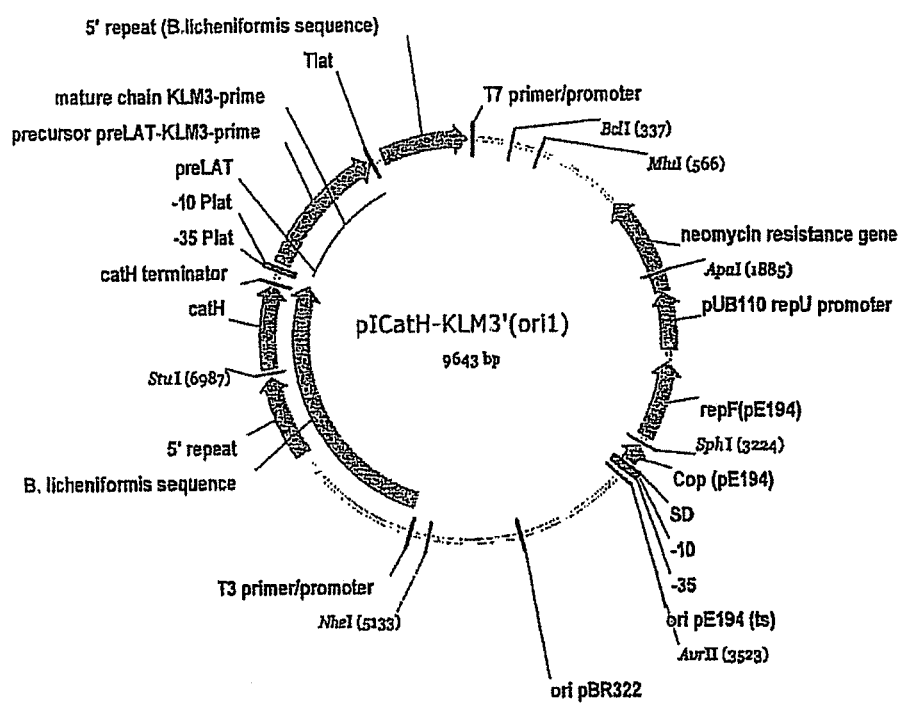
FIG. 54 shows a codon optimised gene construct (no. 052907) used in Example 1.

A nucleotide sequence (SEQ ID NO: 49) encoding a lipid acyltransferase (SEQ. ID No. 16, hereinafter KLM3') was expressed in *Bacillus licheniformis* as a fusion protein with the signal peptide of *B. licheniformis* [alpha]-amylase (LAT) (see FIGS. 53 and 54). For optimal expression in *Bacillus*, a codon optimized gene construct (no. 052907) was ordered at Geneart (Geneart AG, Regensburg, Germany).

Construct no. 052907 contains an incomplete LAT promoter (only the −10 sequence) in front of the LAT-KLM3' precursor gene and the LAT transcription (Tlat) downstream of the LAT-KLM3' precursor gene (see FIGS. 53 and 55). To create a XhoI fragment that contains the LAT-KLM3' precursor gene flanked by the complete LAT promoter at the 5' end and the LAT terminator at the 3' end, a PCR (polymerase chain reaction) amplification was performed with the primers Plat5XhoI_FW and EBS2XhoI_RV and gene construct 052907 as template.

Plat5XhoI_FW:
(SEQ ID NO: 69)
ccccgctcgaggcttttcttttggaagaaatatagggaaaatggtactt gttaaaaattcggaatatttatacaatatcatatgtttcacattgaaa gggg EBS2XhoI_RV:
(SEQ ID NO: 70)
tggaatctcgaggttttatcctttaccttgtctcc PCR was performed on a thermocycler with Phusion High Fidelity DNA polymerase (Finnzymes OY, Espoo, Finland) according to the instructions of the manufacturer (annealing temperature of 55[deg.] C.).

The resulting PCR fragment was digested with restriction enzyme XhoI and ligated with T4 DNA ligase into XhoI digested pICatH according to the instructions of the supplier (Invitrogen, Carlsbad, Calif. USA).

The ligation mixture was transformed into *B. subtilis* strain SC6.1 as described in U.S. Patent Application US20020182734 (International Publication WO 02/14490). The sequence of the XhoI insert containing the LAT-KLM3' precursor gene was confirmed by DNA sequencing (Base-Clear, Leiden, The Netherlands) and one of the correct plasmid clones was designated pICatH-KLM3'(ori1) (FIG. 53). pICatH-KLM3'(ori1) was transformed into *B. licheniformis* strain BML780 (a derivative of BRA7 and BML612, see WO2005111203) at the permissive temperature (37[deg.] C.).

Figure 56:
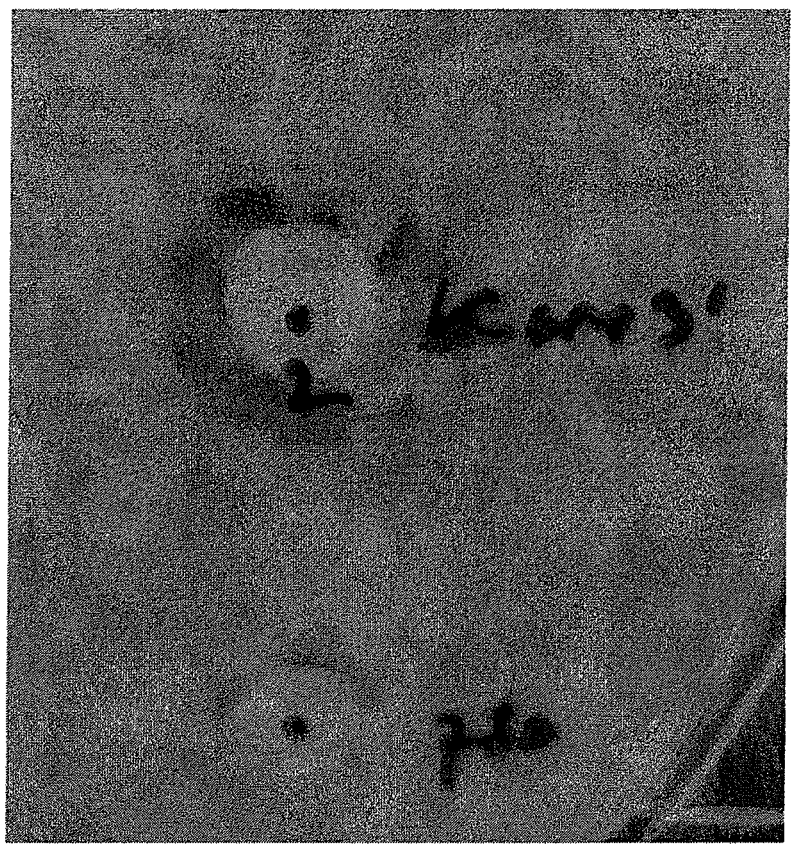
FIG. 56 shows BML780-KLM3'CAP50 (comprising SEQ ID NO: 16—upper colony) and BML780 (the empty host strain—lower colony) after 48 h growth at 37.degree. C. on 1% tributyrin agar.

One neomycin resistant (neoR) and chloramphenicol resistant (CmR) transformant was selected and designated BML780(pICatH-KLM3'(ori1)). The plasmid in BML780 (pICatH-KLM3'(ori1)) was integrated into the catH region on the *B. licheniformis* genome by growing the strain at a non-permissive temperature (50[deg.] C.) in medium with 5 [mu] g/ml chloramphenicol. One CmR resistant clone was selected and designated BML780-pICatH-KLM3'(ori1). BML780-pICatH-KLM3' (ori1) was grown again at the permissive temperature for several generations without antibiotics to loop-out vector sequences and then one neomycin sensitive (neoS), CmR clone was selected. In this clone, vector sequences of pICatH on the chromosome are excised (including the neomycin resistance gene) and only the catH-LATKLM3' cassette is left. Next, the catH-LATKLM3' cassette on the chromosome was amplified by growing the strain in/on media with increasing concentrations of chloramphenicol. After various rounds of amplification, one clone (resistant against 50 [mu]g/ml chloramphenicol) was selected and designated BML780-KLM3'CAP50. To verify KLM3' expression, BML780-KLM3'CAP50 and BML780 (the empty host strain) were grown for 48 h at 37 [deg.] C on a Heart Infusion (Bacto) agar plate with 1% tributyrin. A clearing zone, indicative for lipid acyltransferase activity, was clearly visible around the colony of BML780-KLM3'CAP50 but not around the host strain BML780 (see FIG. 56). This result shows that a substantial amount of KLM3' is expressed in *B. licheniformis* strain BML780-KLM3'CAP50 and that these KLM3' molecules are functional.

COMPARATIVE EXAMPLE 1

Vector Construct

The plasmid construct is pCS32new N80D, which is a pCCmini derivative carrying the sequence encoding the mature form of the native *Aeromonas salmonicida* Glycerophospholipid-cholesterol acyltransferase with a Asn to Asp substitution at position 80 (KLM3'), under control of the p32 promoter and with a CGTase signal sequence.

The host strain used for the expression, is in the *bacillus subtilis* OS21ΔAprE strain The expression level is measured as transferase activity, expressed as % cholesterol esterified, calculated from the difference in free cholesterol in the reference sample and free cholesterol in the enzyme sample in reactions with PC ($T_{PC}$) as donor and cholesterol as acceptor molecule.

Culture Conditions 5 ml of LB broth (Casein enzymatic digest, 10 g/l; low-sodium Yeast extract, 5 g/l; Sodium Chloride, 5 g/l; Inert tableting aids, 2 g/l) supplemented with 50 mg/l kanamycin, was inoculated with a single colony and incubated at 30° C. for 6 hours at 205 rpm. 0.7 ml of this culture was used to inoculate 50 ml of SAS media ($K_2HPO_4$, 10 g/l; MOPS (3-morpholinopropane sulfonic acid), 40 g/l; Sodium Chloride, 5 g/l; Antifoam (Sin 260), 5 drops/l; Soy flour degreased, 20 g/l; Biospringer 106 (100% dw YE), 20 g/l) supplemented with 50 mg/l kanamycin and a solution of high maltose starch hydrolysates (60 g/l). Incubation was continued for 40 hours at 30° C. and 180 rpm before the culture supernatant was separated by centrifugation at 19000 rpm for 30 min. The supernatant was transferred into a clean tube and directly used for transferase activity measurement.

Preparation of Substrates and Enzymatic Reaction

PC (Avanti Polar Lipids #441601) and cholesterol (Sigma C8503) was scaled in the ratio 9:1, dissolved in chloroform, and evaporated to dryness.

The substrate was prepared by dispersion of 3% PC:Cholesterol 9:1 in 50 mM Hepes buffer pH 7.

0.250 ml substrate solution was transferred into a 3 ml glass tube with screw lid. 0.025 ml culture supernatant was added and the mixture was incubated at 40° C. for 2 hours. A reference sample with water instead of enzyme was also prepared. Heating the reaction mixture in a boiling water bath for 10 minutes stopped the enzyme reaction. 2 ml of 99% ethanol was added to the reaction mixture before submitted to cholesterol assay analysis.

Cholesterol Assay

100 μl substrate containing 1.4 U/ml Cholesterol oxidase (SERVA Electrophoresis GmbH cat. No 17109), 0.4 mg/ml ABTS (Sigma A-1888), 6 U/ml Peroxidase (Sigma 6782) in 0.1 M Tris-HCl, pH 6.6 and 0.5% Triton X-100 (Sigma X-100) was incubated at 37° C. for 5 minutes before 5 μl enzyme reaction sample was added and mixed. The reaction mixture was incubated for further 5 minutes and $OD_{405}$ was measured. The content of cholesterol was calculated from the analyses of standard solutions of cholesterol containing 0.4 mg/ml, 0.3 mg/ml, 0.20 mg/ml, 0.1 mg/ml, 0.05 mg/ml, and 0 mg/ml cholesterol in 99% EtOH.

Results

The table shows the average of 8 separate expression cultures

| Strain | $T_{PC}$[a] |
|---|---|
| OS21ΔAprE[pCS32new] | 7.42 ± 10.1[b] |

[a]$T_{PC}$ is the transferase activity, expressed as % cholesterol esterified, calculated from the difference in free cholesterol in the reference sample and free cholesterol in the enzyme sample in reactions with PC as donor molecule and cholesterol as acceptor molecule.
[b]Average of 8 separate expression cultures

EXAMPLE 2

Emulsion Stability, Removal of Cholesterol in UHT Milk

The use of the lipid acyltransferase shown here as SEQ ID NO: 68 (hereinafter referred to as "KLM3") for interesterification and/or transesterification between phospholipids and cholesterol in UHT milk has an effect on improving the emulsion stability, comparing results in ordinary UHT milk and Flavoured UHT milk, produced on basis of fresh milk as well as recombined milk.

For the avoidance of doubt recombined milk is a general term for milk, which is produced from original milk based solid components mixed with water and processed in such a way to produce milk with similar characteristics as the original milk.

Test of KLM3 in UHT Milk and Cream

TIPU Assay
Substrate 0.6% L-α Phosphatidylcholine 95% Plant (Avanti #441601), 0.4% Triton-X 100 (Sigma X-100) and 5 mM $CaCl_2$ was dissolved in 0.05M HEPES buffer pH 7.

Assay Procedure:

400 µl substrate was added to an 1.5 ml Eppendorf tube and placed in an Eppendorf Thermomixer at 37° C. for 5 minutes. At time T=0 min, 50 µl enzyme solution was added. Also a blank with water instead of enzyme was analyzed. The sample was mixed at 10*100 rpm in an Eppendorf Thermomixer at 37° C. for 10 minutes. At time T=10 min the Eppendorf tube was placed in another thermomixer at 99° C. for 10 minutes to stop the reaction.

Free fatty acid in the samples was analyzed by using the NEFA C kit from WAKO GmbH.

Enzyme activity TIPU pH 7 was calculated as micromole fatty acid produced per minute under assay conditions.

| COMPOSITION IN PERCENTAGES | 1 | 2 | 3 | 4 | 5 | 6 | 7 | 8 |
|---|---|---|---|---|---|---|---|---|
| Milk 3.5% fat | 99.90 | 99.90 | 99.90 | 94.16 | | | | |
| Skim milk powder | | | | | 9.00 | 9.00 | 9.00 | 9.00 |
| Butter oil (AMF) | | | | | 3.50 | 3.50 | 3.50 | 3.50 |
| Sucrose | | | | 5.50 | | | | 5.50 |
| Strawberry Flavouring T10063 | | | | 0.12 | | | | 0.12 |
| Carmine Extract (red) | | | | 0.02 | | | | 0.02 |
| RECODAN ™ RS 100 | 0.10 | 0.10 | 0.10 | 0.20 | 0.15 | 0.15 | 0.15 | 0.20 |
| K460 (KLM3) Units/liter | | 75 U/L | 40 U/L | 75 U/L | | 75 U/L | 40 U/L | 75 U/L |
| Water (Tap) | | | | | 87.35 | 87.35 | 87.35 | 81.66 |
| Total percentage | 100.00 | 100.00 | 100.00 | 100.00 | 100.00 | 100.00 | 100.00 | 100.00 |

The samples (recombined milk) were processed in Dairy Pilot Plant as follows:

Pilot (Batch Preparation)
1.—Heat water/milk to 40° C. in mixer tank and add enzymes
2.—Add skimmed milk powder, sugar, other dry ingredients to the water and keep for 30 minutes
3.—Melt butteroil at 70° C.
4.—Add stabiliser/emulsifier to the melted butteroil
5.—Add butteroil, stabiliser/emulsifier to the milk
6.—Add flavorings.
7.—Premix on silverson—medium speed for 1 minute
8.—Dearate for approximately 30 minutes in the bucket
The fresh milk followed step 1, 2, 6, 7 and 8.
UHT—(PHE)
9.—Preheat to 90° C. (holding cell at 30 seconds)
10.—Indirect heating 142° C. for 3 seconds
11.—Downstream homogenisation 200 bar, 75° C.
12.—Cool to 15° C.
13.—Aseptic Filling The ingredients used for the trials were commercially purchased whole milk and/or standard raw materials used for majority of trials in the Dairy Pilot Plant.

The enzyme solution used was a sample of KLM3 (K460—shown as SEQ ID NO: 68 herein). The K460 contains 1400 TIPU units/ml.

The dosage level of enzymes was 75 and 40 units per liter. Reaction time and temperature was in this experiment constant at 40° C. for 30 min.

In order to evaluate results from the trial, all samples were analysed as follows:

Remaining content of cholesterol and phospholipids

Particle size distribution in water and with 1% SDS added

Viscosity and sediment (DLA standard methods in Dairy Pilot Plant) Viscosity is measured in centipoises on a Brookfield Viscosimeter with spindle 2 at 60 rpm and 4° C. Sedimentation is measured by the Sedimentation test in % when subjecting a product sample to centrifugal force of 2800 g for 20 minutes and 20° C. (Ultracentrifuge) and then calculate pellet at % of total sample.

Particle size was measured by Malvern Mastersizer S long bed, configuration Alpha, Linse 300R. The instrument was calibrated with a polymer standard to a specification of 0.993 µm±0.021 µm. The sample is diluted in water (2 g sample to 10 ml water with 1% SDS). SDS was added to avoid particles aggregation, as aggregation will give a false result.

Results
Analysis Results:

|  | Sample 1 | Sample 2 | Sample 3 | Sample 4 | Sample 5 | Sample 6 | Sample 7 | Sample 8 |
|---|---|---|---|---|---|---|---|---|
| Cholesterol | Normal level | Completely esterified | Completely esterified | Completely esterified | Normal level | Partly esterified | Partly esterified | Partly esterified |
| Phospholipids | Normal level | Not present | Not present | Not present | Normal level | Not present | Not present | Not present |

Particle Size Analysis:

|  | Sample 1 | Sample 2 | Sample 3 | Sample 4 | Sample 5 | Sample 6 | Sample 7 | Sample 8 |
|---|---|---|---|---|---|---|---|---|
| Mean particle diameter μm | 0.57 | 0.58 | 0.58 | 0.53 | 0.55 | 0.54 | 0.53 | 0.49 |

All samples have a mean particle size under 1 μm.

Samples are weighed and then subjected to ultracentrifugation at 2800 G for 20 minutes and at 20° C. After centrifugation the supernatant is removed and the dry pellet is weighed and sediment is calculated as percentage of original sample size. As noted above viscosity is measured in centipoises and sedimentation in %.

|  | Sample 1 | Sample 2 | Sample 3 | Sample 4 | Sample 5 | Sample 6 | Sample 7 | Sample 8 |
|---|---|---|---|---|---|---|---|---|
| Viscosity | 5 | 6 | 6 | 22 | 15 | 15 | 17 | 28 |
| Sediment | 2.1 | 0.8 | 1.2 | 0.7 | 1.4 | 0.6 | 0.5 | 0.5 |

Results show that use of KLM3 can improve the emulsion stability in UHT milk, and remove the cholesterol.

EXAMPLE 3

Effect of KLM-3 Enzyme in Pasteurized or UHT Treated Milk

Materials and Methods
Glycerophospholipid cholesterol acyltransferase KLM3 (K460)
Recodan RS 100: Stabilizer system
Cream: Commercial source
Skim milk: Commercial source.

EXPERIMENTAL

In order to further establish whether the use of KLM3 in milk has an effect on improving the emulsion stability the following trial run was made, comparing results in ordinary UHT milk and pasteurised milk, produced on basis of recombined fresh milk. In this experiment the enzyme reaction was conducted at 5° C.

Test of KLM3 in pasteurised (sample 11 and 12) and UHT milk (sample 13 and 14)

| Composition in % | 11 | 12 | 13 | 14 |
|---|---|---|---|---|
| RECODAN RS 100 | 0.15 | 0.15 | 0.13 | 0.13 |
| Cream 38% fat | 8.61 | 8.61 | 8.66 | 8.66 |

-continued

| Composition in % | 11 | 12 | 13 | 14 |
|---|---|---|---|---|
| Skimmed milk | 91.24 | 91.24 | 91.21 | 91.21 |
| KLM3, 100 U/ml | − | + | − | + |

-continued

| Composition in % | 11 | 12 | 13 | 14 |
|---|---|---|---|---|
| Temperature ° C. | 90 | 90 | 142 | 142 |
| Holding time in seconds | 30 | 30 | 3 | 3 |

The said samples were processed in the Dairy Pilot Plant as follows:
Sample 11, 12, 13 and 14:
UHT milk—Pilot (PHE)
1.—Mix skim milk and cream
2.—Add KLM 3 enzyme and stir well.
3.—Leave in cold store overnight (20 hr.)
4.—Heat milk to 60° C. and add Recodan
Sample 13 and 14:
5.—Preheat to 90° C. (holding cell at 30 seconds)
6.—Indirect heating 142° C. for 3 seconds
7.—Downstream homogenisation 200 bar, 75° C.
8.—Cool to 15° C.
9.—Aseptic Filling
Sample 11 and 12:
10.—Homogenise up stream at 70° C. and 200 bar
11.—Pasteurise at 90° C. for 30 sec
12.—Cool to 5° C. and fill The ingredients used for the trials were commercially purchased whole milk and/or standard raw materials used for majority of trials in the Dairy Pilot Plant.

The dosage level of enzymes was the same as in the other examples herein showing with KLM3 enzymation of milk at 5° C.

In order to evaluate results from the trial, all samples were analysed as follows:
Turbiscan over 5 days
Stress test of the UHT samples (long term stability)
Surface Tension.
Cholesterol and phosphatidylethanolamine
Sensoric analysis by Triangle Test Turbiscan:

Turbiscan MA 2000 was used to measure the stability of emulsions by measuring the backscatter of a laser beam from the product.

The milk samples were filled aseptically into a sterile test tube, the test tubes were kept at ambient temperature. The samples were measured at regular intervals over a period of 5-7 days.

Samples were measured from top 5 mm and bottom 5 mm of the test tube, where increase in back scattering from the top layer indicates creaming and increase in the bottom indicates sedimentation of particles in the sample.

STRESS Test of Neutral UHT Milk Products
1. After aseptic filling (typically at ambient temp.) Sample 13 and 14 were placed overnight in cold store at 5° C.
2. Samples were then transferred to an incubator at 35° C. for 24 hours
3. Samples were transferred to Cold Store at 5° C. for 24 hours
4. Samples were transferred to ambient temperature of 20-25° C. for 24 hours
5. Samples were transferred to Cold Store at 5° C. for 24 hours After said temperature treatment, the samples were left at ambient temperature for 2-3 days and is then evaluated visually for Creaming, flocculation, Sedimentation and possible phase separations.

The correlation of this test with actual long-life stability of products has through 2 years observations proved to be having a very high correlation.

Surface Tension:

The surface tension of the milk samples was measured with a Wilhelmy plate using a Tensiometer K10 from Krüss Gas Chromatography:

Gas Chromatography was used to measure the content of cholesterol and cholesterol-ester in the milk samples.
The following CG setup was used:
Perkin Elmer Autosystem 9000 Capillary Gas Chromatograph equipped with WCOT fused silica column 12.5 m×0.25 mm ID×0.1μ film thickness 5% phenyl-methyl-silicone (CP Sil 8 CB from Chrompack).
Carrier gas: Helium.
Injector. PSSI cold split injection (initial temp 50° C. heated to 385° C.), volume 1.0 μl
Detector FID: 395° C.

| | Oven program: | | |
|---|---|---|---|
| | 1 | 2 | 3 |
| Oven temperature, ° C. | 90 | 280 | 350 |
| Isothermal, time, min. | 1 | 0 | 10 |
| Temperature rate, ° C./min. | 15 | 4 | |

Preparation of Milk Samples for Gc Analysis:

The milk lipids are extracted according to Mojonnier AOAC 989.05 using ethanol, $NH_3$, MTBE (methyl-tert-butyl ether) and p-ether. The lipid fraction is redissolved in heptane/pyridine (2:1) containing heptadecan as internal standard and cholesterol is measured by GC.

Preparing samples for cholesterol-ester measurements Squalane is added as an additional internal standard. The lipid fraction is redissolved in hexane and cholesterol-esters are concentrated using a $NH_2$ Bond Elut column and hexane eluation. Samples are redissolved in heptane/pyridine (2:1) and cholesterol-esters are measured by CG.

HPTLC:

HPTLC is used to measure the content of phosphatidylethanolamine (PE) in pasteurised milk samples and UHT milk samples.
Applicator: CAMAG applicator AST4.
HPTLC plate: 20×10 cm (Merck no. 1.05641)
The plate is activated before use by drying in an oven at 160° C. for 20-30 minutes.
Application: 6.0 μl of extracted lipids dissolved in $CHCl_3$:Methanol (2:1) are applied to the HPTLC plate using AST4 applicator.
0.1, 0.3, 0.5, 0.8, 1.5 μl of a standard solution containing standard components with known concentration are also applied to the HPTLC plate
Running-buffer 6: Methylacetate:$CHCl_3$:1-propanol:MeOH:0.25% KCl (25:25:25:10:9)
Elution length: 7 cm
Developing fluid: 6% Cupriacetate in 16% $H_3PO_4$
After elution the plate is dried in an oven at 160° C. for 10 minutes, cooled and immersed in the developing fluid (10 sec) and then dried additional for 6 minutes at 160° C. The plate is evaluated visually and scanned (Camag TLC scanner).

Triangle Test.

ISO 4120:2004 Sensory analysis—Methodology—Triangle test

ISO 4120:2004 describes a procedure for determining whether a perceptible sensory difference or similarity exists between samples of two products. The triangle test is a three-alternative test in which one sample is different from the other two.

The test is counterbalanced for the identity of the odd sample (both ABB and BAA used) and its position in tasting (ABB, BAB, BBA, AAB, ABA, BAA). Chance performance is one third, and performance in a group above that level provides evidence for a perceivable difference. The method is a forced-choice procedure. The method applies whether a difference can exist in a single sensory attribute or in several attributes.

Results

TURBISCAN Measurements

Figure 74:
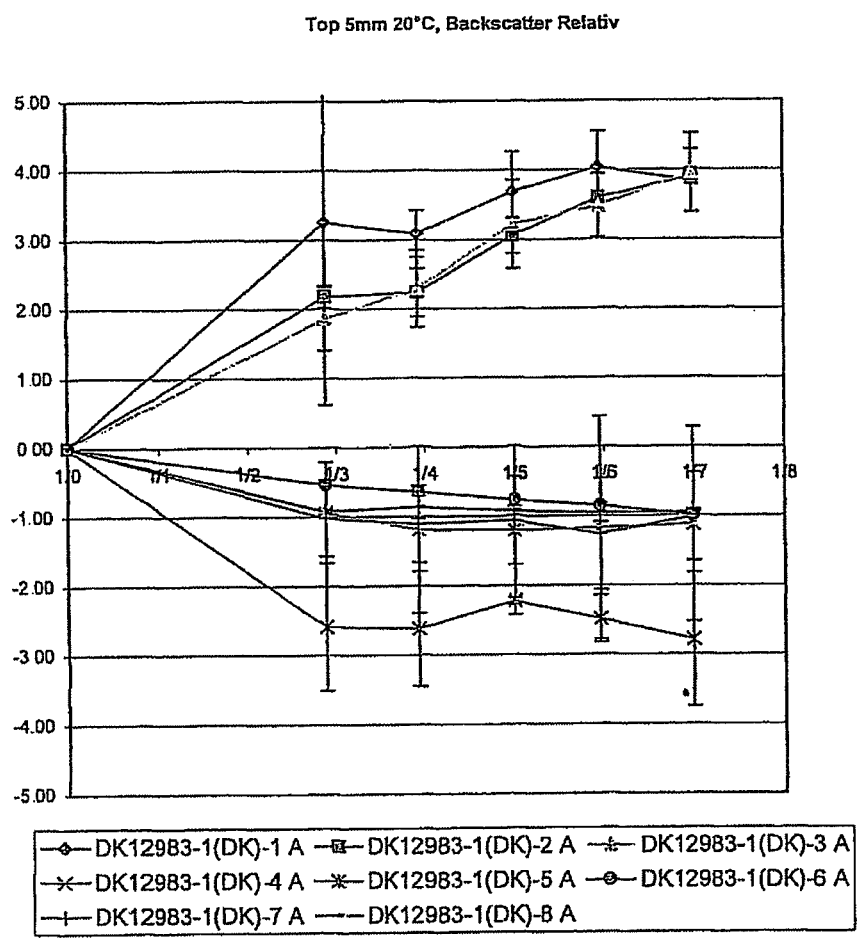
FIG. 74 shows a turbiscan measurement from the top 5 mm.
Figure 75:
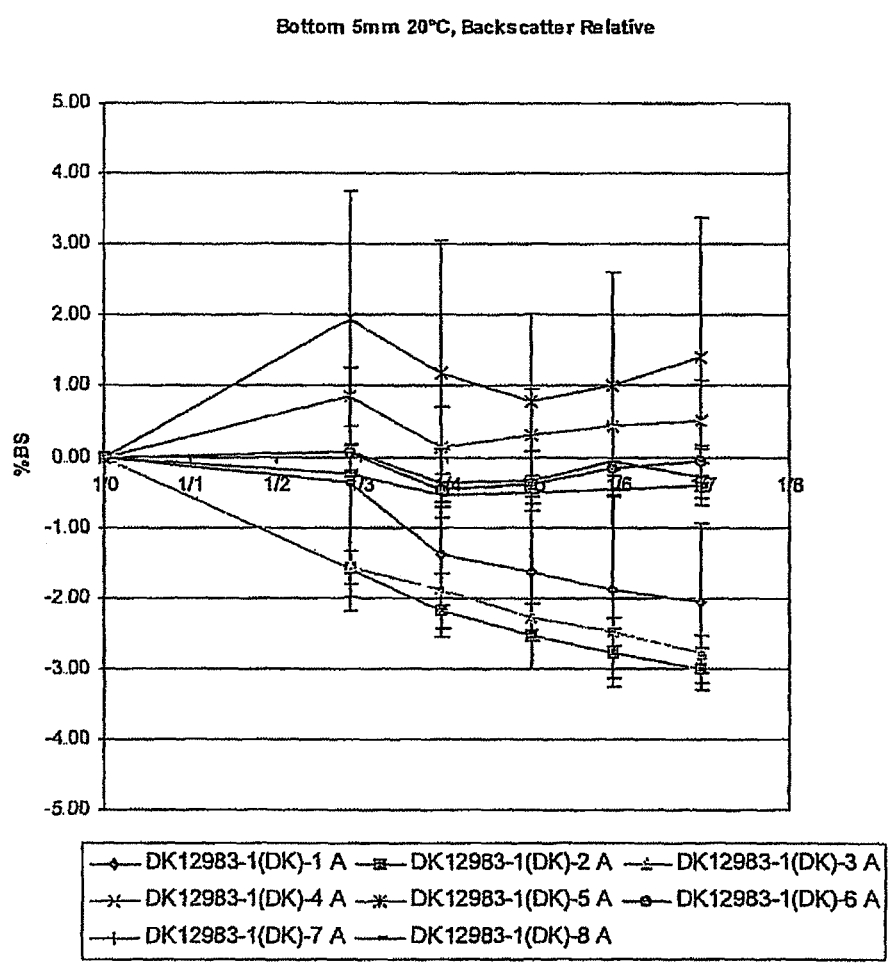
FIG. 75 shows a turbiscan measurement from the bottom 5 mm.

Results from Turbiscan measurements of pasteurized or UHT milk are shown in the Table below and also in FIG. 74 and FIG. 75.

TABLE

Turboscan measurement of Pasteurized milk 12983-1-11 (control), 12983-1-12 (enzyme treated) and UHT milk 12983-1-13 (control), 12983-1-14 (enzyme treated)

| | Average top 5 mm | | | |
|---|---|---|---|---|
| Time (min) | Relative 12983-1-11 | 12983-1-12 | 12983-1-13 | 12983-1-14 |
| 0 | 0.00 | 0.00 | 0.00 | 0.00 |
| 1 | −0.04 | −0.51 | −0.11 | 0.08 |
| 1225 | 1.31 | 2.55 | −0.53 | −0.68 |
| 2683 | 2.11 | 2.81 | −1.09 | −0.02 |
| 6951 | 4.30 | 2.89 | −0.58 | 0.04 |

TABLE-continued

Turboscan measurement of Pasterurized milk 12983-1-11 (control), 12983-1-12 (enzyme treated) and UHT milk 12983-1-13 (control), 12983-1-14 (enzyme treated)

| | Average bottom 5 mm | | | |
|---|---|---|---|---|
| Time (min) | 12983-1-11 | 12983-1-12 | 12983-1-13 | 12983-1-14 |
| 0 | 0.00 | 0.00 | 0.00 | 0.00 |
| 1 | −0.25 | 0.09 | −0.06 | −0.12 |
| 1225 | −1.80 | −1.91 | −0.10 | 0.11 |
| 2683 | −3.03 | −2.21 | −0.50 | 0.12 |
| 6951 | −4.22 | −2.71 | −0.65 | 0.17 |

The TURBISCAN measurements show decreased creaming and decreased sedimentation in the pasteurised samples, the storage time was too short to determine the effect in UHT milk. Storage stability of the UHT milk was therefore determined by the Stress test.

Stress Test of Enzymatically Treated Milk in Trial DK 12938

| Sample | Evaluation after stress test, placed 3 weeks at 30° C. |
|---|---|
| 13 (no enzymatic treatment) | Slight creaming 0-1 mm |
| 14 (enzymatic treatment) | Sample stable |

After 3 weeks at 30° C. a significant difference was observed between the control and the enzyme treated sample.

Surface Tension

The surface tension of the milk samples were measured at 20° C. using a Kruss Tensiometer.

Figure 76:
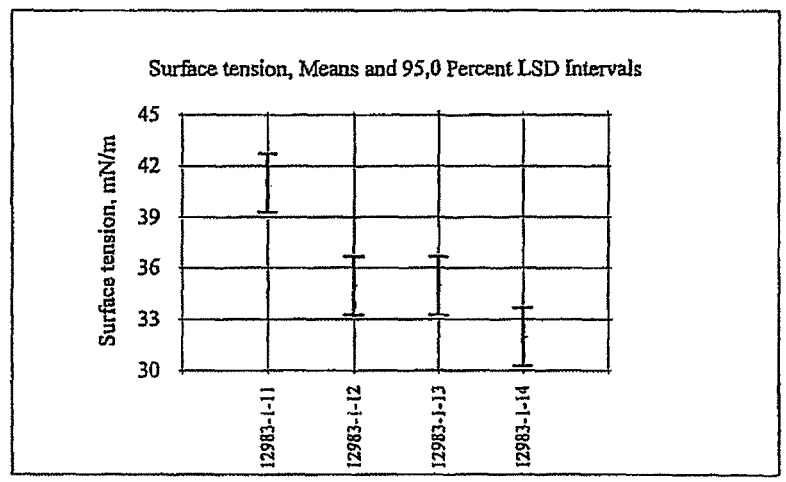
FIG. 76 shows the surface tension of Pasteurized milk 12983-1-11 (control), 12983-1-12 (enzyme treated) and UHT milk 12983-1-13 (control), 12983-1-14 (enzyme treated)

The results are illustrated in FIG. 76.

The results form surface measurement indicates a significant effect of enzymatic treatment of milk with KLM3.

Gas Chromatography of Free Cholesterol and Cholesterol-Ester.

Figure 77:
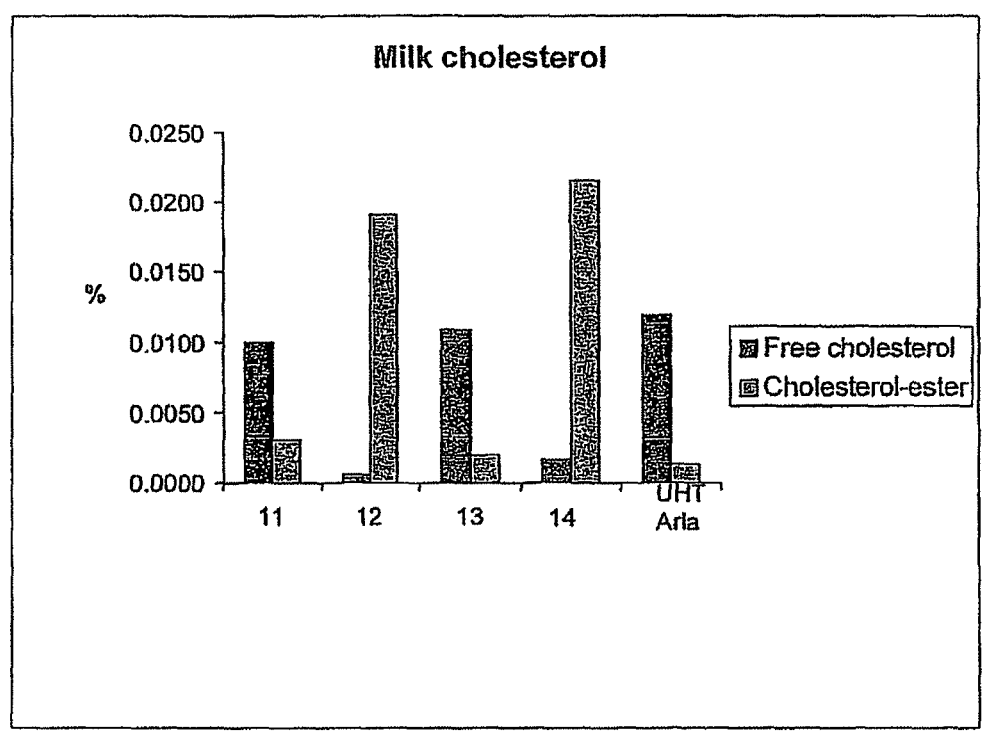
FIG. 77 shows measurements of Milk free cholesterol and cholesterol-ester by Gas Chromatography. 11 and 12 were pasteurised milk and 13 and 14 were UHT milk. Sample −12 and −14 were enzymatically treated with KLM3 at 5° C. for 20 hours. A commercially available UHT milk from Arla was included in the analysis in comparison.

Results of Gas Chromatography measurements of milk cholesterol and cholesterol-ester are shown in FIG. 77.

In general GC results from enzymatic treatment of both pasteurised and UHT milk with KLM3 acyltransferase confirms the ability of this enzyme to convert cholesterol into cholesterol-ester. KLM3 treatment of milk samples reduces free cholesterol by 85-90% in UHT as well as pasteurized milk. In addition KLM3 treatment increased cholesterol-ester level in pasteurized and UHT milk by a factor ~6 and ~10, respectively. A clear effect is thus observed from KLM3 treatment of pasteurized and UHT milk with respect to reduction of free cholesterol.

Pasteurised and UHT milk controls both resembled the commercial UHT milk from ARLA with respect to free cholesterol and cholesterol-ester levels.

Figure 78:
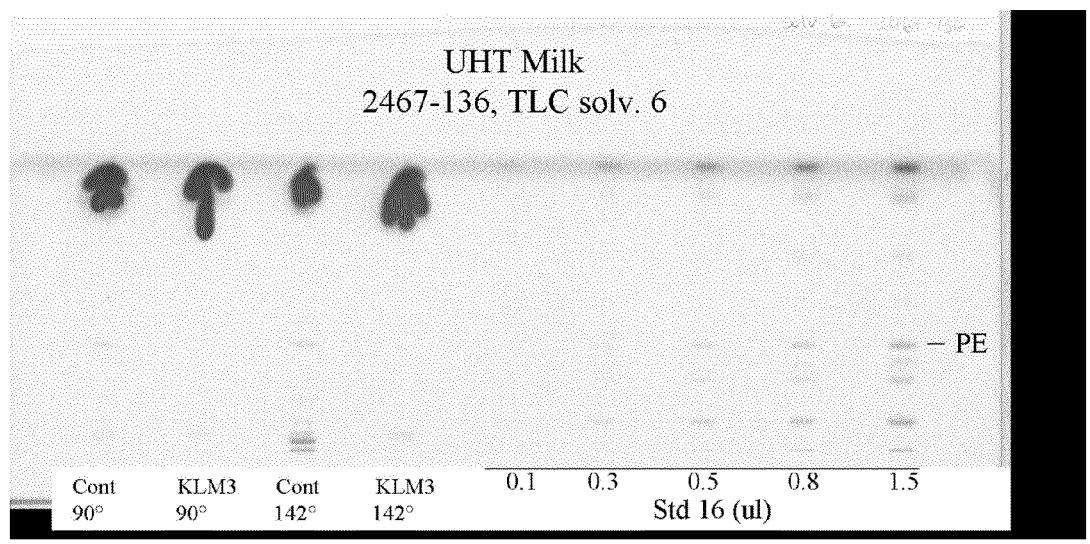
FIG. 78 shows HPTLC of extracted pasteurised (90° C.) and UHT (142° C.) milk lipids dissolved in $CHCl_3$:MeOH (2:1). Standard (Std) 16 contains SpectraLipid Soy Lecithin Mix Standard (No. SLM43) dissolved in $CHCl_3$:MeOH (2:1)

HPTLC of Milk Phosphatidylethanolamine:

Results of milk lipids extracted from pasteurised and UHT milk and measured by HPTLC are shown in FIG. 78.

HPTLC Measurements.

Enzymatic treatment of both pasteurised and UHT milk with KLM3 show a marked reduction in milk phosphatidylethanolamine (PE) content as presented in the table below.

TABLE

Milk phosphatidylethanolamine quantified from HPTLC plate scan. SpectraLipid, Soy Lecithin Mix Standard (No. SLM43) was used in the quantification.

| Pasteurised milk | | UHT milk | |
|---|---|---|---|
| 12983-1-11 | 12983-1-12 | 12983-1-13 | 12983-1-14 |
| 18.7 ppm | 1.5 ppm | 23.3 ppm | 3.4 ppm |

The reduction in milk PE content as a response of KLM3 enzymatic treatment and thus the formation of partially hydrolyzed PE (Lyso-PE) correspond to a better emulsion stability and less tendency to creaming over time. In addition, the reduced milk PE corresponds to the formation of cholesterol-esters and a reduction of free cholesterol as given in FIG. 77, and further a better emulsion stability.

Triangle Test

Organoleptic differences between control and enzyme treated pasteurised or UHT milk were evaluated by a triangle test. The results from the tests is outlined in the table below:

TABLE

Triangle tests of UHT milk and Pasteurised (PAST) milk.

| Test no | Results of tests (Alpha risks) | Without Answer | Answers Taken | Answers Right | Signif. |
|---|---|---|---|---|---|
| 1 | UHT without enzyme/UHT with enzyme | 0 | 8 | 1 | 0.961 |
| 3 | UHT without enzyme/UHT with enzyme | 0 | 8 | 4 | 0.259 |
| 5 | UHT without enzyme/UHT with enzyme | 0 | 8 | 5 | 0.088 |
| Average 1-3-5 | UHT without enzyme/UHT with enzyme | 0 | 24 | 10 | 0.2538 |
| 2 | PAST without enzyme/PAST with enzyme | 0 | 8 | 3 | 0.532 |
| 4 | PAST without enzyme/PAST with enzyme | 0 | 8 | 2 | 0.805 |
| 6 | PAST without enzyme/PAST with enzyme | 0 | 8 | 5 | 0.088 |
| Average 2-4-6 | PAST without enzyme/PAST with enzyme | 0 | 24 | 10 | 0.2538 |

The triangle test shows that treatment with the enzyme (KLM3) does not adversely affect the taste of UHT milk or pasteurized milk compared with milk without enzyme addition.

EXAMPLE 4

Preparation of Chocolate Milk

Materials and Methods

Glycerophospholipid cholesterol acyltransferase KLM3 (K932) (SEQ ID NO: 68): 1128 LATU/g Soy Lecithin Mix Standard (ST16) from Spectra Lipid, Germany.

Recipe

| Ingredient Name | Sample no 1 DK14636-2-3 | Sample no 2 DK14636-2-4 |
|---|---|---|
| Skimmed milk | 89.496 | 89.496 |
| Cream 38% fat | 2.804 | 2.804 |
| Sucrose | 6.000 | 6.000 |
| Cocoa powder D-11A (light alk.) | 1.500 | 1.500 |
| GRINDSTED ® Carrageenan CL 220 | 0.020 | 0.020 |
| CREMODAN ® SUPER Mono-diglyceride | 0.180 | 0.180 |
| KLM3 | +0.01 LATU/ml | |
| Total % | 100 | 100 |

Process

Add KLM3 (100 U/ml) to the pasteurised skimmed milk for sample DK14636-2-3, at a dosage of 0.100 ml KLM3 per liter milk
Agitate for two minutes
Place in cold store at 5° C. for 24 hours
Also place the milk for sample no DK14636-2-4 in the cold store at 5° C. for 24 hours.
After 24 hours storage at 5° C., heat the milk to 70° C. and add all other ingredients
Heat to 90° C. for 30 seconds
UHT treatment (plate heat exchanger) 139-142° C./2-4 sec.
Homogenise at 150 bar/50 bar and 75° C.
Cool to 10-15° C.
Transfer to cold store
Store at below 5° C.
Preparation of Cocoa Milk Samples for GC and TLC Analysis:

2 gram Cocoa milk was scaled in a 12 ml test tube with screw lid. 10 Hexan:Isopropanol 3:2 was added.

The sample was mixed on a Whirley and extracted on a rotamix 30 rpm for 30 minutes.

The test tube was centrifugated at 1720 rcf for 10 minutes. The upper phase accounting 8.5 ml was isolated.

5 ml solvent phase was transferred to a 10 ml Dramglass an evaporated to dryness at 50° C. under a steam of nitrogen. The sample was re-dissolved in 0.400 ml Chloroform:Methanol 2:1 and used for TLC analysis.

Another 2 ml of the solvent phase was isolated, evaporated at 50° C. under a stream of Nitrogen and used for GLC analysis Gas Chromatography:

Gas Chromatography is used to measure the content of cholesterol and cholesterol-ester in the lipid from Cocoa milk samples.

The following CG setup is used:
Perkin Elmer Autosystem 9000 Capillary Gas Chromatograph equipped with WCOT fused silica column 12.5 m×0.25 mm ID×0.1μ film thickness 5% phenyl-methyl-silicone (CP Sil 8 CB from Chrompack).
Carrier gas: Helium.
Injector. PSSI cold split injection (initial temp 50° C. heated to 385° C.), volume 1.0 μl
Detector FID: 395° C.

| | Oven program | | |
|---|---|---|---|
| | 1 | 2 | 3 |
| Oven temperature, ° C. | 90 | 280 | 350 |
| Isohtermal, time, min. | 1 | 0 | 10 |
| Temperature rate, ° C./min. | 15 | 4 | |

HPTLC:

HPTLC is used to measure the content of phosphatidylethanolamine (PE) and Phosphatidylcholine (PC) in the isolated lipid from Cocoa milk samples.
Applicator: CAMAG applicator AST4.
HPTLC plate: 20×10 cm (Merck no. 1.05641)
The plate is activated before use by drying in an oven at 160° C. for 10 minutes.
Application: 6.0 μl of extracted lipids dissolved in $CHCl_3$: Methanol (2:1) are applied to the HPTLC plate using AST4 applicator.
0.1, 0.3, 0.5, 0.8, 1.5 μl of a standard solution containing standard components of phospholipids with known concentration are also applied to the HPTLC plate
Running-buffer 6: Methylacetate:$CHCl_3$:1-propanol:MeOH: 0.25% KCl (25:25:25:10:9)
Elution length: 7 cm
Developing fluid: 6% Cupriacetate in 16% $H_3PO_4$
After elution the plate is dried in an oven at 160° C. for 10 minutes, cooled and immersed in the developing fluid (10 sec) and then dried additional for 6 minutes at 160° C. The plate is evaluated visually and scanned (Camag TLC scanner). Phospholipid components are quantified based on calibration curves from the standard phospholipid composition.

Turbiscan:

Turbiscan MA 2000 is used to measure the stability of emulsions by measuring the backscatter of a laser beam (Lumifugation) from the product.

Results

The results from GLC and TLC analysis of lipid extracted form Cocoamilk treated with KLM3' and a control sample without enzyme treatment is seen in Table 1.

TABLE 1

GLC and TLC analysis of lipid from Cocoa milk

| | Cocoa milk Enzyme treated ppm | Cocoa milk Control Ppm |
|---|---|---|
| GLC-analysis | | |
| Free fatty acids | 300 | 292 |
| Cholesterol | 33 | 60 |
| Cholesterol ester | 48 | 6 |

TABLE 1-continued

GLC and TLC analysis of lipid from Cocoa milk

|  | Cocoa milk Enzyme treated ppm | Cocoa milk Control Ppm |
|---|---|---|
| TLC-analysis |  |  |
| Phosphatidylethanolamine | 10.5 | 27.3 |
| Phosphatidylcholine | 2.8 | 24.9 |

The results in Table 1 indicate that almost half of the cholesterol in the Cocoa milk has been esterified by the enzyme treatment. And the amount of phospholipids in the enzyme treated sample was reduced. The results indicate that KLM3' is more active on phosphatidylcholine than on phosphatidylethanolamine in the Cocoa milk.

Lumifugation of Chocolate Milk with and without KLM 3 (DK14636-2)

Figure 79:
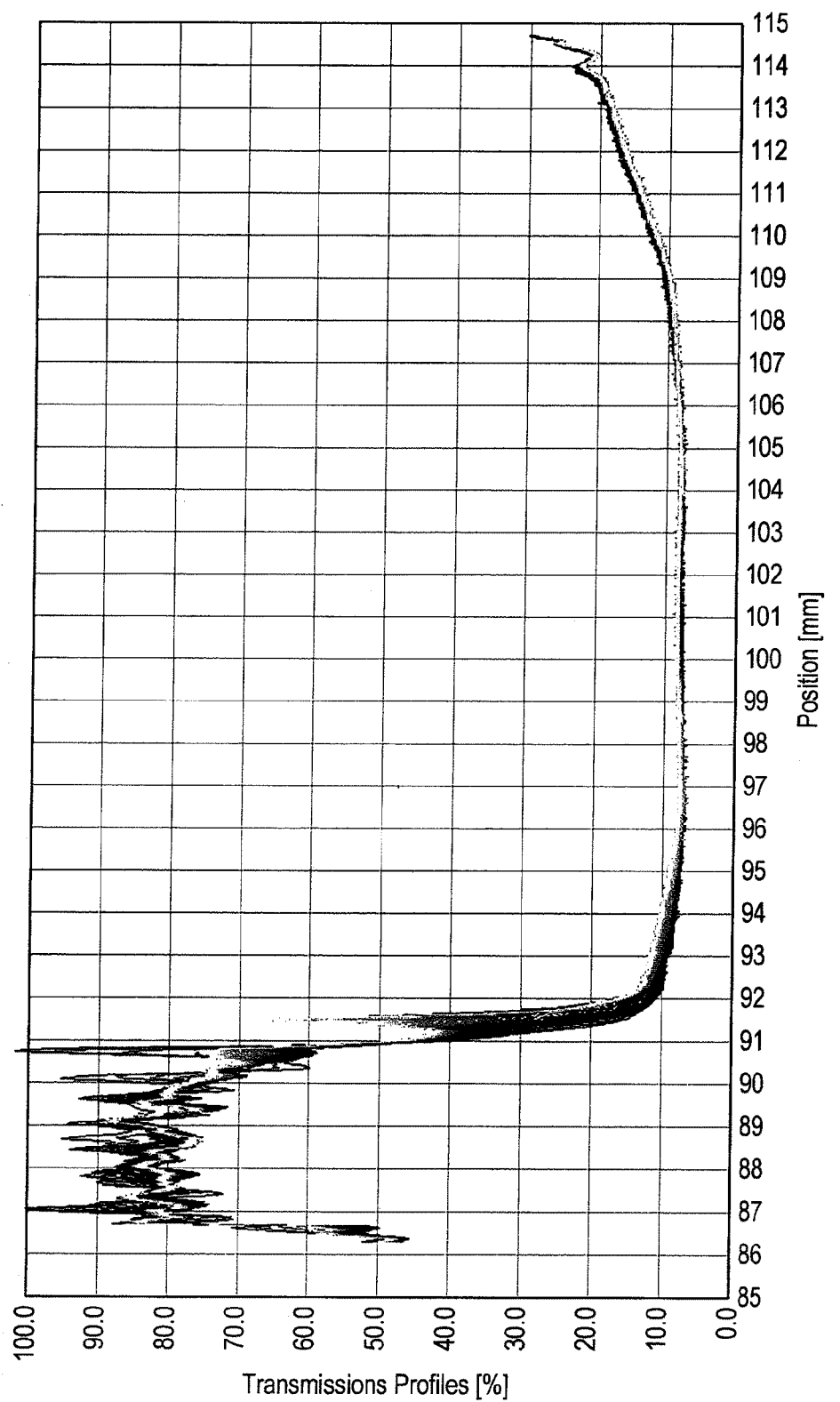
FIG. 79 shows the results of Lumifugation of Chocolate milk with KLM3 ((DK 14636-2-3)
Figure 80:
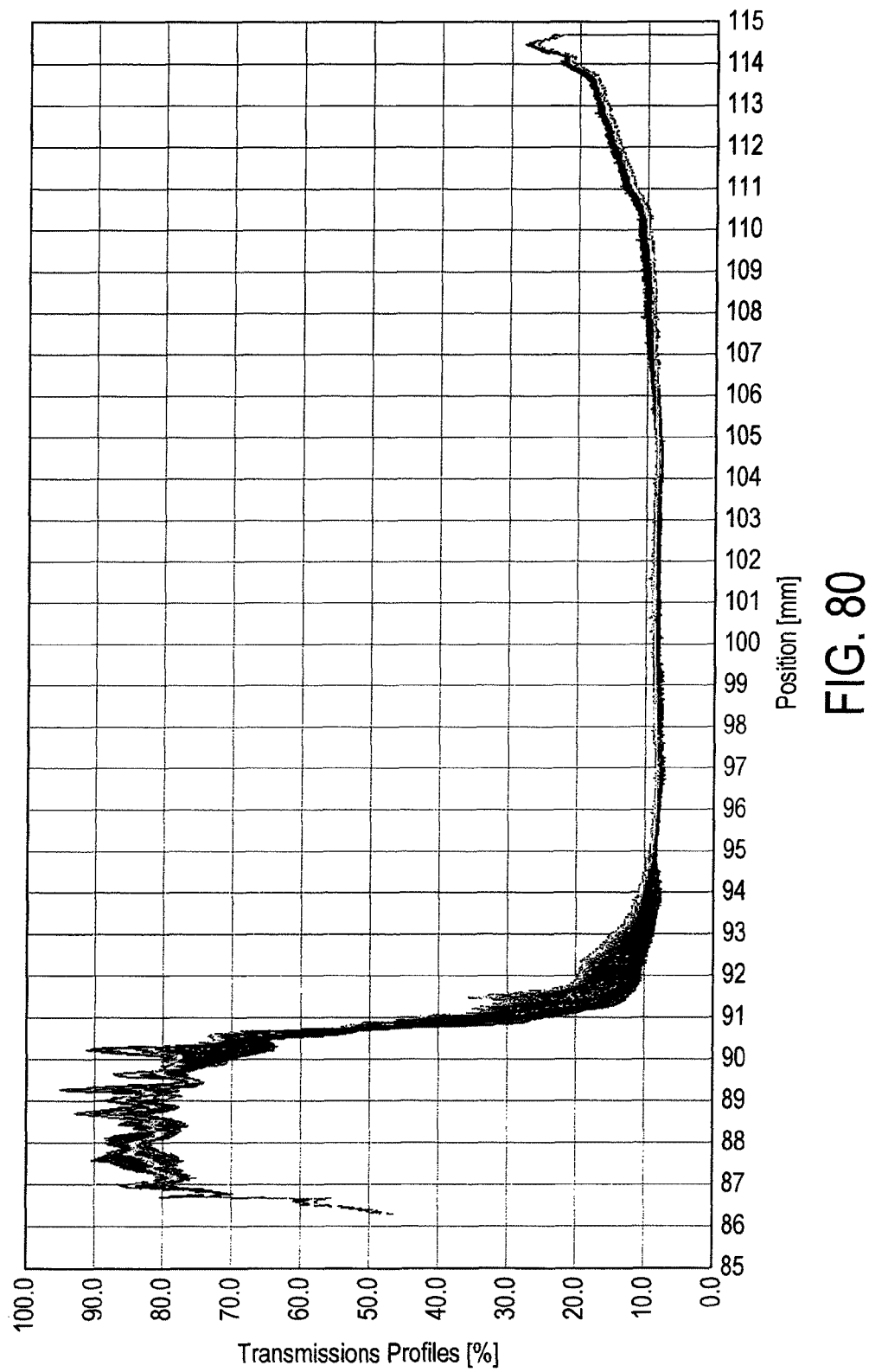
FIG. 80 shows the results of Lumifugation of Chocolate milk without KLM 3 (DK14636-2-4)

Experimental: Lumifugation has been carried out with 300 rpm (12×g), centrifugation glass no. 2 and the results are shown in FIG. 79 (DK 14636-2-3) and FIG. 80 (DK14636-2-4).

Clarification (% Integral Transmission):

| Sample no. | % Change in Transmission/hour ×10³ |
|---|---|
| Sample 1 DK 14636-2-3 | 64 |
| Sample 2 DK14636-2-4 | 72 |

Figure 81:
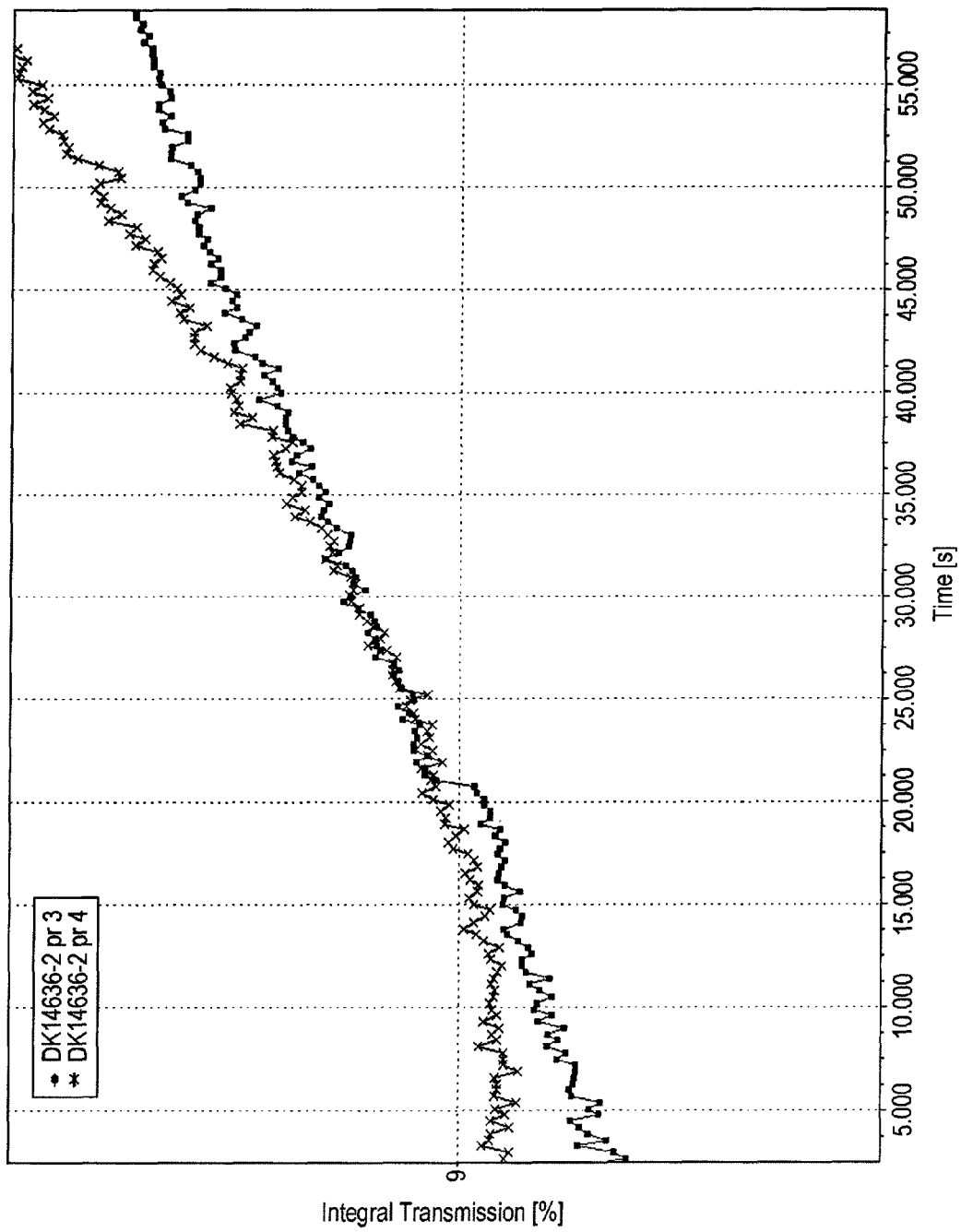
FIG. 81 shows Clarification (% Integral Transmission)

The results are shown in FIG. 81.

As the change in the transmission is a measure of the rate in the clearance, sample 2 is the most unstable.

In order to investigate the rate of clearance front tracking has been performed.

Figure 82:
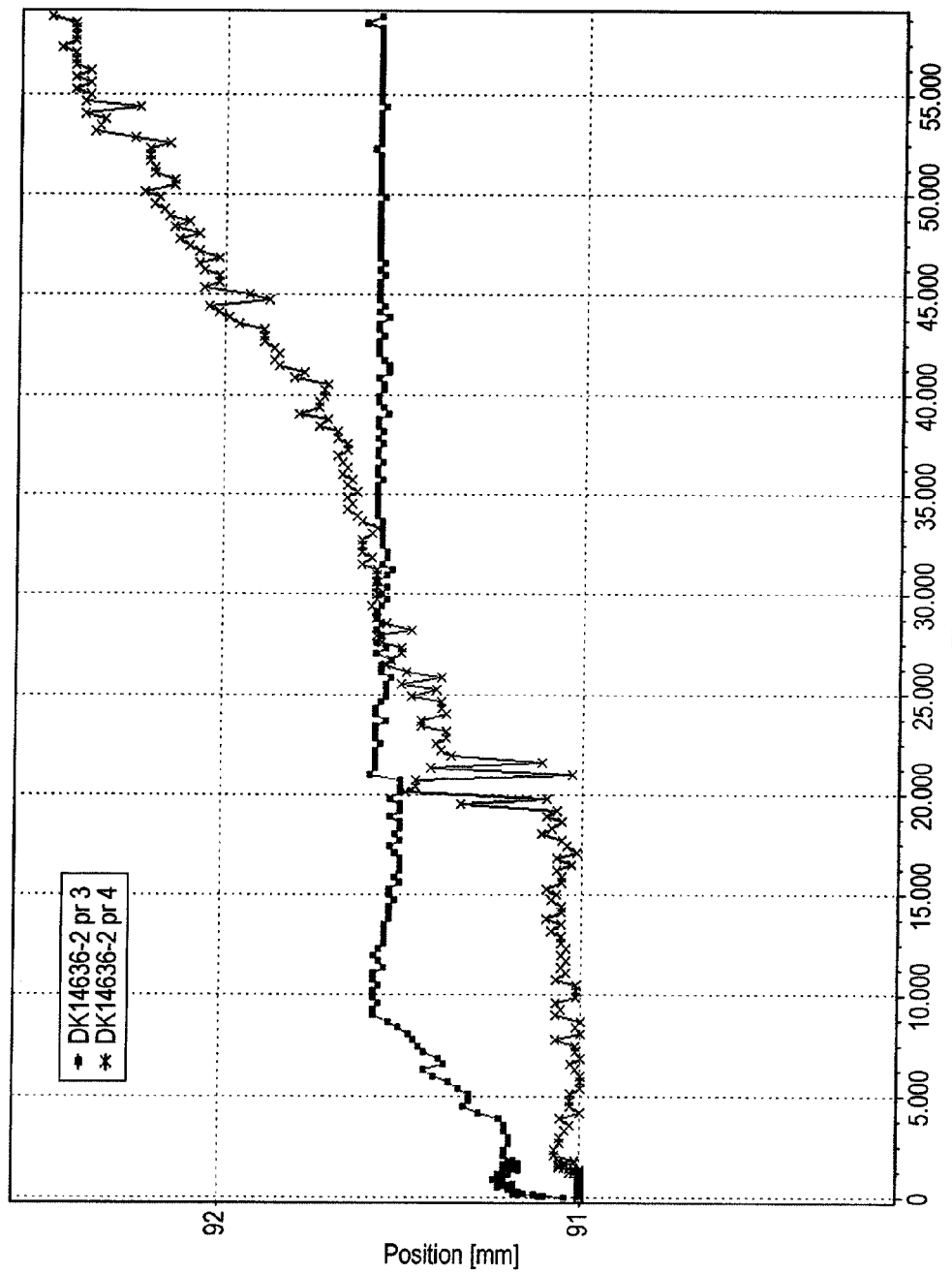
FIG. 82 shows the results of Front tracking, i.e. monitoring the movement of the front of clearance at 15% transmission.

Front tracking, i.e. monitoring the movement of the front of clearance, at 15% transmission (see FIG. 82)

| Sample no | μm/sec at 12xg | mm/month at 1xg |
|---|---|---|
| Sample 1 DK 14636-2-3 | 0.0067 | 1.45 |
| Sample 2 DK 14636-2-4 | 0.0242 | 5.23 |

Figure 83:
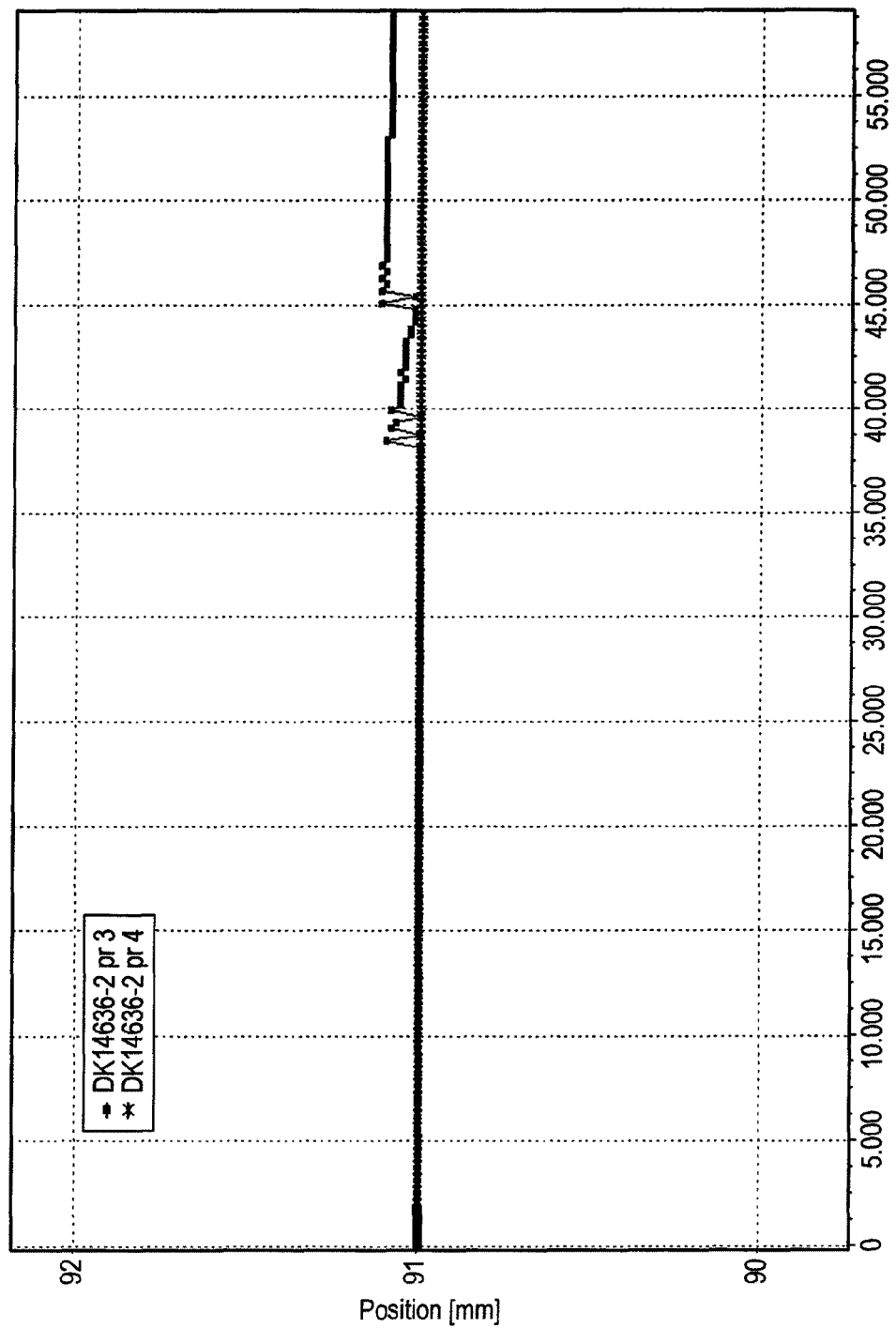
FIG. 83 shows the results of Front tracking, i.e. monitoring the movement of the front of clearance at 50% transmission.

Front tracking at 50% transmission (see FIG. 83) together with the front tracking at 15% (see FIG. 82) shows the difference in the clearance of the two samples, as sample 1 has approx. 1 mm clearance (50% T) supernatant, while sample 2 has a 2 mm less transparent supernatant. This is the result of a broader particle size distribution in sample 2.

Conclusion:

The enzyme treated sample is the most stable sample and further it has the most narrow particle size distribution

EXAMPLE 5

Comparison of KLM3' (K932) with Different Phospholipases

Materials and Methods

Lipid acyltransferase—KLM3' (K932)

A fungal lipolytic enzyme obtainable from *Fusarium heterosporum* CBS 782.83 (hereinafter referred to a "KLM1" from Danisco A/S) as taught in WO2005/087818.

Phospholipase A1 from *Fusarium oxysporum* (LIPOPAN F™) from Novozymes

Pphospholipase A2 from Porcine pancreas (LIPOMOD 699 L™) from Biocatalysts, UK

Standard pasteurised Whole Milk (3.5% fat) from ARLA in Denmark

Enzymated milk was investigated in comparison to reference milk in terms of stability against creaming visual evaluation of creaming, sedimentation and phase separation in samples stored over 60 days.

Furthermore the amount of free fatty acids in the milk was analyzed to evaluate level of rancidity in final product, and amount of cholesterol and/or phospholipids was analyzed to get an indication of enzymatic reaction level.

EXPERIMENTAL

Preparation of Milk

TABLE

| | Recipe Ingredients in % | | | | | |
|---|---|---|---|---|---|---|
| Ingredient Name | 1 | 2 | 3 | 4 | 5 | 6 |
| Whole milk 3.5% fat | 100.000 | 100.000 | 100.000 | 100.000 | 100.000 | 100.000 |
| KLM1 |  |  |  | 10 LATU/ml |  |  |
| KLM3' |  | 0.01 LATU/ml |  |  |  | 0.25 LATU/ml |
| LIPOPAN F |  |  | 5 LATU/ml |  |  |  |
| Lipomod 699 L |  |  |  |  | 0.25 e-PLU/ml |  |
| Total % | 100 | 100 | 100 | 100 | 100 | 100 |

Process

1. Cold milk was mixed with enzyme portion and mixture was left in cold store overnight
2. Preheating to 90° C. for 30 sec
3. UHT treatment at 142° C. for 3 sec
4. Homogenise at 75° C. and 200 bar
5. Cool to 20° C. and fill aseptically in 6 bottles

TABLE

Real time shelf-life test

| | Sample 1 | Sample 2 | Sample 3 | Sample 4 | Sample 5 | Sample 6 |
|---|---|---|---|---|---|---|
| Cream Layer | 4 mm | 1 mm | 3 mm | 2 mm | 3 mm | 2 mm |
| Sediment layer | 0 mm | 0 mm | 12 mm | 1 mm | 2 mm | <1 mm |
| Organoleptic evaluation | Typical UHT flavour, slightly cooked | As sample 1, however, slightly less cooked | Grainy texture with very strong rancidity | As sample 1 | As sample 1 | As sample 1 |

Samples prepared by UHT processing as described earlier were stored at ambient temperatures (18-25° C.) for a period of 60 days, where after the samples were evaluated for creaming layer as well as eventual phase separation or sedimentation in the bottom of the bottles.

Samples were furthermore tested by a trained panel of 6 persons, with a tasting session made as a randomised triangle test with sample 1 (plain UHT milk) used as the reference sample in all test sessions.

Both for real time observation of stability as well as organoleptic evaluation, it can be seen that sample 3 (enzymated with LIPOPAN F™) gives significantly deviating results, with lower stability and strong lipolytic flavour in samples.

KLM3' (samples 2 and 6) reduced the cream layer without forming a sediment layer and showed a marked improvement compared with the control 1.

The phospholipase treated samples 3, 4 and 5 may also reduced the cream layer compared with the control (although not to the same degree as KLM3'), but this was at the expense of forming a sediment layer.

With regard to organoleptic properties, sample 2 (KLM3') had a slightly less cooked taste compared with the control 1. Hence sample 2 has an improved taste compared with the control 1. Lipopan F™ (sample 3) produced milk with bad organoleptic properties, probably due to the high level of free fatty acids produced.

HPTLC and GLC Analysis

Enzyme treated UHT milk according to the recipes shown in the table was extracted with organic solvents and the isolated lipids were analyzed for phospholipids by HPTLC and for cholesterol, cholesterol ester and free fatty acids (FFA) by Gaschromatography (GLC).

TABLE

HPTLC analysis of main phospholipids in milk
PC = phosphatidylcholine
PE = phosphatidylethanolamine.

| Sample | Dosage | PC ppm | PE ppm | Sum PC + PE Ppm | Degree of hydrolysis % |
|---|---|---|---|---|---|
| Control | | 26.6 | 61.4 | 88.0 | 0 |
| KLM3* | 0.01 TIPU/ml | 9.0 | 10.9 | 19.9 | 77 |
| Lipopan F | 5 TIPU/ml | 3.9 | 7.8 | 11.8 | 87 |
| KLM1 | 10 TIPU/ml | 14.6 | 14.6 | 29.2 | 67 |
| Lipomod 699L | 0.25 e-PLU/ml | 5.1 | 2.0 | 7.2 | 92 |
| KLM3' | TIPU/ml | 5.0 | 2.0 | 7.0 | 92 |

TABLE

GLC analysis of cholesterol, cholesterol ester and free fatty acids (FFA)

| Sample | Dosage | FFA total % | Cholesterol % | Cholesterol ester % |
|---|---|---|---|---|
| Control | 0 | 0.022 | 0.015 | 0.0012 |
| KLM3* | 0.01 TIPU/g | 0.029 | 0.009 | 0.0106 |
| Lipopan F | 5 TIPU/g | 0.620 | 0.016 | 0.0014 |
| KLM1 | 10 TIPU/g | 0.159 | 0.016 | 0.0015 |
| Lipomod 699L | 0.25 e-PLU | 0.042 | 0.014 | 0.0010 |
| KLM3' | TIPU/g | 0.065 | 0.001 | 0.0215 |

The results form HPTLC analysis (see Table above) indicate that all enzymes tested were able to hydrolyse a main part of the phospholipids in the milk accounting from 77% to 92%, but only the lipid acyltransferease KLM3' were able to make a transfer reaction of fatty acid to cholesterol during formation of cholesterol ester.

Although all enzymes produced a high degree of phospholipid hydrolysis the amount of free fatty acids produced were significantly different. Based of the amount of phospholipid hydrolysis and free fatty acid produced it is possible to calculate on a molar basis the amount of free fatty acid relative to the amount of phospholipids produced (see the table below). These results clearly demonstrate that the microbial phospholipases A1 produces much more free fatty acid that KLM3, because these phospholipases are not specific but also hydrolysis triglycerides (milk fat). Pancreas phospholipase (Lipomod 699 L) is known to be very specific for the phospholipids, but still produces more free fatty acids than the low dosage of KLM3'. At the high dosage of KLM3' more fatty acid are produced than pancreas phospholipase, but this is explained by activity on lyso-phospholipids. Lipopan F produced the highest amount of free fatty acid because of the hydrolytic activity on triglycerides, which contributed to the negative evaluation in the organoleptic test.

TABLE

Formation of free fatty acid (FFA) relative to the amount of hydrolysed phospholipids

| Sample | Dosage | FFA change mmol/kg | PL change mmol/kg | FFA/PL mol. ratio |
|---|---|---|---|---|
| Control | 0 | 0 | 0 | — |
| KLM3* | 0.01 TIPU/g | 0.279 | 0.093 | 3 |
| Lipopan F | 5 TIPU/g | 21.7 | 0.103 | 210 |
| KLM1 | 10 TIPU/g | 4.98 | 0.080 | 62 |
| Lipomod 699L | 0.25 e-PLU | 0.742 | 0.110 | 7 |
| KLM3' | TIPU/g | 1.58 | 0.110 | 14 |

In conclusion: KLM3' showed an enhanced stability (with a reduced cream layer without formation of a sediment layer)

compared with both the control (without enzyme) and the comparative phospholipase enzymes. Without wishing to be bound by theory the reason for the enhanced stability may be due to a reduced particle size distribution of the fat globules in milk treated with KLM3'.

A further important effect is that KLM3' produces much less free fatty acid compared with the same concentration of phospholipase. During extended storage at ambient temperatures free fatty acid can easily result in more oxidation of the milk and thus later cause organoleptic problems. Thus high free fatty acid content may cause significant problems in UHT milk which is typically stored at ambient temperatures for more than a month.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention is further described by the following numbered paragraphs:

1. A method of producing UHT milk, wherein said method comprises admixing a lipid acyltransferase and milk or a fraction thereof and treating the enzyme treated milk by ultra-heat treatment to produce UHT milk.
2. A method according to paragraph 1 wherein the lipid acyltransferase is added to the UHT milk and incubated therewith at a temperature of less than about 20° C., preferably less than about 10° C.
3. A method according to paragraph 1 or paragraph 2 wherein the lipid acyltransferase is added to the UHT milk and incubated therewith at a temperature of between about 1° C. and about 10° C., preferably between about 3° C. and about 7° C., more preferably about 5° C.
4. A method according to any one of paragraphs 1 to 3 wherein the lipid acyltransferase comprises a GDSx (SEQ ID NO: 120) motif and/or a GANDY (SEQ ID NO: 118) motif.
5. A method according to any one of the preceding paragraphs wherein the lipid acyltransferase enzyme is characterised as an enzyme which possesses acyltransferase activity and which comprises the amino acid sequence motif GDSX (SEQ ID NO: 117), wherein X is one or more of the following amino acid residues L, A, V, I, F, Y, H, Q, T, N, M or S.
6. A method according to any one of the preceding paragraphs wherein the lipid acyltransferase for use in any one of the methods and/or uses of the present invention may be obtainable, preferably obtained, from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.
7. A method according to paragraph 6 wherein the lipid acyltransferase is obtainable, preferably obtained, from an organism from the genus *Aeromonas*.
8. A method according to any on the preceding paragraphs wherein said lipid acyltransferase is a polypeptide having lipid acyltranferase activity which polypeptide is obtained by expression of any one of the nucleotide sequences shown as SEQ ID NO: 36, SEQ ID NO: 38, SEQ ID NO: 39, SEQ ID NO: 42, SEQ ID NO: 44, SEQ ID NO: 46, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62 or SEQ ID NO: 63 or a nucleotide sequence which as has 75% or more identity therewith.
9. A method according to any one of the preceding paragraphs wherein said lipid acyltranferase is a polypeptide having lipid acyltranferase activity which polypeptide is obtained by expression of:
   a) the nucleotide sequence shown as SEQ ID NO: 49 or a nucleotide sequence which as has 75% or more identity therewith;
   b) a nucleic acid which encodes said polypeptide wherein said polypeptide is at least 70% identical with the polypeptide sequence shown in SEQ ID NO: 16 or with the polypeptide sequence shown in SEQ ID NO: 68;
   c) or a nucleic acid which hybridises under medium stringency conditions to a nucleic probe comprising the nucleotide sequence shown as SEQ ID NO: 49.
10. A method according to any on the preceding paragraphs wherein said lipid acyltransferase is a polypeptide having lipid acyltranferase activity which polypeptide comprises any one of the amino acid sequences shown as SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 17, SEQ ID NO: 16, SEQ ID NO: 17, SEQ ID NO: 18, SEQ ID NO: 34, SEQ ID NO: 35, SEQ ID NO: 68 or an amino acid sequence sequence which as has 75% or more identity therewith.
11. A method according to any one of the preceding paragraphs wherein said lipid acyltranferase is a polypeptide having lipid acyltranferase activity which polypeptide comprises the amino acid sequence shown as SEQ ID NO: 68 or an amino acid sequence sequence which as has 75% or more identity therewith.
12. Use of a lipid acyltransferase in the manufacture of UHT milk for improving the stability, particularly the long term stability, of the UHT milk.

Use of a lipid acyltransferase in the manufacture of UHT milk for improving the perceptible sensory difference of the UHT milk.

14. Use of a lipid acyltransferase in the manufacture of UHT milk for improving smell and/or taste of the UHT milk.
15. Use of a lipid acyltransferase in the manufacture of UHT milk for reducing the cholesterol content in the UHT milk.
16. Use of a lipid acyltransferase in the manufacture of UHT milk for eliminating or reducing creaming in the UHT milk.
17. Use according to any one of paragraphs 12-16 wherein the lipid acyltransferase is added to the UHT milk and incubated therewith at a temperature of less than about 20° C., preferably less than about 10° C.
18. Use according to any one of paragraphs 12-17 wherein the lipid acyltransferase is added to the UHT milk and incubated therewith at a temperature of between about 1° C. and about 10° C., preferably between about 3° C. and about 7° C., more preferably about 5° C.
19. Use according to any one of paragraphs 12 to 18 wherein the lipid acyltransferase comprises a GDSX (SEQ ID NO: 120) motif and/or a GANDY (SEQ ID NO: 118) motif.
20. Use according to any one of paragraphs 12-19 wherein the lipid acyltransferase enzyme is characterised as an enzyme which possesses acyltransferase activity and which comprises the amino acid sequence motif GDSX (SEQ ID NO:

117), wherein X is one or more of the following amino acid residues L, A, V, I, F, Y, H, Q, T, N, M or S.

21. Use according to any one of paragraphs 12-20 wherein the lipid acyltransferase for use in any one of the methods and/or uses of the present invention may be obtainable, preferably obtained, from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

22. Use according to paragraph 21 wherein the lipid acyltransferase is obtainable, preferably obtained, from an organism from the genus *Aeromonas*.

23. Use according to any one of paragraphs 12-22 wherein said lipid acyltransferase is a polypeptide having lipid acyltransferase activity which polypeptide is obtained by expression of any one of the nucleotide sequences shown as SEQ ID NO: 36, SEQ ID NO: 38, SEQ ID NO: 39, SEQ ID NO: 42, SEQ ID NO: 44, SEQ ID NO: 46, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62 or SEQ ID NO: 63 or a nucleotide sequence which as has 75% or more identity therewith.

24. Use according to any one of claims 12-23 wherein said lipid acyltransferase is a polypeptide having lipid acyltransferase activity which polypeptide is obtained by expression of:
   a. the nucleotide sequence shown as SEQ ID NO: 49 or a nucleotide sequence which as has 75% or more identity therewith;
   b. a nucleic acid which encodes said polypeptide wherein said polypeptide is at least 70% identical with the polypeptide sequence shown in SEQ ID NO: 16 or with the polypeptide sequence shown in SEQ ID NO: 68; or
   c. a nucleic acid which hybridises under medium stringency conditions to a nucleic probe comprising the nucleotide sequence shown as SEQ ID NO: 49.

25. Use according to any one of paragraphs 12-24 wherein said lipid acyltransferase is a polypeptide having lipid acyltransferase activity which polypeptide comprises any one of the amino acid sequences shown as SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 17, SEQ ID NO: 16, SEQ ID NO: 17, SEQ ID NO: 18, SEQ ID NO: 34, SEQ ID NO: 35, SEQ ID NO: 68 or an amino acid sequence which as has 75% or more identity therewith.

26. Use according to any one of paragraphs 12-25 wherein said lipid acyltransferase is a polypeptide having lipid acyltransferase activity which polypeptide comprises the amino acid sequence shown as SEQ ID NO: 68 or an amino acid sequence which as has 75% or more identity therewith.

27. A method according to any one of paragraphs 9-11 wherein the polypeptide is obtained by expression in *Bacillus licheniformis*.

28. A use according to any one of paragraphs 24-26 wherein the polypeptide is obtained by expression in *Bacillus licheniformis*.

29. A method as generally defined herein with reference to the examples and figures.

30. A use as generally defined herein with reference to the examples and figures.

---

What is claimed is:

1. A method of producing ultra-heat treatment (UHT) milk comprising: mixing a lipid acyltransferase with milk, or a milk fraction, and heating mixture with an ultra-heat treatment to thereby produce UHT milk,
   wherein the lipid acyltransferase has at least 5% transferase activity when calculated with an assay for transferase activity,
   wherein the assay comprises measuring a molar amount of cholesterol ester formed by acyltransfer from phospholipids or triacylglycerides in milk to cholesterol relative to the amount of cholesterol originally available with a formula:

Transferase activity=(Mol/l cholesterol ester(*t*)−Mol/l cholesterol ester(0))×100 Mol/l cholesterol(0); and wherein cholesterol ester(t)=the amount of cholesterol ester to the time t,
   Cholesterol ester(0)=the amount of cholesterol ester to the time 0,
   Cholesterol (0)=the amount of cholesterol in milk to the time 0 and
   Cholesterol and cholesterol ester are determined by gas liquid chromatography (GLC).

2. The method of claim 1, wherein the lipid acyltransferase is added prior to ultra-heat treatment or after ultra-heat treatment.

3. The method of claim 1, wherein the mixture is incubated at a temperature of less than about 20° C.

4. The method of claim 1, wherein the mixture is incubated at a temperature of between about 1° C. and about 10° C.

5. The method of claim 1, wherein the lipid acyltransferase comprises the amino acid sequence motif GDSX (SEQ ID NO: 120) and/or GANDY (SEQ ID NO: 118).

6. The method of claim 1, wherein the lipid acyltransferase possesses acyltransferase activity and comprises the amino acid sequence motif GDSX (SEQ ID NO: 117), wherein X is one or more of the following amino acid residues L, A, V, I, F, Y, H, Q, T, N, M or S.

7. The method of claim 1, wherein the lipid acyltransferase is from an organism in a genera selected from the group consisting of: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas* and *Candida*.

8. The method of claim 7, wherein the lipid acyltransferase is from an organism from the genus *Aeromonas*.

9. The method of claim 1, wherein the lipid acyltransferase is a polypeptide having lipid acyltransferase activity and is produced by expressing a nucleotide sequence selected from the group consisting of: SEQ ID NO: 36, SEQ ID NO: 39, SEQ ID NO: 42, SEQ ID NO: 44, SEQ ID NO: 46, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62 and SEQ ID NO: 63.

10. The method of claim 1, wherein the lipid acyltransferase is a polypeptide having lipid acyltransferase activity and is produced by expressing a nucleotide sequence having 90% or more identity with a nucleotide sequence selected from the group consisting of: SEQ ID NO: 36, SEQ ID NO: 39, SEQ ID NO: 42, SEQ ID NO: 44, SEQ ID NO: 46, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62 and SEQ ID NO: 63.

11. The method of claim 1, wherein the lipid acyltransferase is a polypeptide having lipid acyltransferase activity and is produced by expressing:
   SEQ ID NO: 49 or a nucleotide sequence having 90% or more identity therewith;
   a nucleic acid encoding a polypeptide having at least 90% identity with SEQ ID NO: 16 or with SEQ ID NO: 68, or
   a nucleic acid which hybridises under high stringency conditions (65° C. and 0.1.times.SSC {1×SSC=0.15 M NaCl, 0.015 M Na-citrate pH 7.0}) to a probe comprising SEQ ID NO: 49.

12. The method of claim 1, wherein the lipid acyltransferase is a polypeptide having lipid acyltransferase activity and comprises an amino acid sequence selected from the group consisting of: SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 17, SEQ ID NO: 16, SEQ ID NO: 17, SEQ ID NO: 18, SEQ ID NO: 34, SEQ ID NO: 35 and SEQ ID NO: 68.

13. The method of claim 1, wherein the lipid acyltransferase is a polypeptide having lipid acyltransferase activity and comprises an amino acid sequence having 90% or more identity with an amino acid sequence selected from the group consisting of: SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 17, SEQ ID NO: 16, SEQ ID NO: 17, SEQ ID NO: 18, SEQ ID NO: 34, SEQ ID NO: 35 and SEQ ID NO: 68.

14. The method of claim 1, wherein the lipid acyltransferase is a polypeptide having lipid acyltransferase activity and comprises SEQ ID NO: 68.

15. The method of claim 1, wherein the lipid acyltransferase is a polypeptide having lipid acyltransferase activity and comprises an amino acid sequence having 90% or more identity with SEQ ID NO: 68.

16. The method of claim 11, wherein the polypeptide is expressed in *Bacillus licheniformis*.

17. The method of claim 3, wherein the mixture is incubated at a temperature of less than about 10° C.

18. The method of claim 4, wherein the mixture is incubated at a between about 3° C. and about 7° C.

19. The method of claim 18, wherein the mixture is incubated at about 5° C.

* * * * *

SEQUENCE LISTING

```
<160> NUMBER OF SEQ ID NOS: 137

<210> SEQ ID NO 1
<211> LENGTH: 335
<212> TYPE: PRT
<213> ORGANISM: Aeromonas hydrophila

<400> SEQUENCE: 1

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
                20                  25                  30

Asp Ser Leu Ser Asp Thr Gly Lys Met Tyr Ser Lys Met Arg Gly Tyr
            35                  40                  45

Leu Pro Ser Ser Pro Pro Tyr Tyr Glu Gly Arg Phe Ser Asn Gly Pro
        50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
```

```
                130                 135                 140
Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
                180                 185                 190

His Val Ser Ala Tyr His Asn Gln Leu Leu Asn Leu Ala Arg Gln
                195                 200                 205

Leu Ala Pro Thr Gly Met Val Lys Leu Phe Glu Ile Asp Lys Gln Phe
210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
                275                 280                 285

Met Ala Arg Arg Ser Ala Ser Pro Leu Asn Cys Glu Gly Lys Met Phe
290                 295                 300

Trp Asp Gln Val His Pro Thr Thr Val Val His Ala Ala Leu Ser Glu
305                 310                 315                 320

Arg Ala Ala Thr Phe Ile Ala Asn Gln Tyr Glu Phe Leu Ala His
                325                 330                 335

<210> SEQ ID NO 2
<211> LENGTH: 361
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 2

Ile Val Ala Phe Gly Asp Ser Leu Thr Asp Gly Glu Ala Tyr Tyr Gly
1               5                   10                  15

Asp Ser Asp Gly Gly Gly Trp Gly Ala Gly Leu Ala Ser Arg Leu Thr
                20                  25                  30

Ala Leu Leu Arg Leu Arg Ala Arg Pro Arg Gly Val Asp Val Phe Asn
                35                  40                  45

Arg Gly Ile Ser Gly Arg Thr Ser Asp Gly Arg Leu Ile Val Asp Ala
50                  55                  60

Leu Val Ala Leu Leu Phe Leu Ala Gln Ser Leu Gly Leu Pro Asn Leu
65                  70                  75                  80

Pro Pro Tyr Leu Ser Gly Asp Phe Leu Arg Gly Ala Asn Phe Ala Ser
                85                  90                  95

Ala Gly Ala Thr Ile Leu Pro Thr Ser Gly Pro Phe Leu Ile Gln Val
                100                 105                 110

Gln Phe Lys Asp Phe Lys Ser Gln Val Leu Glu Leu Arg Gln Ala Leu
                115                 120                 125

Gly Leu Leu Gln Glu Leu Leu Arg Leu Pro Val Leu Asp Ala Lys
                130                 135                 140

Ser Pro Asp Leu Val Thr Ile Met Ile Gly Thr Asn Asp Leu Ile Thr
145                 150                 155                 160

Ser Ala Phe Phe Gly Pro Lys Ser Thr Glu Ser Asp Arg Asn Val Ser
```

```
                        165                 170                 175
Val Pro Glu Phe Lys Asp Asn Leu Arg Gln Leu Ile Lys Arg Leu Arg
            180                 185                 190

Ser Asn Asn Gly Ala Arg Ile Ile Val Leu Ile Thr Leu Val Ile Leu
            195                 200                 205

Asn Leu Gly Pro Leu Gly Cys Leu Pro Leu Lys Leu Ala Leu Ala Leu
            210                 215                 220

Ala Ser Ser Lys Asn Val Asp Ala Ser Gly Cys Leu Glu Arg Leu Asn
225                 230                 235                 240

Glu Ala Val Ala Asp Phe Asn Glu Ala Leu Arg Glu Leu Ala Ile Ser
                245                 250                 255

Lys Leu Glu Asp Gln Leu Arg Lys Asp Gly Leu Pro Asp Val Lys Gly
            260                 265                 270

Ala Asp Val Pro Tyr Val Asp Leu Tyr Ser Ile Phe Gln Asp Leu Asp
            275                 280                 285

Gly Ile Gln Asn Pro Ser Ala Tyr Val Tyr Gly Phe Glu Thr Thr Lys
            290                 295                 300

Ala Cys Cys Gly Tyr Gly Gly Arg Tyr Asn Tyr Asn Arg Val Cys Gly
305                 310                 315                 320

Asn Ala Gly Leu Cys Asn Val Thr Ala Lys Ala Cys Asn Pro Ser Ser
                325                 330                 335

Tyr Leu Leu Ser Phe Leu Phe Trp Asp Gly Phe His Pro Ser Glu Lys
                340                 345                 350

Gly Tyr Lys Ala Val Ala Glu Ala Leu
            355                 360

<210> SEQ ID NO 3
<211> LENGTH: 335
<212> TYPE: PRT
<213> ORGANISM: Aeromonas hydrophila

<400> SEQUENCE: 3

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
```

```
                      180                 185                 190
His Val Ser Ala Tyr His Asn Gln Leu Leu Asn Leu Ala Arg Gln
                195                 200                 205
Leu Ala Pro Thr Gly Met Val Lys Leu Phe Glu Ile Asp Lys Gln Phe
210                 215                 220
Ala Glu Met Leu Arg Asp Pro Gln Asn Phe Gly Leu Ser Asp Gln Arg
225                 230                 235                 240
Asn Ala Cys Tyr Gly Gly Ser Tyr Val Trp Lys Pro Phe Ala Ser Arg
                245                 250                 255
Ser Ala Ser Thr Asp Ser Gln Leu Ser Ala Phe Asn Pro Gln Glu Arg
                260                 265                 270
Leu Ala Ile Ala Gly Asn Pro Leu Leu Ala Gln Ala Val Ala Ser Pro
                275                 280                 285
Met Ala Ala Arg Ser Ala Ser Thr Leu Asn Cys Glu Gly Lys Met Phe
                290                 295                 300
Trp Asp Gln Val His Pro Thr Thr Val Val His Ala Ala Leu Ser Glu
305                 310                 315                 320
Pro Ala Ala Thr Phe Ile Glu Ser Gln Tyr Glu Phe Leu Ala His
                325                 330                 335

<210> SEQ ID NO 4
<211> LENGTH: 336
<212> TYPE: PRT
<213> ORGANISM: Aeromonas salmonicida

<400> SEQUENCE: 4

Met Lys Lys Trp Phe Val Cys Leu Leu Gly Leu Ile Ala Leu Thr Val
1               5                   10                  15
Gln Ala Ala Asp Thr Arg Pro Ala Phe Ser Arg Ile Val Met Phe Gly
                20                  25                  30
Asp Ser Leu Ser Asp Thr Gly Lys Met Tyr Ser Lys Met Arg Gly Tyr
                35                  40                  45
Leu Pro Ser Ser Pro Pro Tyr Tyr Glu Gly Arg Phe Ser Asn Gly Pro
                50                  55                  60
Val Trp Leu Glu Gln Leu Thr Lys Gln Phe Pro Gly Leu Thr Ile Ala
65                  70                  75                  80
Asn Glu Ala Glu Gly Gly Ala Thr Ala Val Ala Tyr Asn Lys Ile Ser
                85                  90                  95
Trp Asn Pro Lys Tyr Gln Val Tyr Asn Asn Leu Asp Tyr Glu Val Thr
                100                 105                 110
Gln Phe Leu Gln Lys Asp Ser Phe Lys Pro Asp Asp Leu Val Ile Leu
                115                 120                 125
Trp Val Gly Ala Asn Asp Tyr Leu Ala Tyr Gly Trp Asn Thr Glu Gln
                130                 135                 140
Asp Ala Lys Arg Val Arg Asp Ala Ile Ser Asp Ala Ala Asn Arg Met
145                 150                 155                 160
Val Leu Asn Gly Ala Lys Gln Ile Leu Leu Phe Asn Leu Pro Asp Leu
                165                 170                 175
Gly Gln Asn Pro Ser Ala Arg Ser Gln Lys Val Val Glu Ala Val Ser
                180                 185                 190
His Val Ser Ala Tyr His Asn Lys Leu Leu Leu Asn Leu Ala Arg Gln
                195                 200                 205
Leu Ala Pro Thr Gly Met Val Lys Leu Phe Glu Ile Asp Lys Gln Phe
210                 215                 220
Ala Glu Met Leu Arg Asp Pro Gln Asn Phe Gly Leu Ser Asp Val Glu
```

```
            225                 230                 235                 240
Asn Pro Cys Tyr Asp Gly Gly Tyr Val Trp Lys Pro Phe Ala Thr Arg
                    245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
            275                 280                 285

Met Ala Arg Arg Ser Ala Ser Pro Leu Asn Cys Glu Gly Lys Met Phe
        290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
            20                  25                  30

Pro Ala Gln Ala Thr Pro Thr Leu Asp Tyr Val Ala Leu Gly Asp Ser
        35                  40                  45

Tyr Ser Ala Gly Ser Gly Val Leu Pro Val Asp Pro Ala Asn Leu Leu
    50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
    210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
```

```
                275                 280                 285

Met Asp Val Leu Gly Leu Asp
    290                 295

<210> SEQ ID NO 6
<211> LENGTH: 295
<212> TYPE: PRT
<213> ORGANISM: Streptomyces coelicolor

<400> SEQUENCE: 6

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
            20                  25                  30

Pro Ala Gln Ala Thr Pro Thr Leu Asp Tyr Val Ala Leu Gly Asp Ser
        35                  40                  45

Tyr Ser Ala Gly Ser Gly Val Leu Pro Val Asp Pro Ala Asn Leu Leu
    50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
    130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
    210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
        275                 280                 285

Met Asp Val Leu Gly Leu Asp
    290                 295

<210> SEQ ID NO 7
<211> LENGTH: 238
<212> TYPE: PRT
<213> ORGANISM: Saccharomyces cerevisiae

<400> SEQUENCE: 7

Met Asp Tyr Glu Lys Phe Leu Leu Phe Gly Asp Ser Ile Thr Glu Phe
1               5                   10                  15
```

Ala Phe Asn Thr Arg Pro Ile Glu Asp Gly Lys Asp Gln Tyr Ala Leu
            20                  25                  30

Gly Ala Ala Leu Val Asn Glu Tyr Thr Arg Lys Met Asp Ile Leu Gln
        35                  40                  45

Arg Gly Phe Lys Gly Tyr Thr Ser Arg Trp Ala Leu Lys Ile Leu Pro
    50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
            100                 105                 110

His Ile Arg Pro Ile Ile Gly Pro Gly Leu Val Asp Arg Glu Lys
        115                 120                 125

Trp Glu Lys Glu Lys Ser Glu Glu Ile Ala Leu Gly Tyr Phe Arg Thr
    130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
    210                 215                 220

Asp Trp Arg Asp Val Leu Asp Asp Gly Ser Asn Ile Met Ser
225                 230                 235

<210> SEQ ID NO 8
<211> LENGTH: 347
<212> TYPE: PRT
<213> ORGANISM: Ralstonia sp.

<400> SEQUENCE: 8

Met Asn Leu Arg Gln Trp Met Gly Ala Ala Thr Ala Ala Leu Ala Leu
1               5                   10                  15

Gly Leu Ala Ala Cys Gly Gly Gly Thr Asp Gln Ser Gly Asn Pro
        20                  25                  30

Asn Val Ala Lys Val Gln Arg Met Val Val Phe Gly Asp Ser Leu Ser
            35                  40                  45

Asp Ile Gly Thr Tyr Thr Pro Val Ala Gln Val Gly Gly Gly Lys
    50                  55                  60

Phe Thr Thr Asn Pro Gly Pro Ile Trp Ala Glu Thr Val Ala Ala Gln
65                  70                  75                  80

Leu Gly Val Thr Leu Thr Pro Ala Val Met Gly Tyr Ala Thr Ser Val
                85                  90                  95

Gln Asn Cys Pro Lys Ala Gly Cys Phe Asp Tyr Ala Gln Gly Gly Ser
            100                 105                 110

Arg Val Thr Asp Pro Asn Gly Ile Gly His Asn Gly Ala Gly Ala
        115                 120                 125

Leu Thr Tyr Pro Val Gln Gln Leu Ala Asn Phe Tyr Ala Ala Ser
    130                 135                 140

Asn Asn Thr Phe Asn Gly Asn Asn Asp Val Val Phe Val Leu Ala Gly
145                 150                 155                 160

```
Ser Asn Asp Ile Phe Phe Trp Thr Thr Ala Ala Thr Ser Gly Ser
                165                 170                 175

Gly Val Thr Pro Ala Ile Ala Thr Ala Gln Val Gln Gln Ala Ala Thr
            180                 185                 190

Asp Leu Val Gly Tyr Val Lys Asp Met Ile Ala Lys Gly Ala Thr Gln
            195                 200                 205

Val Tyr Val Phe Asn Leu Pro Asp Ser Ser Leu Thr Pro Asp Gly Val
210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
                260                 265                 270

Phe Gly Phe Ala Asn Thr Ser Ala Arg Ala Cys Asp Ala Thr Lys Ile
            275                 280                 285

Asn Ala Leu Val Pro Ser Ala Gly Gly Ser Ser Leu Phe Cys Ser Ala
290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
                340                 345

<210> SEQ ID NO 9
<211> LENGTH: 261
<212> TYPE: PRT
<213> ORGANISM: Streptomyces coelicolor

<400> SEQUENCE: 9

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190
```

```
Arg Val Pro Ala Asp Pro Asp Gln Pro Trp Pro Pro Leu Pro Pro Arg
            195                 200                 205

Gly Thr Leu Asp Val Arg Arg Asp Val His Trp Ala Arg Glu Tyr
            210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
            245                 250                 255

Ile Ala Ala Val Ala
            260

<210> SEQ ID NO 10
<211> LENGTH: 260
<212> TYPE: PRT
<213> ORGANISM: Streptomyces coelicolor

<400> SEQUENCE: 10

Met Gln Thr Asn Pro Ala Tyr Thr Ser Leu Val Ala Val Gly Asp Ser
1               5                   10                  15

Phe Thr Glu Gly Met Ser Asp Leu Leu Pro Asp Gly Ser Tyr Arg Gly
            20                  25                  30

Trp Ala Asp Leu Leu Ala Thr Arg Met Ala Ala Arg Ser Pro Gly Phe
        35                  40                  45

Arg Tyr Ala Asn Leu Ala Val Arg Gly Lys Leu Ile Gly Gln Ile Val
    50                  55                  60

Asp Glu Gln Val Asp Val Ala Ala Ala Met Gly Ala Asp Val Ile Thr
65                  70                  75                  80

Leu Val Gly Gly Leu Asn Asp Thr Leu Arg Pro Lys Cys Asp Met Ala
                85                  90                  95

Arg Val Arg Asp Leu Leu Thr Gln Ala Val Glu Arg Leu Ala Pro His
            100                 105                 110

Cys Glu Gln Leu Val Leu Met Arg Ser Pro Gly Arg Gln Gly Pro Val
        115                 120                 125

Leu Glu Arg Phe Arg Pro Arg Met Glu Ala Leu Phe Ala Val Ile Asp
    130                 135                 140

Asp Leu Ala Gly Arg His Gly Ala Val Val Asp Leu Tyr Gly Ala
145                 150                 155                 160

Gln Ser Leu Ala Asp Pro Arg Met Trp Asp Val Asp Arg Leu His Leu
                165                 170                 175

Thr Ala Glu Gly His Arg Arg Val Ala Glu Ala Val Trp Gln Ser Leu
            180                 185                 190

Gly His Glu Pro Glu Asp Pro Glu Trp His Ala Pro Ile Pro Ala Thr
        195                 200                 205

Pro Pro Pro Gly Trp Val Thr Arg Arg Thr Ala Asp Val Arg Phe Ala
    210                 215                 220

Arg Gln His Leu Leu Pro Trp Ile Gly Arg Arg Leu Thr Gly Arg Ser
225                 230                 235                 240

Ser Gly Asp Gly Leu Pro Ala Lys Arg Pro Asp Leu Leu Pro Tyr Glu
                245                 250                 255

Asp Pro Ala Arg
            260

<210> SEQ ID NO 11
<211> LENGTH: 454
<212> TYPE: PRT
<213> ORGANISM: Streptomyces coelicolor
```

<400> SEQUENCE: 11

```
Met Thr Arg Gly Arg Asp Gly Gly Ala Gly Ala Pro Pro Thr Lys His
1               5                   10                  15

Arg Ala Leu Leu Ala Ala Ile Val Thr Leu Ile Val Ala Ile Ser Ala
            20                  25                  30

Ala Ile Tyr Ala Gly Ala Ser Ala Asp Asp Gly Ser Arg Asp His Ala
        35                  40                  45

Leu Gln Ala Gly Gly Arg Leu Pro Arg Gly Asp Ala Ala Pro Ala Ser
    50                  55                  60

Thr Gly Ala Trp Val Gly Ala Trp Ala Thr Ala Pro Ala Ala Ala Glu
65                  70                  75                  80

Pro Gly Thr Glu Thr Thr Gly Leu Ala Gly Arg Ser Val Arg Asn Val
                85                  90                  95

Val His Thr Ser Val Gly Gly Thr Gly Ala Arg Ile Thr Leu Ser Asn
            100                 105                 110

Leu Tyr Gly Gln Ser Pro Leu Thr Val Thr His Ala Ser Ile Ala Leu
        115                 120                 125

Ala Ala Gly Pro Asp Thr Ala Ala Ile Ala Asp Thr Met Arg Arg
    130                 135                 140

Leu Thr Phe Gly Gly Ser Ala Arg Val Ile Ile Pro Ala Gly Gly Gln
145                 150                 155                 160

Val Met Ser Asp Thr Ala Arg Leu Ala Ile Pro Tyr Gly Ala Asn Val
                165                 170                 175

Leu Val Thr Thr Tyr Ser Pro Ile Pro Ser Gly Pro Val Thr Tyr His
            180                 185                 190

Pro Gln Ala Arg Gln Thr Ser Tyr Leu Ala Asp Gly Asp Arg Thr Ala
        195                 200                 205

Asp Val Thr Ala Val Ala Tyr Thr Thr Pro Thr Pro Tyr Trp Arg Tyr
    210                 215                 220

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
                245                 250                 255

Asn His Arg Trp Thr Asp Val Leu Ala Ala Arg Leu His Glu Ala Ala
            260                 265                 270

Gly Asp Gly Arg Asp Thr Pro Arg Tyr Ser Val Val Asn Glu Gly Ile
        275                 280                 285

Ser Gly Asn Arg Leu Leu Thr Ser Arg Pro Gly Arg Pro Ala Asp Asn
    290                 295                 300

Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
                325                 330                 335

Pro Glu Leu Ala Asp Arg Asp Ala Ile Leu Thr Gly Leu Arg Thr Leu
            340                 345                 350

Val Asp Arg Ala His Ala Arg Gly Leu Arg Val Gly Ala Thr Ile
        355                 360                 365

Thr Pro Phe Gly Tyr Gly Gly Tyr Thr Glu Ala Arg Glu Thr Met
    370                 375                 380

Arg Gln Glu Val Asn Glu Glu Ile Arg Ser Gly Arg Val Phe Asp Thr
385                 390                 395                 400

Val Val Asp Phe Asp Lys Ala Leu Arg Asp Pro Tyr Asp Pro Arg Arg
                405                 410                 415
```

```
Met Arg Ser Asp Tyr Asp Ser Gly Asp His Leu His Pro Gly Asp Lys
            420                 425                 430
Gly Tyr Ala Arg Met Gly Ala Val Ile Asp Leu Ala Ala Leu Lys Gly
        435                 440                 445
Ala Ala Pro Val Lys Ala
    450

<210> SEQ ID NO 12
<211> LENGTH: 340
<212> TYPE: PRT
<213> ORGANISM: Streptomyces coelicolor

<400> SEQUENCE: 12

Met Thr Ser Met Ser Arg Ala Arg Val Ala Arg Ile Ala Ala Gly
1               5                   10                  15
Ala Ala Tyr Gly Gly Gly Ile Gly Leu Ala Gly Ala Ala Val
            20                  25                  30
Gly Leu Val Val Ala Glu Val Gln Leu Ala Arg Arg Val Gly Val
            35                  40                  45
Gly Thr Pro Thr Arg Val Pro Asn Ala Gln Gly Leu Tyr Gly Gly Thr
    50                  55                  60
Leu Pro Thr Ala Gly Asp Pro Pro Leu Arg Leu Met Met Leu Gly Asp
65                  70                  75                  80
Ser Thr Ala Ala Gly Gln Gly Val His Arg Ala Gly Gln Thr Pro Gly
                85                  90                  95
Ala Leu Leu Ala Ser Gly Leu Ala Val Ala Glu Arg Pro Val Arg
                100                 105                 110
Leu Gly Ser Val Ala Gln Pro Gly Ala Cys Ser Asp Asp Leu Asp Arg
            115                 120                 125
Gln Val Ala Leu Val Leu Ala Glu Pro Asp Arg Val Pro Asp Ile Cys
    130                 135                 140
Val Ile Met Val Gly Ala Asn Asp Val Thr His Arg Met Pro Ala Thr
145                 150                 155                 160
Arg Ser Val Arg His Leu Ser Ser Ala Val Arg Arg Leu Arg Thr Ala
                165                 170                 175
Gly Ala Glu Val Val Val Gly Thr Cys Pro Asp Leu Gly Thr Ile Glu
            180                 185                 190
Arg Val Arg Gln Pro Leu Arg Trp Leu Ala Arg Arg Ala Ser Arg Gln
            195                 200                 205
Leu Ala Ala Ala Gln Thr Ile Gly Ala Val Glu Gln Gly Gly Arg Thr
    210                 215                 220
Val Ser Leu Gly Asp Leu Leu Gly Pro Glu Phe Ala Gln Asn Pro Arg
225                 230                 235                 240
Glu Leu Phe Gly Pro Asp Asn Tyr His Pro Ser Ala Glu Gly Tyr Ala
                245                 250                 255
Thr Ala Ala Met Ala Val Leu Pro Ser Val Cys Ala Ala Leu Gly Leu
            260                 265                 270
Trp Pro Ala Asp Glu Glu His Pro Asp Ala Leu Arg Arg Glu Gly Phe
        275                 280                 285
Leu Pro Val Ala Arg Ala Ala Glu Ala Ala Ser Glu Ala Gly Thr
    290                 295                 300
Glu Val Ala Ala Ala Met Pro Thr Gly Pro Arg Gly Pro Trp Ala Leu
305                 310                 315                 320
Leu Lys Arg Arg Arg Arg Arg Val Ser Glu Ala Glu Pro Ser Ser
                325                 330                 335
```

```
Pro Ser Gly Val
            340

<210> SEQ ID NO 13
<211> LENGTH: 305
<212> TYPE: PRT
<213> ORGANISM: Streptomyces coelicolor

<400> SEQUENCE: 13

Met Gly Arg Gly Thr Asp Gln Arg Thr Arg Tyr Gly Arg Arg Ala
1               5                   10                  15

Arg Val Ala Leu Ala Ala Leu Thr Ala Ala Val Leu Gly Val Gly Val
            20                  25                  30

Ala Gly Cys Asp Ser Val Gly Gly Asp Ser Pro Ala Pro Ser Gly Ser
            35                  40                  45

Pro Ser Lys Arg Thr Arg Thr Ala Pro Ala Trp Asp Thr Ser Pro Ala
        50                  55                  60

Ser Val Ala Ala Val Gly Asp Ser Ile Thr Arg Gly Phe Asp Ala Cys
65                  70                  75                  80

Ala Val Leu Ser Asp Cys Pro Glu Val Ser Trp Ala Thr Gly Ser Ser
                85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
            115                 120                 125

Leu Thr Ala Gln Val Thr Arg Ala Ala Gln Arg Glu Pro Glu Leu Val
        130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
                165                 170                 175

Thr Leu Arg Lys Lys Leu Pro Lys Ala Gln Val Tyr Val Ser Ser Ile
            180                 185                 190

Pro Asp Leu Lys Arg Leu Trp Ser Gln Gly Arg Thr Asn Pro Leu Gly
            195                 200                 205

Lys Gln Val Trp Lys Leu Gly Leu Cys Pro Ser Met Leu Gly Asp Ala
        210                 215                 220

Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255

Arg Arg Cys Arg Ser Asp Gly Ala Val His Glu Phe Arg Phe Gly
            260                 265                 270

Thr Asp Gln Leu Ser His Trp Asp Trp Phe His Pro Ser Val Asp Gly
        275                 280                 285

Gln Ala Arg Leu Ala Glu Ile Ala Tyr Arg Ala Val Thr Ala Lys Asn
    290                 295                 300

Pro
305

<210> SEQ ID NO 14
<211> LENGTH: 268
<212> TYPE: PRT
<213> ORGANISM: Streptomyces rimosus

<400> SEQUENCE: 14
```

```
Met Arg Leu Ser Arg Ala Ala Thr Ala Ser Ala Leu Leu Leu Thr
1               5                  10                  15

Pro Ala Leu Ala Leu Phe Gly Ala Ser Ala Ala Val Ser Ala Pro Arg
            20                  25                  30

Ile Gln Ala Thr Asp Tyr Val Ala Leu Gly Asp Ser Tyr Ser Ser Gly
            35                  40                  45

Val Gly Ala Gly Ser Tyr Asp Ser Ser Gly Ser Cys Lys Arg Ser
50                  55                  60

Thr Lys Ser Tyr Pro Ala Leu Trp Ala Ala Ser His Thr Gly Thr Arg
65                  70                  75                  80

Phe Asn Phe Thr Ala Cys Ser Gly Ala Arg Thr Gly Asp Val Leu Ala
                85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
            115                 120                 125

Leu Gln Gly Glu Ser Ala Cys Leu Ala Arg Ile Ala Lys Ala Arg Ala
            130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Leu Gly Tyr Pro
            165                 170                 175

Arg Phe Tyr Lys Leu Gly Gly Ser Cys Ala Val Gly Leu Ser Glu Lys
            180                 185                 190

Ser Arg Ala Ala Ile Asn Ala Ala Asp Asp Ile Asn Ala Val Thr
            195                 200                 205

Ala Lys Arg Ala Ala Asp His Gly Phe Ala Phe Gly Asp Val Asn Thr
210                 215                 220

Thr Phe Ala Gly His Glu Leu Cys Ser Gly Ala Pro Trp Leu His Ser
225                 230                 235                 240

Val Thr Leu Pro Val Glu Asn Ser Tyr His Pro Thr Ala Asn Gly Gln
            245                 250                 255

Ser Lys Gly Tyr Leu Pro Val Leu Asn Ser Ala Thr
            260                 265

<210> SEQ ID NO 15
<211> LENGTH: 336
<212> TYPE: PRT
<213> ORGANISM: Aeromonas salmonicida

<400> SEQUENCE: 15

Met Lys Lys Trp Phe Val Cys Leu Leu Gly Leu Ile Ala Leu Thr Val
1               5                  10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110
```

```
Gln Phe Leu Gln Lys Asp Ser Phe Lys Pro Asp Asp Leu Val Ile Leu
            115                 120                 125
Trp Val Gly Ala Asn Asp Tyr Leu Ala Tyr Gly Trp Asn Thr Glu Gln
130                 135                 140
Asp Ala Lys Arg Val Arg Asp Ala Ile Ser Asp Ala Ala Asn Arg Met
145                 150                 155                 160
Val Leu Asn Gly Ala Lys Gln Ile Leu Leu Phe Asn Leu Pro Asp Leu
                165                 170                 175
Gly Gln Asn Pro Ser Ala Arg Ser Gln Lys Val Val Glu Ala Val Ser
            180                 185                 190
His Val Ser Ala Tyr His Asn Lys Leu Leu Asn Leu Ala Arg Gln
        195                 200                 205
Leu Ala Pro Thr Gly Met Val Lys Leu Phe Glu Ile Asp Lys Gln Phe
    210                 215                 220
Ala Glu Met Leu Arg Asp Pro Gln Asn Phe Gly Leu Ser Asp Val Glu
225                 230                 235                 240
Asn Pro Cys Tyr Asp Gly Gly Tyr Val Trp Lys Pro Phe Ala Thr Arg
                245                 250                 255
Ser Val Ser Thr Asp Arg Gln Leu Ser Ala Phe Ser Pro Gln Glu Arg
            260                 265                 270
Leu Ala Ile Ala Gly Asn Pro Leu Leu Ala Gln Ala Val Ala Ser Pro
        275                 280                 285
Met Ala Arg Arg Ser Ala Ser Pro Leu Asn Cys Glu Gly Lys Met Phe
    290                 295                 300
Trp Asp Gln Val His Pro Thr Thr Val Val His Ala Ala Leu Ser Glu
305                 310                 315                 320
Arg Ala Ala Thr Phe Ile Glu Thr Gln Tyr Glu Phe Leu Ala His Gly
                325                 330                 335

<210> SEQ ID NO 16
<211> LENGTH: 318
<212> TYPE: PRT
<213> ORGANISM: Aeromonas salmonicida

<400> SEQUENCE: 16

Ala Asp Thr Arg Pro Ala Phe Ser Arg Ile Val Met Phe Gly Asp Ser
1               5                   10                  15
Leu Ser Asp Thr Gly Lys Met Tyr Ser Lys Met Arg Gly Tyr Leu Pro
            20                  25                  30
Ser Ser Pro Pro Tyr Tyr Glu Gly Arg Phe Ser Asn Gly Pro Val Trp
        35                  40                  45
Leu Glu Gln Leu Thr Lys Gln Phe Pro Gly Leu Thr Ile Ala Asn Glu
    50                  55                  60
Ala Glu Gly Gly Ala Thr Ala Val Ala Tyr Asn Lys Ile Ser Trp Asp
65                  70                  75                  80
Pro Lys Tyr Gln Val Ile Asn Asn Leu Asp Tyr Glu Val Thr Gln Phe
                85                  90                  95
Leu Gln Lys Asp Ser Phe Lys Pro Asp Asp Leu Val Ile Leu Trp Val
            100                 105                 110
Gly Ala Asn Asp Tyr Leu Ala Tyr Gly Trp Asn Thr Glu Gln Asp Ala
        115                 120                 125
Lys Arg Val Arg Asp Ala Ile Ser Asp Ala Ala Asn Arg Met Val Leu
    130                 135                 140
Asn Gly Ala Lys Gln Ile Leu Leu Phe Asn Leu Pro Asp Leu Gly Gln
145                 150                 155                 160
```

```
Asn Pro Ser Ala Arg Ser Gln Lys Val Val Glu Ala Val Ser His Val
            165                 170                 175

Ser Ala Tyr His Asn Lys Leu Leu Leu Asn Leu Ala Arg Gln Leu Ala
        180                 185                 190

Pro Thr Gly Met Val Lys Leu Phe Glu Ile Asp Lys Gln Phe Ala Glu
    195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
            245                 250                 255

Ile Ala Gly Asn Pro Leu Leu Ala Gln Ala Val Ala Ser Pro Met Ala
        260                 265                 270

Arg Arg Ser Ala Ser Pro Leu Asn Cys Glu Gly Lys Met Phe Trp Asp
    275                 280                 285

Gln Val His Pro Thr Thr Val Val His Ala Ala Leu Ser Glu Arg Ala
290                 295                 300

Ala Thr Phe Ile Glu Thr Gln Tyr Glu Phe Leu Ala His Gly
305                 310                 315

<210> SEQ ID NO 17
<211> LENGTH: 465
<212> TYPE: PRT
<213> ORGANISM: Candida parapsilosis

<400> SEQUENCE: 17

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
50                  55                  60

Asn Ala Trp Gln Leu Leu Val Arg Ser Glu Thr Phe Gly Asn Pro
65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
        115                 120                 125

Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220
```

```
Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
    450                 455                 460

Phe
465

<210> SEQ ID NO 18
<211> LENGTH: 471
<212> TYPE: PRT
<213> ORGANISM: Candida parapsilosis

<400> SEQUENCE: 18

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
                20                  25                  30

Pro Gln Gly Tyr Glu Ala Gln Pro Leu Gly Ser Ile Leu Lys Thr Arg
            35                  40                  45

Asn Val Pro Asn Pro Leu Thr Asn Val Phe Thr Pro Lys Val Gln
        50                  55                  60

Asn Ala Trp Gln Leu Leu Val Arg Ser Glu Asp Thr Phe Gly Asn Pro
65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr
        115                 120                 125
```

```
Thr Gln Gly Glu Met Tyr Tyr Ile Ser Ala Leu Leu Asp Gln Gly Tyr
            130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
    450                 455                 460

Phe His His His His His
465                 470

<210> SEQ ID NO 19
<211> LENGTH: 261
<212> TYPE: PRT
<213> ORGANISM: Streptomyces coelicolor

<400> SEQUENCE: 19

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30
```

```
Ala Val Leu Leu Ala Asp Arg Arg Pro Glu Gly Asp Phe Thr Tyr Thr
            35                  40                  45

Asn Leu Ala Val Arg Gly Arg Leu Leu Asp Gln Ile Val Ala Glu Gln
 50                  55                  60

Val Pro Arg Val Val Gly Leu Ala Pro Asp Leu Val Ser Phe Ala Ala
 65                  70                  75                  80

Gly Gly Asn Asp Ile Ile Arg Pro Gly Thr Asp Pro Asp Glu Val Ala
                 85                  90                  95

Glu Arg Phe Glu Leu Ala Val Ala Ala Leu Thr Ala Ala Ala Gly Thr
               100                 105                 110

Val Leu Val Thr Thr Gly Phe Asp Thr Arg Gly Val Pro Val Leu Lys
           115                 120                 125

His Leu Arg Gly Lys Ile Ala Thr Tyr Asn Gly His Val Arg Ala Ile
       130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
               165                 170                 175

Glu Gly His Thr Arg Val Ala Leu Arg Ala Gly Gln Ala Leu Gly Leu
           180                 185                 190

Arg Val Pro Ala Asp Pro Asp Gln Pro Trp Pro Pro Leu Pro Pro Arg
       195                 200                 205

Gly Thr Leu Asp Val Arg Arg Asp Val His Trp Ala Arg Glu Tyr
210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
               245                 250                 255

Ile Ala Ala Val Ala
               260

<210> SEQ ID NO 20
<211> LENGTH: 230
<212> TYPE: PRT
<213> ORGANISM: Aspergillus aculeatus

<400> SEQUENCE: 20

Thr Thr Val Tyr Leu Ala Gly Asp Ser Thr Met Ala Lys Asn Gly Gly
 1               5                  10                  15

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
            35                  40                  45

Thr Arg Glu Gly Arg Phe Glu Asn Ile Ala Asp Val Val Thr Ala Gly
 50                  55                  60

Asp Tyr Val Ile Val Glu Phe Gly His Asn Asp Gly Gly Ser Leu Ser
 65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
               100                 105                 110

Tyr Leu Glu Asn Ala Ala Lys Leu Phe Thr Ala Lys Gly Ala Lys Val
           115                 120                 125

Ile Leu Ser Ser Gln Thr Pro Asn Asn Pro Trp Glu Thr Gly Thr Phe
       130                 135                 140
```

```
Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
                195                 200                 205

Leu Lys Ala Val Val Cys Thr Gly Thr Ser Leu Lys Ser Val Leu Thr
        210                 215                 220

Thr Thr Ser Phe Glu Gly
225                 230

<210> SEQ ID NO 21
<211> LENGTH: 18
<212> TYPE: PRT
<213> ORGANISM: Aeromonas sp.

<400> SEQUENCE: 21

Met Lys Lys Trp Phe Val Cys Leu Leu Gly Leu Ile Ala Leu Thr Val
1               5                   10                  15

Gln Ala

<210> SEQ ID NO 22
<211> LENGTH: 29
<212> TYPE: PRT
<213> ORGANISM: Bacillus subtilis

<400> SEQUENCE: 22

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 23
<211> LENGTH: 29
<212> TYPE: PRT
<213> ORGANISM: Bacillus licheniformis

<400> SEQUENCE: 23

Met Met Arg Lys Lys Ser Phe Trp Phe Gly Met Leu Thr Ala Phe Met
1               5                   10                  15

Leu Val Phe Thr Met Glu Phe Ser Asp Ser Ala Ser Ala
            20                  25

<210> SEQ ID NO 24
<211> LENGTH: 1047
<212> TYPE: DNA
<213> ORGANISM: Aeromonas hydrophila

<400> SEQUENCE: 24
atgtttaagt ttaaaaagaa tttcttagtt ggattatcgg cagctttaat gagtattagc      60
ttgttttcgg caaccgcctc tgcagctagc gccgacagcc gtcccgcctt ttcccggatc     120
gtgatgttcg gcgacagcct ctccgatacc ggcaaaatgt acagcaagat gcgcggttac     180
ctcccctcca gcccgcccta ctatgagggc cgtttctcca acggacccgt ctggctggag     240
cagctgacca acagttccc  gggtctgacc atcgccaacg aagcggaagg cggtgccact     300
gccgtggctt acaacaagat ctcctggaat cccaagtatc aggtcatcaa caacctggac     360
tacgaggtca cccagttctt gcagaaagac agcttcaagc cggacgatct ggtgatcctc     420
```

```
tgggtcggtg ccaatgacta tctggcctat ggctggaaca cggagcagga tgccaagcgg    480
gttcgcgatg ccatcagcga tgcggccaac cgcatggtac tgaacggtgc caagcagata    540
ctgctgttca acctgccgga tctgggccag aacccgtcag ctcgcagtca gaaggtggtc    600
gaggcggtca gccatgtctc cgcctatcac aaccagctgc tgctgaacct ggcacgccag    660
ctggccccca ccggcatggt aaagctgttc gagatcgaca gcaaatttgc cgagatgctg    720
cgtgatccgc agaacttcgg cctgagcgac gtcgagaacc cctgctacga cggcggctat    780
gtgtggaagc cgtttgccac ccgcagcgtc agcaccgacc gccagctctc cgccttcagt    840
ccgcaggaac gcctcgccat cgccggcaac ccgctgctgg cacaggccgt tgccagtcct    900
atggcccgcc gcagcgccag ccccctcaac tgtgagggca agatgttctg ggatcaggta    960
cacccgacca ctgtcgtgca cgcagccctg agcgagcgcg ccgccacctt catcgcgaac   1020
cagtacgagt tcctcgccca ctgatga                                       1047
```

<210> SEQ ID NO 25
<211> LENGTH: 347
<212> TYPE: PRT
<213> ORGANISM: Artificial Sequence
<220> FEATURE:
<223> OTHER INFORMATION: Description of Artificial Sequence: Synthetic fusion construct

<400> SEQUENCE: 25

```
Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Ala Asp
                20                  25                  30

Ser Arg Pro Ala Phe Ser Arg Ile Val Met Phe Gly Asp Ser Leu Ser
            35                  40                  45

Asp Thr Gly Lys Met Tyr Ser Lys Met Arg Gly Tyr Leu Pro Ser Ser
        50                  55                  60

Pro Pro Tyr Tyr Glu Gly Arg Phe Ser Asn Gly Pro Val Trp Leu Glu
65                  70                  75                  80

Gln Leu Thr Lys Gln Phe Pro Gly Leu Thr Ile Ala Asn Glu Ala Glu
                85                  90                  95

Gly Gly Ala Thr Ala Val Ala Tyr Asn Lys Ile Ser Trp Asn Pro Lys
            100                 105                 110

Tyr Gln Val Ile Asn Asn Leu Asp Tyr Glu Val Thr Gln Phe Leu Gln
        115                 120                 125

Lys Asp Ser Phe Lys Pro Asp Leu Val Ile Leu Trp Val Gly Ala
        130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
        195                 200                 205

Tyr His Asn Gln Leu Leu Leu Asn Leu Ala Arg Gln Leu Ala Pro Thr
    210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
```

```
                245                 250                 255
Asp Gly Gly Tyr Val Trp Lys Pro Phe Ala Thr Arg Ser Val Ser Thr
            260                 265                 270

Asp Arg Gln Leu Ser Ala Phe Ser Pro Gln Glu Arg Leu Ala Ile Ala
        275                 280                 285

Gly Asn Pro Leu Leu Ala Gln Ala Val Ala Ser Pro Met Ala Arg Arg
        290                 295                 300

Ser Ala Ser Pro Leu Asn Cys Glu Gly Lys Met Phe Trp Asp Gln Val
305                 310                 315                 320

His Pro Thr Thr Val Val His Ala Ala Leu Ser Glu Arg Ala Ala Thr
                325                 330                 335

Phe Ile Ala Asn Gln Tyr Glu Phe Leu Ala His
                340                 345

<210> SEQ ID NO 26
<211> LENGTH: 267
<212> TYPE: PRT
<213> ORGANISM: Streptomyces sp.

<400> SEQUENCE: 26

Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
    210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265
```

```
<210> SEQ ID NO 27
<211> LENGTH: 548
<212> TYPE: PRT
<213> ORGANISM: Thermobifida sp.

<400> SEQUENCE: 27

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
        35                  40                  45

Val Pro Pro Leu Thr Leu Pro Gly Asp Gly Val Leu Cys Thr Thr Ser
    50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
        115                 120                 125

Gly Asp Ser Ser Pro Pro Phe Arg Ala Gly Trp Ser Leu Pro Pro Lys
    130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Arg Leu Phe Leu Gly
            180                 185                 190

Ile Pro Ala Leu Val Leu Val Thr Ala Leu Thr Leu Val Leu Ala Val
        195                 200                 205

Pro Thr Gly Arg Glu Thr Leu Trp Arg Met Trp Cys Glu Ala Thr Gln
    210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
            260                 265                 270

Asp Tyr Tyr Pro Gly Thr Ala Val Lys Gly Gly Cys Trp Arg Ser Ala
        275                 280                 285

Asn Ala Tyr Pro Glu Leu Val Ala Glu Ala Tyr Asp Phe Ala Gly His
    290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
            340                 345                 350

Val Leu Lys Thr Cys Met Val Arg Val Pro Leu Leu Asp Ser Lys Ala
        355                 360                 365

Cys Thr Asp Gln Glu Asp Ala Ile Arg Lys Arg Met Ala Lys Phe Glu
    370                 375                 380

Thr Thr Phe Glu Glu Leu Ile Ser Glu Val Arg Thr Arg Ala Pro Asp
```

```
            385                 390                 395                 400
Ala Arg Ile Leu Val Val Gly Tyr Pro Arg Ile Phe Pro Glu Glu Pro
                    405                 410                 415

Thr Gly Ala Tyr Tyr Thr Leu Thr Ala Ser Asn Gln Arg Trp Leu Asn
            420                 425                 430

Glu Thr Ile Gln Glu Phe Asn Gln Gln Leu Ala Glu Ala Val Ala Val
        435                 440                 445

His Asp Glu Glu Ile Ala Ala Ser Gly Gly Val Gly Ser Val Glu Phe
    450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
        515                 520                 525

Tyr Ala Thr Phe Ala Val Val Ala Gly Ala Thr Val Asp Thr Leu Ala
    530                 535                 540

Gly Glu Val Gly
545

<210> SEQ ID NO 28
<211> LENGTH: 372
<212> TYPE: PRT
<213> ORGANISM: Thermobifida sp.

<400> SEQUENCE: 28

Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
                20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
        50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
```

```
            210                 215                 220
Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
                260                 265                 270

His Asp Glu Glu Ile Ala Ala Ser Gly Gly Val Gly Ser Val Glu Phe
                275                 280                 285

Val Asp Val Tyr His Ala Leu Asp Gly His Glu Ile Gly Ser Asp Glu
290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
                340                 345                 350

Tyr Ala Thr Phe Ala Val Val Ala Gly Ala Thr Val Asp Thr Leu Ala
                355                 360                 365

Gly Glu Val Gly
        370

<210> SEQ ID NO 29
<211> LENGTH: 300
<212> TYPE: PRT
<213> ORGANISM: Corynebacterium efficiens

<400> SEQUENCE: 29

Met Arg Thr Thr Val Ile Ala Ala Ser Ala Leu Leu Leu Leu Ala Gly
1               5                   10                  15

Cys Ala Asp Gly Ala Arg Glu Glu Thr Ala Gly Ala Pro Pro Gly Glu
                20                  25                  30

Ser Ser Gly Gly Ile Arg Glu Glu Gly Ala Glu Ala Ser Thr Ser Ile
            35                  40                  45

Thr Asp Val Tyr Ile Ala Leu Gly Asp Ser Tyr Ala Ala Met Gly Gly
        50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
                100                 105                 110

Thr Leu Pro Ala Gln Val Asp Ala Leu Thr Glu Asp Thr Thr Leu Val
            115                 120                 125

Thr Leu Ser Ile Gly Gly Asn Asp Leu Gly Phe Gly Glu Val Ala Gly
        130                 135                 140

Cys Ile Arg Glu Arg Ile Ala Gly Glu Asn Ala Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
                180                 185                 190

Val Val Val Thr Gly Tyr Leu Pro Leu Val Ser Ala Gly Asp Cys Pro
            195                 200                 205

Glu Leu Gly Asp Val Ser Glu Ala Asp Arg Arg Trp Ala Val Glu Leu
```

```
                210                 215                 220
Thr Gly Gln Ile Asn Glu Thr Val Arg Glu Ala Ala Glu Arg His Asp
225                 230                 235                 240

Ala Leu Phe Val Leu Pro Asp Ala Asp Glu His Thr Ser Cys Ala
                245                 250                 255

Pro Pro Gln Gln Arg Trp Ala Asp Ile Gln Gly Gln Thr Asp Ala
                260                 265                 270

Tyr Pro Leu His Pro Thr Ser Ala Gly His Glu Ala Met Ala Ala Ala
                275                 280                 285

Val Arg Asp Ala Leu Gly Leu Glu Pro Val Gln Pro
290                 295                 300

<210> SEQ ID NO 30
<211> LENGTH: 284
<212> TYPE: PRT
<213> ORGANISM: Novosphingobium aromaticivorans

<400> SEQUENCE: 30

Met Gly Gln Val Lys Leu Phe Ala Arg Cys Ala Pro Val Leu Leu
1               5                   10                  15

Ala Leu Ala Gly Leu Ala Pro Ala Ala Thr Val Ala Arg Glu Ala Pro
                20                  25                  30

Leu Ala Glu Gly Ala Arg Tyr Val Ala Leu Gly Ser Ser Phe Ala Ala
                35                  40                  45

Gly Pro Gly Val Gly Pro Asn Ala Pro Gly Ser Pro Glu Arg Cys Gly
                50                  55                  60

Arg Gly Thr Leu Asn Tyr Pro His Leu Leu Ala Glu Ala Leu Lys Leu
65                  70                  75                  80

Asp Leu Val Asp Ala Thr Cys Ser Gly Ala Thr Thr His His Val Leu
                85                  90                  95

Gly Pro Trp Asn Glu Val Pro Pro Gln Ile Asp Ser Val Asn Gly Asp
                100                 105                 110

Thr Arg Leu Val Thr Leu Thr Ile Gly Gly Asn Asp Val Ser Phe Val
                115                 120                 125

Gly Asn Ile Phe Ala Ala Ala Cys Glu Lys Met Ala Ser Pro Asp Pro
                130                 135                 140

Arg Cys Gly Lys Trp Arg Glu Ile Thr Glu Glu Glu Trp Gln Ala Asp
145                 150                 155                 160

Glu Glu Arg Met Arg Ser Ile Val Arg Gln Ile His Ala Arg Ala Pro
                165                 170                 175

Leu Ala Arg Val Val Val Val Asp Tyr Ile Thr Val Leu Pro Pro Ser
                180                 185                 190

Gly Thr Cys Ala Ala Met Ala Ile Ser Pro Asp Arg Leu Ala Gln Ser
                195                 200                 205

Arg Ser Ala Ala Lys Arg Leu Ala Arg Ile Thr Ala Arg Val Ala Arg
210                 215                 220

Glu Gly Ala Ser Leu Leu Lys Phe Ser His Ile Ser Arg Arg His
225                 230                 235                 240

His Pro Cys Ser Ala Lys Pro Trp Ser Asn Gly Leu Ser Ala Pro Ala
                245                 250                 255

Asp Asp Gly Ile Pro Val His Pro Asn Arg Leu Gly His Ala Glu Ala
                260                 265                 270

Ala Ala Ala Leu Val Lys Leu Val Lys Leu Met Lys
                275                 280
```

```
<210> SEQ ID NO 31
<211> LENGTH: 268
<212> TYPE: PRT
<213> ORGANISM: Streptomyces coelicolor

<400> SEQUENCE: 31

Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Ala Glu Ala
    130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
        195                 200                 205

Gln Arg Ala Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
            260                 265

<210> SEQ ID NO 32
<211> LENGTH: 269
<212> TYPE: PRT
<213> ORGANISM: Streptomyces avermitilis

<400> SEQUENCE: 32

Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
    50                  55                  60

Ser Lys Ala Tyr Pro Tyr Leu Trp Gln Ala Ala His Ser Pro Ser Ser
65                  70                  75                  80
```

```
Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
        115                 120                 125

Leu Gln Ser Asp Ser Ala Cys Leu Ser Arg Ile Asn Thr Ala Lys Ala
    130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Ala Asp Tyr Leu Asn Ser Ala Ile
        195                 200                 205

Ala Lys Arg Ala Ala Asp His Gly Phe Thr Phe Gly Asp Val Lys Ser
    210                 215                 220

Thr Phe Thr Gly His Glu Ile Cys Ser Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265

<210> SEQ ID NO 33
<211> LENGTH: 267
<212> TYPE: PRT
<213> ORGANISM: Streptomyces sp.

<400> SEQUENCE: 33

Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Asn Tyr Ile Asn Thr
    130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190
```

```
Ala Ile Asn Thr Thr Ala Asp Thr Leu Asn Ser Val Ile Ser Ser Arg
            195                 200                 205

Ala Thr Ala His Gly Phe Arg Phe Gly Asp Val Arg Pro Thr Phe Asn
        210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265

<210> SEQ ID NO 34
<211> LENGTH: 317
<212> TYPE: PRT
<213> ORGANISM: Aeromonas hydrophila

<400> SEQUENCE: 34

Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Asn Glu Phe Pro Gly Leu Thr Ile Ala Asn Glu
    50                  55                  60

Ala Glu Gly Gly Pro Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Glu Ile Leu Leu Phe Asn Leu Pro Asp Leu Gly Gln
145                 150                 155                 160

Asn Pro Ser Ala Arg Ser Gln Lys Val Val Glu Ala Ala Ser His Val
                165                 170                 175

Ser Ala Tyr His Asn Gln Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Gln Arg Asn Ala
    210                 215                 220

Cys Tyr Gly Gly Ser Tyr Val Trp Lys Pro Phe Ala Ser Arg Ser Ala
225                 230                 235                 240

Ser Thr Asp Ser Gln Leu Ser Ala Phe Asn Pro Gln Glu Arg Leu Ala
                245                 250                 255

Ile Ala Gly Asn Pro Leu Leu Ala Gln Ala Val Ala Ser Pro Met Ala
            260                 265                 270

Ala Arg Ser Ala Ser Thr Leu Asn Cys Glu Gly Lys Met Phe Trp Asp
        275                 280                 285

Gln Val His Pro Thr Thr Val Val His Ala Ala Leu Ser Glu Pro Ala
    290                 295                 300
```

```
Ala Thr Phe Ile Glu Ser Gln Tyr Glu Phe Leu Ala His
305                 310                 315
```

<210> SEQ ID NO 35
<211> LENGTH: 318
<212> TYPE: PRT
<213> ORGANISM: Aeromonas salmonicida

<400> SEQUENCE: 35

```
Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
    210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His Gly
305                 310                 315
```

<210> SEQ ID NO 36
<211> LENGTH: 1371
<212> TYPE: DNA
<213> ORGANISM: Streptomyces thermosacchari

<400> SEQUENCE: 36

-continued

```
acaggccgat gcacggaacc gtacctttcc gcagtgaagc gctctccccc catcgttcgc    60
cgggacttca tccgcgattt tggcatgaac acttccttca acgcgcgtag cttgctacaa   120
gtgcggcagc agacccgctc gttggaggct cagtgagatt gacccgatcc ctgtcggccg   180
catccgtcat cgtcttcgcc ctgctgctcg cgctgctggg catcagcccg cccaggcag    240 ccggcccggc ctatgtggcc ctgggggatt cctattcctc gggcaacggc gccggaagtt   300
acatcgattc gagcggtgac tgtcaccgca gcaacaacgc gtaccccgcc cgctgggcgg   360
cggccaacgc accgtcctcc ttcaccttcg cggcctgctc gggagcggtg accacggatg   420
tgatcaacaa tcagctgggc gccctcaacg cgtccaccgg cctggtgagc atcaccatcg   480
gcggcaatga cgcgggcttc gcggacgcga tgaccacctg cgtcaccagc tcggacagca   540
cctgcctcaa ccggctggcc accgccacca actacatcaa caccaccctg ctcgcccggc   600
tcgacgcggt ctacagccag atcaaggccc gtgcccccaa cgcccgcgtg gtcgtcctcg   660 gctaccgcg catgtacctg gcctcgaacc cctggtactg cctgggcctg agcaacacca   720
agcgcgcggc catcaacacc accgccgaca ccctcaactc ggtgatctcc tcccgggcca   780
ccgcccacgg attccgattc ggcgatgtcc gcccgacctt caacaaccac gaactgttct   840
tcggcaacga ctggctgcac tcactcaccc tgccggtgtg ggagtcgtac caccccacca   900
gcacgggcca tcagagcggc tatctgccgg tcctcaacgc caacagctcg acctgatcaa   960
cgcacggccg tgcccgcccc gcgcgtcacg ctcggcgcgg gcgccgcagc gcgttgatca  1020
gcccacagtg ccggtgacgg tcccaccgtc acggtcgagg gtgtacgtca cggtggcgcc  1080
gctccagaag tggaacgtca gcaggaccgt ggagccgtcc ctgacctcgt cgaagaactc  1140
cggggtcagc gtgatcaccc ctcccccgta gccggggggcg aaggcggcgc cgaactcctt  1200
gtaggacgtc cagtcgtgcg gcccggcgtt gccaccgtcc gcgtagaccg cttccatggt  1260
cgccagccgg tccccgcgga actcggtggg gatgtccgtg cccaaggtgg tcccggtggt  1320
gtccgagagc accgggggct cgtaccggat gatgtgcaga tccaaagaat t          1371
```

<210> SEQ ID NO 37
<211> LENGTH: 267
<212> TYPE: PRT
<213> ORGANISM: Streptomyces thermosacchari

<400> SEQUENCE: 37

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
                20                  25                  30

Ala Tyr Val Ala Leu Gly Asp Ser Tyr Ser Ser Gly Asn Gly Ala Gly
            35                  40                  45

Ser Tyr Ile Asp Ser Ser Gly Asp Cys His Arg Ser Asn Asn Ala Tyr
        50                  55                  60

Pro Ala Arg Trp Ala Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140
```

```
Thr Leu Leu Ala Arg Leu Asp Ala Val Tyr Ser Gln Ile Lys Ala Arg
145                 150                 155                 160

Ala Pro Asn Ala Arg Val Val Leu Gly Tyr Pro Arg Met Tyr Leu
            165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
        210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265

<210> SEQ ID NO 38
<211> LENGTH: 548
<212> TYPE: PRT
<213> ORGANISM: Thermobifida fusca

<400> SEQUENCE: 38

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
        35                  40                  45

Val Pro Pro Leu Thr Leu Pro Gly Asp Gly Val Leu Cys Thr Thr Ser
    50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
        115                 120                 125

Gly Asp Ser Ser Pro Pro Phe Arg Ala Gly Trp Ser Leu Pro Pro Lys
    130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Leu Phe Leu Gly
            180                 185                 190

Ile Pro Ala Leu Val Leu Val Thr Ala Leu Thr Leu Val Leu Ala Val
        195                 200                 205

Pro Thr Gly Arg Glu Thr Leu Trp Arg Met Trp Cys Glu Ala Thr Gln
    210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255
```

Asn Tyr Tyr Ala Leu Gly Asp Ser Tyr Ser Ser Gly Asp Gly Ala Arg
            260                 265                 270

Asp Tyr Tyr Pro Gly Thr Ala Val Lys Gly Gly Cys Trp Arg Ser Ala
            275                 280                 285

Asn Ala Tyr Pro Glu Leu Val Ala Glu Ala Tyr Asp Phe Ala Gly His
            290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
            340                 345                 350

Val Leu Lys Thr Cys Met Val Arg Val Pro Leu Leu Asp Ser Lys Ala
            355                 360                 365

Cys Thr Asp Gln Glu Asp Ala Ile Arg Lys Arg Met Ala Lys Phe Glu
370                 375                 380

Thr Thr Phe Glu Glu Leu Ile Ser Glu Val Arg Thr Arg Ala Pro Asp
385                 390                 395                 400

Ala Arg Ile Leu Val Val Gly Tyr Pro Arg Ile Phe Pro Glu Glu Pro
                405                 410                 415

Thr Gly Ala Tyr Tyr Thr Leu Thr Ala Ser Asn Gln Arg Trp Leu Asn
            420                 425                 430

Glu Thr Ile Gln Glu Phe Asn Gln Gln Leu Ala Glu Ala Val Ala Val
            435                 440                 445

His Asp Glu Glu Ile Ala Ala Ser Gly Gly Val Gly Ser Val Glu Phe
            450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                485                 490                 495

Val Asp Arg Ser Thr Phe His Pro Asn Ala Ala Gly His Arg Ala Val
            500                 505                 510

Gly Glu Arg Val Ile Glu Gln Ile Glu Thr Gly Pro Gly Arg Pro Leu
            515                 520                 525

Tyr Ala Thr Phe Ala Val Val Ala Gly Ala Thr Val Asp Thr Leu Ala
            530                 535                 540

Gly Glu Val Gly
545

<210> SEQ ID NO 39
<211> LENGTH: 3000
<212> TYPE: DNA
<213> ORGANISM: Thermobifida fusca

<400> SEQUENCE: 39
ggtggtgaac cagaacaccc ggtcgtcggc gtgggcgtcc aggtgcaggt gcaggttctt     60
caactgctcc agcaggatgc cgccgtggcc gtgcacgatg ccttgggca ggcctgtggt    120 ccccgacgag tacagcaccc atagcggatg gtcgaacggc agcggggtga actccagttc    180
cgcgccttcg cccgcggctt cgaactccgc ccaggacagg gtgtcggcga cagggccgca    240
gcccaggtac ggcaggacga cggtgtgctg caggctgggc atgccgtcgc gcagggcttt    300
gagcacgtca cggcggtcga agtccttacc gccgtagcgg tagccgtcca ggccagcag    360 cactttcggt tcgatctgcg cgaaccggtc gaggacgctg cgcaccccga agtcggggga    420

```
acaggacgac caggtcgcac cgatcgcggc gcaggcgagg aatgcggccg tcgcctcggc    480
gatgttcggc aggtaggcca cgacccggtc gccggggccc accccgaggc tgcggagggc    540
cgcagcgatc gcggcggtgc gggtccgcag ttctccccag gtccactcgg tcaacggccg    600
gagttcggac gcgtgccgga tcgccacggc tgatgggtca cggtcgcgga agatgtgctc    660
ggcgtagttg agggtggcgc cggggaacca gacggcgccg ggcatggcgt cggaggcgag    720
cactgtggtg tacggggtgg cggcgcgcac ccggtagtac tcccagatcg cggaccagaa    780
tccttcgagg tcggttaccg accagcgcca cagtgcctcg tagtccggtg cgtccacacc    840
gcggtgctcc cgcacccagc gggtgaacgc ggtgaggttg gcgcgttctt tgcgctcctc    900
gtcgggactc cacaggatcg gcggctgcgg cttgagtgtc atgaaacgcg accccttcgt    960
ggacggtgcg gatgcggtga gcgtcggdtg cctcccctaa cgctcccccgg tgacggagtg   1020 ttgtgcacca catctagcac gcgggacgcg gaaaccgtat ggagaaaaca cctacaaccc   1080
cggccggacg tgggtttcg gccacactta ggggtcgggt gcctgcttgc cgggcagggc    1140
agtcccgggg tgctgtggtg cgggcgggag ggctgtcgct tcgaggtgtg ccggcgggac   1200
actccgggcc tcagccgtac ccgcaacggg gacagttctc ctcccttccg ggctggatgg   1260 tccctcccc cgaaatgcgg cgagatctcc cagtcagccc ggaaaacacc cgctgtgccc    1320
aggtactctt tgcttcgaac agacaggccg gacggtccac gggggaggtt tgtgggcagc   1380
ggaccacgtg cggcgaccag acgacggttg ttcctcggta tccccgctct tgtacttgtg   1440
acagcgctca cgctggtctt ggctgtcccg acggggcgcg agacgctgtg gcgcatgtgg   1500
tgtgaggcca cccaggactg gtgcctgggg gtgccggtcg actcccgcgg acagcctgcg   1560
gaggacggcg agtttctgct gctttctccg gtccaggcag cgacctgggg gaactattac   1620
gcgctcgggg attcgtactc ttcggggac ggggcccgcg actactatcc cggcaccgcg    1680
gtgaagggcg gttgctggcg gtccgctaac gcctatccgg agctggtcgc cgaagcctac   1740
gacttcgccg gacacttgtc gttcctggcc tgcagcggcc agcgcggcta cgccatgctt   1800
gacgctatcg acgaggtcgg ctcgcagctg gactggaact cccctcacac gtcgctggtg   1860
acgatcggga tcgcggcaa cgatctgggg ttctccacgg ttttgaagac ctgcatggtg    1920
cgggtgccgc tgctggacag caaggcgtgc acggaccagg aggacgctat ccgcaagcgg   1980
atggcgaaat tcgagacgac gtttgaagag ctcatcagcg aagtgcgcac ccgcgcgccg   2040
gacgcccgga tccttgtcgt gggctacccc cggattttc cggaggaacc gaccggcgcc    2100
tactacacgc tgaccgcgag caaccagcgg tggctcaacg aaaccattca ggagttcaac   2160
cagcagctcg ccgaggctgt cgcggtccac gacgaggaga ttgccgcgtc gggcggggtg   2220
ggcagcgtga agttcgtgga cgtctaccac gcgttggacg gccacgagat cggctcggac   2280
gagccgtggg tgaacggggt gcagttgcgg gacctcgcca ccggggtgac tgtggaccgc   2340
agtaccttcc accccaacgc cgctgggcac cgggcggtcg gtgagcgggt catcgagcag   2400
atcgaaaccg gcccgggccg tccgctctat gccactttcg cggtggtggc ggggcgacc    2460 gtggacactc tcgcgggcga ggtggggtga cccggcttac cgtccggccc gcaggtctgc   2520
gagcactgcg gcgatctggt ccactgccca gtgcagttcg tcttcggtga tgaccagcgg   2580
cggggagagc cggatcgttg agccgtcgcg gtctttgacg agcacacccc gctgcaggag   2640
ccgttcgcac agttctcttc cggtggccag agtcgggtcg acgtcgatcc cagcccacag   2700
gccgatgctg cgggccgcga ccacgccgtt gccgaccagt tggtcgaggc ggggcgcag    2760 cacggggcg agggcgcgga catggtccag gtaagggccg tcgcggacga ggctcaccac   2820
```

-continued

```
ggcagtgccg accgcgcagg cgagggcgtt gccgccgaag gtgctgccgt gctggccggg    2880
gcggatcacg tcgaagactt ccgcgtcgcc taccgccgcc gccacgggca ggatgccgcc    2940
gcccagcgct ttgccgaaca ggtagatatc ggcgtcgact ccgctgtggt cgcaggcccg    3000
```

<210> SEQ ID NO 40
<211> LENGTH: 372
<212> TYPE: PRT
<213> ORGANISM: Thermobifida fusca

<400> SEQUENCE: 40

```
Val Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Ala Val
            20                  25                  30

Pro Thr Gly Arg Glu Thr Leu Trp Arg Met Trp Cys Glu Ala Thr Gln
        35                  40                  45

Asp Trp Cys Leu Gly Val Pro Val Asp Ser Arg Gly Gln Pro Ala Glu
    50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Val Gly Ser Val Glu Phe
        275                 280                 285

Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350
```

```
Tyr Ala Thr Phe Ala Val Val Ala Gly Ala Thr Val Asp Thr Leu Ala
        355                 360                 365
Gly Glu Val Gly
    370

<210> SEQ ID NO 41
<211> LENGTH: 300
<212> TYPE: PRT
<213> ORGANISM: Corynebacterium efficiens

<400> SEQUENCE: 41

Met Arg Thr Thr Val Ile Ala Ala Ser Ala Leu Leu Leu Ala Gly
1               5                   10                  15

Cys Ala Asp Gly Ala Arg Glu Glu Thr Ala Gly Ala Pro Pro Gly Glu
                20                  25                  30

Ser Ser Gly Gly Ile Arg Glu Glu Gly Ala Glu Ala Ser Thr Ser Ile
            35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Cys Val Asp
145                 150                 155                 160

Leu Leu Gly Glu Thr Ile Gly Gly Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
    210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Thr Asp Ala
            260                 265                 270

Tyr Pro Leu His Pro Thr Ser Ala Gly His Glu Ala Met Ala Ala Ala
        275                 280                 285

Val Arg Asp Ala Leu Gly Leu Glu Pro Val Gln Pro
    290                 295                 300

<210> SEQ ID NO 42
<211> LENGTH: 3000
<212> TYPE: DNA
<213> ORGANISM: Corynebacterium efficiens

<400> SEQUENCE: 42
ttctggggtg ttatgggtt gttatcggct cgtcctgggt ggatcccgcc aggtggggta      60
```

```
ttcacgggggg acttttgtgt ccaacagccg agaatgagtg ccctgagcgg tgggaatgag      120
gtgggcgggg ctgtgtcgcc atgagggggc ggcgggctct gtggtgcccc gcgaccccg       180 gccccggtga gcggtgaatg aaatccggct gtaatcagca tcccgtgccc accccgtcgg      240
ggaggtcagc gcccggagtg tctacgcagt cggatcctct cggactcggc catgctgtcg     300
gcagcatcgc gctcccgggt cttggcgtcc ctcggctgtt ctgcctgctg tccctggaag     360
gcgaaatgat caccggggag tgatacaccg gtggtctcat cccggatgcc cacttcggcg     420
ccatccggca attcgggcag ctccgggtgg aagtaggtgg catccgatgc gtcggtgacg     480
ccatagtggg cgaagatctc atcctgctcg agggtgctca ggccactctc cggatcgata    540 tcggggcgt ccttgatggc gtccttgctg aaaccgaggt gcagcttgtg ggcttccaat      600
ttcgcaccac ggagcgggac gaggctggaa tgacggccga agagcccgtg gtggacctca    660
acgaaggtgg gtagtcccgt gtcatcattg aggaacacgc cctccaccgc acccagcttg   720
tggccggagt tgtcgtaggc gctggcatcc agaaggggaaa cgatctcata tttgtcggtg   780
tgctcagaca tgatcttcct ttgctgtcgg tgtctggtac taccacggta gggctgaatg   840
caactgttat ttttctgtta ttttaggaat tggtccatat cccacaggct ggctgtggtc    900
aaatcgtcat caagtaatcc ctgtcacaca aaatgggtgg tgggagccct ggtcgcggtt    960 ccgtggggagg cgccgtgccc cgcaggatcg tcggcatcgg cggatctggc cggtaccccg   1020
cggtgaataa aatcattctg taaccttcat cacggttggt tttaggtatc cgccccttc    1080 gtcctgaccc cgtccccggc gcgcgggagc ccgcggttg cggtagacag gggagacgtg    1140
gacaccatga ggacaacggt catcgcagca agcgcattac tccttctcgc cggatgcgcg   1200
gatgggcccc gggaggagac cgccggtgca ccgccgggtg agtcctccgg gggcatccgg   1260
gaggaggggg cggaggcgtc gacaagcatc accgacgtct acatcgccct cggggattcc    1320
tatgcggcga tgggcgggcg ggatcagccg ttacggggtg agccgttctg cctgcgctcg    1380
tccggtaatt acccggaact cctccacgca gaggtcaccg atctcacctg ccaggggggcg   1440 gtgaccgggg atctgctcga acccaggacg ctggggggagc gcacgctgcc ggcgcaggtg   1500
gatgcgctga cggaggacac caccctggtc accctctcca tcgggggcaa tgacctcgga   1560
ttcggggagg tggcgggatg catccgggaa cggatcgccg gggagaacgc tgatgattgc    1620
gtggacctgc tgggggaaac catcgggggag cagctcgatc agcttccccc gcagctggac   1680
cgcgtgcacg aggctatccg ggaccgcgcc ggggacgcgc aggttgtggt caccggttac    1740
ctgccgctcg tgtctgccgg ggactgcccc gaactggggg atgtctccga gcggatcgt    1800 cgttgggcgg ttgagctgac cgggcagatc aacgagaccg tgcgcgaggc ggccgaacga    1860
cacgatgccc tctttgtcct gcccgacgat gccgatgagc acaccagttg tgcaccccca   1920
cagcagcgct gggcggatat ccagggccaa cagaccgatg cctatccgct gcacccgacc    1980
tccgccggcc atgaggcgat ggccgccgcc gtccgggacg cgctgggcct ggaaccggtc    2040
cagccgtagc gccgggcgcg cgcttgtcga cgaccaaccc atgccaggct gcagtcacat    2100
ccgcacatag cgcgcgcggg cgatggagta cgcaccatag aggatgagcc cgatgccgac    2160
gatgatgagc agcacactgc cgaagggttg ttccccgagg gtgcgcagag ccgagtccag   2220
acctgcggcc tgctccggat catgggccca accggcgatg acgatcaaca ccccccaggat    2280 cccgaaggcg ataccacggg cgacataacc ggctgttccg gtgatgatga tcgcggtccc    2340
gacctgccct gaccccgcac ccgcctccag atcctcccgg aaatcccggg tggccccctt    2400
ccagaggttg tagacacccg cccccagtac caccagcccg gcgaccacaa ccagcaccac   2460
```

```
accccagggt tgggatagga cggtggcggt gacatcggtg gcggtctccc catcggaggt      2520
gctgccgccc cgggcgaagg tggaggtggt caccgccagg gagaagtaga ccatggccat      2580
gaccgccccc ttggcccttt ccttgaggtc ctcgcccgcc agcagctggc tcaattgcca      2640
gagtcccagg gccgccaggg cgatgacggc aacccacagg aggaactgcc cacccggagc      2700
ctccgcgatg gtggccaggg cacctgaatt cgaggcctca tcacccgaac cgccggatcc      2760
agtggcgatg cgcaccgcga tccacccgat gaggatgtgc agtatgccca ggacaatgaa      2820
accacctctg gccagggtgg tcagcgcggg gtggtcctcg gcctggtcgg cagcccgttc      2880
gatcgtccgt ttcgcggatc tggtgtcgcc cttatccata gctcccattg aaccgccttg      2940
aggggtgggc ggccactgtc agggcggatt gtgatctgaa ctgtgatgtt ccatcaaccc      3000
```

<210> SEQ ID NO 43
<211> LENGTH: 268
<212> TYPE: PRT
<213> ORGANISM: Streptomyces coelicolor

<400> SEQUENCE: 43

```
Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Ala Glu Ala
    130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
        195                 200                 205

Gln Arg Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
            260                 265
```

<210> SEQ ID NO 44

```
<211> LENGTH: 2000
<212> TYPE: DNA
<213> ORGANISM: Streptomyces coelicolor

<400> SEQUENCE: 44
cccggcggcc cgtgcaggag cagcagccgg cccgcgatgt cctcgggcgt cgtcttcatc      60
aggccgtcca tcgcgtcggc gaccggcgcc gtgtagttgg cccggacctc gtcccaggtg     120
cccgcggcga tctggcgggt ggtgcggtgc gggccgcgcc gaggggagac gtaccagaag     180
cccatcgtca cgttctccgg ctgcggttcg ggctcgtccg ccgctccgtc cgtcgcctcg     240
ccgagcacct tctcggcgag gtcggcgctg gtcgccgtca ccgtgacgtc ggcgccccgg     300
ctccagcgcg agatcagcag cgtccagccg tcgccctccg ccagcgtcgc gctgcggtcg     360
tcgtcgcggg cgatccgcag cacgcgcgcg ccgggcggca gcagcgtggc gccggaccgt     420
acgcggtcga tgttcgccgc gtgcgagtac ggctgctcac ccgtggcgaa acggccgagg     480
aacagcgcgt cgacgacgtc ggacggggag tcgctgtcgt ccacgttgag ccggatcggc     540
agggcttcgt gcgggttcac ggacatgtcg ccatgatcgg gcacccggcc gccgcgtgca     600
cccgcttttcc cggcacgca cgacaggggc tttctcgccg tcttccgtcc gaacttgaac     660
gagtgtcagc catttcttgg catggacact tccagtcaac gcgcgtagct gctaccacgg     720
ttgtggcagc aatcctgcta agggaggttc catgagacgt ttccgacttg tcggcttcct     780
gagttcgctc gtcctcgccg ccggcgccgc cctcaccggg gcagcgaccg cccaggcgg     840
ccaacccgcc gccgccgacg gctatgtggc cctcggcgac tcctactcct ccggggtcgg     900
agcgggcagc tacatcagct cgagcggcga ctgcaagcgc agcacgaagg cccatccta      960
cctgtgggcg gccgcccact cgccctccac gttcgacttc accgcctgtt ccggcgcccg    1020
tacgggtgat gttctctccg gacagctcgg cccgctcagc tccggcaccg gcctcgtctc    1080
gatcagcatc ggcggcaacg acgccggttt cgccgacacc atgacgacct gtgtgctcca    1140
gtccgagagc tcctgcctgt cgcggatcgc caccgccgag gcgtacgtcg actcgacgct    1200
gcccggcaag ctcgacggcg tctactcggg aatcagcgac aaggcgccga acgcccacgt    1260
cgtcgtcatc ggctacccgc gcttctacaa gctcggcacc acctgcatcg gcctgtccga    1320
gaccaagcgg acggcgatca acaaggcctc cgaccacctc aacaccgtcc tcgcccagcg    1380
cgccgccgcc cacggcttca ccttcggcga cgtacgcacc accttcaccg gccacgagct    1440
gtgctccggc agccctggc tgcacagcgt caactggctg aacatcggcg agtcgtacca    1500
ccccaccgcg gccggccagt ccggtggcta cctgccggtc ctcaacggcg ccgcctgacc    1560
tcaggcggaa ggagaagaag aaggagcgga gggagacgag gagtgggagg ccccgcccga    1620
cggggtcccc gtccccgtct ccgtctccgt cccggtcccg caagtcaccg agaacgccac    1680
cgcgtcggac gtggcccgca ccggactccg cacctccacg cgcacggcac tctcgaacgc    1740
gccggtgtcg tcgtgcgtcg tcaccaccac gccgtcctgg cgcgagcgct cgccgcccga    1800
cgggaaggac agcgtccgcc acccggatc ggagaccgac ccgtccgcgg tcacccaccg    1860
gtagccgacc tccgcgggca gccgcccgac cgtgaacgtc gccgtgaacg cgggtgcccg    1920
gtcgtgcggc ggcggacagg ccccgagta gtgggtgcgc gagcccacca cggtcacctc    1980
caccgactgc gctgcggggc                                                2000

<210> SEQ ID NO 45
<211> LENGTH: 269
<212> TYPE: PRT
<213> ORGANISM: Streptomyces avermitilis
```

<400> SEQUENCE: 45

Met Arg Arg Ser Arg Ile Thr Ala Tyr Val Thr Ser Leu Leu Ala
1               5                   10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
                35                  40                  45

Val Gly Ala Gly Ser Tyr Leu Ser Ser Ser Gly Asp Cys Lys Arg Ser
    50                  55                  60

Ser Lys Ala Tyr Pro Tyr Leu Trp Gln Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
                100                 105                 110

Ile Gly Gly Asn Asp Ala Gly Phe Ser Asp Val Met Thr Thr Cys Val
                115                 120                 125

Leu Gln Ser Asp Ser Ala Cys Leu Ser Arg Ile Asn Thr Ala Lys Ala
        130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
                180                 185                 190

Lys Arg Ser Ala Ile Asn Asp Ala Ala Asp Tyr Leu Asn Ser Ala Ile
        195                 200                 205

Ala Lys Arg Ala Ala Asp His Gly Phe Thr Phe Gly Asp Val Lys Ser
    210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
                260                 265

<210> SEQ ID NO 46
<211> LENGTH: 1980
<212> TYPE: DNA
<213> ORGANISM: Streptomyces avermitilis

<400> SEQUENCE: 46
ccaccgccgg gtcggcggcg agtctcctgg cctcggtcgc ggagaggttg gccgtgtagc      60
cgttcagcgc ggcgccgaac gtcttcttca ccgtgccgcc gtactcgttg atcaggccct     120
tgcccttgct cgacgcggcc ttgaagccgg tgcccttctt gagcgtgacg atgtagctgc     180
ccttgatcgc ggtggggag ccggcggcga gcaccgtgcc ctcggccggg gtggcctggg      240
cgggcagtgc ggtgaatccg cccacgaggg cgccggtcgc cacggcggtt atcgcggcga     300
tccggatctt cttgctacgc agctgtgcca tacgagggag tcctcctctg ggcagcggcg     360
cgcctgggtg gggcgcacgg ctgtgggggg tgcgcgcgtc atcacgcaca cggccctgga     420
gcgtcgtgtt ccgccctggg ttgagtaaag cctcggccat ctacggggt ggctcaaggg     480 agttgagacc ctgtcatgag tctgacatga gcacgcaatc aacggggccg tgagcacccc     540
ggggcgaccc cggaaagtgc cgagaagtct tggcatggac acttcctgtc aacacgcgta     600

```
gctggtacga cggttacggc agagatcctg ctaaagggag gttccatgag acgttcccga    660
attacggcat acgtgacctc actcctcctc gccgtcggct gcgccctcac cggggcagcg    720
acggcgcagg cgtccccagc cgccgcggcc acgggctatg tggccctcgg cgactcgtac    780
tcgtccggtg tcggcgccgg cagctacctc agctccagcg gcgactgcaa gcgcagttcg    840
aaggcctatc cgtacctctg caggccgcg cattcaccct cgtcgttcag tttcatggct    900
tgctcgggcg ctcgtacggg tgatgtcctg gccaatcagc tcggcaccct gaactcgtcc    960
accggcctgg tctccctcac catcggaggc aacgacgcgg gcttctccga cgtcatgacg   1020
acctgtgtgc tccagtccga cagcgcctgc ctctcccgca tcaacacggc gaaggcgtac   1080
gtcgactcca ccctgccggg ccaactcgac agcgtgtaca cggcgatcag cacgaaggcc   1140
ccgtcggccc atgtggccgt gctgggctac ccccgcttct acaaactggg cggctcctgc   1200
ctcgcgggcc tctcggagac caagcggtcc gccatcaacg acgcggccga ctatctgaac   1260
agcgccatcg ccaagcgcgc cgccgaccac ggcttcacct cggcgacgt caagagcacc   1320 ttcaccggcc atgagatctg ctccagcagc acctggctgc acagtctcga cctgctgaac   1380 atcgccagt cctaccaccc gaccgcgcc ggccagtccg gcggctatct gccggtcatg   1440
aacagcgtgg cctgagctcc cacggcctga attttaagg cctgaattt taaggcgaag   1500 gtgaaccgga agcggaggcc ccgtccgtcg ggtctccgt cgcacaggtc accgagaacg   1560
gcacggagtt ggacgtcgtg cgcaccgggt cgcgcacctc gacggcgatc tcgttcgaga   1620
tcgttccgct cgtgtcgtac gtggtgacga acacctgctt ctgctgggtc tttccgccgc   1680
tcgccgggaa ggacagcgtc ttccagcccg gatccgggac ctcgcccttc ttggtcaccc   1740
agcggtactc cacctcgacc ggcacccggc ccaccgtgaa ggtcgccgtg aacgtgggcg   1800
cctgggcggt gggcggcggg caggcaccgg agtagtcggt gtgcacgccg gtgaccgtca   1860
ccttcacgga ctgggccggc ggggtcgtcg taccgccgcc gccaccgccg cctcccggag   1920
tggagcccga gctgtggtcg ccccccgccgt cggcgttgtc gtcctcgggg gttttcgaac   1980
```

<210> SEQ ID NO 47
<211> LENGTH: 372
<212> TYPE: PRT
<213> ORGANISM: Thermobifida fusca

<400> SEQUENCE: 47

```
Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
            20                  25                  30

Pro Thr Gly Arg Glu Thr Leu Trp Arg Met Trp Cys Glu Ala Thr Gln
        35                  40                  45

Asp Trp Cys Leu Gly Val Pro Val Asp Ser Arg Gly Gln Pro Ala Glu
    50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
```

```
            130                 135                 140
Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
                180                 185                 190

Cys Thr Asp Gln Glu Asp Ala Ile Arg Lys Arg Met Ala Lys Phe Glu
                195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
                260                 265                 270

His Asp Glu Glu Ile Ala Ala Ser Gly Gly Val Gly Ser Val Glu Phe
                275                 280                 285

Val Asp Val Tyr His Ala Leu Asp Gly His Glu Ile Gly Ser Asp Glu
290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
                340                 345                 350

Tyr Ala Thr Phe Ala Val Val Ala Gly Ala Thr Val Asp Thr Leu Ala
                355                 360                 365

Gly Glu Val Gly
    370

<210> SEQ ID NO 48
<211> LENGTH: 968
<212> TYPE: DNA
<213> ORGANISM: Thermobifida fusca

<400> SEQUENCE: 48
ctgcagacac ccgccccgcc ttctcccgga tcgtcatgtt cggcgactcc ctcagcgaca       60
ccggcaagat gtactccaag atgcgcggct acctgccgtc ctccccgccg tactacgagg      120
gccgcttctc gaacggcccg gtctggctgg agcagctgac gaagcagttc cccggcctga      180
cgatcgccaa cgaggccgag ggggcgcgca ccgcagtcgc ctacaacaag atctcctgga      240
acccgaagta ccaggtcatt aacaacctcg actacgaggt cacccagttc ttgcagaagg      300
actcgttcaa gcccgacgac ctggtcatcc tgtgggtggg cgccaacgac tacctggcct      360
acggttggaa cacggagcag gacgccaagc gggtgcgcga cgccatctcg gacgcggcaa      420
accgcatggt cctgaacggc gcgaagcaga tcctgctgtt caacctgccc gacctgggcc      480
agaacccgtc cgcccgctcc agaaggtcg tcgaggccgt ctcgcacgtg tccgcctacc      540
acaacaagct gctcctcaac ctcgcccggc agctcgcccc gacgggcatg gtcaagctgt      600
tcgagatcga caagcagttc gcggagatgc tgcgcgaccc ccagaacttc ggcctgagcg      660
acgtggagaa cccgtgctac gacggcggct acgtgtggaa gccgttcgcc acccggtccg      720
tctcgaccga ccggcagctg tcggccttct cgccccagga gcgcctggcg atcgctggca      780
```

| | |
|---|---|
| acccgctcct ggcacaggcg gtagcttcgc cgatggcccg ccgctcggcc tcgcccctca | 840 |
| actgcgaggg caagatgttc tgggaccagg tccaccccac caccgtggtc cacgccgccc | 900 |
| tctcggagcg cgccgccacc ttcatcgaga cccagtacga gttcctcgcc cactagtcta | 960 |
| gaggatcc | 968 |

<210> SEQ ID NO 49
<211> LENGTH: 1044
<212> TYPE: DNA
<213> ORGANISM: Aeromonas salmonicida

<400> SEQUENCE: 49

| | |
|---|---|
| atgaaacaac aaaaacggct ttacgcccga ttgctgacgc tgttatttgc gctcatcttc | 60 |
| ttgctgcctc attctgcagc ttcagcagca gatacaagac cggcgtttag ccggatcgtc | 120 |
| atgtttggag atagcctgag cgatacgggc aaaatgtata gcaaaatgag aggctatctt | 180 |
| ccgtcaagcc cgccgtatta tgaaggccgc tttagcaatg gaccggtctg gctggaacaa | 240 |
| ctgacgaaac aatttccggg actgacgatc gctaatgaag cagaaggagg agcaacagcg | 300 |
| gtcgcctata caaaatcag ctgggacccg aaatatcagg tcatcaacaa cctggactat | 360 |
| gaagtcacac agtttcttca gaaagacagc tttaaaccgg atgatctggt catcctttgg | 420 |
| gtcggcgcca atgattatct ggcgtatggc tggaacacag aacaagatgc caaagagtc | 480 |
| agagatgcca tcagcgatgc cgctaataga atggtcctga acggcgccaa acaaatcctg | 540 |
| ctgtttaacc tgccggatct gggacaaaat ccgagcgcca gaagccaaaa agtcgtcgaa | 600 |
| gcagtcagcc atgtcagcgc ctatcataac aaactgctgc tgaacctggc aagacaattg | 660 |
| gcaccgacgg gaatggttaa attgtttgaa attgacaaac agtttgccga atgctgaga | 720 |
| gatccgcaaa attttggcct gagcgatgtc gaaaacccgt gctatgatgg cggatatgtc | 780 |
| tggaaaccgt ttgccacaag aagcgtcagc acggatagca aactgtcagc gtttagcccg | 840 |
| caagaaagac tggcaatcgc cggaaatccg cttttggcac aagcagttgc ttcaccgatg | 900 |
| gcaagaagat cagcaagccc gctgaattgc gaaggcaaaa tgttttggga tcaggtccat | 960 |
| ccgacaacag ttgtccatgc tgcccttca gaaagagcgg cgacgtttat cgaaacacag | 1020 |
| tatgaatttc tggcccatgg ctga | 1044 |

<210> SEQ ID NO 50
<211> LENGTH: 1005
<212> TYPE: DNA
<213> ORGANISM: Aeromonas hydrophila

<400> SEQUENCE: 50

| | |
|---|---|
| atgaaaaaat ggtttgtgtg tttattggga ttggtcgcgc tgacagttca ggcagccgac | 60 |
| agccgtcccg ccttctcccg gatcgtgatg tttggcgaca gcctctccga taccggcaag | 120 |
| atgtacagca agatgcgcgg ttacctcccc tccagccccc cctactatga gggccgcttc | 180 |
| tccaacgggc ccgtctggct ggagcagctg accaacgagt tcccgggcct gaccatagcc | 240 |
| aacgaggcgg aaggcggacc gaccgccgtg gcttacaaca gatctcctg gaatcccaag | 300 |
| tatcaggtca tcaacaacct ggactacgag gtcacccagt cctgcaaaa agacagcttc | 360 |
| aagccggacg atctggtgat cctctgggtc ggcgccaacg actatctggc ctatggctgg | 420 |
| aacacagagc aggatgccaa gcgggtgcgc gacgccatca gcgatgcggc caaccgcatg | 480 |
| gtgctgaacg cgccaaggaa gatactgctg ttcaacctgc cggatctggg ccagaacccc | 540 |
| tcggcccgca gccagaaggt ggtcgaggcg gccagccatg tctccgccta ccacaaccag | 600 |

```
ctgctgctga acctggcacg ccagctggct cccaccggca tggtgaagct gttcgagatc     660
gacaagcagt tgccgagat gctgcgtgat ccgcagaact tcggcctgag cgaccagagg      720
aacgcctgct acggtggcag ctatgtatgg aagccgtttg cctcccgcag cgccagcacc    780
gacagccagc tctccgcctt caacccgcag gagcgcctcg ccatcgccgg caacccgctg    840
ctggcccagg ccgtcgccag ccccatggct gcccgcagcg ccagcaccct caactgtgag    900
ggcaagatgt tctgggatca ggtccacccc accactgtcg tgcacgccgc cctgagcgag    960
cccgccgcca ccttcatcga gagccagtac gagttcctcg cccac                   1005
```

<210> SEQ ID NO 51
<211> LENGTH: 1011
<212> TYPE: DNA
<213> ORGANISM: Aeromonas salmonicida

<400> SEQUENCE: 51

```
atgaaaaaat ggtttgtttg tttattgggg ttgatcgcgc tgacagttca ggcagccgac     60
actcgccccg ccttctcccg gatcgtgatg ttcggcgaca gcctctccga taccggcaaa    120
atgtacagca gatgcgcggg ttacctcccc tccagcccgc cctactatga gggccgtttc    180
tccaacggac ccgtctggct ggagcagctg accaagcagt tcccgggtct gaccatcgcc    240
aacgaagcgg aaggcggtgc cactgccgtg gcttacaaca gatctcctg gaatcccaag     300 tatcaggtct acaacaacct ggactacgag gtcacccagt tcttgcagaa agacagcttc    360
aagccggacg atctggtgat cctctgggtc ggtgccaatg actatctggc atatggctgg    420
aatacggagc aggatgccaa gcgagttcgc gatgccatca gcgatgcggc caaccgcatg    480
gtactgaacg gtgccaagca gatactgctg ttcaacctgc cggatctggg ccagaacccg    540
tcagcccgca gtcagaaggt ggtcgaggcg gtcagccatg tctccgccta tcacaacaag    600
ctgctgctga acctggcacg ccagctggcc cccaccggca tggtaaagct gttcgagatc    660
gacaagcaat tgccgagat gctgcgtgat ccgcagaact tcggcctgag cgacgtcgag     720
aaccgctgct acgacggcgg ctatgtgtgg aagccgtttg ccaccccgcag cgtcagcacc    780 gaccgccagc tctccgcctt cagtccgcag gaacgcctcg ccatcgccgg caacccgctg    840
ctggcacagg ccgttgccag tcctatggcc cgccgcagcg ccagcccct caactgtgag    900 ggcaagatgt tctgggatca ggtacacccg accactgtcg tgcacgcagc cctgagcgag    960
cgcgccgcca ccttcatcga gacccagtac gagttcctcg cccacggatg a            1011
```

<210> SEQ ID NO 52
<211> LENGTH: 888
<212> TYPE: DNA
<213> ORGANISM: Streptomyces coelicolor

<400> SEQUENCE: 52

```
atgccgaagc ctgcccttcg ccgtgtcatg accgcgacag tcgccgccgt cggcacgctc     60
gccctcggcc tcaccgacgc caccgcccac gccgcgcccg cccaggccac tccgaccctg    120
gactacgtcg ccctcggcga cagctacagc gccggctccg gcgtcctgcc cgtcgacccc    180
gccaacctgc tctgtctgcg ctcgacggcc aactacccc acgtcatcgc ggacacgacg    240
ggcgcccgcc tcacggacgt cacctgcggc gccgcgcaga ccgccgactt cacgcgggcc    300
cagtacccgg gcgtcgcacc ccagttggac gcgctcggca ccggcacgga cctggtcacg    360
ctcaccatcg gcggcaacga caacagcacc ttcatcaacg ccatcacggc ctgcggcacg    420
gcgggtgtcc tcagcggcgg caagggcagc ccctgcaagg acaggcacgg cacctccttc    480
```

```
gacgacgaga tcgaggccaa cacgtacccc gcgctcaagg aggcgctgct cggcgtccgc    540
gccagggctc cccacgccag ggtggcggct ctcggctacc cgtggatcac cccggccacc    600
gccgacccgt cctgcttcct gaagctcccc ctcgccgccg gtgacgtgcc ctacctgcgg    660
gccatccagg cacacctcaa cgacgcggtc cggcgggccg ccgaggagac cggagccacc    720
tacgtggact tctccggggt gtccgacggc acgacgcct gcgaggcccc cggcacccgc    780
tggatcgaac cgctgctctt cgggcacagc ctcgttcccg tccaccccaa cgccctgggc    840
gagcggcgca tggccgagca cacgatggac gtcctcggcc tggactga                888
```

<210> SEQ ID NO 53
<211> LENGTH: 888
<212> TYPE: DNA
<213> ORGANISM: Streptomyces coelicolor

<400> SEQUENCE: 53

```
tcagtccagg ccgaggacgt ccatcgtgtg ctcggccatg cgccgctcgc ccagggcgtt     60
ggggtggacg ggaacgaggc tgtgcccgaa gagcagcggt tcgatccagc gggtgccggg    120
ggcctcgcag gcgtcgtggc cgtcggacac cccggagaag tccacgtagg tggctccggt    180
ctcctcggcg gcccgccgga ccgcgtcgtt gaggtgtgcc tggatggccc gcaggtaggg    240
cacgtcaccg gcggcgaggg ggagcttcag gaagcaggac gggtcggcgg tggccggggt    300
gatccacggg tagccgagag ccgccaccct ggcgtgggga gccctggcgc ggacgccgag    360
cagcgcctcc ttgagcgcgg ggtacgtgtt ggcctcgatc tcgtcgtcga aggaggtgcc    420
gtgcctgtcc ttgcagggc tgcccttgcc gccgctgagg acacccgccg tgccgcaggc    480
cgtgatggcg ttgatgaagg tgctgttgtc gttgccgccg atggtgagcg tgaccaggtc    540
cgtgccggtg ccgagcgcgt ccaactgggg tgcgacgccc gggtactggg cccgcgtgaa    600
gtcggcggtc tgcgcggcgc cgcaggtgac gtccgtgagg cggcgcccg tcgtgtccgc    660 gatgacgtgg gggtagttgg ccgtcgagcg cagacagagc aggttggcgg ggtcgacggg    720
caggacgccg gagccggcgc tgtagctgtc gccgaggcg acgtagtcca gggtcggagt    780
ggcctgggcg ggcgcggcgt gggcggtggc gtcggtgagg ccgagggcga gcgtgccgac    840
ggcggcgact gtcgcggtca tgacacggcg aagggcaggc ttcggcat                888
```

<210> SEQ ID NO 54
<211> LENGTH: 717
<212> TYPE: DNA
<213> ORGANISM: Saccharomyces cerevisiae

<400> SEQUENCE: 54

```
atggattacg agaagtttct gttatttggg gattccatta ctgaatttgc ttttaatact     60
aggcccattg aagatggcaa agatcagtat gctcttggag ccgcattagt caacgaatat    120
acgagaaaaa tggatattct tcaaagaggg ttcaaggggt acacttctag atgggcgttg    180
aaaatacttc ctgagatttt aaagcatgaa tccaatattg tcatggccac aatattttg    240 ggtgccaacg atgcatgctc agcaggtccc caaagtgtcc ccctcccgga tttatcgat    300 aatattcgtc aaatggtatc tttgatgaag tcttaccata tccgtcctat tataatagga    360
ccggggctag tagatagaga gaagtgggaa aagaaaaat ctgaagaaat agctctcgga    420
tacttccgta ccaacgagaa ctttgccatt tattccgatg ccttagcaaa actagccaat    480
gaggaaaaag ttccccttcgt ggctttgaat aaggcgttc aacaggaagg tggtgatgct    540
tggcaacaac tgctaacaga tggactgcac ttttccggaa aagggtacaa aatttttcat    600
```

```
gacgaattat tgaaggtcat tgagacattc tacccccaat atcatcccaa aaacatgcag    660
tacaaactga aagattggag agatgtgcta gatgatggat ctaacataat gtcttga      717

<210> SEQ ID NO 55
<211> LENGTH: 1044
<212> TYPE: DNA
<213> ORGANISM: Ralstonia sp.

<400> SEQUENCE: 55
atgaacctgc gtcaatggat gggcgccgcc acggctgccc ttgccttggg cttggccgcg     60
tgcgggggcg gtgggaccga ccagagcggc aatcccaatg tcgccaaggt gcagcgcatg    120
gtggtgttcg gcgacagcct gagcgatatc ggcacctaca cccccgtcgc gcaggcggtg    180
ggcggcggca agttcaccac caacccgggc ccgatctggg ccgagaccgt ggccgcgcaa    240
ctgggcgtga cgctcacgcc ggcggtgatg ggctacgcca cctccgtgca gaattgcccc    300
aaggccggct gcttcgacta tgcgcagggc ggctcgcgcg tgaccgatcc gaacggcatc    360
ggccacaacg gcggcgcggg ggcgctgacc tacccggttc agcagcagct cgccaacttc    420
tacgcggcca gcaacaacac attcaacggc aataacgatg tcgtcttcgt gctggccggc    480
agcaacgaca tttcttctg gaccactgcg gcggccacca gcggctccgg cgtgacgccc    540
gccattgcca cggcccaggt gcagcaggcc gcgacggacc tggtcggcta tgtcaaggac    600
atgatcgcca agggtgcgac gcaggtctac gtgttcaacc tgcccgacag cagcctgacg    660
ccggacggcc tggcaagcgg cacgaccggc caggcgctgc tgcacgcgct ggtgggcacg    720
ttcaacacga cgctgcaaag cgggctggcc ggcacctcgg cgcgcatcat cgacttcaac    780
gcacaactga ccgcggcgat ccagaatggc gcctcgttcg gcttcgccaa caccagcgcc    840
cgggcctgcg acgccaccaa gatcaatgcc ctggtgccga gcgccggcgg cagctcgctg    900
ttctgctcgg ccaacacgct ggtggcttcc ggtgcggacc agagctacct gttcgccgac    960
ggcgtgcacc cgaccacggc cggccatcgc ctgatcgcca gcaacgtgct ggcgcgcctg   1020
ctggcggata acgtcgcgca ctga                                          1044

<210> SEQ ID NO 56
<211> LENGTH: 786
<212> TYPE: DNA
<213> ORGANISM: Streptomyces coelicolor

<400> SEQUENCE: 56
gtgatcgggt cgtacgtggc ggtggggac agcttcaccg agggcgtcgg cgaccccggc     60
cccgacgggg cgttcgtcgg ctgggccgac cggctcgccg tactgctcgc ggaccggcgc    120
cccgagggcg acttcacgta cacgaacctc gccgtgcgcg gcaggctcct cgaccagatc    180
gtggcggaac aggtcccgcg ggtcgtcgga ctcgcgcccg acctcgtctc gttcgcggcg    240
ggcggcaacg acatcatccg gcccggcacc gatcccgacg aggtcgccga gcggttcgag    300
ctggcggtgg ccgcgctgac cgccgcggcc ggaaccgtcc tggtgaccac cgggttcgac    360
acccgggggg tgcccgtcct caagcacctg cgcggcaaga tcgccacgta caacgggcac    420
gtccgcgcca tcgccgaccg ctacggctgc ccggtgctcg acctgtggtc gctgcggagc    480
gtccaggacc gcagggcgtg ggacgccgac cggctgcacc tgtcgccgga ggggcacacc    540
cgggtggcgc tgcgcgcggg gcaggccctg gcctgcgcg tcccggccga ccctgaccag    600
ccctggccgc ccctgccgcc gcggcggcacg ctcgacgtcc ggcgcgacga cgtgcactgg    660
gcgcgcgagt acctggtgcc gtggatcggg cgccggctgc ggggcgagtc gtcgggcgac    720
```

```
cacgtgacgg ccaaggggac gctgtcgccg gacgccatca agacgcggat cgccgcggtg    780
gcctga                                                                786

<210> SEQ ID NO 57
<211> LENGTH: 783
<212> TYPE: DNA
<213> ORGANISM: Streptomyces coelicolor

<400> SEQUENCE: 57
atgcagacga accccgcgta caccagtctc gtcgccgtcg gcgactcctt caccgagggc     60
atgtcggacc tgctgcccga cggctcctac cgtggctggg ccgacctcct cgccacccgg    120
atggcggccc gctcccccgg cttccggtac gccaacctgg cggtgcgcgg gaagctgatc    180
ggacagatcg tcgacgagca ggtggacgtg gccgccgcca tgggagccga cgtgatcacg    240
ctggtcggcg gctcaacga cacgctgcgg cccaagtgcg acatggcccg ggtgcgggac    300
ctgctgaccc aggccgtgga acggctcgcc ccgcactgcg agcagctggt gctgatgcgc    360
agtcccggtc gccagggtcc ggtgctggag cgcttccggc cccgcatgga ggccctgttc    420
gccgtgatcg acgacctggc cgggcggcac ggcgccgtgg tcgtcgacct gtacggggcc    480
cagtcgctgg ccgaccctcg gatgtgggac gtggaccggc tgcacctgac cgccgagggc    540
caccgccggg tcgcggaggc ggtgtggcag tcgctcggcc acgagcccga ggaccccgag    600
tggcacgcgc cgatcccggc gacgccgccg ccggggtggg tgacgcgcag gaccgcggac    660
gtccggttcg cccggcagca cctgctgccc tggataggcc gcaggctgac cgggcgctcg    720
tccggggacg gcctgccggc caagcgcccg gacctgctgc cctacgagga ccccgcacgg    780
tga                                                                   783

<210> SEQ ID NO 58
<211> LENGTH: 1365
<212> TYPE: DNA
<213> ORGANISM: Streptomyces coelicolor

<400> SEQUENCE: 58
atgacccggg gtcgtgacgg gggtgcgggg gcgcccccca ccaagcaccg tgccctgctc     60
gcggcgatcg tcaccctgat agtggcgatc tccgcggcca tataccgcgg agcgtccgcg    120
gacgacggca gcagggacca cgcgctgcag gccggaggcc gtctcccacg aggagacgcc    180 gccccgcgt ccaccggtgc ctgggtgggc gcctgggcca ccgcaccggc cgcggccgag    240
ccgggcaccg agacgaccgg cctggcgggc cgctccgtgc gcaacgtcgt gcacacctcg    300
gtcggcggca ccggcgcgcg gatcaccctc tcgaacctgt acgggcagtc gccgctgacc    360
gtcacacacg cctcgatcgc cctggccgcc gggcccgaca ccgccgccgc gatcgccgac    420
accatgcgcc ggctcaccct cggcggcagc gcccgggtga tcatcccggc gggcggccag    480
gtgatgagcg acaccgcccg cctcgccatc ccctacgggg cgaacgtcct ggtcaccacg    540 tactcccccca tcccgtccgg gccggtgacc taccatccgc aggcccggca gaccagctac    600
ctggccgacg gcgaccgcac ggcggacgtc accgccgtcg cgtacaccac ccccacgccc    660
tactggcgct acctgaccgc cctcgacgtg ctgagccacg aggccgacgg cacggtcgtg    720
gcgttcggcg actccatcac cgacggcgcc cgctcgcaga gcgacgccaa ccaccgctgg    780
accgacgtcc tcgccgcacg cctgcacgag gcgcgggcg acggccggga cacgccccgc    840
tacagcgtcg tcaacgaggg catcagcggc aaccggctcc tgaccagcag gccggggcgg    900
ccggccgaca acccgagcgg actgagccgg ttccagcggg acgtgctgga acgcaccaac    960
```

| | | |
|---|---|---|
| gtcaaggccg | tcgtcgtcgt cctcggcgtc aacgacgtcc tgaacagccc ggaactcgcc | 1020 |
| gaccgcgacg | ccatcctgac cggcctgcgc accctcgtcg accgggcgca cgcccgggga | 1080 |
| ctgcgggtcg | tcggcgccac gatcacgccg ttcggcggct acggcggcta caccgaggcc | 1140 |
| cgcgagacga | tgcggcagga ggtcaacgag gagatccgct ccggccgggt cttcgacacg | 1200 |
| gtcgtcgact | tcgacaaggc cctgcgcgac ccgtacgacc cgcgccggat gcgctccgac | 1260 |
| tacgacagcg | cgaccaccct gcaccccggc gacaaggggt acgcgcgcat gggcgcggtc | 1320 |
| atcgacctgg | ccgcgctgaa gggcgcggcg ccggtcaagg cgtag | 1365 |

<210> SEQ ID NO 59
<211> LENGTH: 1023
<212> TYPE: DNA
<213> ORGANISM: Streptomyces coelicolor

<400> SEQUENCE: 59

| | | |
|---|---|---|
| atgacgagca | tgtcgagggc gagggtggcg cggcggatcg cggccggcgc ggcgtacggc | 60 |
| ggcggcggca | tcggcctggc gggagcggcg gcggtcggtc tggtggtggc cgaggtgcag | 120 |
| ctggccagac | gcagggtggg ggtgggcacg ccgacccggg tgccgaacgc gcagggactg | 180 |
| tacggcggca | ccctgcccac ggccggcgac ccgccgctgc ggctgatgat gctgggcgac | 240 |
| tccacgccg | ccgggcaggg cgtgcaccgg gccgggcaga cgccgggcgc gctgctggcg | 300 |
| tccgggctcg | cggcggtggc ggagcggccg gtgcggctgg ggtcggtcgc ccagccgggg | 360 |
| gcgtgctcgg | acgacctgga ccggcaggtg gcgctggtgc tcgccgagcc ggaccgggtg | 420 |
| cccgacatct | gcgtgatcat ggtcggcgcc aacgacgtca cccaccggat gccggcgacc | 480 |
| cgctcggtgc | ggcaccctgtc ctcggcggta cggcggctgc gcacggccgg tgcggaggtg | 540 |
| gtggtcggca | cctgtccgga cctgggcacg atcgagcggg tgcggcagcc gctgcgctgg | 600 |
| ctggcccggc | gggcctcacg gcagctcgcg gcggcacaga ccatcggcgc cgtcgagcag | 660 |
| ggcgggcgca | cggtgtcgct gggcgacctg ctgggtccgg agttcgcgca gaacccgcgg | 720 |
| gagctcttcg | gccccgacaa ctaccacccc tccgccgagg ggtacgccac ggccgcgatg | 780 |
| gcggtactgc | cctcggtgtg cgccgcgctc ggcctgtggc cggccgacga ggagcacccg | 840 |
| gacgcgctgc | cccgcgaggg cttcctgccg gtggcgcgcg cggcggcgga ggcggcgtcc | 900 |
| gaggcgggta | cggaggtcgc cgccgccatg cctacggggc ctcgggggcc ctgggcgctg | 960 |
| ctgaagcgcc | ggagacggcg tcgggtgtcg gaggcggaac cgtccagccc gtccggcgtt | 1020 |
| tga | | 1023 |

<210> SEQ ID NO 60
<211> LENGTH: 918
<212> TYPE: DNA
<213> ORGANISM: Streptomyces coelicolor

<400> SEQUENCE: 60

| | | |
|---|---|---|
| atgggtcgag | ggacggacca gcggacgcgc tacggccgtc gccgggcgcg tgtcgcgctc | 60 |
| gccgccctga | ccgccgccgt cctgggcgtg ggcgtggcgg gctgcgactc cgtgggcggc | 120 |
| gactcacccg | ctccttccgg cagcccgtcg aagcggacga ggacggcgcc cgcctgggac | 180 |
| accagcccg | cgtccgtcgc cgccgtgggc gactccatca cgcgcggctt cgacgcctgt | 240 |
| gcggtgctgt | cggactgccc ggaggtgtcg tgggcgaccg gcagcagcgc gaaggtcgac | 300 |
| tcgctggccc | tacggctgct ggggaaggcg gacgcggccc agcacagctg gaactacgcg | 360 |
| gtcaccgggg | cccggatggc ggacctgacc gctcaggtga cgcgggcggc gcagcgcgag | 420 |

```
ccggagctgg tggcggtgat ggccggggcg aacgacgcgt gccggtccac gacctcggcg      480
atgacgccgg tggcggactt ccgggcgcag ttcgaggagg cgatggccac cctgcgcaag      540
aagctcccca aggcgcaggt gtacgtgtcg agcatcccgg acctcaagcg gctctggtcc      600
cagggccgca ccaacccgct gggcaagcag gtgtggaagc tcggcctgtg cccgtcgatg      660
ctgggcgacg cggactccct ggactcggcg gcgaccctgc ggcgcaacac ggtgcgcgac      720
cgggtggcgg actacaacga ggtgctgcgg gaggtctgcg cgaaggaccg gcggtgccgc      780
agcgacgacg gcgcggtgca cgagttccgg ttcggcacgg accagttgag ccactgggac      840
tggttccacc cgagtgtgga cggccaggcc cggctggcgg agatcgccta ccgcgcggtc      900
accgcgaaga atccctga                                                   918

<210> SEQ ID NO 61
<211> LENGTH: 1068
<212> TYPE: DNA
<213> ORGANISM: Streptomyces rimosus

<400> SEQUENCE: 61
ttcatcacaa cgatgtcaca acaccggcca tccgggtcat ccctgatcgt gggaatgggt       60
gacaagcctt cccgtgacga aagggtcctg ctacatcaga aatgacagaa atcctgctca      120
gggaggttcc atgagactgt cccgacgcgc ggccacggcg tccgcgctcc tcctcacccc      180
ggcgctcgcg ctcttcggcg cgagcgccgc cgtgtccgcg ccgcgaatcc aggccaccga      240
ctacgtggcc ctcggcgact cctactcctc ggggtcggc gcgggcagct acgacagcag      300
cagtggctcc tgtaagcgca gcaccaagtc ctacccggcc ctgtgggccg cctcgcacac      360
cggtacgcgg ttcaacttca ccgcctgttc gggcgcccgc acaggagacg tgctggccaa      420
gcagctgacc ccggtcaact ccggcaccga cctggtcagc attaccatcg gcggcaacga      480
cgcgggcttc gccgacacca tgaccaccctg caacctccag ggcgagagcg cgtgcctggc      540
gcggatcgcc aaggcgcgcg cctacatcca gcagacgctg cccgcccagc tggaccaggt      600
ctacgacgcc atcgacagcc gggccccgc agcccaggtc gtcgtcctgg gctacccgcg      660
cttctacaag ctgggcggca gctgcgccgt cggtctctcg gagaagtccc gcgcggccat      720
caacgccgcc gccgacgaca tcaacgccgt caccgccaag cgcgccgcg accacggctt      780 cgccttcggg gacgtcaaca cgaccttcgc cgggcacgag ctgtgctccg cgccccctg      840 gctgcacagc gtcaccccttc ccgtggagaa ctcctaccac cccacggcca acggacagtc      900
caagggctac ctgcccgtcc tgaactccgc cacctgatct cgcggctact ccgcccctga      960
cgaagtcccg ccccccgggcg gggcttcgcc gtaggtgcgc gtaccgccgt cgcccgtcgc     1020
gccggtggcc ccgccgtacg tgccgccgcc cccggacgcg gtcggttc                  1068

<210> SEQ ID NO 62
<211> LENGTH: 1008
<212> TYPE: DNA
<213> ORGANISM: Aeromonas hydrophila

<400> SEQUENCE: 62
atgaaaaaat ggtttgtgtg tttattggga ttggtcgcgc tgacagttca ggcagccgac       60
agtcgccccg cctttttccccg gatcgtgatg ttcggcgaca gcctctccga taccggcaaa      120
atgtacagca agatgcgcgg ttacctcccc tccagcccgc cctactatga gggccgtttc      180
tccaacggac ccgtctgggct ggagcagctg accaaaacagt tcccgggtct gaccatcgcc      240
aacgaagcgg aaggcggtgc cactgccgtg gcttacaaca agatctcctg gaatcccaag      300
```

```
tatcaggtca tcaacaacct ggactacgag gtcacccagt tcttgcagaa agacagcttc    360
aagccggacg atctggtgat cctctgggtc ggtgccaatg actatctggc ctatggctgg    420
aacacggagc aggatgccaa gcgggttcgc gatgccatca gcgatgcggc caaccgcatg    480
gtactgaacg gtgccaagca gatactgctg ttcaacctgc cggatctggg ccagaacccg    540
tcagctcgca gtcagaaggt ggtcgaggcg gtcagccatg tctccgccta tcacaaccag    600
ctgctgctga acctggcacg ccagctggcc cccaccggca tggtaaagct gttcgagatc    660
gacaagcaat tgccgagat gctgcgtgat ccgcagaact tcggcctgag cgacgtcgag    720
aacccctgct acgacggcgg ctatgtgtgg aagccgtttg ccacccgcag cgtcagcacc    780
gaccgccagc tctccgcctt cagtccgcag gaacgcctcg ccatcgccgg caacccgctg    840
ctggcacagg ccgttgccag tcctatggcc cgccgcagcg ccagccccct caactgtgag    900
ggcaagatgt tctgggatca ggtacacccg accactgtcg tgcacgcagc cctgagcgag    960
cgcgccgcca ccttcatcgc gaaccagtac gagttcctcg cccactga                1008
```

<210> SEQ ID NO 63
<211> LENGTH: 1011
<212> TYPE: DNA
<213> ORGANISM: Aeromonas salmonicida

<400> SEQUENCE: 63

```
atgaaaaaat ggtttgtttg tttattgggg ttgatcgcgc tgacagttca ggcagccgac     60
actcgccccg ccttctcccg gatcgtgatg ttcggcgaca gcctctccga taccggcaaa    120
atgtacagca agatgcgcgg ttacctcccc tccagcccgc cctactatga gggccgtttc    180
tccaacggac ccgtctggct ggagcagctg accaagcagt tcccgggtct gaccatcgcc    240
aacgaagcgg aaggcggtgc cactgccgtg gcttacaaca agatctcctg gaatcccaag    300
tatcaggtca tcaacaacct ggactacgag gtcacccagt tcttgcagaa agacagcttc    360
aagccggacg atctggtgat cctctgggtc ggtgccaatg actatctggc atatggctgg    420
aatacggagc aggatgccaa gcgagttcgc gatgccatca gcgatgcggc caaccgcatg    480
gtactgaacg gtgccaagca gatactgctg ttcaacctgc cggatctggg ccagaacccg    540
tcagcccgca gtcagaaggt ggtcgaggcg gtcagccatg tctccgccta tcacaacaag    600
ctgctgctga acctggcacg ccagctggcc cccaccggca tggtaaagct gttcgagatc    660
gacaagcaat tgccgagat gctgcgtgat ccgcagaact tcggcctgag cgacgtcgag    720
aacccctgct acgacggcgg ctatgtgtgg aagccgtttg ccacccgcag cgtcagcacc    780
gaccgccagc tctccgcctt cagtccgcag gaacgcctcg ccatcgccgg caacccgctg    840
ctggcacagg ccgttgccag tcctatggcc cgccgcagcg ccagccccct caactgtgag    900
ggcaagatgt tctgggatca ggtacacccg accactgtcg tgcacgcagc cctgagcgag    960
cgcgccgcca ccttcatcga gacccagtac gagttcctcg cccacggatg a             1011
```

<210> SEQ ID NO 64
<211> LENGTH: 51
<212> TYPE: DNA
<213> ORGANISM: Artificial Sequence
<220> FEATURE:
<223> OTHER INFORMATION: Description of Artificial Sequence: Synthetic terminator oligonucleotide

<400> SEQUENCE: 64

```
cgggacttac cgaaagaaac catcaatgat ggtttctttt tgttcataa a                51
```

<210> SEQ ID NO 65
<211> LENGTH: 59
<212> TYPE: DNA
<213> ORGANISM: Artificial Sequence
<220> FEATURE:
<223> OTHER INFORMATION: Description of Artificial Sequence: Synthetic
      terminator oligonucleotide

<400> SEQUENCE: 65
caagactaaa gaccgttcgc ccgttttttgc aataagcggg cgaatcttac ataaaaata    59

<210> SEQ ID NO 66
<211> LENGTH: 61
<212> TYPE: DNA
<213> ORGANISM: Artificial Sequence
<220> FEATURE:
<223> OTHER INFORMATION: Description of Artificial Sequence: Synthetic
      terminator oligonucleotide

<400> SEQUENCE: 66
acggccgtta gatgtgacag cccgttccaa aaggaagcgg gctgtcttcg tgtattattg    60
t                                                                    61

<210> SEQ ID NO 67
<211> LENGTH: 54
<212> TYPE: DNA
<213> ORGANISM: Artificial Sequence
<220> FEATURE:
<223> OTHER INFORMATION: Description of Artificial Sequence: Synthetic
      terminator oligonucleotide

<400> SEQUENCE: 67
tcttttaaag gaaaggctgg aatgcccggc attccagcca catgatcatc gttt          54

<210> SEQ ID NO 68
<211> LENGTH: 280
<212> TYPE: PRT
<213> ORGANISM: Aeromonas salmonicida

<400> SEQUENCE: 68

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asp
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val

```
                165                 170                 175
Ser Ala Tyr His Asn Lys Leu Leu Asn Leu Ala Arg Gln Leu Ala
        180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Val Glu Asn Pro
        210                 215                 220

Cys Tyr Asp Gly Gly Tyr Val Trp Lys Pro Phe Arg Ser Ala Ser Pro
225                 230                 235                 240

Leu Asn Cys Glu Gly Lys Met Phe Trp Asp Gln Val His Pro Thr Thr
                245                 250                 255

Val Val His Ala Ala Leu Ser Glu Arg Ala Ala Thr Phe Ile Glu Thr
            260                 265                 270

Gln Tyr Glu Phe Leu Ala His Gly
        275                 280

<210> SEQ ID NO 69
<211> LENGTH: 102
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ccccgctcga ggcttttctt ttggaagaaa atatagggaa aatggtactt gttaaaaatt      60
cggaatattt atacaatatc atatgtttca cattgaaagg gg                        102

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tggaatctcg aggttttatc ctttaccttg tctcc                                35

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 71

Met Arg Arg Ser Arg Phe Leu Ala
1               5

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 72

Ala Leu Ile Leu Leu Thr Leu Ala
1               5
```

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 73

Ala Arg Ala Ala Pro
1               5

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 74

Tyr Val Ala Leu Gly Asp Ser Tyr Ser Ser Gly
1               5                   10

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 75

Gly Ala Gly Ser Tyr
1               5

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 76

Ser Ser Gly Asp
1

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 77

Arg Ser Thr Lys Ala Tyr Pro Ala Leu Trp Ala Ala Ala His Ala
1               5                   10                  15

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 78

```
Ser Ser Phe Ser Phe
1               5

<210> SEQ ID NO 79
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 79

Ala Cys Ser Gly Ala Arg Thr Tyr Asp Val Leu Ala
1               5                   10

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 80

Leu Val Ser Ile Thr Ile Gly Gly Asn Asp Ala Gly Phe Ala Asp
1               5                   10                  15

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 81

Met Thr Thr Cys Val Leu
1               5

<210> SEQ ID NO 82
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 82

Ser Asp Ser Ala Cys Leu
1               5

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 83

Thr Leu Pro Ala
1

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
```

-continued consensus peptide

<400> SEQUENCE: 84

Arg Leu Asp Ser Val Tyr Ser Ala Ile
1               5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 85

Thr Arg Ala Pro
1

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 86

Ala Arg Val Val Val Leu Gly Tyr Pro Arg Ile Tyr
1               5                   10

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 87

Leu Gly Leu Ser
1

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 88

Thr Lys Arg Ala Ala Ile Asn Asp Ala Ala Asp
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 89

Leu Asn Ser Val Ile Ala Lys Arg Ala Ala Asp His
1               5                   10

<210> SEQ ID NO 90
<211> LENGTH: 7

```
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 90

Gly Phe Thr Phe Gly Asp Val
1               5

<210> SEQ ID NO 91
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 91

Gly His Glu Leu Cys Ser Ala
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 92

Pro Trp Leu His Ser Leu Thr Leu Pro
1               5

<210> SEQ ID NO 93
<211> LENGTH: 6
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 93

Ser Tyr His Pro Thr Ala
1               5

<210> SEQ ID NO 94
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 94

Gly His Ala Ala Gly Tyr Leu Pro Val Leu Asn Ser Ile
1               5                   10

<210> SEQ ID NO 95
<211> LENGTH: 232
<212> TYPE: PRT
<213> ORGANISM: Aspergillus aculeatus

<400> SEQUENCE: 95

Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
                20                  25                  30
```

```
Ala Thr Val Val Asn Asp Ala Val Ala Gly Arg Ser Ala Arg Ser Tyr
             35                  40                  45

Thr Arg Glu Gly Arg Phe Glu Asn Ile Ala Asp Val Val Thr Ala Gly
 50                  55                  60

Asp Tyr Val Ile Val Glu Phe Gly His Asn Asp Gly Gly Ser Leu Ser
 65                  70                  75                  80

Thr Asp Asn Gly Arg Thr Asp Cys Ser Gly Thr Gly Ala Glu Val Cys
                 85                  90                  95

Tyr Ser Val Tyr Asp Gly Val Asn Glu Thr Ile Leu Thr Phe Pro Ala
                100                 105                 110

Tyr Leu Glu Asn Ala Ala Lys Leu Phe Thr Ala Lys Gly Ala Lys Val
            115                 120                 125

Ile Leu Ser Ser Gln Thr Pro Asn Asn Pro Trp Glu Thr Gly Thr Phe
130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
        195                 200                 205

Leu Lys Ala Val Val Cys Thr Gly Thr Ser Leu Lys Ser Val Leu Thr
210                 215                 220

Thr Thr Ser Phe Glu Gly Thr Cys
225                 230

<210> SEQ ID NO 96
<211> LENGTH: 184
<212> TYPE: PRT
<213> ORGANISM: Escherichia coli

<400> SEQUENCE: 96

Ala Asp Thr Leu Leu Ile Leu Gly Asp Ser Leu Ser Ala Gly Tyr Arg
 1               5                  10                  15

Met Ser Ala Ser Ala Ala Trp Pro Ala Leu Leu Asn Asp Lys Trp Gln
             20                  25                  30

Ser Lys Thr Ser Val Val Asn Ala Ser Ile Ser Gly Asp Thr Ser Gln
             35                  40                  45

Gln Gly Leu Ala Arg Leu Pro Ala Leu Leu Lys Gln His Gln Pro Arg
 50                  55                  60

Trp Val Leu Val Glu Leu Gly Gly Asn Asp Gly Leu Arg Gly Phe Gln
65                   70                  75                  80

Pro Gln Gln Thr Glu Gln Thr Leu Arg Gln Ile Leu Gln Asp Val Lys
                 85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
            115                 120                 125

Ala Lys Glu Phe Asp Val Pro Leu Leu Pro Phe Phe Met Glu Glu Val
130                 135                 140

Tyr Leu Lys Pro Gln Trp Met Gln Asp Gly Ile His Pro Asn Arg Asp
145                 150                 155                 160

Asp Ala Gln Pro Phe Ile Ala Asp Trp Met Ala Lys Gln Leu Gln Pro
                165                 170                 175
```

```
Leu Val Asn His Asp Ser Leu Glu
            180
```

```
<210> SEQ ID NO 97
<211> LENGTH: 308
<212> TYPE: PRT
<213> ORGANISM: Aeromonas hydrophila

<400> SEQUENCE: 97
```

```
Ile Val Met Phe Gly Asp Ser Leu Ser Asp Thr Gly Lys Met Tyr Ser
1               5                   10                  15

Lys Met Arg Gly Tyr Leu Pro Ser Pro Pro Tyr Tyr Glu Gly Arg
            20                  25                  30

Phe Ser Asn Gly Pro Val Trp Leu Glu Gln Leu Thr Asn Glu Phe Pro
            35                  40                  45

Gly Leu Thr Ile Ala Asn Glu Ala Glu Gly Gly Pro Thr Ala Val Ala
        50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205

Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala Ala Thr Phe Ile Glu Ser Gln Tyr Glu
    290                 295                 300

Phe Leu Ala His
305
```

```
<210> SEQ ID NO 98
<211> LENGTH: 167
<212> TYPE: PRT
<213> ORGANISM: Escherichia coli

<400> SEQUENCE: 98
```

```
Leu Leu Ile Leu Gly Asp Ser Leu Ser Ala Gly Tyr Arg Met Ser Ala
1               5                   10                  15

Ser Ala Ala Trp Pro Ala Leu Leu Asn Asp Lys Trp Gln Ser Lys Thr
            20                  25                  30

Ser Val Val Asn Ala Ser Ile Ser Gly Asp Thr Ser Gln Gln Gly Leu
        35                  40                  45

Ala Arg Leu Pro Ala Leu Leu Lys Gln His Gln Pro Arg Trp Val Leu
    50                  55                  60

Val Glu Leu Gly Gly Asn Asp Gly Leu Arg Gly Phe Gln Pro Gln Gln
65                  70                  75                  80

Thr Glu Gln Thr Leu Arg Gln Ile Leu Gln Asp Val Lys Ala Ala Asn
                85                  90                  95

Ala Glu Pro Leu Leu Met Gln Ile Arg Leu Pro Ala Asn Tyr Gly Arg
            100                 105                 110

Arg Tyr Asn Glu Ala Phe Ser Ala Ile Tyr Pro Lys Leu Ala Lys Glu
        115                 120                 125

Phe Asp Val Pro Leu Leu Pro Phe Phe Met Glu Glu Val Tyr Leu Lys
    130                 135                 140

Pro Gln Trp Met Gln Asp Asp Gly Ile His Pro Asn Arg Asp Ala Gln
145                 150                 155                 160

Pro Phe Ile Ala Asp Trp Met
                165
```

<210> SEQ ID NO 99
<211> LENGTH: 295
<212> TYPE: PRT
<213> ORGANISM: Aeromonas hydrophila

<400> SEQUENCE: 99

```
Ile Val Met Phe Gly Asp Ser Leu Ser Asp Thr Gly Lys Met Tyr Ser
1               5                   10                  15

Lys Met Arg Gly Tyr Leu Pro Ser Pro Pro Tyr Tyr Glu Gly Arg
            20                  25                  30

Phe Ser Asn Gly Pro Val Trp Leu Glu Gln Leu Thr Asn Glu Phe Pro
        35                  40                  45

Gly Leu Thr Ile Ala Asn Glu Ala Glu Gly Gly Pro Thr Ala Val Ala
    50                  55                  60

Tyr Asn Lys Ile Ser Trp Asn Pro Lys Tyr Gln Val Ile Asn Asn Leu
65                  70                  75                  80

Asp Tyr Glu Val Thr Gln Phe Leu Gln Lys Asp Ser Phe Lys Pro Asp
                85                  90                  95

Asp Leu Val Ile Leu Trp Val Gly Ala Asn Asp Tyr Leu Ala Tyr Gly
            100                 105                 110

Trp Asn Thr Glu Gln Asp Ala Lys Arg Val Arg Asp Ala Ile Ser Asp
        115                 120                 125

Ala Ala Asn Arg Met Val Leu Asn Gly Ala Lys Glu Ile Leu Leu Phe
    130                 135                 140

Asn Leu Pro Asp Leu Gly Gln Asn Pro Ser Ala Arg Ser Gln Lys Val
145                 150                 155                 160

Val Glu Ala Ala Ser His Val Ser Ala Tyr His Asn Gln Leu Leu Leu
                165                 170                 175

Asn Leu Ala Arg Gln Leu Ala Pro Thr Gly Met Val Lys Leu Phe Glu
            180                 185                 190

Ile Asp Lys Gln Phe Ala Glu Met Leu Arg Asp Pro Gln Asn Phe Gly
        195                 200                 205
```

```
Leu Ser Asp Gln Arg Asn Ala Cys Tyr Gly Gly Ser Tyr Val Trp Lys
    210                 215                 220

Pro Phe Ala Ser Arg Ser Ala Ser Thr Asp Ser Gln Leu Ser Ala Phe
225                 230                 235                 240

Asn Pro Gln Glu Arg Leu Ala Ile Ala Gly Asn Pro Leu Leu Ala Gln
                245                 250                 255

Ala Val Ala Ser Pro Met Ala Ala Arg Ser Ala Ser Thr Leu Asn Cys
            260                 265                 270

Glu Gly Lys Met Phe Trp Asp Gln Val His Pro Thr Thr Val Val His
        275                 280                 285

Ala Ala Leu Ser Glu Pro Ala
        290                 295

<210> SEQ ID NO 100
<211> LENGTH: 335
<212> TYPE: PRT
<213> ORGANISM: Aeromonas hydrophila

<400> SEQUENCE: 100

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
                20                  25                  30

Asp Ser Leu Ser Asp Thr Gly Lys Met Tyr Ser Lys Met Arg Gly Tyr
            35                  40                  45

Leu Pro Ser Ser Pro Tyr Tyr Glu Gly Arg Phe Ser Asn Gly Pro
    50                  55                  60

Val Trp Leu Glu Gln Leu Thr Asn Glu Phe Pro Gly Leu Thr Ile Ala
65                  70                  75                  80

Asn Glu Ala Glu Gly Gly Pro Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
                165                 170                 175

Gly Gln Asn Pro Ser Ala Arg Ser Gln Lys Val Val Glu Ala Ala Ser
            180                 185                 190

His Val Ser Ala Tyr His Asn Gln Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
        275                 280                 285
```

```
Met Ala Ala Arg Ser Ala Ser Thr Leu Asn Cys Glu Gly Lys Met Phe
            290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 101
<211> LENGTH: 318
<212> TYPE: PRT
<213> ORGANISM: Aeromonas salmonicida

<400> SEQUENCE: 101

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
                20                  25                  30

Ser Ser Pro Pro Tyr Tyr Glu Gly Arg Phe Ser Asn Gly Pro Val Trp
            35                  40                  45

Leu Glu Gln Leu Thr Lys Gln Phe Pro Gly Leu Thr Ile Ala Asn Glu
50                  55                  60

Ala Glu Gly Gly Ala Thr Ala Val Ala Tyr Asn Lys Ile Ser Trp Asn
65                  70                  75                  80

Pro Lys Tyr Gln Val Tyr Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
290                 295                 300

Ala Thr Phe Ile Glu Thr Gln Tyr Glu Phe Leu Ala His Gly
305                 310                 315

<210> SEQ ID NO 102
<211> LENGTH: 50
```

```
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 102

Arg Pro Ala Phe Ser Arg Ile Val Met Phe Gly Asp Ser Leu Ser Asp
1               5                   10                  15

Thr Gly Lys Met Tyr Ser Lys Met Arg Gly Tyr Leu Pro Ser Ser Pro
            20                  25                  30

Pro Tyr Tyr Glu Gly Arg Phe Ser Asn Gly Pro Val Trp Leu Glu Gln
        35                  40                  45

Leu Thr
    50

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 103

Phe Pro Gly Leu Thr Ile Ala Asn Glu Ala Glu Gly Gly
1               5                   10

<210> SEQ ID NO 104
<211> LENGTH: 79
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 104

Thr Ala Val Ala Tyr Asn Lys Ile Ser Trp Asn Pro Lys Tyr Gln Val
1               5                   10                  15

Ile Asn Asn Leu Asp Tyr Glu Val Thr Gln Phe Leu Gln Lys Asp Ser
            20                  25                  30

Phe Lys Pro Asp Asp Leu Val Ile Leu Trp Val Gly Ala Asn Asp Tyr
        35                  40                  45

Leu Ala Tyr Gly Trp Asn Thr Glu Gln Asp Ala Lys Arg Val Arg Asp
    50                  55                  60

Ala Ile Ser Asp Ala Ala Asn Arg Met Val Leu Asn Gly Ala Lys
65                  70                  75

<210> SEQ ID NO 105
<211> LENGTH: 23
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 105

Ile Leu Leu Phe Asn Leu Pro Asp Leu Gly Gln Asn Pro Ser Ala Arg
1               5                   10                  15

Ser Gln Lys Val Val Glu Ala
            20

<210> SEQ ID NO 106
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 106

Ser His Val Ser Ala Tyr His Asn
1               5

<210> SEQ ID NO 107
<211> LENGTH: 38
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 107

Leu Leu Leu Asn Leu Ala Arg Gln Leu Ala Pro Thr Gly Met Val Lys
1               5                   10                  15

Leu Phe Glu Ile Asp Lys Gln Phe Ala Glu Met Leu Arg Asp Pro Gln
            20                  25                  30

Asn Phe Gly Leu Ser Asp
        35

<210> SEQ ID NO 108
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 108

Tyr Val Trp Lys Pro Phe Ala
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 109

Gln Leu Ser Ala Phe
1               5

<210> SEQ ID NO 110
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 110

Pro Gln Glu Arg Leu Ala Ile Ala Gly Asn Pro Leu Leu Ala Gln Ala
1               5                   10                  15

Val Ala Ser Pro Met Ala
            20

<210> SEQ ID NO 111
<211> LENGTH: 4
<212> TYPE: PRT
```

-continued

<213> ORGANISM: Artificial Sequence
<220> FEATURE:
<223> OTHER INFORMATION: Description of Artificial Sequence: Synthetic
      consensus peptide

<400> SEQUENCE: 111

Arg Ser Ala Ser
1

<210> SEQ ID NO 112
<211> LENGTH: 24
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 112

Leu Asn Cys Glu Gly Lys Met Phe Trp Asp Gln Val His Pro Thr Thr
1               5                   10                  15

Val Val His Ala Ala Leu Ser Glu
            20

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 113

Ala Ala Thr Phe Ile
1               5

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      consensus peptide

<400> SEQUENCE: 114

Gln Tyr Glu Phe Leu Ala His
1               5

<210> SEQ ID NO 115
<211> LENGTH: 1225
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: XhoI insert containing the LAT-KLM3' precursor
      gene
<220> FEATURE:
<221> NAME/KEY: CDS
<222> LOCATION: (101)..(1141)

<400> SEQUENCE: 115
gcttttcttt tggaagaaaa tatagggaaa atggtacttg ttaaaaattc ggaatattta      60
tacaatatca tatgtttcac attgaaaggg gaggagaatc atg aaa caa caa aaa      115
                                            Met Lys Gln Gln Lys
                                            1               5 cgg ctt tac gcc cga ttg ctg acg ctg tta ttt gcg ctc atc ttc ttg      163
Arg Leu Tyr Ala Arg Leu Leu Thr Leu Leu Phe Ala Leu Ile Phe Leu

```
                10                  15                  20
ctg cct cat tct gca gct tca gca gca gat aca aga ccg gcg ttt agc       211
Leu Pro His Ser Ala Ala Ser Ala Ala Asp Thr Arg Pro Ala Phe Ser
            25                  30                  35 cgg atc gtc atg ttt gga gat agc ctg agc gat acg ggc aaa atg tat       259
Arg Ile Val Met Phe Gly Asp Ser Leu Ser Asp Thr Gly Lys Met Tyr
        40                  45                  50 agc aaa atg aga ggc tat ctt ccg tca agc ccg ccg tat tat gaa ggc       307
Ser Lys Met Arg Gly Tyr Leu Pro Ser Ser Pro Pro Tyr Tyr Glu Gly
    55                  60                  65 cgc ttt agc aat gga ccg gtc tgg ctg gaa caa ctg acg aaa caa ttt       355
Arg Phe Ser Asn Gly Pro Val Trp Leu Glu Gln Leu Thr Lys Gln Phe
70                  75                  80                  85 ccg gga ctg acg atc gct aat gaa gca gaa gga gga gca aca gcg gtc       403
Pro Gly Leu Thr Ile Ala Asn Glu Ala Glu Gly Gly Ala Thr Ala Val
                90                  95                 100 gcc tat aac aaa atc agc tgg gac ccg aaa tat cag gtc atc aac aac       451
Ala Tyr Asn Lys Ile Ser Trp Asp Pro Lys Tyr Gln Val Ile Asn Asn
            105                 110                 115 ctg gac tat gaa gtc aca cag ttt ctt cag aaa gac agc ttt aaa ccg       499
Leu Asp Tyr Glu Val Thr Gln Phe Leu Gln Lys Asp Ser Phe Lys Pro
        120                 125                 130 gat gat ctg gtc atc ctt tgg gtc ggc gcc aat gat tat ctg gcg tat       547
Asp Asp Leu Val Ile Leu Trp Val Gly Ala Asn Asp Tyr Leu Ala Tyr
    135                 140                 145 ggc tgg aac aca gaa caa gat gcc aaa aga gtc aga gat gcc atc agc       595
Gly Trp Asn Thr Glu Gln Asp Ala Lys Arg Val Arg Asp Ala Ile Ser
150                 155                 160                 165 gat gcc gct aat aga atg gtc ctg aac ggc gcc aaa caa atc ctg ctg       643
Asp Ala Ala Asn Arg Met Val Leu Asn Gly Ala Lys Gln Ile Leu Leu
                170                 175                 180 ttt aac ctg ccg gat ctg gga caa aat ccg agc gcc aga agc caa aaa       691
Phe Asn Leu Pro Asp Leu Gly Gln Asn Pro Ser Ala Arg Ser Gln Lys
            185                 190                 195 gtc gtc gaa gca gtc agc cat gtc agc gcc tat cat aac aaa ctg ctg       739
Val Val Glu Ala Val Ser His Val Ser Ala Tyr His Asn Lys Leu Leu
        200                 205                 210 ctg aac ctg gca aga caa ttg gca ccg acg gga atg gtt aaa ttg ttt       787
Leu Asn Leu Ala Arg Gln Leu Ala Pro Thr Gly Met Val Lys Leu Phe
    215                 220                 225 gaa att gac aaa cag ttt gcc gaa atg ctg aga gat ccg caa aat ttt       835
Glu Ile Asp Lys Gln Phe Ala Glu Met Leu Arg Asp Pro Gln Asn Phe
230                 235                 240                 245 ggc ctg agc gat gtc gaa aac ccg tgc tat gat ggc gga tat gtc tgg       883
Gly Leu Ser Asp Val Glu Asn Pro Cys Tyr Asp Gly Gly Tyr Val Trp
                250                 255                 260 aaa ccg ttt gcc aca aga agc gtc agc acg gat aga caa ctg tca gcg       931
Lys Pro Phe Ala Thr Arg Ser Val Ser Thr Asp Arg Gln Leu Ser Ala
            265                 270                 275 ttt agc ccg caa gaa aga ctg gca atc gcc gga aat ccg ctt ttg gca       979
Phe Ser Pro Gln Glu Arg Leu Ala Ile Ala Gly Asn Pro Leu Leu Ala
        280                 285                 290 caa gca gtt gct tca ccg atg gca aga aga tca gca agc ccg ctg aat      1027
Gln Ala Val Ala Ser Pro Met Ala Arg Arg Ser Ala Ser Pro Leu Asn
    295                 300                 305 tgc gaa ggc aaa atg ttt tgg gat cag gtc cat ccg aca aca gtt gtc      1075
Cys Glu Gly Lys Met Phe Trp Asp Gln Val His Pro Thr Thr Val Val
310                 315                 320                 325 cat gct gcc ctt tca gaa aga gcg gcg acg ttt atc gaa aca cag tat      1123
His Ala Ala Leu Ser Glu Arg Ala Ala Thr Phe Ile Glu Thr Gln Tyr
```

```
                        330             335             340
gaa ttt ctg gcc cat ggc tgagttaaca gaggacggat ttcctgaagg          1171
Glu Phe Leu Ala His Gly
                345 aaatccgttt ttttatttta agcttggaga caaggtaaag gataaaacct cgag       1225
```

<210> SEQ ID NO 116
<211> LENGTH: 347
<212> TYPE: PRT
<213> ORGANISM: Artificial Sequence
<220> FEATURE:
<223> OTHER INFORMATION: Description of Artificial Sequence: Synthetic
      construct polypeptide

<400> SEQUENCE: 116

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ser Ala Ala Asp Thr
            20                  25                  30

Arg Pro Ala Phe Ser Arg Ile Val Met Phe Gly Asp Ser Leu Ser Asp
        35                  40                  45

Thr Gly Lys Met Tyr Ser Lys Met Arg Gly Tyr Leu Pro Ser Ser Pro
50                  55                  60

Pro Tyr Tyr Glu Gly Arg Phe Ser Asn Gly Pro Val Trp Leu Glu Gln
65                  70                  75                  80

Leu Thr Lys Gln Phe Pro Gly Leu Thr Ile Ala Asn Glu Ala Glu Gly
                85                  90                  95

Gly Ala Thr Ala Val Ala Tyr Asn Lys Ile Ser Trp Asp Pro Lys Tyr
            100                 105                 110

Gln Val Ile Asn Asn Leu Asp Tyr Glu Val Thr Gln Phe Leu Gln Lys
        115                 120                 125

Asp Ser Phe Lys Pro Asp Asp Leu Val Ile Leu Trp Val Gly Ala Asn
    130                 135                 140

Asp Tyr Leu Ala Tyr Gly Trp Asn Thr Glu Gln Asp Ala Lys Arg Val
145                 150                 155                 160

Arg Asp Ala Ile Ser Asp Ala Ala Asn Arg Met Val Leu Asn Gly Ala
                165                 170                 175

Lys Gln Ile Leu Leu Phe Asn Leu Pro Asp Leu Gly Gln Asn Pro Ser
            180                 185                 190

Ala Arg Ser Gln Lys Val Val Glu Ala Val Ser His Val Ser Ala Tyr
        195                 200                 205

His Asn Lys Leu Leu Leu Asn Leu Ala Arg Gln Leu Ala Pro Thr Gly
    210                 215                 220

Met Val Lys Leu Phe Glu Ile Asp Lys Gln Phe Ala Glu Met Leu Arg
225                 230                 235                 240

Asp Pro Gln Asn Phe Gly Leu Ser Asp Val Glu Asn Pro Cys Tyr Asp
                245                 250                 255

Gly Gly Tyr Val Trp Lys Pro Phe Ala Thr Arg Ser Val Ser Thr Asp
            260                 265                 270

Arg Gln Leu Ser Ala Phe Ser Pro Gln Glu Arg Leu Ala Ile Ala Gly
        275                 280                 285

Asn Pro Leu Leu Ala Gln Ala Val Ala Ser Pro Met Ala Arg Arg Ser
    290                 295                 300

Ala Ser Pro Leu Asn Cys Glu Gly Lys Met Phe Trp Asp Gln Val His
305                 310                 315                 320

Pro Thr Thr Val Val His Ala Ala Leu Ser Glu Arg Ala Ala Thr Phe
```

```
                      325                 330                 335
Ile Glu Thr Gln Tyr Glu Phe Leu Ala His Gly
            340                 345

<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence: Synthetic
      motif peptide
<220> FEATURE:
<221> NAME/KEY: MOD_RES
<222> LOCATION: (4)..(4)
<223> OTHER INFORMATION: Leu, Ala, Val, Ile, Phe, Tyr, His, Gln, Thr,
      Asn, Met or Ser
<220> FEATURE:
<223> OTHER INFORMATION: See specification as filed for detailed
      description of substitutions and preferred embodiments

<400> SEQUENCE: 117

Gly Asp Ser Xaa
1

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 118

Gly Ala Asn Asp Tyr
1               5

<210> SEQ ID NO 119
<211> LENGTH: 56
<212> TYPE: DNA
<213> ORGANISM: Artificial Sequence
<220> FEATURE:
<223> OTHER INFORMATION: Description of Artificial Sequence: Synthetic
      terminator oligonucleotide

<400> SEQUENCE: 119
gctgacaaat aaaagaagc aggtatggag gaacctgctt cttttttacta ttattg        56

<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Synthetic
      motif peptide
<220> FEATURE:
<221> NAME/KEY: MOD_RES
<222> LOCATION: (4)..(4)
<223> OTHER INFORMATION: Any amino acid

<400> SEQUENCE: 120

Gly Asp Ser Xaa
1

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence: Synthetic
      motif peptide
```

```
<220> FEATURE:
<221> NAME/KEY: MOD_RES
<222> LOCATION: (4)..(4)
<223> OTHER INFORMATION: Leu or Tyr

<400> SEQUENCE: 121

Gly Asp Ser Xaa
1

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 122

Gly Asp Ser Leu
1

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 123

Gly Gly Asn Asp Ala
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 124

Gly Gly Asn Asp Leu
1               5

<210> SEQ ID NO 125
<211> LENGTH: 4
<212> TYPE: PRT
<213> ORGANISM: Artificial Sequence
<220> FEATURE:
<223> OTHER INFORMATION: Description of Artificial Sequence: Synthetic
      motif peptide

<400> SEQUENCE: 125

Gly Asp Ser Tyr
1

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      motif peptide
<220> FEATURE:
<221> NAME/KEY: MOD_RES
<222> LOCATION: (5)..(5)
<223> OTHER INFORMATION: Any amino acid

<400> SEQUENCE: 126
```

```
Gly Gly Asn Asp Xaa
1               5

<210> SEQ ID NO 127
<211> LENGTH: 5
<212> TYPE: PRT
<213> ORGANISM: Aeromonas hydrophila

<400> SEQUENCE: 127

Gly Asp Ser Leu Ser
1               5

<210> SEQ ID NO 128
<211> LENGTH: 8
<212> TYPE: PRT
<213> ORGANISM: Aeromonas hydrophila

<400> SEQUENCE: 128

Glu Leu Gly Gly Asn Asp Gly Leu
1               5

<210> SEQ ID NO 129
<211> LENGTH: 5
<212> TYPE: PRT
<213> ORGANISM: Aeromonas hydrophila

<400> SEQUENCE: 129

Gln Ile Arg Leu Pro
1               5

<210> SEQ ID NO 130
<211> LENGTH: 14
<212> TYPE: PRT
<213> ORGANISM: Aeromonas hydrophila

<400> SEQUENCE: 130

Gly Gln Asn Pro Ser Ala Arg Ser Gln Lys Val Val Glu Ala
1               5                   10

<210> SEQ ID NO 131
<211> LENGTH: 5
<212> TYPE: PRT
<213> ORGANISM: Aeromonas hydrophila

<400> SEQUENCE: 131

Asp Gly Ile His Pro
1               5

<210> SEQ ID NO 132
<211> LENGTH: 5
<212> TYPE: PRT
<213> ORGANISM: Aeromonas hydrophila

<400> SEQUENCE: 132

Gly Asp Ser Leu Ser
1               5

<210> SEQ ID NO 133
<211> LENGTH: 8
<212> TYPE: PRT
<213> ORGANISM: Aeromonas hydrophila

<400> SEQUENCE: 133

Trp Val Gly Ala Asn Asp Tyr Leu
1               5
```

<210> SEQ ID NO 134
<211> LENGTH: 5
<212> TYPE: PRT
<213> ORGANISM: Aeromonas hydrophila

<400> SEQUENCE: 134

Asp Gln Val His Pro
1               5

<210> SEQ ID NO 135
<211> LENGTH: 4
<212> TYPE: PRT
<213> ORGANISM: Aeromonas hydrophila

<400> SEQUENCE: 135

Tyr His Asn Gln
1

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 136

His His His His His His
1               5

<210> SEQ ID NO 137
<211> LENGTH: 317
<212> TYPE: PRT
<213> ORGANISM: Aeromonas hydrophila

<400> SEQUENCE: 137

Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
    130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Gln Leu Leu Leu Asn Leu Ala Arg Gln Leu Ala
            180                 185                 190

```
Pro Thr Gly Met Val Lys Leu Phe Glu Ile Asp Lys Gln Phe Ala Glu
        195             200             205
Met Leu Arg Asp Pro Gln Asn Phe Gly Leu Ser Asp Val Glu Asn Pro
    210             215             220
Cys Tyr Asp Gly Gly Tyr Val Trp Lys Pro Phe Ala Thr Arg Ser Val
225             230             235             240
Ser Thr Asp Arg Gln Leu Ser Ala Phe Ser Pro Gln Glu Arg Leu Ala
            245             250             255
Ile Ala Gly Asn Pro Leu Leu Ala Gln Ala Val Ala Ser Pro Met Ala
            260             265             270
Arg Arg Ser Ala Ser Pro Leu Asn Cys Glu Gly Lys Met Phe Trp Asp
        275             280             285
Gln Val His Pro Thr Thr Val Val His Ala Ala Leu Ser Glu Arg Ala
    290             295             300
Ala Thr Phe Ile Ala Asn Gln Tyr Glu Phe Leu Ala His
305             310             315
```